(12) United States Patent
Vu et al.

(10) Patent No.: US 10,253,104 B2
(45) Date of Patent: Apr. 9, 2019

(54) BISPECIFIC ANTIBODIES AGAINST CD3ε AND BCMA

(71) Applicant: ENGMAB AG, Pfäffikon (CH)

(72) Inventors: Minh Diem Vu, Wollerau (CH); Klaus Strein, Weinheim (DE); Oliver Ast, Bassersdorf (CH); Marina Bacac, Zurich (CH); Lydia Jasmin Hanisch, Birmensdorf (CH); Tanja Fauti, Zurich (CH); Anne Freimoser-Grundschober, Zurich (CH); Ralf Hosse, Cham (CH); Christian Klein, Bonstetten (CH); Ekkehard Moessner, Kreuzlingen (CH); Samuel Moser, Rotkreuz (CH); Ramona Murr, Zurich (CH); Pablo Umana, Wollerau (CH); Sabine Jung-Imhof, Planegg (DE); Stefan Klostermann, Neuried (DE); Michael Molhoj, Munich (DE); Joerg Regula, Munich (DE); Wolfgang Schaefer, Mannheim (DE)

(73) Assignee: ENGMAB AG, Wilen (CH)

( * ) Notice: Subject to any disclaimer, the term of this patent is extended or adjusted under 35 U.S.C. 154(b) by 0 days.

(21) Appl. No.: 15/501,620

(22) PCT Filed: Aug. 3, 2015

(86) PCT No.: PCT/EP2015/067841
§ 371 (c)(1),
(2) Date: Feb. 3, 2017

(87) PCT Pub. No.: WO2016/020332
PCT Pub. Date: Feb. 11, 2016

(65) Prior Publication Data
US 2017/0306036 A1    Oct. 26, 2017

(30) Foreign Application Priority Data

Aug. 4, 2014    (EP) .................................. 14179705

(51) Int. Cl.
| | | |
|---|---|---|
| *C07K 16/00* | (2006.01) | |
| *C07K 16/28* | (2006.01) | |
| *C07K 16/46* | (2006.01) | |
| *C07K 16/30* | (2006.01) | |
| *A61K 39/00* | (2006.01) | |

(52) U.S. Cl.
CPC ...... *C07K 16/2878* (2013.01); *C07K 16/2809* (2013.01); *C07K 16/3061* (2013.01); *C07K 16/468* (2013.01); *A61K 2039/505* (2013.01); *C07K 2317/21* (2013.01); *C07K 2317/31* (2013.01); *C07K 2317/33* (2013.01); *C07K 2317/35* (2013.01); *C07K 2317/522* (2013.01); *C07K 2317/526* (2013.01); *C07K 2317/55* (2013.01); *C07K 2317/56* (2013.01); *C07K 2317/565* (2013.01); *C07K 2317/64* (2013.01); *C07K 2317/66* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,202,238 A | 4/1993 | Fell et al. |
| 5,204,244 A | 4/1993 | Fell et al. |
| 6,331,415 B1 | 12/2001 | Cabilly et al. |

FOREIGN PATENT DOCUMENTS

| | | |
|---|---|---|
| EP | 1870459 A1 | 12/2007 |
| EP | 2647707 A1 | 10/2013 |
| WO | 96/27011 A1 | 9/1996 |
| WO | 1996/027011 A1 | 9/1996 |
| WO | 98/050431 A2 | 11/1998 |
| WO | 2000/041474 A2 | 7/2000 |
| WO | 2001/024811 A1 | 4/2001 |
| WO | 2001/024812 A1 | 4/2001 |
| WO | 2002/066516 A2 | 8/2002 |
| WO | 2007/110205 A2 | 10/2007 |
| WO | 2007/117600 A2 | 10/2007 |
| WO | 2007/147901 A1 | 12/2007 |
| WO | 2009/080251 A1 | 7/2009 |
| WO | 2009/080525 A1 | 7/2009 |
| WO | 2009/089004 A1 | 7/2009 |
| WO | 2009/132058 A2 | 10/2009 |
| WO | 2010/104949 A2 | 9/2010 |
| WO | 2010/129304 A2 | 11/2010 |
| WO | 2011/090754 A1 | 7/2011 |
| WO | 2011/143545 A1 | 11/2011 |
| WO | 2012/058768 A1 | 5/2012 |
| WO | 2012/066058 A1 | 5/2012 |
| WO | 2012/131555 A2 | 10/2012 |
| WO | 2012/143498 A1 | 10/2012 |
| WO | 2012/163802 A1 | 12/2012 |
| WO | 2013/002362 A1 | 1/2013 |
| WO | 2013/026833 A1 | 2/2013 |
| WO | 2013/072406 A1 | 5/2013 |
| WO | 2013/072415 A1 | 5/2013 |
| WO | 2013/096291 A2 | 6/2013 |
| WO | 2013/154760 A1 | 10/2013 |
| WO | 2013/157953 A1 | 10/2013 |
| WO | 2013/157954 A1 | 10/2013 |

*Primary Examiner* — Sean E Aeder
(74) *Attorney, Agent, or Firm* — Patrick H. Higgins; Eckert Seamas Cherin & Mellot, LLC

(57) ABSTRACT

A bispecific bi- or trivalent antibody specifically binding to the two targets which are extracellular domain of human B cell maturation antigen (BCMA) and human CD3ε, wherein the variable domains VL and VH in a light chain and the respective heavy chain are replaced by each other, characterized in comprising a constant domain CL wherein the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D) (numbering according to EU index of Kabat). Also the manufacture and use of said antibody.

16 Claims, 49 Drawing Sheets
Specification includes a Sequence Listing.

FIG. 1
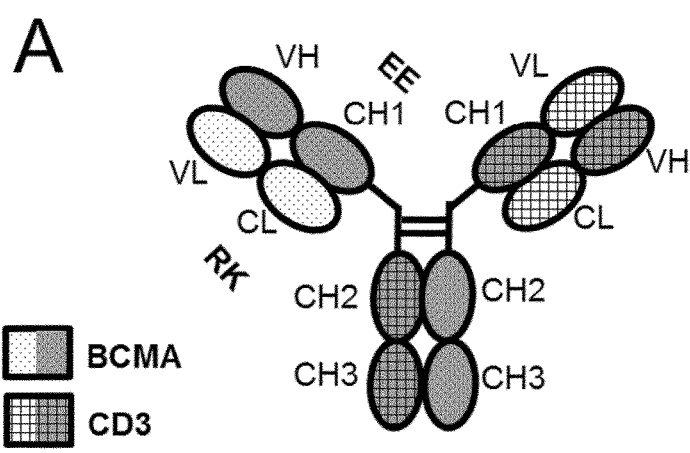
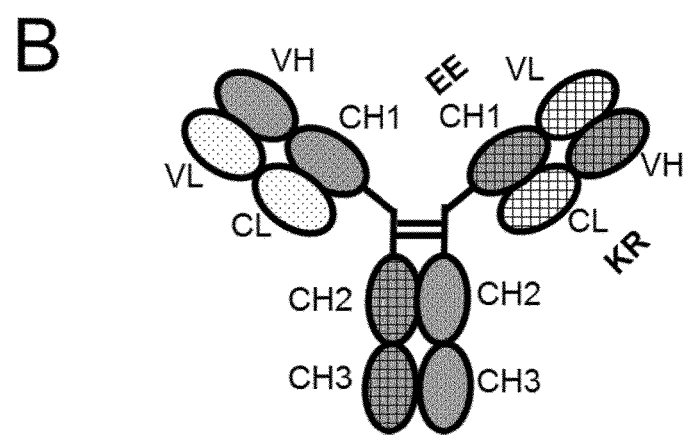

FIG. 8
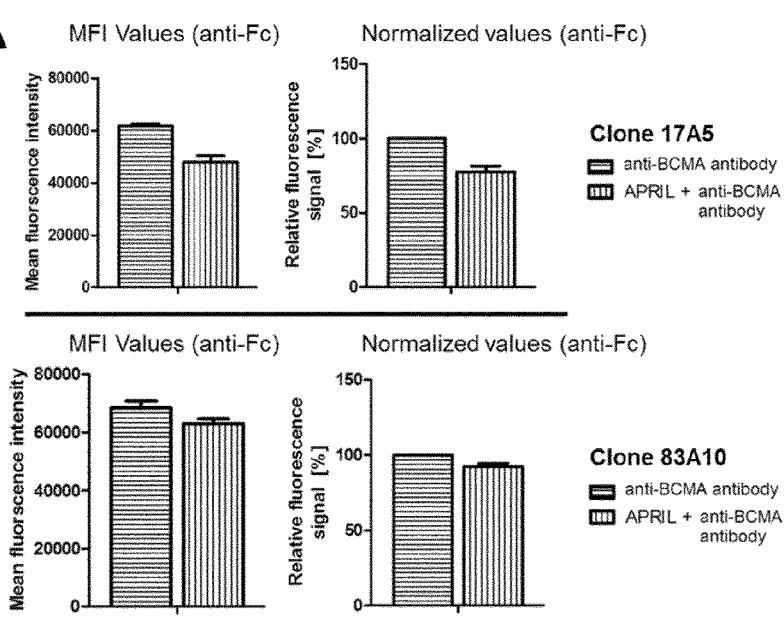
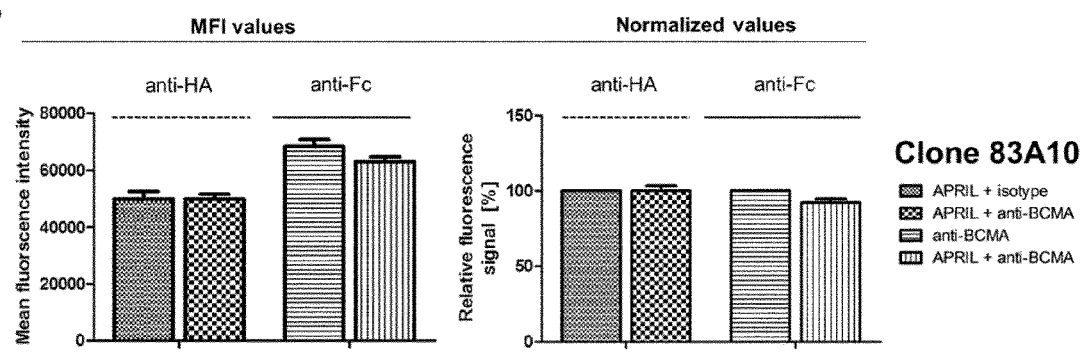

FIG. 11
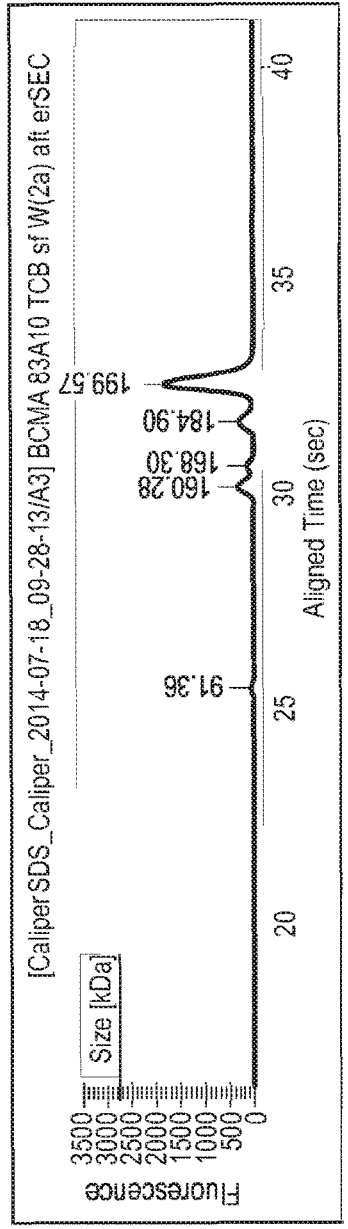
C. 83A10-TCB
Pur. methods: PA + SEC
Purity: 69.5%
Yield: 14.1 mg/L
Amount: 13.1 mg
Monomer: 74.7%
LC-MS: 40-60% correct molecule
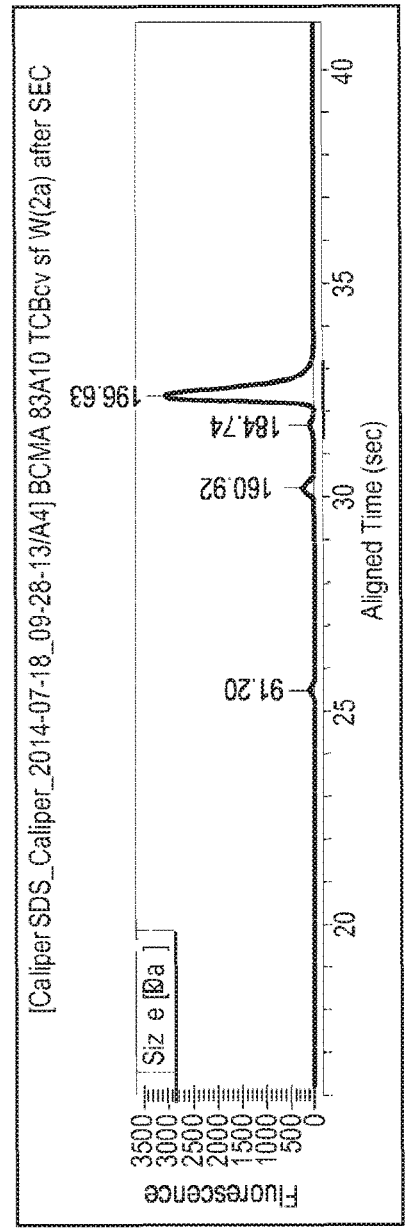
D. 83A10-TCBcv
Pur. methods: PA + SEC
Purity: 91.0%
Yield: 10.3 mg/L
Amount: 10.0 mg
Monomer: 83.9%
LC-MS: 90% correct molecule

FIG. 12
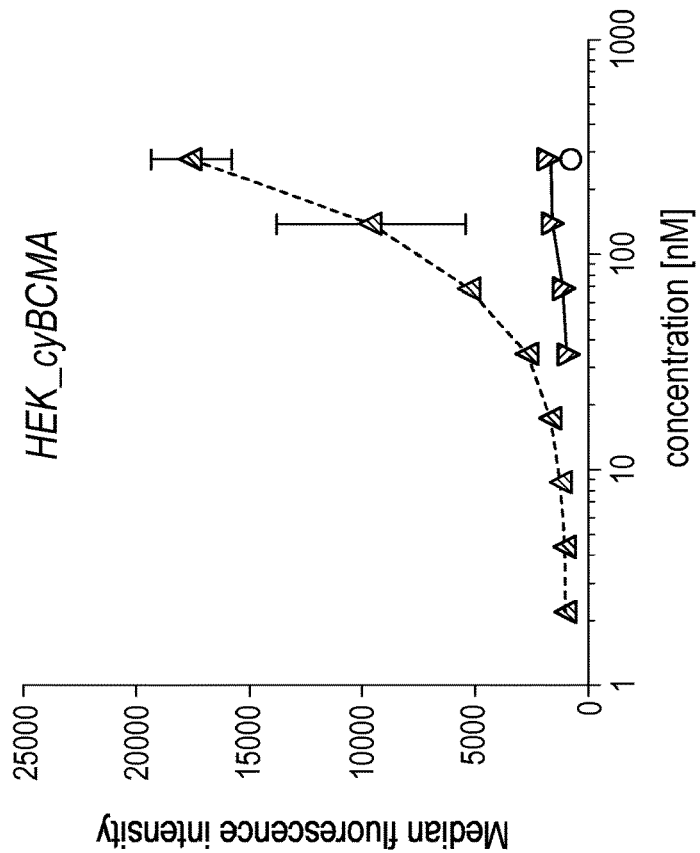
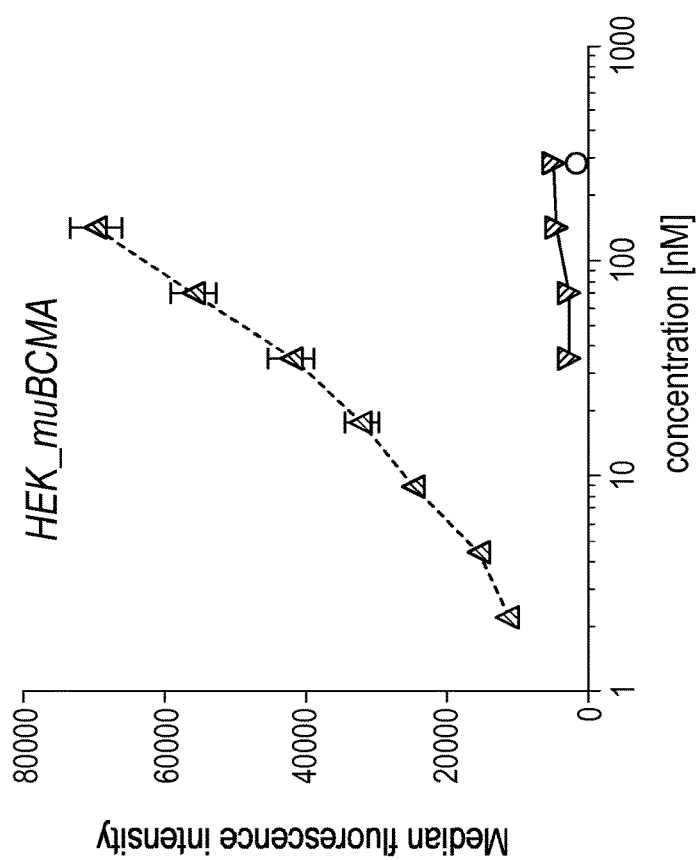

FIG. 15
A
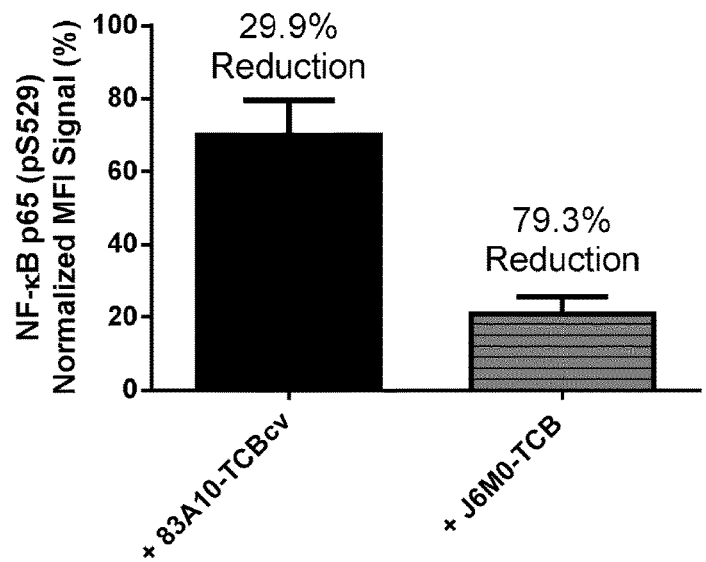
B
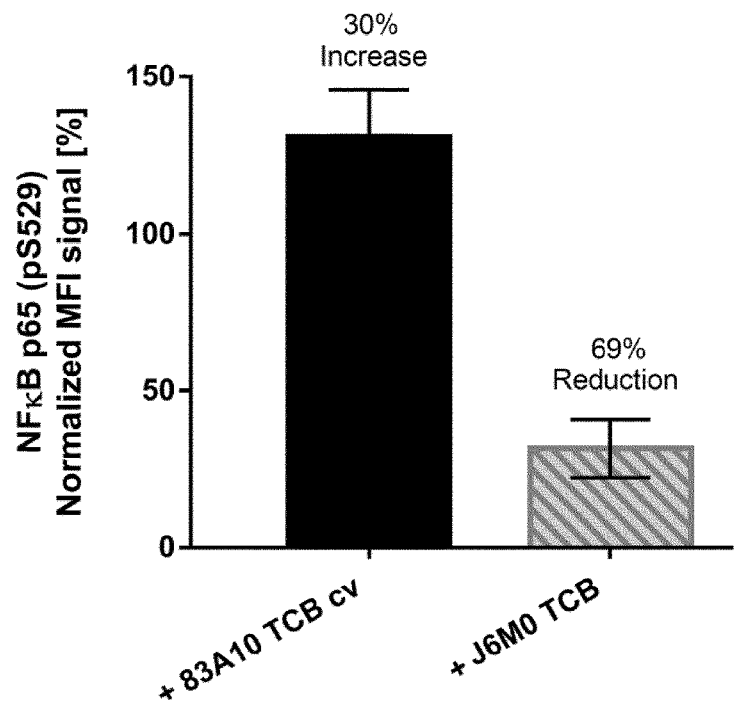

FIG. 16
A
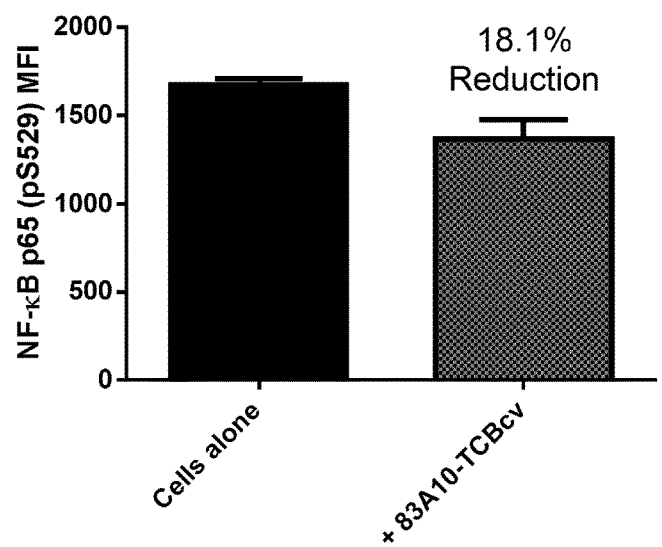
B
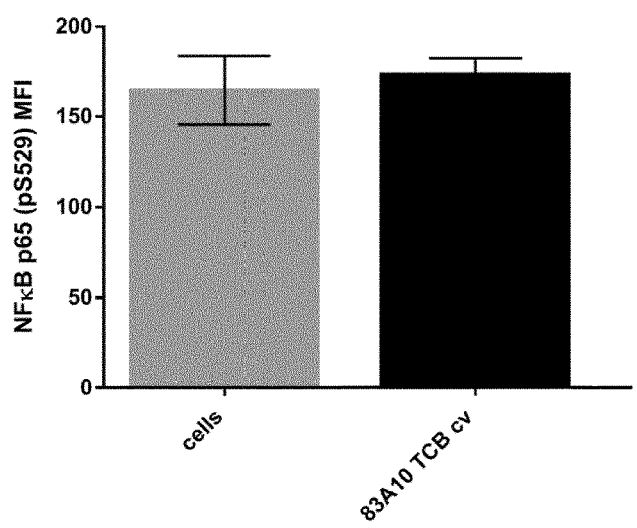

FIG. 19
A
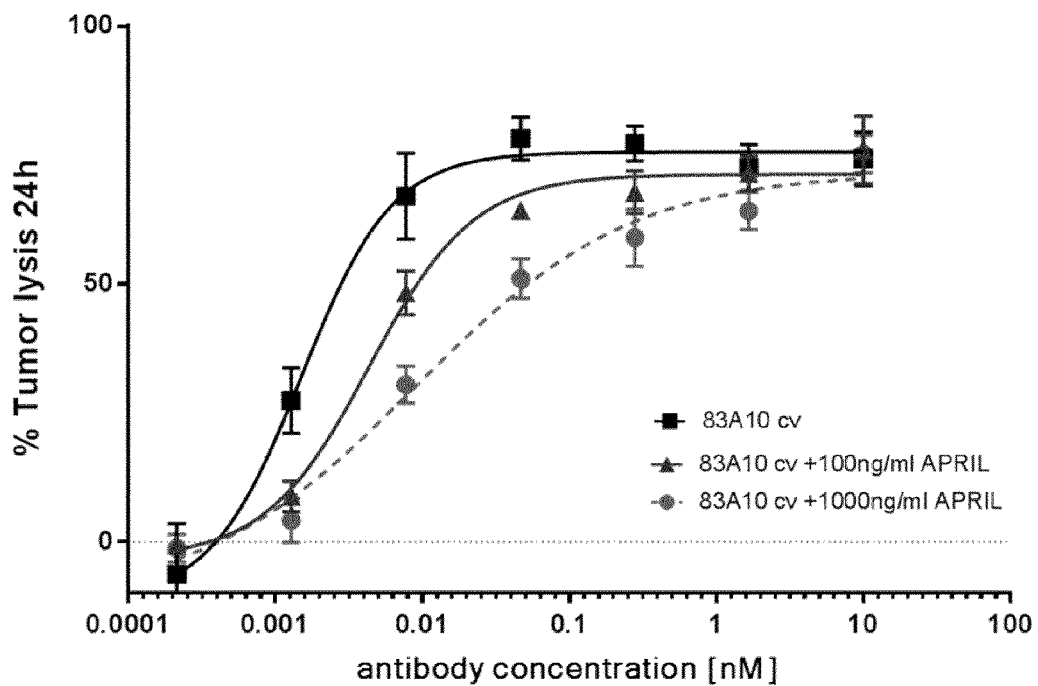
B
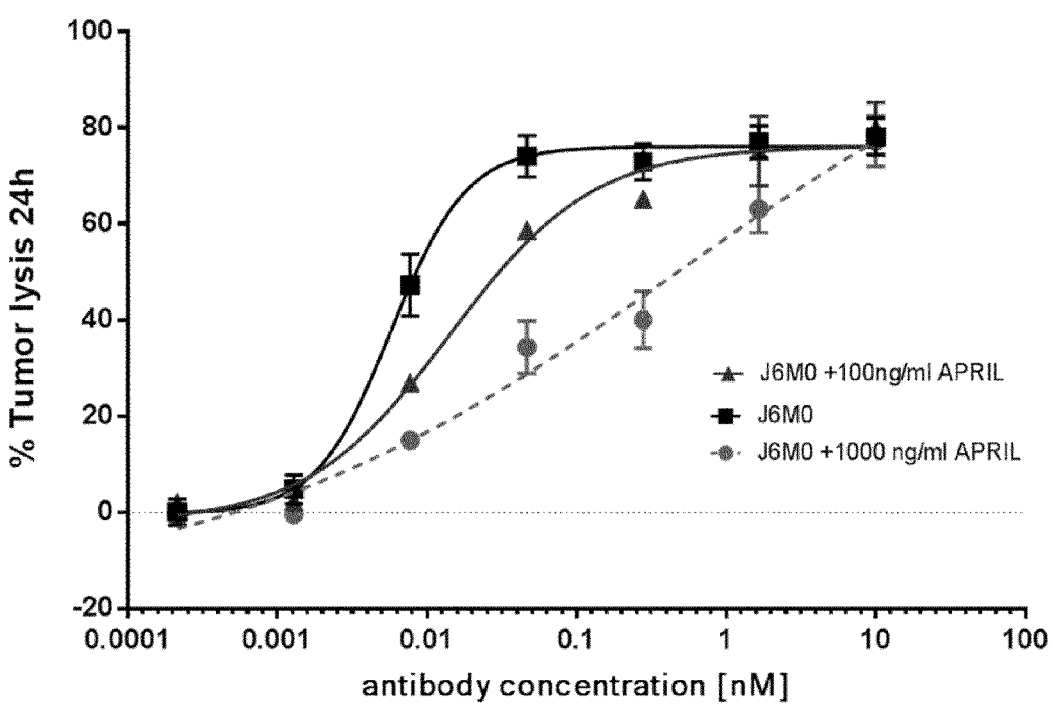

FIG. 20
B
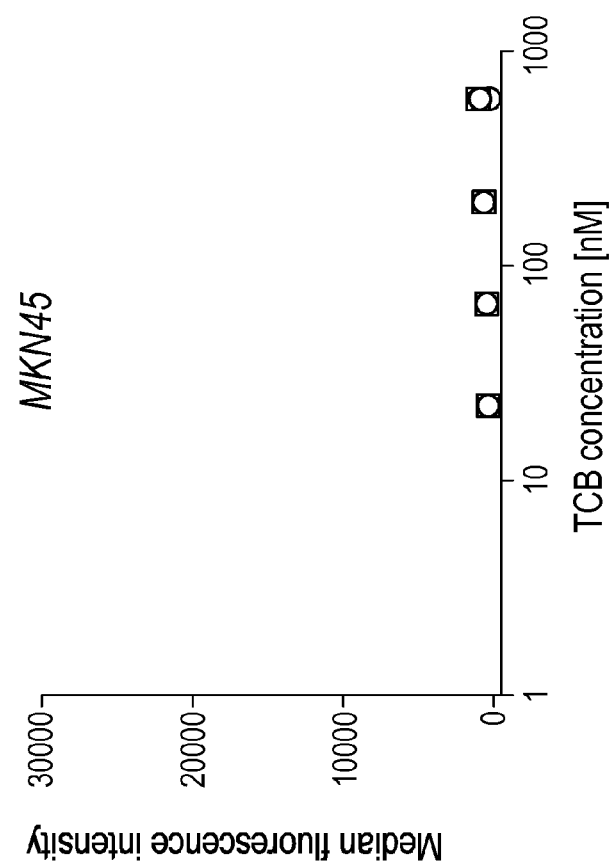
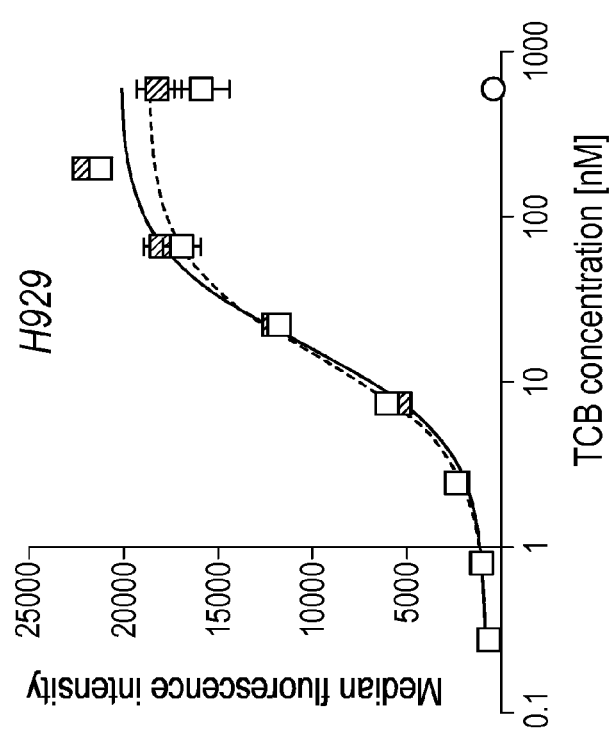

FIG. 23
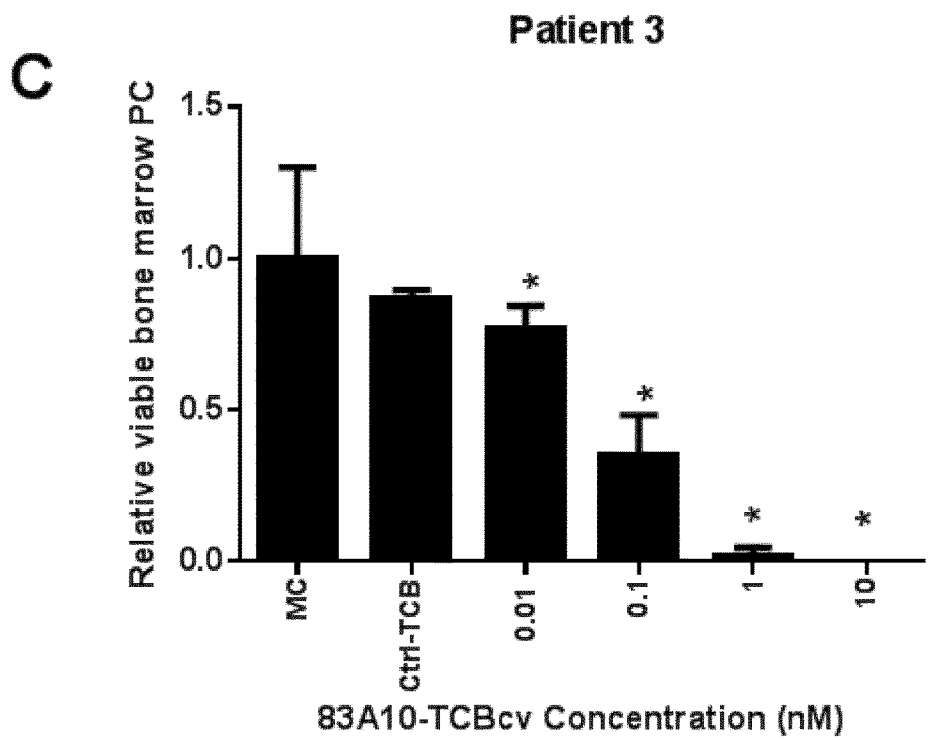
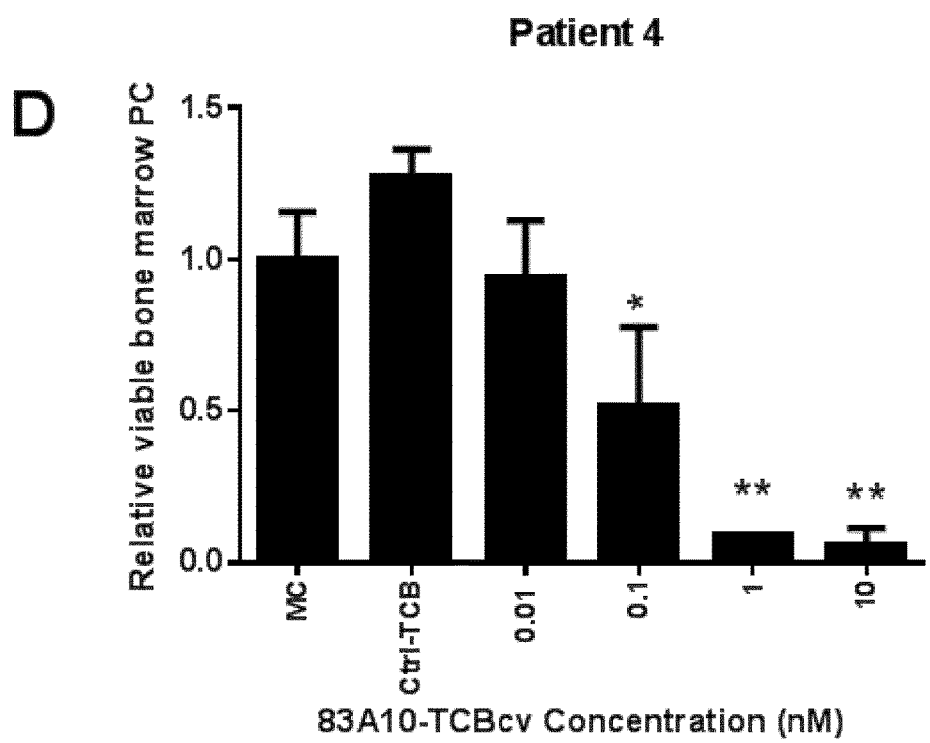

FIG. 23
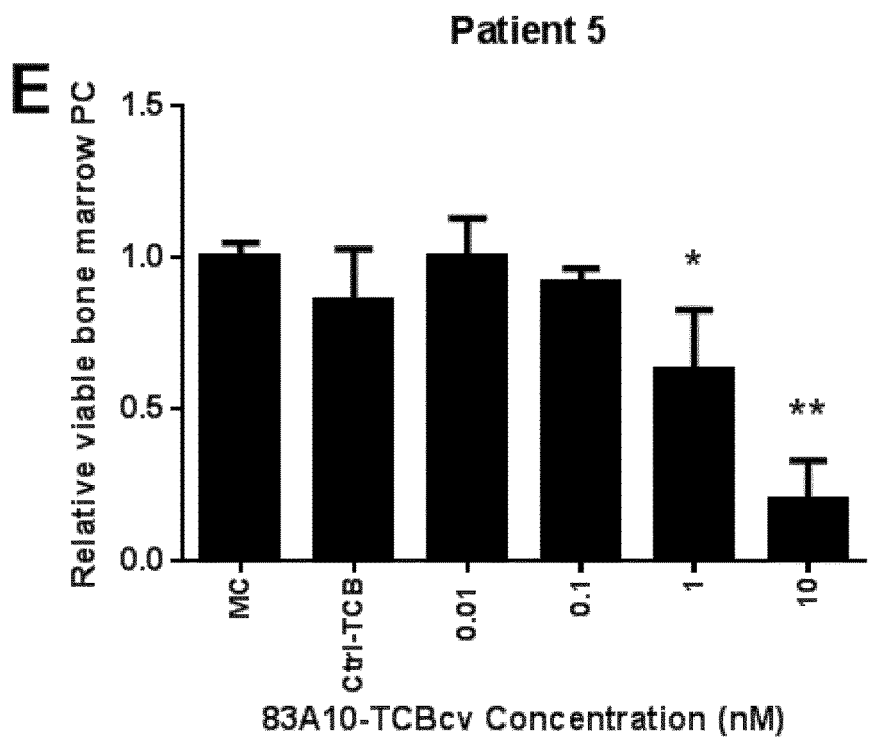
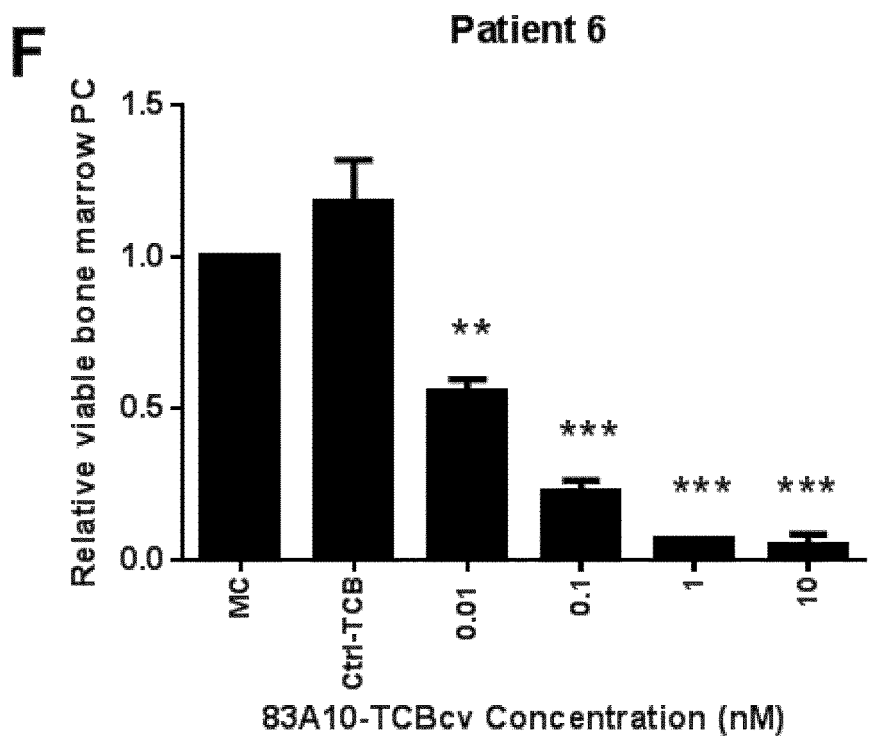

BISPECIFIC ANTIBODIES AGAINST CD3ε AND BCMA

REFERENCE TO SEQUENCE LISTING SUBMITTED ELECTRONICALLY

The content of the electronically submitted sequence listing (Name 3681_0030001_SeqListing_txt; Size: 109,134 bytes; and Date of Creation: Jan. 23, 2017) is incorporated herein by reference in its entirety.

The present invention relates to novel bispecific antibodies against CD3ε and BCMA, their manufacture and use.

BACKGROUND OF THE INVENTION

Human B cell maturation antigen also known as BCMA; TR17_HUMAN, TNFRSF17 (UniProt Q02223), is a member of the tumor necrosis receptor superfamily that is preferentially expressed in differentiated plasma cells (Laabi et al. 1992; Madry et al. 1998). BCMA is a non glycosylated type III transmembrane protein, which is involved in B cell maturation, growth and survival. BCMA is a receptor for two ligands of the TNF superfamily: APRIL (a proliferation-inducing ligand), the high-affinity ligand to BCMA and the B cell activation factor BAFF, the low-affinity ligand to BCMA (THANK, BlyS, B lymphocyte stimulator, TALL-1 and zTNF4). APRIL and BAFF show structural similarity and overlapping yet distinct receptor binding specificity. The negative regulator TACI also binds to both BAFF and APRIL. The coordinate binding of APRIL and BAFF to BCMA and/or TACI activates transcription factor NF-κB and increases the expression of pro-survival Bcl-2 family members (e.g. Bcl-2, Bcl-xL, Bcl-w, Mcl-1, A1) and the downregulation of pro-apoptotic factors (e.g. Bid, Bad, Bik, Bim, etc.), thus inhibiting apoptosis and promoting survival. This combined action promotes B cell differentiation, proliferation, survival and antibody production (as reviewed in Rickert R C et al., Immunol Rev (2011) 244 (1): 115-133).

The TCR/CD3 complex of T-lymphocytes consists of either a TCR alpha (α)/beta (β) or TCR gamma (γ)/delta (δ) heterodimer coexpressed at the cell surface with the invariant subunits of CD3 labeled gamma (γ), delta (δ), epsilon (ε), zeta (ζ), and eta (η). Human CD3ε is described under UniProt P07766 (CD3ε_HUMAN). An anti CD3ε antibody described in the state of the art is SP34 (Yang S J, The Journal of Immunology (1986) 137; 1097-1100). SP34 reacts with both primate and human CD3. SP34 is available from PharMingen. A further anti CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti et al., Transplantation 54: 844 (1992)).

A wide variety of recombinant bispecific antibody formats have been developed in the recent past, e.g. by fusion of, e.g. an IgG antibody format and single chain domains (see Kontermann R E, mAbs 4:2, (2012) 1-16). Bispecific antibodies wherein the variable domains VL and VH or the constant domains CL and CH1 are replaced by each other are described in WO2009080251 and WO2009080252.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway J B, Presta L G, Carter P; Protein Eng. 9, 617-621 (1996); and WO1996027011). The percentage of heterodimer could be further increased by remodeling the interaction surfaces of the two CH3 domains using a phage display approach and the introduction of a disulfide bridge to stabilize the heterodimers (Merchant A. M, et al, Nature Biotech 16 (1998) 677-681; Atwell S, Ridgway J B, Wells J A, Carter P., J Mol Biol 270 (1997) 26-35). New approaches for the knobs-into-holes technology are described in e.g. in EP 1870459A1. Although this format appears very attractive, no data describing progression towards the clinic are currently available. One important constraint of this strategy is that the light chains of the two parent antibodies have to be identical to prevent mispairing and formation of inactive molecules. Thus this technique is not appropriate for easily developing recombinant, bispecific antibodies against two targets starting from two antibodies against the first and the second target, as either the heavy chains of these antibodies and/or the identical light chains have to be optimized. Xie, Z., et al, J Immunol Methods 286 (2005) 95-101 refers to a format of bispecific antibody using scFvs in combination with knobs-into-holes technology for the FC part. WO2012116927 and WO2010145792 mention exchanging the CH1 and CL domains. WO2009080254 mentions knob in hole constructs for producing bispecific antibodies. WO 2006093794 relates to heterodimeric protein binding compositions. WO199937791 describes multipurpose antibody derivatives. Morrison, S. L., et al., J. Immunol. 160 (1998) 2802-2808 refers to the influence of variable region domain exchange on the functional properties of IgG.

WO 201302362 relate to heterodimerized polypeptides. WO201312733 relates to polypeptides comprising heterodimeric Fc regions. WO2012131555 relates to engineered heterodimeric immunoglobulins. EP 2647707 relates to engineered hetero-dimeric immunoglobulins. WO2009080251, WO 2009080252, WO 2009080253, WO 2009080254 and Schaefer, W. et al, PNAS, 108 (2011) 11187-1191 relate to bivalent, bispecific IgG antibodies with a domain crossover. The multispecific antibodies with VH/VL replacement/exchange in one binding to prevent light chain mispairing (CrossMabVH-VL) which are described in WO2009080252, (see also Schaefer, W. et al, PNAS, 108 (2011) 11187-1191) clearly reduce the byproducts caused by the mismatch of a light chain against a first antigen with the wrong heavy chain against the second antigen (compared to approaches without such domain exchange). However their preparation is not completely free of side products. The main side product is based on a Bence-Jones-type interaction (Schaefer, W. et al, PNAS, 108 (2011) 11187-1191).

Antibodies against BCMA are described e.g. in Gras M-P. et al. Int Immunol. 7 (1995) 1093-1106, WO200124811, WO200124812, WO2010104949 and WO2012163805. Antibodies against BCMA and their use for the treatment of lymphomas and multiple myeloma are mentioned e.g. in WO2002066516 and WO2010104949. WO2013154760 relates to chimeric antigen receptors (CAR) comprising a BCMA recognition moiety and a T-cell activation moiety.

Ryan, M C et al., Mol. Cancer Ther. 6 (2007) 3009-3018 relate to targeting of BCMA for plasma cell malignancies. Antibody SG1, with ligand blocking activity could promote cytotoxicity of multiple myeloma (MM) cell lines as naked antibodies or as antibody-drug conjugates (ADC). SG1, an inhibitory BCMA antibody, blocks APRIL-dependent activation of nuclear factor-κB in a dose-dependent manner in vitro. Cytotoxicity of SG1 was assessed as a naked antibody after chimerization with and without Fc mutations that enhance FcγRIIIA binding. Ryan also mentions antibody SG2 which does not significantly inhibit APRIL binding to BCMA. However SG2 showed a 20 fold higher $IC_{50}$ value as SG1 measured as cytotoxic activity of a drug conjugate against BCMA positive myeloma cell lines. Ryan conclude that BCMA antibodies can act on myeloma cell lines through multiple mechanisms that include inhibition of APRIL-dependent NF-κB activation, promotion of tumor cell lysis by natural killer cell-mediated ADCC activity, and induction of cytotoxicity by ADCs.

Bispecific antibodies against CD3 and BCMA are mentioned in WO2007117600, WO2009132058, WO2012066058, WO2012143498, and WO2013072415. PCT/EP2014/052189 and PCT/EP2014/052190 describe antibodies against BCMA and bispecific antibodies against CD3 and BCMA comprising certain CDRs and variable domains disclosed also in the present invention.

Accordingly there is a need for bispecific antibodies against CD3ε and BCMA with VH/VL exchange which can be produced in high yield and easily purified.

SUMMARY OF THE INVENTION

The invention relates to a bispecific bi- or trivalent antibody specifically binding to the two targets which are the extracellular domain of human BCMA (further named also as "BCMA") and human CD3ε (further named also as "CD3") wherein the variable domains VL and VH in a light chain and the respective heavy chain are replaced by each other, characterized in comprising a constant domain CL wherein the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D) (numbering according to EU index of Kabat). Preferably the antibody is monovalent for CD3 binding. Preferably in addition to the amino acid replacement at position 124 in the constant domain CL the amino acid at position 123 is substituted independently by lysine (K), arginine (R) or histidine (H). Preferably the antibody is monovalent for CD3 binding and amino acid 124 is K, amino acid 147 is E, amino acid 213 is E, and amino acid 123 is R.

The invention relates to a bispecific antibody specifically binding to the two targets which are the extracellular domain of human BCMA (further named also as "BCMA") and human CD3ε (further named also as "CD3"), characterized in comprising
a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and
c) wherein in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 and the amino acid at position 213 is substituted independently by glutamic acid (E), or aspartic acid (D) (numbering according to EU index of Kabat) (see e.g. FIGS. 1A, 2A, 2C, 3A, 3C).

Preferably said bispecific antibody described in the last preceding paragraph is further characterized in that said bispecific antibody comprises in addition a Fab fragment of said first antibody (further named also as "BCMA-Fab") and in the constant domain CL said BCMA-Fab the amino acid at position 124 is substituted independently by lysine (K), arginine (R) or histidine (H) (numbering according to Kabat), and wherein in the constant domain CH1 of said BCMA-Fab the amino acid at positions 147 and the amino acid at position 213 is substituted independently by glutamic acid (E), or aspartic acid (D) (numbering according to EU index of Kabat) (see e.g. FIGS. 2A, 2C).

The invention further relates to a bispecific antibody specifically binding to the two targets which are the extracellular domain of human BCMA (further named also as "BCMA") and human CD3ε (further named also as "CD3"), characterized in comprising
a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and wherein
c) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at positions 147 and the amino acid at position 213 is substituted independently by glutamic acid (E), or aspartic acid (D) (numbering according to EU index of Kabat) (see e.g. FIGS. 1B, 2B, 2D, 3B, 3D).

Preferably said bispecific antibody described in the last preceding paragraph is further characterized in that said bispecific antibody comprises in addition a second Fab fragment of said first antibody ("BCMA-Fab") (see e.g. FIG. 2B, 2D).

Amino acid numbering in the constant domain CL is according to Kabat (see below).

Preferably in addition to the amino acid replacement at position 124 in the constant domain CL of the first or second light chain the amino acid at position 123 is substituted independently by lysine (K), arginine (R) or histidine (H).

Preferably in the constant domain CL the amino acid at position 124 is substituted by lysine (K), in the constant domain CH1 the amino acid at position 147 and the amino acid at position 213 are substituted by glutamic acid (E). Preferably in addition in the constant domain CL in the amino acid at position 123 is substituted by arginine (R).

In a preferred embodiment of the invention the antibody according to the invention consists of one Fab fragment of an antibody specifically binding to CD3 (further named also as "CD3-Fab"), and one Fab fragment of an antibody specifically binding to BCMA (further named also as "BCMA-Fab(s)") and a Fc part, wherein the CD3-Fab and the BCMA-Fab are linked via their C-termini to the hinge region of said Fc part. Either the CD3-Fab or the BCMA-Fab comprises aa substitution and the CD3-Fab comprises crossover (FIGS. 1A and 1B).

In a preferred embodiment of the invention the antibody according to the invention consists of one CD3-Fab, and one BCMA-Fab and a Fc part, wherein the CD3-Fab and the BCMA-Fab are linked via their C-termini to the hinge region of said Fc part and a second BCMA-Fab, which is linked with its C-terminus to the N-terminus of the CD3-Fab. The CD3-Fab comprises crossover and either the CD3-Fab or both BCMA-Fabs comprise aa substitution (FIGS. 2A and 2B). Especially preferred is a bispecific antibody comprising BCMA-Fab-Fc-CD3-Fab-BCMA-Fab, wherein both BCMA-Fabs comprise aa substitution and the CD3-Fab comprises VL/VH crossover (FIG. 2A). Especially preferred is a bispecific antibody consisting of BCMA-Fab-Fc-CD3-Fab-BCMA-Fab, wherein both BCMA-Fabs comprise aa substitution Q124K, E123R, K147E and K213E and the CD3-Fab comprises VL/VH crossover. Especially preferred is that both BCMA-Fabs comprise as CDRs the CDRs of antibody 83A10, or as VH/VL the VH/VL of 83A10. Further preferred is that both BCMA-Fabs comprise as CDRs the CDRs of antibody 17A5, or as VH/VL the VH/VL of 17A5. Further preferred is that both BCMA-Fabs comprise as CDRs the CDRs of antibody 13A4, or as VH/VL the VH/VL of 13A4.

In a preferred embodiment of the invention the antibody according to the invention consists of two BCMA-Fabs and a Fc part, wherein the BCMA-Fabs are linked via their C-termini to the hinge region of said Fc part and a CD3-Fab, which is linked with its C-terminus to the N-terminus of one BCMA-Fab. The CD3-Fab comprises crossover and either the CD3-Fab or both BCMA-Fabs comprise aa substitution (FIGS. 2C and 2D).

In a preferred embodiment of the invention the antibody according to the invention consists of one CD3-Fab, which is linked via its C-terminus to the hinge region of said Fc part and a BCMA-Fab, which is linked with its C-terminus to the N-terminus of the CD3-Fab. The CD3-Fab comprises crossover and either the CD3-Fab or the BCMA-Fab comprise aa substitution (FIGS. 3A and 3B).

In a preferred embodiment of the invention the antibody according to the invention consists of one BCMA-Fab, which is linked via its C-terminus to the hinge region of said Fc part and a CD3-Fab, which is linked with its C-terminus to the N-terminus of the BCMA-Fab. The CD3-Fab comprises crossover and either the CD3-Fab or the BCMA-Fab comprise aa substitution (FIGS. 3C and 3D).

The Fab fragments are chemically linked together by the use of an appropriate linker according to the state of the art. Preferably a (Gly4-Ser1)3 linker is used (Desplancq D K et al., Protein Eng. 1994 August; 7(8):1027-33 and Mack M. et al., PNAS Jul. 18, 1995 vol. 92 no. 15 7021-7025). Linkage between two Fab fragments is performed between the heavy chains. Therefore the C-terminus of CH1 of a first Fab fragment is linked to the N-terminus of VH of the second Fab fragment (no crossover) or to VL (crossover). Linkage between a Fab fragment and the Fc part is performed according to the invention as linkage between CH1 and CH2.

The first and a second Fab fragment of an antibody specifically binding to BCMA are preferably derived from the same antibody and preferably identical in the CDR sequences, variable domain sequences VH and VL and/or the constant domain sequences CH1 and CL. Preferably the amino acid sequences of the first and a second Fab fragment of an antibody specifically binding to BCMA are identical. Preferably the BCMA antibody is an antibody comprising the CDR sequences of antibody 83A10, 17A5 or 13A4, an antibody comprising the VH and VL sequences of antibody 83A10, 17A5 or 13A4, or an antibody comprising the VH, VL, CH1, and CL sequences of antibody 83A10, 17A5 or 13A4.

Preferably the bispecific antibody comprises as Fab fragments and Fc part, not more than one Fab fragment of an anti-CD3 antibody, not more than two Fab fragments of an anti-BCMA antibody and not more than one Fc part, preferably a human Fc part. Preferably the second Fab fragment of an anti-BCMA antibody is linked via its C-terminus either to the N-terminus of the Fab fragment of an anti-CD3 antibody or to the hinge region of the Fc part. Preferably linkage is performed between CH1 of BCMA-Fab and VL of CD3-Fab (VL/VH crossover).

Preferably the antibody according to the invention is further characterized in that it binds also specifically to cynomolgus BCMA. Such a preferred antibody according to the invention is the antibody characterized in comprising a heavy and light chain set of polypeptides SEQ ID NO:43, SEQ ID NO:44, SEQ ID NO:45, and SEQ ID NO:46 (set 1).

Preferably the antibody portion specifically binding to human CD3, preferably the Fab fragment, is characterized in comprising a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3 of the anti-CD3ε antibody (CDR MAB CD3). Preferably the antibody portion specifically binding to human CD3 is characterized in that the variable domains are of SEQ ID NO:7 and 8 (VHVL MAB CD3).

Preferably the antibody portion, preferably the Fab fragment, specifically binding to human BCMA is characterized in comprising a variable domain VH comprising the heavy chain CDRs CDR1H of SEQ ID NO:21, a CDR2H of SEQ ID NO:24, a CDR3H of SEQ ID NO: 27 and comprising a variable domain VL comprising the light chain CDRs CDR1L of SEQ ID NO:30, a CDR2L of SEQ ID NO:33, a CDR3L of SEQ ID NO: 36 (CDR MAB 83A10). Preferably the antibody portion, preferably the Fab fragment, specifically binding to human BCMA is characterized in comprising a variable domain VH comprising the heavy chain CDRs CDR1H of SEQ ID NO:22, a CDR2H of SEQ ID NO:25, a CDR3H of SEQ ID NO: 28 and a variable domain VL comprising the light chain CDR1L of SEQ ID NO:31, a CDR2L of SEQ ID NO:34, a CDR3L of SEQ ID NO: 37 (CDR MAB 17A5). Preferably the antibody portion, preferably the Fab fragment, specifically binding to human BCMA is characterized in comprising a variable domain VH comprising the heavy chain CDRs CDR1H of SEQ ID NO:23, a CDR2H of SEQ ID NO:26, a CDR3H of SEQ ID NO: 29 and a variable domain VL comprising the light chain CDR1L of SEQ ID NO:32, a CDR2L of SEQ ID NO:35, a CDR3L of SEQ ID NO: 38 (CDR MAB 13A4).

Preferably the antibody portion, preferably the Fab fragment, specifically binding to human BCMA is characterized in comprising a VH of SEQ ID NO: 15 and a VL of SEQ ID NO: 18 (VHVL MAB 83A10). Preferably the antibody portion, preferably the Fab fragment, specifically binding to human BCMA is characterized in comprising a VH of SEQ ID NO: 16 and a VL of SEQ ID NO: 19 (VHVL MAB 17A5). Preferably the antibody portion, preferably the Fab fragment, specifically binding to human BCMA is characterized in comprising a VH of SEQ ID NO: 17 and a VL of SEQ ID NO: 20 (VHVL MAB 13A4).

The invention relates to a bispecific antibody specifically binding to the extracellular domain of human BCMA and to human CD3ε, characterized in comprising a heavy and light chain set selected from the group consisting of polypeptides i) SEQ ID NO:43, SEQ ID NO:44, SEQ ID NO:45, and SEQ ID NO:46 (set 1), ii) SEQ ID NO:45, SEQ ID NO:47, SEQ ID NO:48, and SEQ ID NO:49 (set 2), and iii) SEQ ID NO:45, SEQ ID NO:50, SEQ ID NO:51, and SEQ ID NO:52 (set 3).

Preferably an antibody according to the invention comprises as anti-BCMA antibody an antibody selected from the group of the BCMA antibody variants of 13A4 and 83A10. Preferably, an antibody to the invention, comprising sequences of 13A4, comprises an amino acid replacement at respective position 95 (N95) or 96 (G96) within CDR3H of SEQ ID NO:29 by either a single amino acid change in position 95, either N95S, N95T, N95E, N95Q, N95A, or N95G, or by a single amino acid change in position 96, either G96A, G96E, or G96Q.

Preferably an antibody according to the invention, comprising sequences of 13A4, comprises an amino acid replacement selected from the group consisting of amino acid replacements at respective positions 27 (N27f) and 28 (G28) within CDR1L of SEQ ID NO:32 by either a single amino acid change in position 27, either N27fS, N27fT, N27fE, N27fQ, N27fA, or N27fG or by a single amino acid change in position 28 either G28A, G28E, or G28Q.

Preferably an antibody according to the invention, comprising sequences of 13A4, comprises an amino acid replacement selected from the group consisting of amino acid replacements at respective positions 54 (D54) and 55 (S55) within CDR2H of SEQ ID NO:26 by either a single amino acid change in position 54, either D54S, D54T, D54E, D54Q, D54A, or D54G or by a single amino acid change in position 55, either S55A, S55E, or S55Q.

Preferably an antibody according to the invention, comprising sequences of 13A4, comprises an amino acid replacement selected from the group consisting of amino acid replacements W at position 33 (W33) within CDR1H of SEQ ID NO:23 by either W33F, W33Y, W33V, W33I, W33L, or W33A.

Preferably an antibody according to the invention, comprising sequences of 13A4, comprises up to two amino acid replacements in N95 and/or W33 or up to two amino acid replacements in G96 and/or W33. Preferably an antibody according to the invention, comprising sequences of 13A4, comprises one amino acid replacement in N95 or G96.

Preferably an antibody according to the invention, comprising sequences of 13A4, comprises up to four amino acid replacements in N95 and/or W33 and/or N27 or G28 and/or D54 or S55 or up to four amino acid replacements in G96 and/or W33 and/or N27 or G28 and/or D54 or S55. Preferably an antibody according to the invention, comprising sequences of 13A4, comprises one amino acid replacement in N95 or G96.

Preferably an antibody according to the invention comprises the first light chain and the first heavy chain of a first antibody specifically binding to BCMA, wherein said light chain comprising as CDRs, CDR2L of SEQ ID NO:35, CDR3L of SEQ ID NO: 38 and CDR1L selected from the group consisting of SEQ ID NO: 32, 71, 73, 75, 77, 79, 81, 83, 85, and 87, and said heavy chain comprising as heavy chain CDRs CDR1H selected from the group consisting of SEQ ID NO:23, 107, 109, 111, 113, 115, and 117, CDR2H selected from the group consisting of SEQ ID NO:26, 89, 91, 93, 95, 97, 99, 101, 103, and 105 CDR3H selected from the group consisting of SEQ ID NO:29, 53, 55, 57, 59, 61, 63, 65, 67, and 69.

Preferably an antibody according to the invention comprises within the first light chain of a first antibody specifically binding to BCMA a variable light chain domain VL selected from the group consisting of SEQ ID NO: 20, 72, 74, 76, 78, 80, 82, 84, 86, and 88, and within the first heavy chain of a first antibody specifically binding to BCMA a variable heavy chain domain VH selected from the group consisting of SEQ ID NO: 17, 54, 56, 58, 60, 62, 64, 66, 68, 70, 90, 92, 94, 96, 98, 100, 102, 104, 106, 108, 110, 112, 114, 116, and 118.

Preferably an antibody according to the invention, comprising sequences of 83A10, comprises an amino acid replacement selected from the group consisting of amino acid replacements at position 98 (W98) within CDR3H of SEQ ID NO:27 by either W98F, W98Y, W98V, W98I, W98L, or W98A.

Preferably an antibody according to the invention comprises the first light chain and the first heavy chain of a first antibody specifically binding to BCMA, wherein said light chain comprising as CDRs CDR1L of SEQ ID NO:30, CDR2L of SEQ ID NO:33, CDR3L of SEQ ID NO: 36 and said heavy chain comprising as heavy chain CDRs CDR1H of SEQ ID NO:21, CDR2H of SEQ ID NO:24, and CDR3H selected from the group consisting of SEQ ID NO: 27, 119, 121, 123, 125, 127, and 129.

Preferably an antibody according to the invention comprises within the first light chain of a first antibody specifically binding to BCMA a variable light chain domain VL of SEQ ID NO:18 and within the first heavy chain of a first antibody specifically binding to BCMA a variable heavy chain domain VH selected from the group consisting of SEQ ID NO: 15, 120, 122, 124, 126, 128, and 130.

The invention relates further to a bispecific antibody specifically binding to the extracellular domain of BCMA and to CD3ε, characterized in comprising as heavy and light chains the polypeptides of SEQ ID NO: 45, 50, 51, and 52 wherein one or more CDRs are replaced by the respective CDRs of the "BCMA antibody variants". The invention relates further to a bispecific antibody specifically binding to the extracellular domain of BCMA and to CD3ε, characterized in comprising as heavy and light chains the polypeptides of SEQ ID NO: 45, 50, 51, and 52 wherein one or more VHs and/or VLs are replaced by the respective VHs and/or VLs of the "BCMA antibody variants". The invention relates further to a bispecific antibody specifically binding to the extracellular domain of BCMA and to CD3ε, characterized in comprising as heavy and light chains the polypeptides of SEQ ID NO: 43, 44, 45, and 46 wherein one or more CDRs are replaced by the respective CDRs of the "BCMA antibody variants". The invention relates further to a bispecific antibody specifically binding to the extracellular domain of BCMA and to CD3ε, characterized in comprising as heavy and light chains the polypeptides of SEQ ID NO: 43, 44, 45, and 46 wherein one or more VHs and/or VLs are replaced by the respective VHs and/or VLs of the "BCMA antibody variants". Preferably an antibody according to the invention shows high affinity to BCMA and low aggregation.

The invention further relates to a nucleic acid set encoding a respective heavy and light chain set.

Preferably the bispecific antibody according to the invention comprising constant heavy regions CH2/CH3 of IgG1 subclass is characterized in comprising the mutations L234A, L235A and P239G (numbering according to EU index of Kabat) to avoid FcR and C1q binding and minimizing ADCC/CDC. The advantage is that such an antibody of the invention mediates its tumor cell killing efficacy purely by the powerful mechanism of T-cell redirection/activation. Additional mechanisms of action like effects on complement system and on effector cells expressing FcR are avoided and the risk of side-effects is decreased.

The invention comprises preferably a heavy chain of an antibody according to the invention consisting of (from N-to-C-terminus) VH(BCMA)-CH1(BCMA)-VL(CD3)-CH1(CD3)-CH2-CH3 of SEQ ID NO: 43, 47, or 50, as well as the respective encoding nucleic acids. These polypeptides and respective nucleic acids are useful for the production of a bispecific antibody according to the invention.

The amino acid (aa) exchanges outside of the CDRs of the bispecific antibodies according to the invention provide considerably improved production/purification without changing biological properties like binding to BCMA. By introduction of the aa exchanges according to the invention light chain LC mispairing and the formation of side products in production is significantly reduced and therefore purification is facilitated.

Preferably an antibody according to the invention is characterized by showing tumor growth inhibition of more than 70%, preferably of more than 85%, preferably of close to 100% in a multiple myeloma xenograft model (e.g. xenograft with NCI-H929 cells or RPMI8226 cells or U266B1 cells or L-363 cells) at a dose of 1 mg/kg body weight (BW) administered intravenously (i.v.) or subcutaneously (s.c.) or intraperitoneal (i.p.) twice a week or once a week, preferably 0.5 mg/kg BW administered i.v. or i.p. or s.c. twice a week or once a week, preferably at 0.1 mg/kg BW administered i.v. or i.p. or s.c. twice a week or once a week, preferably at 0.05 mg/kg BW administered i.v. or i.p. or s.c. twice a week or once a week, preferably at 0.01 mg/kg BW administered i.v. or i.p. or s.c twice a week or once a week, preferably at 5 µg/kg BW administered i.v. or i.p. or s.c. twice a week or once a week.

Preferably an antibody according to the invention is characterized by an elimination half-life in mice, preferably cynomolgus monkeys of longer than 24 hours, preferably 3 days or longer, preferably half-life is measured for the doses which are effective in the xenograft model at twice or once a week administration.

Bispecific antibodies binding to a target on tumor cells and to CD3 and having the molecular format (scFv)$_2$ have very short elimination half-life of 1 to 4 hours. In the clinical trials with the (scFv)$_2$ bispecific CD19×CD3 antibody blinatumomab, this compound had to be administered via a pump carried by the patients over weeks and months (Topp et al. J Clin Oncol 2011; 29(18): 2493-8). Compared to a twice a week or once a week iv or sc administration, treatment administered via a pump is much less convenient for the patients and also much more risky (e.g. failure of pump, issues with the catheter).

Preferably an antibody according to the invention is characterized in showing an EC50 value for binding to NCI-H929 cells (ATCC® CRL-9068™) of 30 nM or lower, preferably an EC50 value of 15 nM and lower.

Preferably an antibody according to the invention is characterized by its capability to induce redirected killing of NCI-H929 tumor cells in the presence of human T cells with an EC50 lower than 0.1 nM, preferably 0.05 nM, preferably 0.02 nM, preferably 0.002 nM and lower.

Preferably the potency of tumor cell killing of a bispecific antibody according to the invention is not or only minimally reduced by clinically relevant concentrations of APRIL; specifically the bispecific antibody of the invention is characterized in that addition of 100 ng/ml APRIL changes the EC50 for redirected T-cell killing of tumor cells by less than a factor of 4, preferably less than a factor of 2, preferably less than a factor of 1.5; In one preferred embodiment, the bispecific antibody of the invention is characterized in that addition of 1000 ng/mL APRIL changes the EC50 for tumor cell killing by less than a factor of 6.5, preferably less than a factor of 5, preferably less than a factor of 4, preferably less than a factor of 3, preferably less than a factor of 2.

APRIL and BAFF have been shown to be important in multiple myeloma pathogenesis. Patients suffering from multiple myeloma have a high variability of plasma concentrations of APRIL and BAFF. In healthy subjects, APRIL plasma concentrations are usually 10 ng/ml or less. In myeloma patients, plasma concentrations of APRIL and/or BAFF range from 10 ng/ml to 100 ng/ml and in a low percentage of patients even up to 300 ng/ml and more (Moreaux et al. 2004; Blood 103(8): 3148-3157). More importantly, APRIL is constitutively expressed in the bone marrow microenvironment being an important survival factor to malignant myeloma cells and also being mainly produced and secreted by bone marrow myeloid precursor cells (Matthes et al. Blood 2011; 118 (7): 1838-1844). Thus, the concentrations of APRIL in the bone marrow of myeloma patients, which are expected to be of higher magnitude, up to 1000 ng/mL or even more, are of high relevance in this context. If the concentrations for redirected T-cell killing of tumor cells by a BCMA×CD3 bispecific antibody are e.g. shifted by 100 ng/ml and/or 1000 ng/mL APRIL to significantly higher concentrations (i.e. if it takes higher concentrations of BCMA×CD3 bispecific antibody to achieve the same value of tumor lysis (%) at a defined time of incubation), at a given clinical dose/concentration of the bispecific antibody patients with low APRIL levels in blood and/or bone marrow may have a therapeutic effect, but patients with e.g. 100 ng/ml APRIL in blood and/or 1000 ng/mL APRIL in bone marrow may respond with a much lower therapeutic effect or even no effect with the treatment with the bispecific antibody. An alternative could be to use rather higher therapeutic doses, but in such case the risks for side-effects would considerably increase (T-cell bispecific antibodies can be associated with dose-dependent side-effects, e.g. as reported for blinatumomab in clinical phase 1 and 2 trials). Such a shift towards higher effective concentrations of the BCMA×CD3 antibody by high levels of APRIL would more likely be caused if the BCMA×CD3 antibody and APRIL ligand compete for the same binding sites on the BCMA receptor. In that case, BCMA receptor occupancy would be reduced by the competing APRIL. Less receptor occupancy with the BCMA×CD3bispecific antibody means lower efficacy. BAFF could also cause such a shift, but given the much lower binding affinity of BAFF to BCMA than of APRIL to BCMA (i.e. up to 1000-fold lower affinity), APRIL plasma concentrations are in this context more relevant than BAFF plasma concentrations.

Preferably the antibody according to the invention is not competing with the binding of a natural ligand of BCMA, preferably not with APRIL.

Preferably an antibody according to the invention is characterized in that the binding of said antibody in a concentration of 1000 nM to human BCMA is not reduced by 140 ng/ml (6.25 nM) murine Δ APRIL for more than 10%, measured in an ELISA assay as OD at 450 nm, compared to the binding of said binder/antibody to human BCMA without APRIL.

Preferably an antibody according to the invention is characterized in that the binding of said antibody in a concentration of 500 nM to human BCMA is not reduced by 1120 ng/ml (50 nM) ΔAPRIL for more than 35%, preferably not reduced by for more than 15% measured in an ELISA assay as OD at 450 nm compared to the binding of said binder/antibody to human BCMA without APRIL. Preferably the antibody according to the invention is characterized in that the binding of said binder/antibody in a concentration of 1000 nM is not reduced by 1120 ng/ml (50 nM) A APRIL for more than 35%, preferably not reduced by for more than 15% measured in an ELISA assay as OD at 450 nm, compared to the binding of said binder/antibody to human BCMA without APRIL.

Preferably an antibody according to the invention is characterized in that the binding of said antibody to BCMA on cells of multiple myeloma cell line NCI-H929 is not reduced by APRIL for more than 25%, preferably not more than 20%, preferably not more than 10%, measured as binding of said binder/antibody in a concentration of 200 nM, preferably 100 nM, preferably 50 nM, and preferably 5 nM to NCI-H929 cells (ATCC® CRL9068™) in presence of APRIL in a concentration of 2.5 µg/ml compared to the binding of said antibody to NCI-H929 cells without APRIL.

Preferably an antibody according to the invention is characterized in that said antibody does not alter (induce or reduce) APRIL-induced (APRIL concentration 1000 ng/mL) NF-κB activation in a concentration of 1 nM, preferably 100 nM, preferably 400 nM for more than 30%, preferably does not alter more than 20%, preferably does not alter more than 10% as compared to APRIL alone, and/or said antibody does not induce NF-κB activation without APRIL in a concentration of 1 nM, preferably 100 nM, preferably 400 nM for more than 20%, preferably for not more than 10%, preferably for not more than 5% as compared without said antibody.

Stability of bispecific antibodies can be affected in practical conditions and clinical applications. Despite recent antibody engineering improvements, some recombinant proteins and molecular formats (e.g. scFVs fragments) tend to denature and form aggregates more easily than other under stress conditions (Worn and Pluckthun. J Mol Biol 2001; 305, 989-1010). Preferably an antibody according to this invention is characterized in that said antibody stored in standard formulation buffer at 37° C. preferably at 40° C., for 10 days, preferably up to 2 weeks, preferably up to 4 weeks, does not result in more than 10% changes (Δ), preferably not more than 5% changes (Δ), in high molecular weight (HMW) species and/or low molecular weight (LMW) species and/or monomer content as compared to the said antibody stored in the same formulation buffer at −80° C. for the same period of storage.

Preferably a bispecific antibody according to the invention is characterized by its capability to induce redirected killing of multiple myeloma patient primary myeloma cells in the presence of human T cells. Preferably the bispecific antibody according to the invention is characterized in that the CH3 domain of one heavy chain and the CH3 domain of the other heavy chain each meet at an interface which comprises an original interface between the antibody CH3 domains; wherein said interface is altered to promote the formation of the bispecific antibody, wherein the alteration is characterized in that:
a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

Preferably the antibody according to the invention is characterized in that said amino acid residue having a larger side chain volume is selected from the group consisting of arginine (R), phenylalanine (F), tyrosine (Y), tryptophan (W). Preferably the antibody according to the invention is characterized in that said amino acid residue having a smaller side chain volume is selected from the group consisting of alanine (A), serine (S), threonine (T), valine (V). Preferably the antibody according to the invention is characterized in that both CH3 domains are further altered by the introduction of cysteine (C) as amino acid in the corresponding positions of each CH3 domain Preferably the antibody according to the invention is characterized in that one of the constant heavy chain domains CH3 of both heavy chains is replaced by a constant heavy chain domain CH1; and the other constant heavy chain domain CH3 is replaced by a constant light chain domain CL.

Preferably the antibody according to the invention is further characterized in that it binds also specifically to cynomolgus BCMA.

A further embodiment of the invention is one or more nucleic acids encoding the amino acid sequences of an antibody according to the invention.

Further embodiments of the invention are expression vectors comprising nucleic acids according to the invention capable of expressing said nucleic acid in a host cell.

A further embodiment of the invention is a method for the preparation of a bispecific antibody according to the invention comprising the steps of
a) transforming a host cell with vectors comprising nucleic acid molecules encoding the light chains and heavy chains of an antibody according to this invention
b) culturing the host cell under conditions that allow synthesis of said antibody molecule, and
c) recovering said antibody molecule from said culture.

A further embodiment of the invention is a host cell comprising vectors comprising nucleic acid molecules encoding the light chains and heavy chains of an antibody according to the invention.

A further preferred embodiment of the invention is a pharmaceutical composition comprising an antibody according to the invention and a pharmaceutically acceptable excipient.

A further embodiment of the invention is a diagnostic composition comprising an antibody according to the invention.

A further embodiment of the invention is a method for the treatment of a patient in need of therapy, characterized by administering to the patient a therapeutically effective amount of a bispecific antibody according to the invention.

A further preferred embodiment of the invention is a pharmaceutical composition comprising an antibody according to the invention for use as a medicament. A further preferred embodiment of the invention is a pharmaceutical composition comprising an antibody according to the invention for use as a medicament in the treatment of plasma cell disorders. A further preferred embodiment of the invention is a pharmaceutical composition comprising an antibody according to the invention for use as a medicament in the treatment of multiple myeloma. A further embodiment of the invention is an antibody according to the invention for the treatment of plasma cell disorders like multiple myeloma or other B-cell disorders expressing BCMA. Multiple myeloma is a B-cell malignancy characterized by a monoclonal expansion and accumulation of abnormal plasma cells in the bone marrow compartment. Multiple myeloma also involves circulating clonal B cells with same IgG gene rearrangement and somatic hypermutation. Multiple myeloma arises from an asymptomatic, premalignant condition called monoclonal gammopathy of unknown significance (MGUS), characterized by low levels of bone marrow plasma cells and a monoclonal protein. Multiple myeloma cells proliferate at low rate. Multiple myeloma results from a progressive occurrence of multiple structural chromosomal changes (e.g. unbalanced translocations). Multiple myeloma involves the mutual interaction of malignant plasma cells and bone marrow microenvironment (e.g. normal bone marrow stromal cells). Clinical signs of active Multiple myeloma include monoclonal antibody spike, plasma cells overcrowding the bone marrow, lytic bone lesions and bone destruction resulting from overstimulation of osteoclasts (Dimopulos & Terpos, Ann Oncol 2010; 21 suppl 7: vii143-150). Another B-cell disorder involving plasma cells i.e. expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol 2010; 6: 326-337). A further preferred embodiment of the invention is pharmaceutical composition comprising an antibody according to the invention for use as a medicament in the treatment of systemic lupus erythematosus.

DESCRIPTION OF THE FIGURES

FIG. 8. Competition of anti-BCMA antibodies with Δ-APRIL in H929 cells after simultaneous incubation as detected by flow cytometry. (A) The median fluorescence intensity and the relative fluorescence signal (Alexa.Fluor 647 signal) of the anti-BCMA antibody clones 13A4, 17A5, 83A10 at the concentration of 20 µg/mL in presence or absence of 2.5 µg/mL Δ-APRIL or (B) the mean fluorescence intensity and the relative fluorescence signal of Δ-APRIL (FITC signal) at a concentration of 2.5 µg/mL Δ-APRIL and the anti-BCMA antibody clone 83A10 (20 µg/mL) (Alexa.Fluor 647 signal) were measured. Detection of anti-BCMA antibody in presence of Δ-APRIL with FITC conjugated anti-human Fc antibody was normalized to the signal of anti-BCMA antibody clone in absence Δ-APRIL. Detection of Δ-APRIL in presence of the anti-BCMA antibody clone with Alexa.Fluor 647 conjugated anti-HA antibody was normalized to Δ-APRIL signal in presence of the isotype control (see Example 5d).

FIG. 12. Binding of anti-BCMA/anti-CD3-TCB antibodies on murine BCMA-expressing HEK cells (A) and and cynomolgus monkey BCMA-expressing HEK cells (B) as detected by flow cytometry (see Example 10).

FIG. 15. Effect of anti-BCMA/anti-CD3-TCBcv antibodies on APRIL-induced NF-κB activation as detected by phosphoflow cytometry. (A) Effect of APRIL non-competing 83A10-TCBcv compared to APRIL competing J6M0-TCB on APRIL (1000 ng/mL) mediated NF-κB activation in H929 cells. (B) Effect of APRIL non-competing 83A10-TCBcv compared to APRIL competing J6M0-TCB on APRIL (saturating concentration of 5000 ng/mL) mediated NF-κB activation in H929 cells. Detection of intracellular phosphorylated NF-κB by phosphoflow cytometry (see Example 13).

FIG. 16. Effect of anti-BCMA/anti-CD3 TCBcv antibodies on NF-κB activation in H929 cells in absence of APRIL as detected by phosphoflow cytometry. (A) Effect of APRIL non-competing 83A10-TCBcv on NF-κB activation in H929 cells in absence of APRIL (experiment 1). (B) Effect of APRIL non-competing 83A10-TCB on NF-κB activation in H929 cells in absence of APRIL (experiment 2). Detection of intracellular phosphorylated NF-κB by phosphoflow cytometry (see Example 14).

FIG. 18-1. Redirected T-cell lysis of H929 MM cells induced by anti-BCMA/anti-CD3 T-cell bispecific antibodies as measured by LDH release. Concentration response curves for lysis of H929 MM cells induced by 83A10-TCBcv (open circle, dotted line). There was a concentration-dependent killing of H929 cells for 83A10-TCBcv antibody while no killing was observed with the control-TCB. Experiments were performed with PBMC donor 1 (A), donor 3 (B), donor 4 (C), donor 5 (D) using an effector cell to tumor target cell (E:T) ratio of 10 PBMCs to 1 MM cell (see Example 18).

FIG. 18-2. Redirected T-cell lysis of L363 MM cells induced by anti-BCMA/anti-CD3 T-cell bispecific antibodies as measured by LDH release. Concentration response curves for lysis of L363 MM cells induced by 83A10-TCBcv (open circle, dotted line). A concentration-dependent killing of L363 cells was observed for 83A10-TCBcv antibody while no killing was observed with the control-TCB. Experiments were performed with PBMC donor 1 (A), donor 2 (B), donor 3 (C), donor 4 (D), donor 5 (E) using an E:T ratio of 10 PBMCs to 1 MM cell (see Example 19).

FIG. 18-3. Redirected T-cell lysis of RPMI-8226 MM cells induced by anti-BCMA/anti-CD3 T-cell bispecific antibodies as measured by LDH release. Concentration response curves for lysis of RPMI-8226 MM cells induced by 83A10-TCBcv (open circle, dotted line). A concentration-dependent killing of RPMI-8226 cells was observed for 83A10-TCB antibody while no killing was observed with the control-TCB. Experiments were performed with PBMC donor 2 (A), donor 3 (B), donor 4 (C), donor 5 (D) using an E:T ratio of 10 PBMCs to 1 MM cell (see Example 19A).

FIG. 18-4. Redirected T-cell lysis of JJN-3 MM cells induced by anti-BCMA/anti-CD3 T-cell bispecific antibodies as measured by flow cytometry. Concentration-dependent killing of JJN-3 MM cells by 83A10-TCBcv (open circle, dotted line). Percentage of annexin-V positive JJN-3 cells (A, C) and tumor cell lysis (B, D) were determined and plotted. The percentage of lysis of JJN-3 cells induced by a specific concentration of anti-BCMA/anti-CD3 T cell bispecific antibody determined as the following: the absolute count of annexin-V-negative JJN-3 cells at a given TCB concentration and subtracting it from the absolute count of annexin-V-negative JJN-3 cells without TCB; divided by the absolute count of annexin-V-negative JJN-3 cells without TCB. Experiments were performed with 2 PBMC donors: donor 1 (A, B) and donor 2 (C, D) using an E:T ratio of 10 PBMCs to 1 MM cell (see Example 19B).

FIG. 19. Anti-BCMA/anti-CD3 TCB antibodies induce T-cell redirected killing of BCMA-positive H929 myeloma cells in presence of APRIL as detected by colorimetric LDH release assay. (A) APRIL non-blocking/non-competing 83A10-TCBcv in the absence of exogenous APRIL and in presence of 100 ng/mL or 1000 ng/mL of exogenous APRIL. (B) APRIL blocking/competing J6M0-TCB absence of exogenous APRIL and in presence of 100 ng/mL or 1000 ng/mL of exogenous APRIL. E:T ratio used as 10 PBMCs:1 H929 cell; cells were incubated for 24 h before measurement of LDH release (see Example 20).

DETAILED DESCRIPTION OF THE INVENTION

Figure 2:
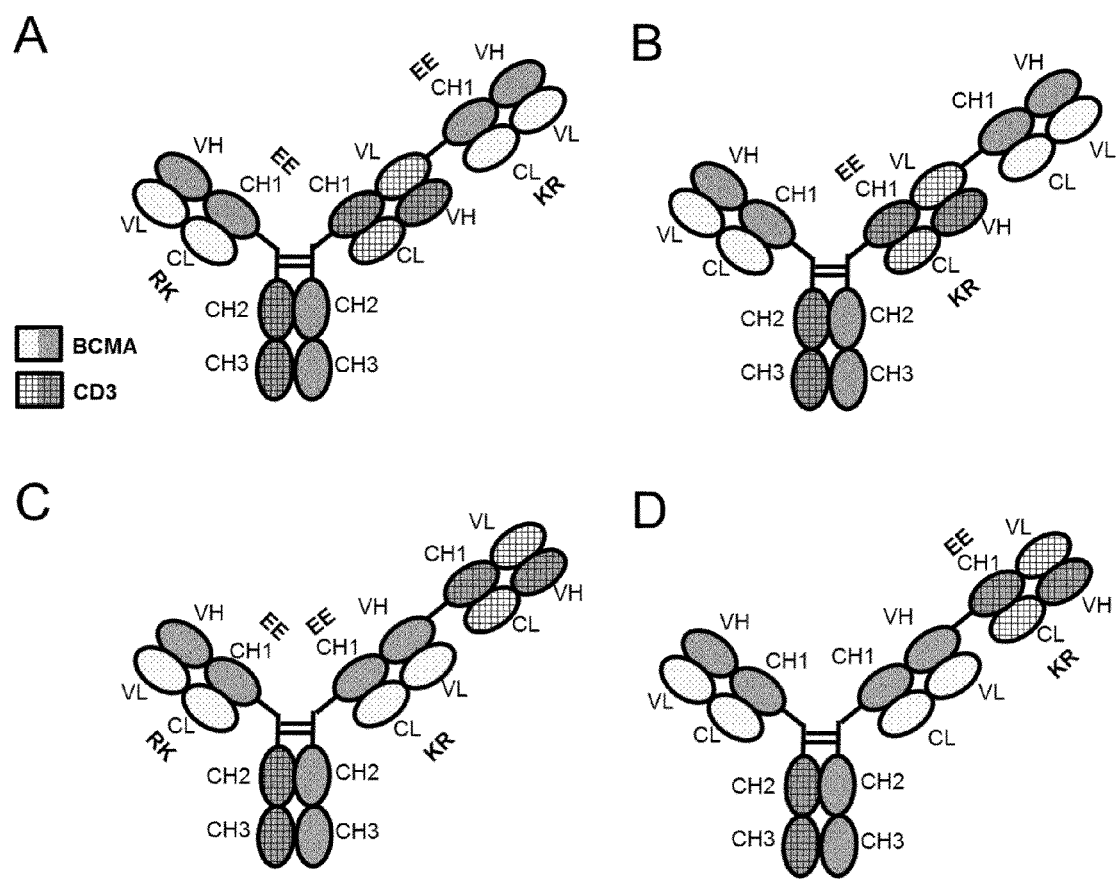
FIG. 2. Preferred bispecific trivalent antibodies comprising only the Fab fragments (specific to CD3 and BCMA) and the Fc part as specified: (A) Fab BCMA(RK/EE)-Fc-Fab CD3-Fab BCMA(RK/EE); (B) Fab BCMA-Fc-Fab CD3 (RK/EE)-Fab BCMA; (C) Fab BCMA(RK/EE)-Fc-Fab BCMA(RK/EE)-Fab CD3; (D) Fab BCMA-Fc-Fab BCMA-Fab CD3(RK/EE). aa substitutions for RK/EE introduced in CL-CH1 to reduce LC mispairing/side-products in production. Preferably, the Fab CD3 includes a VL-VH crossover to reduce LC mispairing and side-products. Preferably, Fab CD3 and Fab BCMA are linked to each other with flexible linkers.

The inventors have found that bispecific antibodies against CD3ε and BCMA with VH/VL exchange can be produced in high yield and easily purified if in the light chain CL of either the antibody portion against CD3ε or BCMA the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D) (numbering according to EU index of Kabat).

Preferably the VH/VL exchange is in the CD3 binding portion. Preferably the bispecific antibody is monovalent for CD3 binding. The amino acid substitutions described above can be either in the BCMA binding portion or in the CD3 binding portion. Therefore in a certain embodiment of the invention the CD3 binding portion can comprise the VH/VL exchange and the amino acid substitutions. In this case the BCMA binding portion does not comprise any VH/VL exchange or amino acid substitutions at amino acids 124, 147, 213, or 123. Preferably the bispecific antibody is monovalent for CD3 binding and bivalent for BCMA binding. As described, the bispecific antibody can therefore comprise a second BCMA binding portion, which is identical to the first one. Therefore if the first BCMA binding portion comprises the amino acid substitutions, the second BCMA binding portion comprises the same substitutions and if the first BCMA binding portion does not comprise the amino acid substitutions, the second BCMA binding portion does also not comprise the substitutions. Preferably amino acid 124 is K, amino acid 147 is E, amino acid 213 is E, and amino acid 123 is R. Preferably the CD3 binding portion and the BCMA binding portion (or both BCMA binding portions if so) are Fab fragments, whereby when two BCMA binding portions are present one BCMA portion is chemically linked to the CD3 binding portion via CH1/VL (C-terminus of BCMA binding portion (CH1) to N-terminus of crossover CD3 binding portion(VL)) or CH1/VH (C-terminus of crossover CD3 binding portion (CH1) to N-terminus of BCMA binding portion(VH)). The bispecific antibody can comprise or not comprise an Fc part.

The term "target" as used herein means either BCMA or CD3. The term "first target and second target" means either CD3 as first target and BCMA as second target or means BCMA as first target and CD3 as second target.

The term "BCMA" as used herein relates to human B cell maturation antigen, also known as BCMA; TR17_HUMAN, TNFRSF17 (UniProt Q02223), which is a member of the tumor necrosis receptor superfamily that is preferentially expressed in differentiated plasma cells. The extracellular domain of BCMA consists according to UniProt of amino acids 1-54 (or 5-51). The term "antibody against BCMA, anti-BCMA antibody" as used herein relates to an antibody specifically binding to BCMA.

The term "CD3ε or CD3" as used herein relates to human CD3ε described under UniProt P07766 (CD3ε_HUMAN). The term "antibody against CD3, anti CD3 antibody" relates to an antibody binding to CD3ε. Preferably the antibody comprises a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3. Preferably the antibody comprises the variable domains of SEQ ID NO:7 (VH) and SEQ ID NO:8 (VL). The term "antibody against CD3, anti CD3 antibody" as used herein relates to an antibody specifically binding to CD3.

"Specifically binding to CD3 or BCMA" refer to an antibody that is capable of binding CD3 or BCMA (the targets) with sufficient affinity such that the antibody is useful as a therapeutic agent in targeting CD3 or BCMA. In some embodiments, the extent of binding of an anti-CD3 or BCMA antibody to an unrelated, non-CD3 or non-BCMA protein is about 10-fold preferably >100-fold less than the binding of the antibody to CD3 or BCMA as measured, e.g., by surface plasmon resonance (SPR) e.g. Biacore®, enzyme-linked immunosorbent (ELISA) or flow cytometry (FACS). Preferably the antibody that binds to CD3 or BCMA has a dissociation constant (Kd) of $10^{-8}$ M or less, preferably from $10^{-8}$ M to $10^{-13}$ M, preferably from $10^{-9}$ M to $10^{-13}$ M. Preferably the anti-CD3 and/or anti-BCMA antibody binds to an epitope of CD3 and/or BCMA that is conserved among CD3 and/or BCMA from different species, preferably among human and cynomolgus. "Bispecific antibody specifically binding to CD3 and BCMA" or "antibody according to the invention" or "bispecific antibody against CD3 and BCMA" refers to a respective definition for binding to both targets. An antibody specifically binding to BCMA (or BCMA and CD3) does not bind to other human antigens. Therefore in an ELISA, OD values for such unrelated targets will be equal or lower to that of the limit of detection of the specific assay, preferably >0.3 ng/mL, or equal or lower to OD values of control samples without plate-bound-BCMA or with untransfected HEK293 cells.

The term "BCMA antibody variant" as used herein relates to an anti-BCMA antibody, which comprises the sequences of antibody 13A4 with an amino acid replacement selected from the group consisting of amino acid replacements at respective position 95 (N95) or 96 (G96) within CDR3H of SEQ ID NO:29 by either a single amino acid change in position 95, either N95S, N95T, N95E, N95Q, N95A, or N95G, or by a single amino acid change in position 96, either G96A, G96E, or G96Q. It also relates to an antibody of the invention, which comprises the sequences of antibody 13A4 with amino acid replacement selected from the group consisting of amino acid replacements at respective positions 27 (N27f) and 28 (G28) within CDR1L of SEQ ID NO:32 by either a single amino acid change in position 27, either N27fS, N27fT, N27fE, N27fQ, N27fA, or N27fG or by a single amino acid change in position 28 either G28A, G28E, or G28Q. It also relates to an antibody of the invention, which comprises the sequences of antibody 13A4 with amino acid replacement selected from the group consisting of amino acid replacements at respective positions 54 (D54) and 55 (S55) within CDR2H of SEQ ID NO:26 by either a single amino acid change in position 54, either D54S, D54T, D54E, D54Q, D54A, or D54G or by a single amino acid change in position 55, either S55A, S55E, or S55Q. It also relates to an antibody of the invention, which comprises the sequences of antibody 13A4 with amino acid replacement selected from the group consisting of amino acid replacements W at position 33 (W33) within CDR1H of SEQ ID NO:23 by either W33F, W33Y, W33V, W33I, W33L, or W33A.

The term "BCMA antibody variant" as used herein relates also to an antibody of the invention, which comprises the sequences of antibody 83A10, with an amino acid replacement selected from the group consisting of amino acid replacements at position 98 (W98) within CDR3H of SEQ ID NO:27 by either W98F, W98Y, W98V, W98I, W98L, or W98A.

The term "APRIL" as used herein relates to recombinant, truncated murine APRIL (Δ-APRIL) (amino acids 106-241; NP_076006). APRIL can be produced as described in Ryan, 2007 (Mol Cancer Ther; 6 (11): 3009-18) and is also commercially available (R&D Systems Europe).

Anti-BCMA antibodies are analyzed by ELISA for binding to human BCMA using plate-bound BCMA in the presence and absence of APRIL. For this assay, an amount of plate-bound BCMA preferably 1.5 µg/mL and concentration(s) preferably ranging from 1 pM to 200 nM of anti-BCMA antibody are used. A BCMA antibody for which its BCMA binding is not inhibited according to the invention is an anti-BCMA antibody "not inhibiting the binding of APRIL to human BCMA in an ELISA assay".

The term "NF-κB" as used herein relates to recombinant NF-κB p50 (accession number (P19838).

NF-κB activity is measured by a DNA-binding ELISA of an extract of NCI-H929 MM cells (CRL-9068™). NCI-H929 MM cells, untreated or treated with 0.1 pM to 200 nM isotype control or with 0.1 pM to 200 nM of anti-BCMA antibodies and incubated for 20 min in the absence of APRIL. NF-κB activity is assayed using a functional ELISA that detects chemiluminescent signal from p65 bound to the NF-κB consensus sequence (U.S. Pat. No. 6,150,090).

Preferably, NF-κB activity is measured by phosphoflow cytometry measuring intracellular phosphorylated NF-κB p65 (pS529) in NCI-H929 MM cells (CRL-9068™). NCI-H929 MM cells, untreated or treated with 1000 ng/mL, preferably 3000 ng/mL, preferably 5000 ng/mL APRIL for 1 min to 30 min, preferably 15 min, and previously incubated with 0.1 pM to 200 nM of anti-BCMA/anti-CD3 TCB antibodies or isotype control antibodies for 20 min without APRIL or concomitantly with APRIL. NF-κB activity is assayed using a functional phosphoflow assay that detects the intracellular signal of phosphorylated 5529 of from p65 bound to the NF-κB consensus sequence (U.S. Pat. No. 6,150,090).

Also if an antibody according to the invention is used in large excess, preferably up to 500 nM or 1000 nM, binding of said antibody to BCMA is not reduced by 140 ng/ml APRIL for more than 10%, preferably not more than 6%, preferably not more than 1%.

Preferably, if an antibody according to the invention is used in large excess, preferably up to 107 nM, binding of 1000 ng/ml APRIL to NCI-H929 cells (CRL-9068™) is not reduced by more than 10%, preferably not more than 5%, preferably not more than 1% in presence of said antibody.

Preferably, if an antibody according to the invention is used in large excess, preferably up to 267 nM, binding of said antibody to RPMI8226 (CCL-155™) is not reduced by 1000 ng/ml APRIL for more than 10%, preferably not more than 5%, preferably not more than 1%.

In a preferred embodiment, if an antibody according to the invention is used in large excess, preferably up to 133 nM, binding of said antibody to NCI-H929 cells (CRL-9068™) is not reduced by 2500 ng/ml APRIL for more than 25%, preferably not more than 20%, preferably not more than 10%.

Preferably, if an antibody according to the invention is used in large excess, preferably up to 400 nM, said antibody does not alter APRIL-induced NF-κB activation in NCI-H929 cells (CRL9068™) for more than 30% in presence of 1000 ng/mL, preferably 3000 ng/mL, preferably 5000 ng/mL APRIL.

In one preferred embodiment, if an antibody according to the invention is used in large excess, preferably up to 400 nM, said antibody does not induce NF-κB activation in NCI-H929 cells (CRL-9068™) for more than 5% in absence of APRIL.

Preferably an antibody according to the invention is characterized in showing an EC50 value for binding to NCI-H929 cells (ATCC® CRL-9068™) of 30 nM or lower, preferably an EC50 value of 15 nM and lower.

Preferably, an antibody according to this invention is characterized by its capability to bind to RPMI8226 (CCL-155™) cells.

In one preferred embodiment, an antibody according to the invention is characterized by its capability to bind to human T cells. The term "TCB" as used herein refer to a bispecific antibody specifically binding to BCMA and CD3.

Preferably, an antibody according to this invention is characterized by its capability to bind to cynomolgus monkey BCMA transiently expressed on HEK-cells.

In a preferred embodiment, an antibody according to this invention is characterized by its capability to induce CD4+ and CD8+ T-cell activation in the presence of tumor cells expressing BCMA.

Preferably an antibody according to the invention is characterized by its capability to induce redirected killing of NCI-H929 tumor cells in the presence of human T cells with an EC50 lower than 0.1 nM, preferably 0.05 nM, preferably 0.02 nM, preferably 0.002 nM and lower.

Preferably, the potency (e.g. EC50) to induce redirected T-cell killing of NCI-H929 cells of an antibody according to the invention is defined by not being reduced or being only minimally reduced by clinically relevant concentrations of APRIL; characterized in that addition of 100 ng/ml APRIL changes the EC50 for NCI-H929 cell killing by less than a factor of 4, preferably less than a factor of 2, preferably less than a factor of 1.5; more preferably that addition of 1000 ng/mL APRIL changes the EC50 for NCI-H929 cell killing by less than a factor of 6.5, preferably less than a factor of 5, preferably less than a factor of 4, preferably less than a factor of 3, preferably less than a factor of 2, preferably less than a factor of 1.5.

The term "antibody" as used herein refers to a monoclonal antibody. An antibody consists of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. Each heavy chain comprises a heavy chain variable region (abbreviated herein as HCVR or VH) and a heavy chain constant region. The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The "constant domains" of the heavy chain and of the light chain are not involved directly in binding of an antibody to a target, but exhibit various effector functions.

The "light chain of an antibody" as used herein is a polypeptide comprising in N-terminal to C-terminal direction a light chain variable domain (VL), and a light chain constant domain (CL), abbreviated as VL-CL. A "crossover light chain (VH-CL)" as used herein is a light chain wherein the VL domain is replaced by the respective VH domain "The "heavy chain of an antibody" as used herein is a polypeptide comprising in N-terminal to C-terminal direction a heavy chain variable domain (VH) and a constant heavy chain domain 1 (CH1). A "crossover heavy chain (VL-CH1)" as used herein is a heavy chain wherein the VH domain is replaced by the respective VL domain.

There exist several approaches for CH3-modifications to enforce the heterodimerization, which are well described e.g. in WO96/27011, WO98/050431, EP1870459, WO2007/110205, WO2007/147901, WO2009/089004, WO2010/129304, WO2011/90754, WO2011/143545, WO2012058768, WO2013157954, WO2013096291. Typically in all such approaches the first CH3 domain and the second CH3 domains are both engineered in a complementary manner so that each CH3 domain (or the heavy chain comprising it) cannot longer homodimerize with itself but is forced to heterodimerize with the complementary engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the antibodies according to the invention which reduce light chain mispairing, e.g. Bence-Jones type side products.

In one preferred embodiment of the invention (in case the antibody according to the invention comprises CH3 domains in the heavy chains) the CH3 domains of said multispecific antibody according to the invention can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681; WO98/050431. In this method the interaction surfaces of the two CH3 domains are altered to increase the heterodimerisation of both heavy chains containing these two CH3 domains. Each of the two CH3 domains (of the two heavy chains) can be the "knob", while the other is the "hole".

Thus in one embodiment of the invention said antibody according to the invention (comprises a CH3 domain in each heavy chain and) is further characterized in that the first CH3 domain of the first heavy chain of the antibody under a) and the second CH3 domain of the second heavy chain of the antibody under b) each meet at an interface which comprises an original interface between the antibody CH3 domains, wherein said interface is altered to promote the formation of the antibody according to the invention, wherein the alteration is characterized in that:

i) the CH3 domain of one heavy chain is altered, so that within the original interface of the CH3 domain of one heavy chain that meets the original interface of the CH3 domain of the other heavy chain within the antibody according to the invention, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the antibody according to the invention an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

In one aspect of the invention both CH3 domains are further altered by the introduction of cysteine (C) as amino acid in the corresponding positions of each CH3 domain such that a disulfide bridge between both CH3 domains can be formed.

Other techniques for CH3-modifications to enforcing the heterodimerization are contemplated as alternatives of the invention and described e.g. in WO96/27011, WO98/050431, EP1870459, WO2007/110205, WO2007/147901, WO2009/089004, WO2010/129304, WO2011/90754, WO2011/143545, WO2012/058768, WO2013/157954, WO2013/157953, WO2013/096291.

In one embodiment the antibody according to the invention is of IgG2 isotype and the heterodimerization approach described in WO2010/129304 can be used alternatively.

The term "antibody" includes e.g. mouse antibodies, human antibodies, chimeric antibodies, humanized antibodies and genetically engineered antibodies (variant or mutant antibodies) as long as their characteristic properties are retained. Especially preferred are human or humanized antibodies, especially as recombinant human or humanized antibodies. The terms "monoclonal antibody" or "monoclonal antibody composition" as used herein refer to a preparation of antibody molecules of a single amino acid composition.

The terms "bispecific antibody" and "antibody according to the invention" as used herein refer to an antibody in which one of the two pairs of heavy chain and light chain (HC/LC) is specifically binding to BCMA and the other one is specifically binding to CD3 or preferably to CD3 and BCMA. The term "valent" as used within the current application denotes the presence of a specified number of binding sites in an antibody molecule. A bivalent antibody according to this invention has two binding sites, one for CD3 and the other for BCMA. As such, the term "trivalent", denote the presence of three binding sites in an antibody according to the invention, which are two binding sites for BCMA and one binding site for CD3.

There are five types of mammalian antibody heavy chains denoted by the Greek letters: α, δ, ε, γ, and μ (Janeway C A, Jr et al (2001). Immunobiology. 5th ed., Garland Publishing). The type of heavy chain present defines the class of antibody; these chains are found in IgA, IgD, IgE, IgG, and IgM antibodies, respectively (Rhoades R A, Pflanzer R G (2002). Human Physiology, 4th ed., Thomson Learning). Distinct heavy chains differ in size and composition; α and γ contain approximately 450 amino acids, while μ and £ have approximately 550 amino acids. Each heavy chain has two regions, the constant region and the variable region. The constant region is identical in all antibodies of the same isotype, but differs in antibodies of different isotype. Heavy chains γ, α and δ have a constant region composed of three constant domains CH1, CH2, and CH3 (in a line), and a hinge region for added flexibility (Woof J, Burton D Nat Rev Immunol 4 (2004) 89-99); heavy chains μ and £ have a constant region composed of four constant domains CH1, CH2, CH3, and CH4 (Janeway C A, Jr et al (2001). Immunobiology. 5th ed., Garland Publishing). The variable region of the heavy chain differs in antibodies produced by different B cells, but is the same for all antibodies produced by a single B cell or B cell clone. The variable region of each heavy chain is approximately 110 amino acids long and is composed of a single antibody domain.

In mammals there are two types of light chain, which are called lambda (λ) and kappa (κ). A light chain has two successive domains: one constant domain CL and one variable domain VL. The approximate length of a light chain is 211 to 217 amino acids. Preferably the light chain is a kappa (κ) light chain, and the constant domain CL is preferably derived from a kappa (κ) light chain (the constant domain CK). Preferably the heavy and light chains constant domains of the antibody according to the invention are human domains.

The "antibodies" according to the invention can be of any class (e.g. IgA, IgD, IgE, IgG, and IgM, preferably IgG or IgE), or subclass (e.g., IgG1, IgG2, IgG3, IgG4, IgA1 and IgA2, preferably IgG1), whereby both antibodies, from which the bivalent bispecific antibody according to the invention is derived, have an Fc part of the same subclass (e.g. IgG1, IgG4 and the like, preferably IgG1), preferably of the same allotype (e.g. Caucasian).

A "Fab fragment of an antibody" as used herein is a fragment on an antibody that binds to antigens. A Fab fragment of an antibody consists of two pairs of domains. In a wild-type antibody it is composed of one constant and one variable domain of each of the heavy chain (CH1 and VH) and the light chain (CL and VL). According to the invention such domain pairs can be, due to a crossover, also VH-CL and VL-CH1. In a wild-type antibody and according to the invention the domain of the heavy and light chain domain pairs of a Fab fragment are not chemically linked together and are therefore not scFvs (single chain variable fragments). "Crossover" according to the invention means that preferably in one Fab the domains VL and VH are replaced by each other.

The term "aa substitution or charge variant" as used herein means amino acid substitution according to the invention in that in a constant domain CL the amino acid at position 124 is substituted independently by lysine (K), arginine (R) or histidine (H) (numbering according to Kabat), and wherein in the respective constant domain CH1 the amino acid at position 147 and the amino acid at position 213 is substituted independently by glutamic acid (E), or aspartic acid (D) (numbering according to EU index of Kabat), and preferably in addition in the constant domain CL in the amino acid at position 123 is substituted independently by lysine (K), arginine (R) or histidine (H) and preferably by arginine (R).

A preferred combination of aa substitution is Q124K, E123R, K147E and K213E (for example: E123R means that glutamic acid (E) at position 123 is replaced by arginine (R).

A "Fc part of an antibody" is a term well known to the skilled artisan and defined on the basis of papain cleavage of antibodies. The antibodies according to the invention contain as Fc part, preferably a Fc part derived from human origin and preferably all other parts of the human constant regions. The Fc part of an antibody is directly involved in complement activation, C1q binding, C3 activation and Fc receptor binding. While the influence of an antibody on the complement system is dependent on certain conditions, binding to C1q is caused by defined binding sites in the Fc part. Such binding sites are known in the state of the art and described e.g. by Lukas, T J., et al., J. Immunol. 127 (1981) 2555-2560; Brunhouse, R., and Cebra, J. J., MoI. Immunol. 16 (1979) 907-917; Burton, D. R., et al., Nature 288 (1980) 338-344; Thommesen, J. E., et al., MoI. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation, C1q binding and C3 activation, whereas IgG4 do not activate the complement system, do not bind C1q and do not activate C3. Preferably the Fc part is a human Fc part.

Preferably the Fc part is a human IgG1Fc part. Preferably the antibody according to the invention comprises in the human IgG1 Fc part amino acid substitution of Pro329 with glycine or arginine and/or substitutions L234A and L235A, preferably Pro329 with glycine and substitutions L234A and L235A.

Preferably the antibody according to the invention comprises as Fc part an Fc variant of a wild-type human IgG Fc region, said Fc variant comprising an amino acid substitution at position Pro329 and at least one further amino acid substitution, wherein the residues are numbered according to the EU index of Kabat, and wherein said antibody exhibits a reduced affinity to the human FcγRIIIA and/or FcγRIIA and/or FcγRI compared to an antibody comprising the wildtype IgG Fc region, and wherein the ADCC induced by said antibody is reduced to at least 20% of the ADCC induced by the antibody comprising a wild-type human IgG Fc region. In a specific embodiment Pro329 of a wild-type human Fc region in the antibody according to the invention is substituted with glycine or arginine or an amino acid residue large enough to destroy the proline sandwich within the Fc/Fcγ receptor interface, that is formed between the proline329 of the Fc and tryptophane residues Trp 87 and Tip 110 of FcγRIII (Sondermann et al.: Nature 406, 267-273 (20 Jul. 2000)). In a further aspect of the invention at least one further amino acid substitution in the Fc variant is S228P, E233P, L234A, L235A, L235E, N297A, N297D, or P331S and still in another embodiment said at least one further amino acid substitution is L234A (denotes that leucine 234 is substituted by alanine) and L235A of the human IgG1 Fc region or S228P and L235E of the human IgG4 Fc region. Such Fc variants are described in detail in WO2012130831.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the targets noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice will result in the production of human antibodies upon target challenge (see, e.g., Jakobovits, A., et al., Proc. Natl. Acad. Sci. USA 90 (1993) 2551-2555; Jakobovits, A., et at, Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH)) as used herein denotes each of the pair of light and heavy chains which is involved directly in binding the antibody to the target. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the target binding site. The antibody heavy and light chain CDR3 regions play a particularly important role in the binding specificity/affinity of the antibodies according to the invention and therefore provide a further object of the invention.

The terms "hypervariable region" or "target-binding portion of an antibody" when used herein refer to the amino acid residues of an antibody which are responsible for target-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to target binding. CDR and FR regions are determined according to the standard definition of Kabat et al., Sequences of Proteins of Immunological Interest, 5th ed., Public Health Service, National Institutes of Health, Bethesda, Md. (1991).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of a target that is bound by an antibody.

For the preparation of a bispecific antibody according to the invention there could be used separate vectors encoding each light and heavy chain or another appropriate amount of vectors. Such vectors can be used in transforming the host cell.

The term "nucleic acid or nucleic acid molecule", as used herein, is intended to include DNA molecules and RNA molecules. A nucleic acid molecule may be single-stranded or double-stranded, but preferably is double-stranded DNA.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen S N, et al, PNAS 1972, 69 (8): 2110-2114.

Recombinant production of antibodies using transformation is well-known in the state of the art and described, for example, in the review articles of Makrides, S. C, Protein Expr. Purif. 17 (1999) 183-202; Geisse, S., et al., Protein Expr. Purif. 8 (1996) 271-282; Kaufman, R J., Mol. Biotechnol. 16 (2000) 151-161; Werner, R. G., et al., Arzneimittelforschung 48 (1998) 870-880 as well as in U.S. Pat. Nos. 6,331,415 and 4,816,567.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The bispecific antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NSO cells, SP2/0 cells, HEK293 cells, COS cells, yeast, or E. coli cells, and the antibody is recovered from the cells (supernatant or cells after lysis). The bispecific antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed., Current Protocols in Molecular Biology, Greene Publishing and Wiley Interscience, New York (1987).

Expression in NSO cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci.

USA 89 (1992) 4285-4289; and Norderhaug, L., et al., J. Immunol. Methods 204 (1997) 77-87. A preferred transient expression system (HEK293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous Linking is accomplished by ligation at convenient restriction sites. If such sites do not exist, the synthetic oligonucleotide adaptors or linkers are used in accordance with conventional practice.

The bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA or RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and target binding, but may improve the yield of the recombinant production, protein stability or facilitate the purification.

T cell bispecific (TCB) binders have very high concentration/tumor-cell-receptor-occupancy dependent potency in cell killing (e.g. EC50 in in vitro cell killing assays in the sub- or low picomolar range; Dreier et al. Int J Cancer 2002), T-cell bispecific binder (TCB) are given at much lower doses than conventional monospecific antibodies. For example, blinatumomab (CD19×CD3) is given at a continuous intravenous dose of 5 to 15 µg/m$^2$/day (i.e. only 0.035 to 0.105 mg/m$^2$/week) for treatment of acute lymphocytic leukemia or 60 µg/m$^2$/day for treatment of Non Hodgkin Lymphoma, and the serum concentrations at these doses are in the range of 0.5 to 4 ng/ml (Klinger et al., Blood 2012; Topp et al., J Clin Oncol 2011; Goebeler et al. Ann Oncol 2011). Because low doses of TCB can exert high efficacy in patients, it is envisaged that for an antibody according to the invention subcutaneous administration is possible and preferred in the clinical settings (preferably in the dose range of 0.25 to 2.5 mg/m$^2$/week). Even at these low concentrations/doses/receptor occupancies, TCB can cause considerable adverse events (Klinger et al., Blood 2012). Therefore it is critical to control tumor cell occupancy/coverage. In patients with high and variable levels of serum APRIL and BAFF (e.g. multiple myeloma patients, Moreaux et al. 2004; Blood 103(8): 3148-3157) number of TCB bound to the tumor cells resp. tumor cell occupancy may be considerably influenced by APRIL (the high affinity ligand which binds to human BCMA with 1000-fold higher affinity than to BAFF). But by using said antibody of this invention, tumor cell occupancy respectively efficacy/safety it may not be required to increase the dose for an antibody according to this invention as said antibody may not be affected by APRIL ligand competition. Another advantage of the antibody according to the invention is based on the inclusion of an Fc portion, which increases the elimination half-life up to ~12 days or even more and offers the opportunity of once or twice/week administrations as compared to TCBs without an Fc portion (e.g. blinatumomab) which are required to be given intravenously and continuously with a pump carried by patients.

With the CD19×CD3 T-cell bispecific (TCB) antibody blinatumomab response rates up to 80% have been shown in patients with relapsed/refractory Acute Lymphocytic Leukemia ALL, As for ALL for Multiple Myeloma and other plasma cell diseases there is still a high medical need. Despite all today available treatment, five years after first diagnosis approx 60% of Multiple Myeloma patients already died. There is still a need for an effective treatment for patients with Multiple Myeloma.

The antibodies according to the invention have unique features and advantages to e.g. blinatumomab and to published BCMA×CD3 TCB antibodies:

long elimination half life (days instead of hours)

convenient twice or once a week administration (instead of administration by a pump to be carried for weeks/months by the patient)

minimal influence of the blood and bone marrow concentrations of APRIL, the natural ligand of BCMA, on BCMA-TCB induced tumor cell killing (patients with multiple myeloma show a huge variability of APRIL concentrations, patients with high APRIL levels could experience reduced or even no efficacy of the drug if efficacy is strongly dependent on APRIL levels)

molecular format and structure providing high stability and low aggregation of the BCMA×CD3 TCB antibodies optimization of the molecular structures to enable high quality manufacturing and to facilitate purification by the following measures:

aa substitutions in CL and CH1 to reduce light chain mispairing

VL-VH crossover to reduce light chain mispairing

Preferably knob into hole technology to improve correct heavy chain pairing

Preferably Pro 329 and L234A and L235A amino acid substitutions in CH3 of Fc to avoid potential side effects from interaction with complement system and/or with FcR carrying effector cells.

TABLE 1

Antibody sequences

| BCMA antibody | SEQ ID NO: | | | | | | | |
|---|---|---|---|---|---|---|---|---|
| | VH | VL | CDR1H | CDR2H | CDR3H | CDR1L | CDR2L | CDR3L |
| 83A10 | 15 | 18 | 21 | 24 | 27 | 30 | 33 | 36 |
| 17A5 | 16 | 19 | 22 | 25 | 28 | 31 | 34 | 37 |
| 13A4 | 17 | 20 | 23 | 26 | 29 | 32 | 35 | 38 |

TABLE 2

Additional constructs

| Construct | SEQ ID NO: |
|---|---|
| BCMA 83A10 VH_CH1 x CD3 VH_CL Fc knob LALA PG | 39 |
| BCMA 83A10 HC hole LALA PG | 40 |
| CD3 VL_CH1 | 41 |
| BCMA 83A10 hum IgG1 LC | 42 |
| BCMA 83A10 VH_CH1cv x CD3 VL_CH1 Fc knob LALA PG | 43 |
| BCMA 83A10cv HC hole LALA PG | 44 |
| CD3 VH_CL | 45 |
| BCMA 83A10cv hum IgG1 LC | 46 |
| BCMA 17A5 VH_CH1cv x CD3 VL_CH1 Fc knob LALA PG | 47 |
| BCMA 17A5cv HC hole LALA PG | 48 |
| BCMA 17A5cv hum IgG1 LC | 49 |
| BCMA 13A4 VH_CH1 cv x CD3 VL_CH1 Fc knob LALA PG | 50 |
| BCMA 13A4cv HC hole LALA PG | 51 |
| BCMA 13A4cv hum IgG1 LC | 52 |

To make the following (2+1) Fc-containing anti-BCMA/anti-CD3 TCBs, the respective "building blocks"/sequence IDs as mentioned in the table 2 above are needed:
83A10-TCB: 39, 40, 41, 42 (comparison)
83A10-TCBcv: 43, 44, 45, 46 (FIG. 2A)
17A5-TCBcv: 45, 47, 48, 49 (FIG. 2A)
13A4-TCBcv: 45, 50, 51, 52 (FIG. 2A)

TABLE 3 aa replacements in CDRs

| | SEQ ID NO: | | | |
|---|---|---|---|---|
| Aa substitution | Original CDR | Variant CDR | Original VL/VH | Variant VL/VH |
| N95S | 29 | 53 | 17 | 54 |
| N95T | 29 | 55 | 17 | 56 |
| N95E | 29 | 57 | 17 | 58 |
| N95Q | 29 | 59 | 17 | 60 |
| N95A | 29 | 61 | 17 | 62 |
| N95G | 29 | 63 | 17 | 64 |
| G96A | 29 | 65 | 17 | 66 |
| G96E | 29 | 67 | 17 | 68 |
| G96Q | 29 | 69 | 17 | 70 |
| N27fS | 32 | 71 | 20 | 72 |
| N27fT | 32 | 73 | 20 | 74 |
| N27fE | 32 | 75 | 20 | 76 |
| N27fQ | 32 | 77 | 20 | 78 |
| N27fA | 32 | 79 | 20 | 80 |
| N27fG | 32 | 81 | 20 | 82 |
| G28A | 32 | 83 | 20 | 84 |
| G28E | 32 | 85 | 20 | 86 |
| G28Q | 32 | 87 | 20 | 88 |
| D54S | 26 | 89 | 17 | 90 |
| D54T | 26 | 91 | 17 | 92 |
| D54E | 26 | 93 | 17 | 94 |
| D54Q | 26 | 95 | 17 | 96 |
| D54A | 26 | 97 | 17 | 98 |
| D54G | 26 | 99 | 17 | 100 |
| S55A | 26 | 101 | 17 | 102 |
| S55E | 26 | 103 | 17 | 104 |
| S55Q | 26 | 105 | 17 | 106 |
| W33F | 23 | 107 | 17 | 108 |
| W33Y | 23 | 109 | 17 | 110 |
| W33V | 23 | 111 | 17 | 112 |
| W33I | 23 | 113 | 17 | 114 |
| W33L | 23 | 115 | 17 | 116 |
| W33A | 23 | 117 | 17 | 118 |
| W98F | 27 | 119 | 15 | 120 |
| W98Y | 27 | 121 | 15 | 122 |
| W98V | 27 | 123 | 15 | 124 |
| W98I | 27 | 125 | 15 | 126 |
| W98L | 27 | 127 | 15 | 128 |
| W98A | 27 | 129 | 15 | 130 |

In the following specific embodiments of the invention are listed:

1. A bispecific bi- or trivalent antibody specifically binding to the two targets which are the extracellular domain of human BCMA (further named also as "BCMA") and human CD3ε (further named also as "CD3") wherein the variable domains VL and VH in a light chain and the respective heavy chain are replaced by each other, characterized in comprising a constant domain CL wherein the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D) (numbering according to EU index of Kabat).

2. A bispecific antibody specifically binding to the two targets which are the extracellular domain of human BCMA and human CD3, characterized in comprising
a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and wherein
c) in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 and the amino acid at position 213 is substituted independently by glutamic acid (E), or aspartic acid (D) (numbering according to EU index of Kabat).

3. A bispecific antibody specifically binding to the two targets which are the extracellular domain of human BCMA and human CD3, characterized in comprising
a) the first light chain and the first heavy chain of a first antibody which specifically binds to BCMA; and
b) the second light chain and the second heavy chain of a second antibody which specifically binds to CD3, and wherein the variable domains VL and VH in the second light chain and second heavy chain of the second antibody are replaced by each other; and wherein
c) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at positions 147 and the amino acid at position 213 is substituted independently by glutamic acid (E), or aspartic acid (D) (numbering according to Kabat).

4. A bispecific antibody according to embodiment 2 above, characterized in that
said bispecific antibody comprises in addition a Fab fragment of said first antibody (further named also as "BCMA-Fab") and in the constant domain CL said BCMA-Fab the amino acid at position 124 is substituted independently by lysine (K), arginine (R) or histidine (H) (numbering according to Kabat), and wherein in the constant domain CH1 of said BCMA-Fab the amino acid at positions 147 and the amino acid at position 213 is substituted independently by glutamic acid (E), or aspartic acid (D) (numbering according to Kabat).

5. A bispecific antibody according to embodiment 3 above, characterized in that
said bispecific antibody comprises in addition a second Fab fragment of said first antibody ("BCMA-Fab").

6. A bispecific antibody according to any one of embodiment 1, characterized in consisting of one Fab fragment of an antibody specifically binding to CD3 (further named also as "CD3-Fab"), and one Fab fragment of an antibody specifically binding to BCMA (further named also as "BCMA-Fab(s)") and a Fc part, wherein the CD3-Fab and the BCMA-Fab are linked via their C-termini to the hinge region of said Fc part and wherein either the CD3-Fab or the BCMA-Fab comprises aa substitution and the CD3-Fab comprises crossover.

7. A bispecific antibody according to embodiment 6, characterized in consisting of one CD3-Fab, and one BCMA-Fab and a Fc part, wherein the CD3-Fab and the BCMA-Fab are linked via their C-termini to the hinge region of said Fc part and a second BCMA-Fab, which is linked with its C-terminus to the N-terminus of the CD3-Fab and wherein the CD3-Fab comprises crossover and either the CD3-Fab or both BCMA-Fabs comprise aa substitution (FIGS. 2A and 2B).

8. A bispecific antibody according to embodiment 7, characterized in consisting of BCMA-Fab-Fc-CD3-Fab-BCMA-Fab, wherein both BCMA-Fabs comprise aa substitution and the CD3-Fab comprises VL/VH crossover.

9. A bispecific antibody according to embodiment 1, characterized in consisting of two BCMA-Fabs and a Fc part, wherein the BCMA-Fabs are linked via their C-termini to the hinge region of said Fc part and a CD3-Fab, which is linked with its C-terminus to the N-terminus of one BCMA-Fab and the CD3-Fab comprises crossover and either the CD3-Fab or both BCMA-Fabs comprise aa substitution (FIGS. 2C and 2D).

Figure 3:
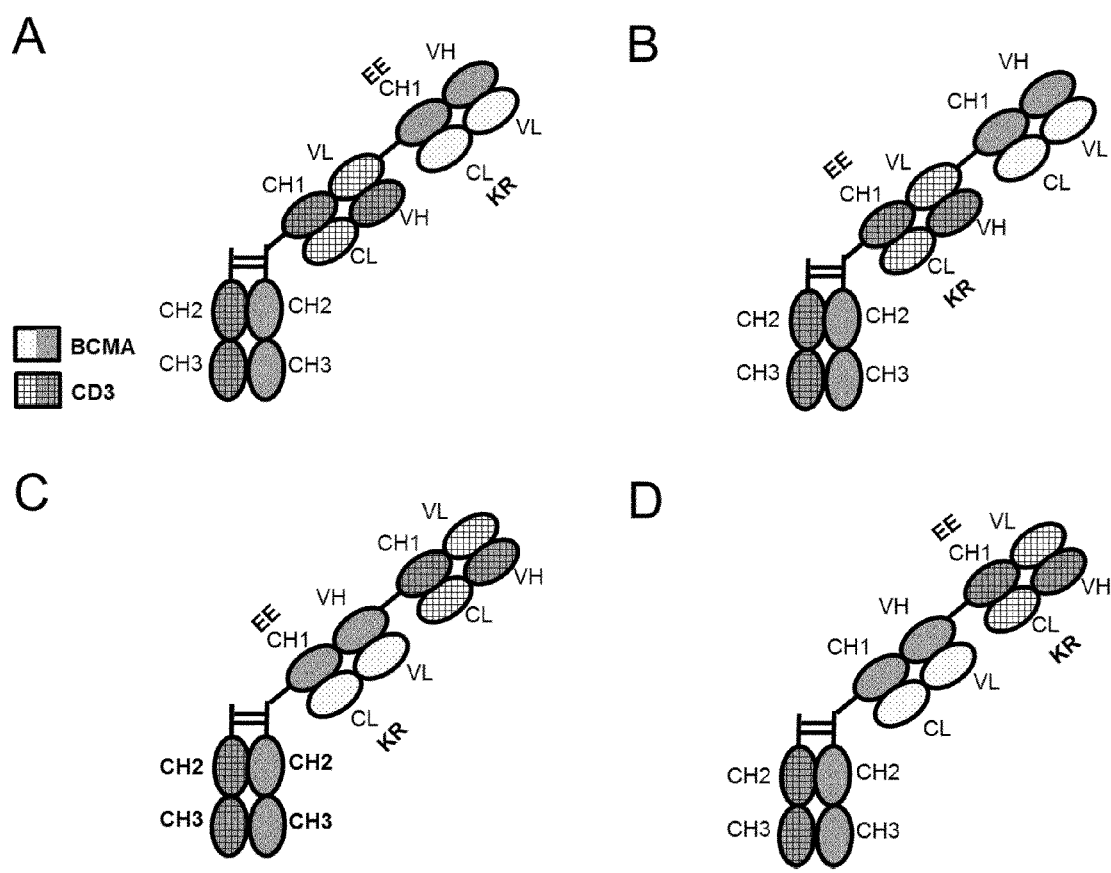
FIG. 3. Bispecific bivalent antibodies comprising only the Fab fragments (specific to CD3 and BCMA) and the Fc part as specified: (A) Fc-Fab CD3-Fab BCMA(RK/EE); (B) Fc-Fab CD3(RK/EE)-Fab BCMA; (C) Fc-Fab BCMA(RK/EE)-Fab CD3; (D) Fc-Fab BCMA-Fab CD3(RK/EE). Preferably, the Fabs CD3 include a VL-VH crossover to reduce LC mispairing and side-products. Fab CD3 and Fab BCMA are linked to each other with flexible linkers.

10. A bispecific antibody according to any one of embodiment 1 to 5, characterized in consisting of one CD3-Fab, which is linked via its C-terminus to the hinge region of said Fc part and a BCMA-Fab, which is linked with its C-terminus to the N-terminus of the CD3-Fab and either the CD3-Fab or the BCMA-Fab comprise aa substitution (FIGS. 3A and 3B).

11. A bispecific antibody according to any one of embodiment 1 to 6, characterized in consisting of one BCMA-Fab, which is linked via its C-terminus to the hinge region of said Fc part and a CD3-Fab, which is linked with its C-terminus to the N-terminus of the BCMA-Fab and either the CD3-Fab or the BCMA-Fab comprise aa substitution (FIGS. 3C and 3D).

12. A bispecific antibody according to any one of embodiment 1 to 6, characterized in comprising the CDR sequences of anti-BCMA antibody 83A10, 17A5 or 13A4, 13. A bispecific antibody according to any one of embodiment 1 to 6, characterized in comprising the VH and VL sequences of anti-BCMA antibody 83A10, 17A5 or 13A4, or an antibody comprising the VH, VL, CH1, and CL sequences of anti-BCMA antibody 83A10, 17A5 or 13A4.

14. A bispecific antibody according to any one of embodiment 1 to 6, characterized in that the antibody portion specifically binding to human CD3, preferably the Fab fragment, is characterized in comprising a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3 of the anti CD3ε antibody (CDR MAB CD3).

15. A bispecific antibody according to any one of embodiment 1 to 6, characterized in that the antibody portion specifically binding to human CD3 is characterized in that the variable domains are of SEQ ID NO:7 and 8 (VHVL MAB CD3).

16. A bispecific antibody according to any one of embodiment 1 to 6, characterized in that the Fab fragment, specifically binding to human BCMA is characterized in comprising a variable domain VH comprising the heavy chain CDRs CDR1H of SEQ ID NO:21, a CDR2H of SEQ ID NO:24, a CDR3H of SEQ ID NO: 27 and comprising a variable domain VL comprising the light chain CDRs CDR1L of SEQ ID NO:30, a CDR2L of SEQ ID NO:33, a CDR3L of SEQ ID NO: 36 (CDR MAB 83A10).

17. A bispecific antibody according to any one of embodiment 1 to 6, characterized in that the Fab fragment, specifically binding to human BCMA is characterized in comprising a variable domain VH comprising the heavy chain CDRs CDR1H of SEQ ID NO:22, a CDR2H of SEQ ID NO:25, a CDR3H of SEQ ID NO: 28 and a variable domain VL comprising the light chain CDR1L of SEQ ID NO:31, a CDR2L of SEQ ID NO:34, a CDR3L of SEQ ID NO: 37 (CDR MAB 17A5).

18. A bispecific antibody according to any one of embodiment 1 to 6, characterized in that the Fab fragment, specifically binding to human BCMA is characterized in comprising a variable domain VH comprising the heavy chain CDRs CDR1H of SEQ ID NO:23, a CDR2H of SEQ ID NO:26, a CDR3H of SEQ ID NO: 29 and a variable domain VL comprising the light chain CDR1L of SEQ ID NO:32, a CDR2L of SEQ ID NO:35, a CDR3L of SEQ ID NO: 38 (CDR MAB 13A4).

19. A bispecific antibody according to any one of embodiment 1 to 6, characterized in that the Fab fragment, specifically binding to human BCMA is characterized in comprising a VH of SEQ ID NO: 15 and a VL of SEQ ID NO: 18 (VHVL MAB 83A10).

20. A bispecific antibody according to any one of embodiment 1 to 6, characterized in that the Fab fragment, specifically binding to human BCMA is characterized in comprising a VH of SEQ ID NO: 16 and a VL of SEQ ID NO: 19 (VHVL MAB 17A5).

21. A bispecific antibody according to any one of embodiment 1 to 6, characterized in that the Fab fragment, specifically binding to human BCMA is characterized in comprising a VH of SEQ ID NO: 17 and a VL of SEQ ID NO: 20 (VHVL MAB 13A4).

22. A bispecific antibody according to any one of embodiment 1 to 21, characterized in that in addition to the amino acid replacement at position 124 in the constant domain CL the amino acid at position 123 is substituted independently by lysine (K), arginine (R) or histidine (H).

23. A bispecific antibody according to any one of embodiment 1 to 22, characterized in that amino acid 124 is K, amino acid 147 is E, amino acid 213 is E, and amino acid 123 is R.

24. A bispecific antibody specifically binding to the extracellular domain of human BCMA and to human CD3ε, characterized in comprising a heavy and light chain set selected from the group consisting of polypeptides i) SEQ ID NO:43, SEQ ID NO:44, SEQ ID NO:45, and SEQ ID NO:46 (set 1), ii) SEQ ID NO:45, SEQ ID NO:47, SEQ ID NO:48, and SEQ ID NO:49 (set 2), and iii) SEQ ID NO:45, SEQ ID NO:50, SEQ ID NO:51, and SEQ ID NO:52 (set 3).

25. An antibody according to embodiment 24, characterized in that in the antibody portion specifically binding to human CD3ε the variable domain VH is replaced by a variable domain VH comprising the heavy chain CDRs of SEQ ID NO: 1, 2 and 3 as respectively heavy chain CDR1, CDR2 and CDR3 and the variable domain VL is replaced by a variable domain VL comprising the light chain CDRs of SEQ ID NO: 4, 5 and 6 as respectively light chain CDR1, CDR2 and CDR3 of the anti CD3ε antibody.

26. An antibody according to any one of embodiments 1 to 25, characterized in that the CH3 domain of one heavy chain and the CH3 domain of the other heavy chain each meet at an interface which comprises an original interface between the antibody CH3 domains; wherein said interface is altered to promote the formation of the bispecific antibody, wherein the alteration is characterized in that:

a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

27. A method for the preparation of an a bispecific antibody according to any one of embodiments 1 to 26 comprising the steps of a) transforming a host cell with vectors comprising nucleic acid molecules encoding the light chain and heavy chain of an antibody according to any one of embodiments 1 to 26, b) culturing the host cell under conditions that allow synthesis of said antibody molecule; and c) recovering said antibody molecule from said culture.

28. A host cell comprising vectors comprising nucleic acid molecules encoding the light chain and heavy chains of an antibody according to any one of embodiments 1 to 26.

29. A pharmaceutical composition comprising an antibody according to any one of embodiments 1 to 26 and a pharmaceutically acceptable excipient.

30. An antibody according to any one of embodiments 1 to 26 or the pharmaceutical composition of embodiment 29 for use as a medicament.

31. An antibody according to any one of embodiments 1 to 26 or the pharmaceutical composition of embodiment 29 for use as a medicament in the treatment of plasma cell disorders.

32. An antibody according to any one of embodiments 1 to 26 or the pharmaceutical composition of embodiment 29 for use as a medicament in the treatment of multiple myeloma.

33. An antibody according to any one of embodiments 1 to 26 or the pharmaceutical composition of embodiment 29 for the treatment of plasma cell disorders like multiple myeloma or other B-cell disorders expressing BCMA.

34. An antibody according to any one of embodiments 1 to 25, characterized in comprising in the human IgG1 Fc part amino acid substitution of Pro329 with glycine or arginine and/or substitutions L234A and L235A.

The following examples, sequence listing and figures are provided to aid the understanding of the present invention, the true scope of which is set forth in the appended claims. It is understood that modifications can be made in the procedures set forth without departing from the spirit of the invention.

Materials & General Methods

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulins light and heavy chains is given in: Kabat, E. A. et al., (1991) Sequences of Proteins of Immunological Interest, 5$^{th}$ ed., NIH Publication No. 91-3242. Amino acids of antibody chains were numbered and referred to according to Kabat, E. A., et al., Sequences of Proteins of Immunological Interest, 5th ed., Public Health Service, National Institutes of Health, Bethesda, Md., (1991).

Gene Synthesis a) Desired gene segments were prepared from oligonucleotides made by chemical synthesis. The 600-1800 bp long gene segments, which were flanked by singular restriction endonuclease cleavage sites, were assembled by annealing and ligation of oligonucleotides including PCR amplification and subsequently cloned via the indicated restriction sites e.g. Kpnl/Sad or Ascl/Pacl into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany).

b) Desired gene segments where required were either generated by PCR using appropriate templates or were synthesized by Geneart AG (Regensburg, Germany) from synthetic oligonucleotides and PCR products by automated gene synthesis. The gene segments flanked by singular restriction endonuclease cleavage sites were cloned into standard expression vectors or into sequencing vectors for further analysis. The plasmid DNA was purified from transformed bacteria using commercially available plasmid purification kits. Plasmid concentration was determined by UV spectroscopy. The DNA sequence of the subcloned gene fragments was confirmed by DNA sequencing. Gene segments were designed with suitable restriction sites to allow subcloning into the respective expression vectors. If required, protein coding genes were designed with a 5'-end DNA sequence coding for a leader peptide which targets proteins for secretion in eukaryotic cells.

DNA Sequence Determination

DNA sequences were determined by double strand sequencing.

DNA and Protein Sequence Analysis and Sequence Data Management

The Clone Manager (Scientific & Educational Software) software package version 9.2 was used for sequence mapping, analysis, annotation and illustration.

Expression Vectors a) The fusion genes comprising the described antibody chains as described below were generated by PCR and/or gene synthesis and assembled with known recombinant methods and techniques by connection of the according nucleic acid segments e.g. using unique restriction sites in the respective vectors. The subcloned nucleic acid sequences were verified by DNA sequencing. For transient transfections larger quantities of the plasmids are prepared by plasmid preparation from transformed *E. coli* cultures (Nucleobond A X, Macherey-Nagel).

b) For the generation of anti-BCMA antibody expression vectors, the variable regions of heavy and light chain DNA sequences were subcloned in frame with either the human IgG1 constant heavy chain or the hum IgG1 constant light chain pre-inserted into the respective generic recipient expression vector optimized for expression in mammalian cell lines. The antibody expression is driven by a chimeric MPSV promoter comprising a CMV enhancer and a MPSV promoter followed by a 5' UTR, an intron and a Ig kappa MAR element. The transcription is terminated by a synthetic polyA signal sequence at the 3' end of the CDS. All vectors carry a 5'-end DNA sequence coding for a leader peptide which targets proteins for secretion in eukaryotic cells. In addition each vector contains an EBV OriP sequence for episomal plasmid replication in EBV EBNA expressing cells.

c) For the generation of BCMA×CD3 bispecific antibody vectors, the IgG1 derived bispecific molecules consist at least of two antigen binding moieties capable of binding specifically to two distinct antigenic determinants CD3 and BCMA. The antigen binding moieties are Fab fragments composed of a heavy and a light chain, each comprising a variable and a constant region. At least one of the Fab fragments was a "Crossfab" fragment, wherein VH and VL were exchanged. The exchange of VH and VL within the Fab fragment assures that Fab fragments of different specificity do not have identical domain arrangements. The bispecific molecule design was monovalent for CD3 and bivalent for BCMA where one Fab fragment was fused to the N-terminus of the inner CrossFab (2+1). The bispecific molecule contained an Fc part in order for the molecule to have a long half-life. A schematic representation of the constructs is given in FIG. 2; the preferred sequences of the constructs are shown in SEQ ID NOs 39 to 52. The molecules were produced by co-transfecting HEK293 EBNA cells growing in suspension with the mammalian expression vectors using polymer-based transfection. For preparation of 2+1 CrossFab-IgG constructs, cells were transfected with the corresponding expression vectors in a 1:2:1:1 ratio ("vector Fc(knob)":"vector light chain":"vector light chain CrossFab":"vector heavy chain-CrossFab").

Cell Culture Techniques

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Expression in HEK293 Cells (HEK293-EBNA System)

Bispecific antibodies were expressed by transient co-transfection of the respective mammalian expression vectors in HEK293-EBNA cells, which were cultivated in suspension, using polymer-based transfection. One day prior to transfection the HEK293-EBNA cells were seeded at 1.5 Mio viable cells/mL in Ex-Cell medium, supplemented with 6 mM of L-Glutamine. For every mL of final production volume 2.0 Mio viable cells were centrifuged (5 minutes at 210×g). The supernatant was aspirated and the cells resuspended in 100 µL of CD CHO medium. The DNA for every mL of final production volume was prepared by mixing 1 µg of DNA (Ratio heavy chain:modified heavy chain:light chain:modified light chain=1:1:2:1) in 100 µL of CD CHO medium. After addition of 0.27 µL of polymer-based solution (1 mg/mL) the mixture was vortexed for 15 seconds and left at room temperature for 10 minutes. After 10 minutes, the resuspended cells and DNA/polymer-based solution mixture were put together and then transferred into an appropriate container which was placed in a shaking device (37° C., 5% $CO_2$). After a 3 hours incubation time 800 µL of Ex-Cell Medium, supplemented with 6 mM L-Glutamine, 1.25 mM valproic acid and 12.5% Pepsoy (50 g/L), was added for every mL of final Production volume. After 24 hours, 70 µL of Feed solution was added for every mL of final production volume. After 7 days or when the cell viability was equal or lower than 70%, the cells were separated from the supernatant by centrifugation and sterile filtration. The antibodies were purified by an affinity step and one or two polishing steps, being cation exchange chromatography and size exclusion chromatography. When required, an additional polishing step was used. The recombinant anti-BCMA human antibody and bispecific antibodies were produced in suspension by co-transfecting HEK293-EBNA cells with the mammalian expression vectors using polymer-based transfection. The cells were transfected with two or four vectors, depending in the format. For the human IgG1 one plasmid encoded the heavy chain and the other plasmid the light chain. For the bispecific antibodies four plasmids were co-transfected. Two of them encoded the two different heavy chains and the other two encoded the two different light chains. One day prior to transfection the HEK293-EBNA cells were seeded at 1.5 Mio viable cells/mL in F17 Medium, supplemented with 6 mM of L-Glutamine.

Protein Determination

Determination of the antibody concentration was done by measurement of the absorbance at 280 nm, using the theoretical value of the absorbance of a 0.1% solution of the antibody. This value was based on the amino acid sequence and calculated by GPMAW software (Lighthouse data).

SDS-Page

The NuPAGE® Pre-Cast gel system (Invitrogen) is used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer is used.

Protein Purification

By Protein a Affinity Chromatography

For the affinity step the supernatant was loaded on a protein A column (HiTrap Protein A FF, 5 mL, GE Healthcare) equilibrated with 6 CV 20 mM sodium phosphate, 20 mM sodium citrate, pH 7.5. After a washing step with the same buffer the antibody was eluted from the column by step elution with 20 mM sodium phosphate, 100 mM sodium chloride, 100 mM Glycine, pH 3.0. The fractions with the desired antibody were immediately neutralized by 0.5 M Sodium Phosphate, pH 8.0 (1:10), pooled and concentrated by centrifugation. The concentrate was sterile filtered and processed further by cation exchange chromatography and/or size exclusion chromatography.

By Cation Exchange Chromatography

For the cation exchange chromatography step the concentrated protein was diluted 1:10 with the elution buffer used for the affinity step and loaded onto a cation exchange colume (Poros 50 HS, Applied Biosystems). After two washing steps with the equilibration buffer and a washing buffer resp. 20 mM sodium phosphate, 20 mM sodium citrate, 20 mM TRIS, pH 5.0 and 20 mM sodium phosphate, 20 mM sodium citrate, 20 mM TRIS, 100 mM sodium chloride pH 5.0 the protein was eluted with a gradient using 20 mM sodium phosphate, 20 mM sodium citrate, 20 mM TRIS, 100 mM sodium chloride pH 8.5. The fractions containing the desired antibody were pooled, concentrated by centrifugation, sterile filtered and processed further a size exclusion step.

By Analytical Size Exclusion Chromatography

For the size exclusion step the concentrated protein was injected in a XK16/60 HiLoad Superdex 200 column (GE Healthcare), and 20 mM Histidine, 140 mM Sodium Chloride, pH 6.0 with or without Tween20 as formulation buffer. The fractions containing the monomers were pooled, concentrated by centrifugation and sterile filtered into a sterile vial.

Measurement of Purity and Monomer Content

Purity and monomer content of the final protein preparation was determined by CE-SDS (Caliper LabChip GXII system (Caliper Life Sciences)) resp. HPLC (TSKgel G3000 SW XL analytical size exclusion column (Tosoh)) in a 25 mM potassium phosphate, 125 mM Sodium chloride, 200 mM L-arginine monohydrochloride, 0.02% (w/v) Sodium azide, pH 6.7 buffer.

Molecular Weight Confirmation by LC-MS Analyses

Deglycosylation

To confirm homogeneous preparation of the molecules final protein solution of was analyzed by LC-MS analyses. To remove heterogeneity introduced by carbohydrates the constructs are treated with PNGaseF (ProZyme). Therefore the pH of the protein solution was adjusted to pH7.0 by adding 2 µl 2 M Tris to 20 µg protein with a concentration of 0.5 mg/ml. 0.8 µg PNGaseF was added and incubated for 12 h at 37° C.

LC-MS Analysis—On Line Detection

The LC-MS method was performed on an Agilent HPLC 1200 coupled to a TOF 6441 mass spectrometer (Agilent). The chromatographic separation was performed on a Macherey Nagel Polysterene column; RP1000-8 (8 µm particle size, 4.6×250 mm; cat. No. 719510). Eluent A was 5% acetonitrile and 0.05% (v/v) formic acid in water, eluent B was 95% acetonitrile, 5% water and 0.05% formic acid. The flow rate was 1 ml/min, the separation was performed at 40° C. and 6 µg (15 µl) of a protein sample obtained with a treatment as described before.

| Time (min.) | % B |
| --- | --- |
| 0.5 | 15 |
| 10 | 60 |
| 12.5 | 100 |
| 14.5 | 100 |
| 14.6 | 15 |
| 16 | 15 |
| 16.1 | 100 |

During the first 4 minutes the eluate was directed into the waste to protect the mass spectrometer from salt contamination. The ESI-source was running with a drying gas flow of 12 l/min, a temperature of 350° C. and a nebulizer pressure of 60 psi. The MS spectra were acquired using a fragmentor voltage of 380 V and a mass range 700 to 3200 m/z in positive ion mode using. MS data were acquired by the instrument software from 4 to 17 minutes.

Isolation of Primary Human Pan T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors. Briefly, blood was diluted with sterile PBS and carefully layered over a Histopaque gradient (Sigma, H8889). After centrifugation for 30 minutes at 450×g at room temperature (brake switched off), part of the plasma above the PBMC containing interphase was discarded. The PBMCs were transferred into new 50 ml Falcon tubes and tubes were filled up with PBS to a total volume of 50 ml. The mixture was centrifuged at room temperature for 10 minutes at 400×g (brake switched on). The supernatant was discarded and the PBMC pellet washed twice with sterile PBS (centrifugation steps at 4° C. for 10 minutes at 350×g). The resulting PBMC population was counted automatically (ViCell) and stored in RPMI1640 medium, containing 10% FCS and 1% L-alanyl-L-glutamine (Biochrom, K0302) at 37° C., 5% $CO_2$ in the incubator until assay start.

T cell enrichment from PBMCs was performed using the Pan T Cell Isolation Kit II (Miltenyi Biotec #130-091-156), according to the manufacturer's instructions. Briefly, the cell pellets were diluted in 40 µî if cold buffer per 10 million cells (PBS with 0.5% BSA, 2 nM EDTA, sterile filtered) and incubated with 10 µî Biotin-Antibody Cocktail per 10 million cells for 10 min at 4° C. 30 µî cold buffer and 20 µî Anti-Biotin magnetic beads per 10 million cells were added, and the mixture incubated for another 15 min at 4° C. Cells were washed by adding 10-20× the current volume and a subsequent centrifugation step at 300×g for 10 min, Up to 100 million cells were resuspended in 500 µî buffer. Magnetic separation of unlabeled human pan T cells was performed using LS columns (Miltenyi Biotec #130-042-401) according to the manufacturer's instructions. The resulting T cell population was counted automatically (ViCell) and stored in AIM-V medium at 37° C., 5% CO$_2$ in the incubator until assay start (not longer than 24 h).

Isolation of Primary Human Naive T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors, T-cell enrichment from PBMCs was performed using the Naive CD8$^+$ T cell isolation Kit from Miltenyi Biotec (#130-093-244), according to the manufacturer's instructions, but skipping the last isolation step of CD8$^+$ T cells (also see description for the isolation of primary human pan T cells).

Isolation of Primary Cynomolgus PBMC's from Heparinized Blood

Peripheral blood mononuclear cells (PBMCs) were prepared by density centrifugation from fresh blood from healthy cynomolgus donors, as follows: Heparinized blood was diluted 1:3 with sterile PBS, and Lymphoprep medium (Axon Lab #1114545) was diluted to 90% with sterile PBS. Two volumes of the diluted blood were layered over one volume of the diluted density gradient and the PBMC fraction was separated by centrifugation for 30 min at 520×g, without brake, at room temperature. The PBMC band was transferred into a fresh 50 ml Falcon tube and washed with sterile PBS by centrifugation for 10 min at 400×g at 4° C. One low-speed centrifugation was performed to remove the platelets (15 min at 150×g, 4° C.), and the resulting PBMC population was automatically counted (Vi-Cell) and immediately used for further assays.

EXAMPLES

Example 1: Generation of Anti-BCMA Antibodies

Example 1.1: Production of Antigens and Tool Reagents

Example 1.1.1: Recombinant, Soluble, Human BCMA Extracellular Domain

The extracellular domains of human, cynomolgus and murine BCMA that were used as antigens for phage display selections were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). The extracellular domains of human, cynomolgus and murine BCMA comprised methionine 4 to asparagine 53, methionine 4 to asparagine 52, and alanine 2 to threonine 49, respectively. These were N-terminally fused to the hinge of a human IgG1 enabling heterodimerization with an unfused human IgG1 Fc portion (hole chain) by knobs-into-holes technology.

For recovering of the extracellular domain of BCMA the following primers were used:

```
                                        (SEQ ID NO: 9)
AAGCTTGGATCCATGTTGCAGATGGCTGGGCAGTGCTCC-3 incorporating a BamHI site (bold, underlined)
and reverse primer
                                       (SEQ ID NO: 10)
5-GAATTCGCGGCCGCTCATCCTTTCACTGAATTGGTCACACTTGCA

TTAC-3 primer
                                       (SEQ ID NO: 11)
5-ACGTTAGATCTCCACTCAGTCCTGCATCTTGTTCCAGTTAAC-3
and reverse primer
                                       (SEQ ID NO: 12)
5-AACGTTGCGGCCGCTAGTTTCACAAACCCCAGG-3

(SEQ ID NO: 13)
GAATTCAAGCTTGCCACCATGTTGCAGATGGCTGGGCAGTGCTCC-3 including a HindIII restriction site (bold, underlined) and Kozak consensus sequence
and reverse primer
                                       (SEQ ID NO: 14)
5-GAATTCTCTAGATTACCTAGCAGAAATTGATTTCTCTATCTCCGT

AGC-3
```

Example 1.1.2: Recombinant, Truncated Murine APRIL

Recombinant, truncated, murine APRIL that was used as tool (competitor) for the phage display selections and ELISAs was transiently expressed as N-terminal monomeric Fc-fusion in HEK EBNA cells. Murine APRIL comprised histidine 106 to leucine 241. It was N-terminally fused to the hinge of a human IgG1 enabling heterodimerization with an unfused human IgG1 Fc portion (hole chain) by knobs-into-holes technology.

Example 1.2: BCMA-Expressing Cells as Tools

Example 1.2.1: Recombinant Cells Expressing Human, Cyno or Mouse BCMA on their Surface a) Production of HEK293-EBNA Cells, Transiently Expressing Full Length BCMA Transiently expressing BCMA HEK293-EBNA cells were produced in suspension by transfecting HEK293-EBNA cells with the mammalian expression vectors using polymer-based transfection. The cells were transfected with vectors containing the gene coding either full length human, murine or cynomolgus BCMA. One day prior to transfection the HEK293-EBNA cells were seeded at 1.5 Mio viable cells/mL in Ex-Cell® GTM-3 medium, supplemented with 6 mM of L-Glutamine.

For every mL of final Production volume 2.0 Mio viable cells were centrifuged (5 minutes at 210×g). The supernatant was aspirated and the cells resuspended in 100 uL of CD CHO medium. The DNA for every mL of final Production volume was prepared by mixing 1 ug of DNA in 100 uL of CD CHO medium. After addition of 0.27 uL of polymer-based solution (1 mg/mL) the mixture was vortexed for 15 seconds and left at RT for 10 minutes. After 10 minutes the resuspended cells and DNA/polymer-based solution mixture were put together. This was transferred into an appropriate container which was placed in a shaking device (37° C., 5% CO2). After 3 hour incubation time 800 uL of F17 Medium, supplemented with 6 mM L-Glutamine, 1.25 mM valproic acid and 12.5% Pepsoy (50 g/L), was added for every mL of final Production volume.

After 2 days incubation the transiently transfected HEK293-EBNA cells were harvested by centrifugation (200*g; 10 min.). After aspiration of the supernatant the cell pellet was gently resuspended with Ex-Cell® GTM-3 medium at the required density (30 Mio cells/mL). Cells were transferred into cryo vials (1 mL/vial), placed in a cryo preservation box, which was previously cooled at four degrees centigrade for at least 12 hours, and stored at −80 degrees centigrade. After 72 hours at −80 degrees centigrade the cells were transferred into liquid nitrogen.

b) Generation of BCMA Expressing CHO Cell Line

CHO cell lines overexpressing human, cyno or murine BCMA were generated by transduction with virus-like particles (VLP). Lentivirus-based virus-like particles were produced by co-transfection of HEK293T (ATCC CRL11268) cells with ViraSafe™ Lentiviral Packaging plasmids (Cell Biolabs, USA) and lentiviral expression vectors coding for either human, murine or cyno BCMA. Plasmid transfections into HEK293T cells were performed with Lipofectamine LTX (Life Technologies, USA) according the manufacturer's instructions. Transfections were done in 6-well plates seeded with $6 \times 10^5$ cells/well the day before transfection and 2.5 µg of plasmid DNA. Each transfection contained 0.4 µg of pRSV-Rev packaging vector, 0.4 µg of pCgpV packaging vector, 0.4 µg of pCMV-VSV-G envelop vector, and 1.3 µg of either human (pETR14305), murine (pETR14304) or cyno (pETR14306) BCMA expression vector. The VLP-containing supernatant was collected after 48 h and filtered through 0.45 µm pore-sized polyethersulfone membrane. To generate stable BCMA expressing cell lines, CHO cells were seeded at $1.0 \times 10^6$ cells/well in 6-well plates and overlaid with 2 mL of VLP-containing supernatant. Transductions were carried out by spinoculation at 800×g and at 32° C. for 30 min in an Eppendorf centrifuge 5810 table-top centrifuge (Eppendorf, Germany). Viral supernatant was exchanged for fresh media 12 h after spinoculation. 3 days after transduction, puromycin was added to 6 µg/mL and the cells were cultured for several passages. A BCMA-positive cell pool was obtained by FACS sorting (FACS ARIA, Becton, Dickinson and Company, USA) using a cross-reactive Alexa Fluor 448-labeled anti-BCMA antibody.

c) Recombinant Cells Stably Expressing Cynomolgus BCMA on their Surface i. Generation of BCMA Stably Expressing HEK293T Cell Line HEK293T (ATCC CRL11268) cell lines overexpressing human or cynomolgus BCMA were generated by transduction with virus-like particles (VLP). Lentivirus-based virus-like particles were produced by co-transfection of HEK293T cells with ViraSafe™ Lentiviral Packaging plasmids (Cell Biolabs) and lentiviral expression vectors coding for either human or cyno BCMA. Plasmid transfections into HEK293T cells were performed with Lipofectamine LTX (Life Technologies) according the manufacturer's instructions. Transfections were done in 6-well plates seeded with 6×105 cells/well the day before transfection and 2.5 µg of plasmid DNA. Each transfection contained 0.4 µg of pRSV-Rev packaging vector, 0.4 µg of pCgpV packaging vector, 0.4 µg of pCMV-VSV-G envelop vector, and 1.3 µg of either human (pETR14305) or cyno (pETR14306) BCMA expression vector. The VLP-containing supernatant was collected after 48 h and filtered through 0.45 µm pore-sized polyethersulfone membrane. To generate stable BCMA expressing cell lines, HEK293T cells were seeded at 1.0×106 cells/well in 6-well plates and overlaid with 1 mL of VLP-containing supernatant. Transductions were carried out by spinoculation at 800×g and at 32° C. for 30 min in an Eppendorf centrifuge 5810 table-top centrifuge (Eppendorf). Viral supernatant was exchanged for fresh media 12 h after spinoculation. 3 days after transduction, puromycin was added to 1 µg/mL and the cells were cultured for several passages. A BCMA-positive cell clone was obtained by FACS sorting (FACS ARIA, Becton, Dickinson and Company) using a human/cyno cross-reactive anti-BCMA antibody (MAB 83A10), and FITC-conjugated Fc gamma-specific goat anti-human IgG (Jackson ImmunoResearch, #109-095-098) as secondary antibody.

ii. Normalization of Human and Cynomolgus BCMA Expression

Flow cytometry analysis using an anti-FLAG M2 antibody (Sigma-Aldrich, #F3165) was used to confirm comparable expression levels of FLAG-tagged cynomolgus and human BCMA in transduced HEK293T cells. An intracellular FLAG-tag was fused to the c-terminus of human and cynomolgus BCMA. For intracellular staining, 106 cells were washed, fixed with paraformaldehyde, permeabilized using 1% saponin in PBS, and then incubated with anti-FLAG M2 antibody for 30 min at 4° C. Cells were rinced with PBS and incubated 30 min with an RPE-conjugated goat-anti-mouse antibody (AbD Serotec, #103001), washed three times with PBS and resuspended in 1 mL PBS/5% FCS for flow cytometry analysis.

Example 1.2.2: Human Myeloma Cell Line Expressing BCMA on their Surface

BCMA expression was assessed on five human myeloma cell lines (NCI-H929, RPMI-8226, U266B1, L-363 and JJN-3) by flow cytometry. NCI-H929 cells ((H929) ATCC® CRL-9068™) were cultured in 80-90% RPMI 1640 with 10-20% heat-inactivated FCS and could contain 2 mM L-glutamine, 1 mM sodium pyruvate and 50 µM mercaptoethanol. RPMI-8226 cells ((RPMI) ATCC® CCL155™) were cultured in a media containing 90% RPMI 1640 and 10% heat-inactivated FCS. U266B1 ((U266) ATCC® TIB-196™) cells were cultured in RPMI-1640 medium modified to contain 2 mM L-glutamine, 10 mM HEPES, 1 mM sodium pyruvate, 4500 mg/L glucose, and 1500 mg/L sodium bicarbonate and 15% heat-inactivated FCS. L-363 cell line (Leibniz Institute DSMZ—German collection of microorganisms and cell cultures; DSMZ No. ACC 49) was cultured in 85% RPMI 1640 and 15% heat-inactivated FCS. JJN-3 cell line (DSMZ No. ACC 541) was cultured in 40% Dulbecco's MEM+40% Iscove's MDM+20% heat-inactivated FBS. Briefly, cells were harvested, washed, counted for viability, resuspended at 50,000 cells/well of a 96-well round bottom plate and incubated with anti-human BCMA antibody (Abcam, #ab54834, mouse IgG1) at 10 µg/ml for 30 min at 4° C. (to prevent internalization). A mouse IgG1 was used as isotype control (BD Biosciences, #554121). Cells were then centrifuged (5 min at 350×g), washed twice and incubated with the FITC-conjugated anti mouse secondary antibody for 30 min at 4° C. At the end of incubation time, cells were centrifuged (5 min at 350×g), washed twice with FACS buffer, resuspended in 100 ul FACS buffer and analyzed on a Cantoll device running FACS Diva software. The relative quantification of BCMA receptor number on the surface membrane of H929, RPMI-8226 and U266B1 myeloma cell lines was assessed by QIFIKIT analysis (Dako, #K0078, following manufacturer's instructions). H929 cells expressed human BCMA with the highest density, up to 5-6-fold higher more than other myeloma cell lines. H929 is considered as a high BCMA-expressing myeloma cell line as compared to RPMI-8226, U266 and L363 which are low BCMA-expressing myeloma cells. Tables 4 and 4A summarize the relative BCMA receptor number on the cell surface of human multiple myeloma cell lines.

TABLE 4

Quantification of BCMA receptor number on membrane surface of NCI-H929, RPMI-8226 and U266B1 myeloma cell lines

| Myeloma cell lines | Relative binding sites per cell |
|---|---|
| H929 | 24981 |
| RPMI-8226 | 3617 |
| U266(B1) | 4794 |

TABLE 4A

Quantification of BCMA receptor number on membrane surface of H929, L363, RPMI-8226, U266B1 and JJN-3 human myeloma cell lines

| Human myeloma cell lines | Specific antigen binding capacity (SABC) | | | | |
|---|---|---|---|---|---|
| | Experiment 1 | Experiment 2 | Experiment 3 | Experiment 4 | Experiment 5 |
| H929 | 19357 | 54981 | 44800 | 100353 | 98050 |
| L363 | 16,970 | / | 11300 | 11228 | / |
| U266(B1) | / | 12852 | 11757 | / | 9030 |
| RPMI-8226 | 1165 | 5461 | / | 11361 | 2072 |
| JJN-3 | / | / | / | / | 650 |

Example 1.3: Obtaining BCMA Binders Out of an In Vitro, Recombinant Library

Example 1.3.1: Construction of Generic Fab-Libraries

Generic antibody libraries in the Fab-format are constructed on the basis of human germline genes using the following V-domain pairings: Vk320 kappa light chain with VH323 heavy chain for the DP47-3 library and Vkl_17 kappa light chain with VH1_69 heavy chain for the DP88-3 library. Both libraries are randomized in CDR3 of the light chain (L3) and CDR3 of the heavy chain (H3) and are assembled from 3 fragments per library by splicing by overlapping extension (SOE) PCR. Fragment 1 comprises the 5' end of the antibody gene including randomized L3, fragment 2 is a central constant fragment spanning from L3 to H3, whereas fragment 3 comprises randomized H3 and the 3' portion of the antibody gene. The following primer combinations are used to generate library fragments for DP47-3 library: fragment 1 (LMB3-LibL1b_new), fragment 2 (MS63-MS64), fragment 3 (Lib2H-fdseqlong). See Table 1 of WO2012020038. The following primer combinations are used to generate library fragments for the DP88-3 library: fragment 1 (LMB3-RJH_LIB3), fragment 2 (RJH31-RJH32) and fragment 3 (LIB882-fdseqlong). See Tables 3 and 4 of WO2012020038.

The PCR protocol for the production of library fragments includes: 5 min of initial denaturation at 94° C.; 25 cycles of 1 min at 94° C., 1 min at 58° C., and 1 min at 72° C.; and terminal elongation for 10 min at 72° C. For assembly PCR, equimolar ratios of the 3 fragments are used as template. The assembly PCR protocol includes: 3 min of initial denaturation at 94° C.; and 5 cycles of 30 seconds at 94° C., 1 min at 58° C., and 2 min at 72° C. At this stage, primers complementary to sequence outside fragments 1-3 are added and an additional 20 cycles are performed prior to a terminal elongation for 10 min at 72° C. After assembly of sufficient amounts of full length randomized Fab constructs, the Fab constructs are digested with NcoI/NotI for the DP47-3 library and with NcoI/NheI for the DP88-3 library alongside with similarly treated acceptor phagemid vector. For the DP47-3 library, 22.8 µg of Fab library is ligated with 16.2 µg of phagemid vector. For the DP88-3 library, 30.6 µg of Fab library is ligated with 30.6 µg of phagemid vector.

Purified ligations are used for 68 transformations for the DP47-3 library and 64 transformations for the DP88-3 library, respectively, to obtain final DP47-3 and DP88-3 libraries. Phagemid particles displaying the Fab libraries are rescued and purified by PEG/NaCl purification to be used for selection of anti-BCMA Fab clones.

Example 1.3.2: Selection of Anti-BCMA Fab Clones

Anti-BCMA Fabs were established by phage display from synthetic Fab libraries consisting of VL and VH pairings derived from different V-domain families Clones 17A5 and 83A10 were generated from Vk3_20/VH3_23 sublibrary and clone 13A4 from Vk2D_28/VH5_1 sublibrary, respectively (Table 5). These libraries are based on entirely human frameworks with sequence diversity in CDR3 of VL (3 different lengths) and VH domains (6 different lengths).

TABLE 5

Anti-BCMA clones and respective VL/VH pairings

| Fab clone | VL domain | VH domain |
|---|---|---|
| 17A5 | Vk3_20 | VH3_23 |
| 83A10 | Vk3_20 | VH3_23 |
| 13A4 | Vk2D_28 | VH5_1 |

Selection rounds (biopanning) were performed in solution according to the following pattern: 1) pre-clearing of ~$10^{12}$ phagemid particles per library pool in immunotubes coated with 10 ug/ml of an unrelated human IgG to deplete the libraries of antibodies recognizing the Fc-portion of the antigens; 2) incubation of the non-Fc-binding phagemid particles with 100 nM biotinylated BCMA for 0.5 h in the presence of 100 nM unrelated non-biotinylated Fc knobs-into-holes construct for further depletion of Fc-binders in a total volume of 2 ml; 3) capture of biotinylated BCMA and specifically binding phage by splitting up and transferring the panning reaction into 16 wells on a neutravidin or streptavidin pre-coated microtiter plate for 20 min on a shaker; 4) washing of respective wells 10-30× with PBS/Tween20 and 10-30× with PBS using a plate washer; 5) optional competitive washing step by addition of 230 nM murine APRIL to displace Fab clones that recognize the binding site of the natural ligand thus selecting for APRIL-non-competing phage antibodies; 6) elution of phage particles by addition of 125 ul 100 mM TEA (triethylamine) per well for 5-10 min and neutralization by addition of an equal volume of 1M Tris/HCl pH 7.4; 7) re-infection of log-phase E. coli TG1 cells with the eluted phage particles, infection with helperphage VCSM13, incubation on a shaker at 30° C. overnight and subsequent PEG/NaCl precipitation of phagemid particles to be used in the next selection round.

Selections were carried out over 3 to 5 rounds using constant antigen concentrations of 100 nM. Apart from selection campaigns during which only human BCMA was used as antigen, additional selection campaigns were carried out during which also cynomolgus or murine BCMA were used in an alternating fashion with human BCMA in order to select for cross-reactive antibodies. Moreover, as an alternative to streptavidin plate-based capture, capture of antigen:phage complexes was performed by addition of $5.4 \times 10^7$ streptavidin-coated magnetic beads to the panning reaction followed by washing steps using respective magnets under the conditions described above.

Specific binders were identified by surface plasmon resonance-screening of Fab-containing bacterial culture supernatants using BioRad's ProteOn XPR36 biosensor. In brief, after infection of log-phase E. coli TG1 cells with the eluted phage particles, single colony forming units (cfu) were plated and picked for inoculation of 1 ml expression cultures in 96-deep well plates. Fabs were captured from the supernatants on a ProteOn GLM chip that was derivatized with 8.000-10.000 RU of a goat anti-human IgG, F(ab')2 fragment specific polyclonal antibody (Jackson ImmunoResearch, #109-005-006) in vertical orientation. Subsequently, human, cynomolgus and murine BCMA as well as an unrelated Fc knobs-into-holes construct were injected as analytes in horizontal orientation. Clones that exhibited significant binding responses to BCMA and did not bind the Fc-portion of the antigens, were bacterially expressed in a 0.5 liter culture volume, affinity purified and kinetically characterized by SPR-analysis using a one-shot-kinetics protocol on BioRad's ProteOn XPR36 biosensor.

Example 2: BCMA Binding Assays: Surface Plasmon Resonance a) Affinities (KD) of anti-BCMA Fab clones were measured by surface plasmon resonance using a ProteOn XPR36 instrument (Biorad) at 25° C. with biotinylated human, cynomolgus and murine BCMA immobilized on NLC chips by neutravidin capture (Table 6). An unrelated biotinylated Fc knobs-into-holes construct was immobilized in a similar fashion as negative control Immobilization of antigens (ligand): Recombinant antigens were diluted with PB ST (10 mM phosphate, 150 mM sodium chloride pH 7.4, 0.005% Tween 20) to 10 ug/ml, then injected at 40 ul/minute for 300 s in vertical orientation. Injection of analytes: For one-shot kinetics measurements, injection direction was changed to horizontal orientation, two-fold dilution series of purified Fab (varying concentration ranges) were injected simultaneously at 40 ul/min along channels 1-5, with association times of 200 or 300 s, and dissociation times of 300 s. Buffer (PBST) was injected along the sixth channel to provide an "in-line" blank for referencing. Association rate constants (kon) and dissociation rate constants (koff) were calculated using a simple one-to-one Langmuir binding model in ProteOn Manager v3.1 software by simultaneously fitting the association and dissociation sensorgrams. The equilibrium dissociation constant (KD) was calculated as the ratio koff/kon. Regeneration was performed in horizontal orientation using 10 mM glycine-HCl pH 1.5 at a flow rate of 100 ul/min for a contact time of 18 s.

TABLE 6

Monovalent affinities of anti-BCMA Fab clones

| Fab clone | $K_D$ human BCMA[nM] | KD cynomolgus BCMA[nM] | KD murine BCMA[nM] |
|---|---|---|---|
| 17A5 | 45 | — | 74 |
| 83A10 | 76 | 1510 | 1130 |
| 13A4 | 1.8 | — | — | b) Assessment of binding of anti-BCMA antibodies to recombinant BCMA by surface plasmon resonance (SPR) as follow. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany) The avidity of the interaction between anti-BCMA antibodies and recombinant BCMA Fc(kih) (human, cynomolgus and murine) was determined. Biotinylated recombinant human, cynomolgus and murine BCMA Fc(kih) were directly coupled on a SA chip following instructions (Biacore, Freiburg/Germany). The immobilization level ranged from 200 to 700 RU. The anti-BCMA antibodies were passed at a 2-fold concentration range (1.95 to 500 nM) with a flow of 30 µL/minutes through the flow cells over 120 seconds. The dissociation was monitored for 180 seconds. Bulk refractive index differences were corrected for by subtracting the response obtained on the reference flow cell. Here, the anti-BCMA antibodies were flown over an empty surface previously activated and deactivated as described in the standard amine coupling kit. Apparent kinetic constants were derived using the Biacore T200 Evaluation Software (vAA, Biacore AB, Uppsala/Sweden), to fit rate equations for 1:1 Langmuir binding by numerical integration, despite the bivalency of the interaction for comparison purposes.

The affinity of the interaction between anti-BCMA antibodies and recombinant human BCMA Fc(kih) was also determined. Anti-human Fab antibody (GE Healthcare) was directly coupled on a CM5 chip at pH 5.0 using the standard amine coupling kit (Biacore, Freiburg/Germany). The immobilization level was about 6500 RU. Anti-BCMA antibody was captured for 90 seconds at 25 nM. Recombinant human BCMA Fc(kih) was passed at a 4-fold concentration range (1.95 to 500 nM) with a flow of 30 µL/minutes through the flow cells over 120 seconds. The dissociation was monitored for 120 seconds. Bulk refractive index differences were corrected for by subtracting the response obtained on reference flow cell. Here, recombinant BCMA was flown over a surface with immobilized anti-human Fab antibody but on which HBS-EP has been injected rather than anti-BCMA antibody. Kinetic constants were derived using the Biacore T100 Evaluation Software (vAA, Biacore AB, Uppsala/Sweden), to fit rate equations for 1:1 Langmuir binding by numerical integration (Table 7). Binding of 83A10 anti-BCMA antibody to recombinant cynomolgus BCMA Fc(kih) and murine BCMA Fc(kih) was also measured (Table 8).

TABLE 7

Affinity constants determined by fitting rate equations for 1:1 Langmuir binding

| Ligand | Analyte | Kon[1/Ms] | Koff[1/s] | KD[M] |
|---|---|---|---|---|
| 17A5 anti-BCMA IgG | huBCMA Fc(kih) | $2.2 \times 10^5$ | $1.9 \times 10^{-3}$ | $8.7 \times 10^{-9}$ |

TABLE 7-continued

Affinity constants determined by fitting rate equations for 1:1 Langmuir binding

| Ligand | Analyte | Kon[1/Ms] | Koff[1/s] | KD[M] |
|---|---|---|---|---|
| 83A10 anti-BCMA IgG | huBCMA Fc(kih) | $6.2 \times 10^5$ | $2.5 \times 10^{-3}$ | $4.1 \times 10^{-9}$ |
| 13A4 anti-BCMA IgG | huBCMA Fc(kih) | $7.2 \times 10^4$ | $3.6 \times 10^{-4}$ | $5.1 \times 10^{-9}$ |

TABLE 8

Binding of recombinant BCMA Fc(kih) to 83A10 anti-BCMA antibody: human BCMA Fc(kih); cynomolgus BCMA Fc(kih); murine BCMA Fc(kih)

| Ligand | Analyte | Kon[1/Ms] | Koff[1/s] | KD[M] |
|---|---|---|---|---|
| 83A10 anti-BCMA IgG | huBCMA Fc(kih) | $6.2 \times 10^5$ | $2.5 \times 10^{-3}$ | $4.1 \times 10^{-9}$ |
| 83A10 anti-BCMA IgG | cyBCMA Fc(kih) | $2.8 \times 10^5$ | $2.0 \times 10^{-2}$ | $7.2 \times 10^{-8}$ |
| 83A10 anti-BCMA IgG | muBCMA Fc(kih) | $2.0 \times 10^5$ | $4.0 \times 10^{-2}$ | $2.0 \times 10^{-7}$ |

Example 3: Specificity Test of Anti-BCMA IgG Antibodies to huTACI-R and huBAFF-R As members of the TNF-TNF-R superfamily, TACI and BAFF receptors are related to BCMA receptor with respectively 22% and 18.5% homology in the extracellular domain Therefore, surface plasmon resonance (SPR) binding experiments are performed to examine the specificity of anti-BCMA IgG antibodies. All SPR experiments are performed on a Biacore T200 (GE Healthcare) at 25° C. with HBS-EP as running buffer (0.01 M HEPES pH 7.4, 0.15 M NaCl, 3 mM EDTA, 0.005% Surfactant P20). Fc fused huBCMA, huBAFF-R and huTACI-R are chemically immobilized with a high immobilization level (~5000 RU) on different flow channels of a Biacore CM5 sensor chip at pH 5.0 using the standard amine coupling kit (GE Healthcare). Initially high concentrated solutions (1.5 µM, dissolved in HBS-EP) of anti-BCMA IgG 83A10 as well as a-huTACI-R IgG and a-huBAFF-R IgG as positive controls are injected (association time: 80 s, dissociation time: 600 s, flow: 30 µl/min) to check if binding occurs. A positive binding event of the a-huTACI-R IgG to huTACI-R as well as for a-huBAFF-R IgG to huBAFF-R and anti-BCMA IgG antibodies to huBCMA indicates that all receptors are still recognized after immobilization. For anti-BCMA IgG antibodies binding with fast kinetic rate constants to huBAFF-R and/or huTACI-R, a careful examination of kinetic parameter with low immobilization levels (300 RU) is performed on a new CM5 sensor chip. Anti-BCMA IgG antibody dilutions at concentrations of 700, 350, 175, 87.5, 43.75, 21.88 nM (dissolved in HBS-EP) are injected (association time: 80 s, dissociation time: 300 s, flow: 30 µl/min), and sample(s) are tested in duplicate. Regeneration is also performed when applicable i.e no fast and complete dissociation. Kinetic evaluation of the interaction between anti-BCMA IgG antibodies and huBAFF-R or huTACI-R is performed by global fitting of the data to a 1:1 interaction model that includes a term for mass transport (Biacore evaluation Version 2.0). A steady state analysis with higher anti-BCMA IgG antibody concentrations is also performed.

Example 4: Binding of BCMA Antibodies to BCMA-Positive Multiple Myeloma Cell Lines (Flow Cytometry)

Figure 4:
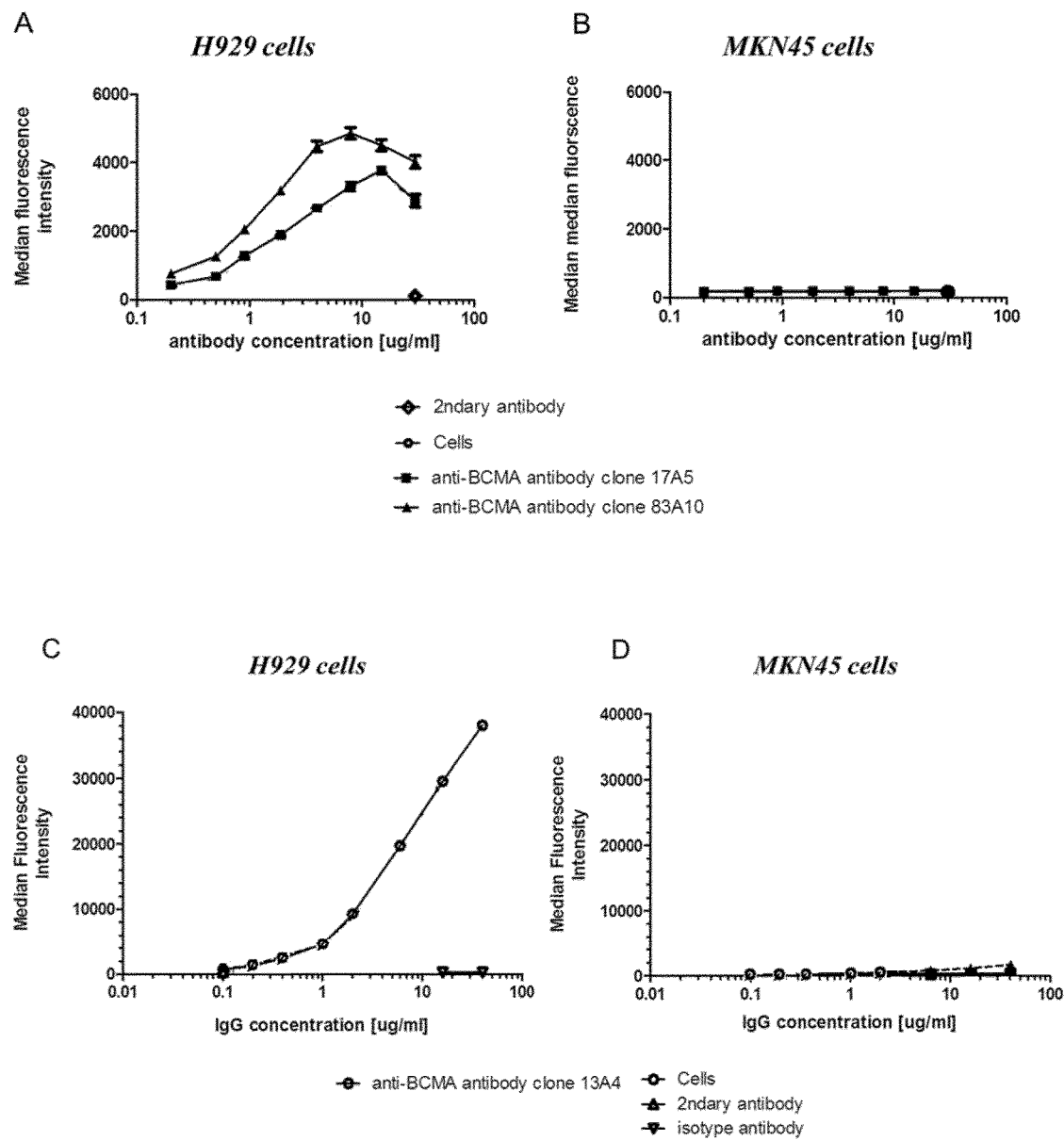
FIG. 4. Binding of anti-BCMA antibodies on BCMA-positive multiple myeloma cells. Mean fluorescence intensity for anti-BCMA IgG clones plotted in function of anti-BCMA antibody concentrations (from 0.2 to 40 µg/mL); (A) clones 17A5 and 83A10 on H929 cells, (B) clones 17A5, 83A10 on MKN45 cells, (C) clones 13A4 on H929 cells (D) clones 13A4 on MKN45 cells (see Example 4).

Anti-BCMA IgG antibodies (clones 17A5, 83A10, 13A4) were analyzed by flow cytometry for binding to human BCMA on BCMA-expressing H929 cells. MKN45 (human gastric adenocarcinoma cell line that does not express BCMA) was used as negative control. Briefly, cultured cells are harvested, counted and cell viability was evaluated using ViCell. Viable cells are then adjusted to $2 \times 10^6$ cells per ml in BSA-containing FACS Stain Buffer (BD Biosciences). 100 µl of this cell suspension were further aliquoted per well into a round-bottom 96-well plate and incubated with 30 µl of the anti-BCMA antibodies or corresponding IgG control for 30 min at 4° c. All anti-BCMA antibodies (and isotype control) were titrated and analyzed in final concentration range between 0.1-40 ug/ml. Cells were then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 ul BD Fixation buffer per well (#BD Biosciences, 554655) at 4° C. for 20 min, resuspended in 120 µl FACS buffer and analyzed using BD FACS Cantoll. FIG. 4 shows the mean fluorescence intensity for anti-BCMA IgG clones plotted in function of anti-BCMA antibody concentration; (A) clones 17A5, 83A10 on H929 cells, (B) clones 17A5, 83A10 on MKN45 cells, (C) clone 13A4 on H929 cells (D) clone 13A4 on MKN45 cells. EC50 values (denoting the antibody concentration required to reach 50% of the maximal binding) for the binding of clones 17A5, 83A10 to H929 cells are summarized in Table 9.

TABLE 9

EC50 values for binding of anti-BCMA antibodies to H929 multiple myeloma cells

| | Anti-BCMA antibody clone 83A10 | Anti-BCMA antibody clone 17A5 |
|---|---|---|
| EC50 (nM) | 12.5 | 9.0 |
| EC50 (µg/ml) | 1.8 | 1.3 |

Figure 5:
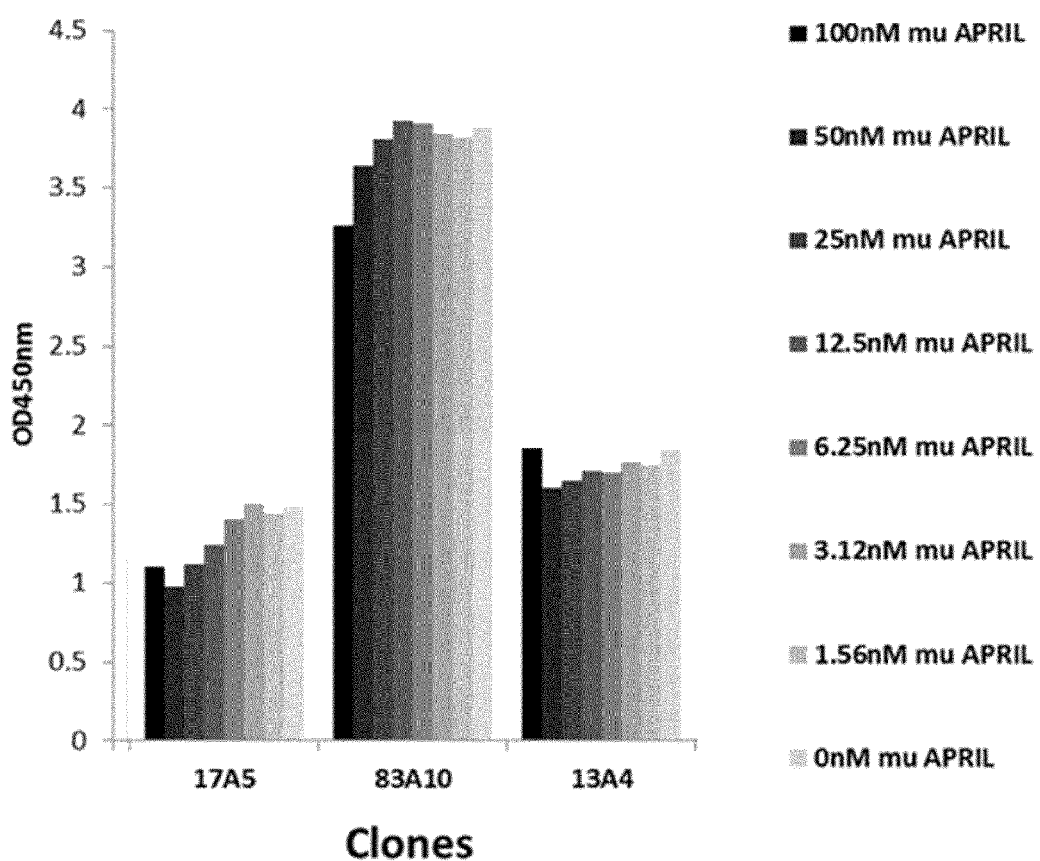
FIG. 5. Competition ELISA. ELISA results of selected anti-BCMA Fab clones (17A5, 83A10, and 13A4), at saturating concentrations of 500 or 1000 nM, binding to immobilized human BCMA in the presence of a concentration range of murine APRIL (from 1.56 to 100 nM) are shown. In case of non-competition, signals remained constant within the variability of the assay across the concentration range and signals in the presence of murine APRIL were comparable to those from the control wells where no murine APRIL was added. In case of competition a concentration dependent reduction of the signal was measured (see Example 5a).

Example 5: 100 ng/mL, Preferably 1000 ng/mL of APRIL does not Alter Binding of BCMA Antibody to Human BCMA (Flow Cytometry and ELISA)

a) Identification of non-APRIL-competing anti-BCMA Fabs or antibodies by ELISA. Binding of Fabs to immobilized human BCMA was assessed in the presence of increasing concentrations of murine APRIL. 25 nM biotinylated human BCMA (100 µl/well) were coated on a neutravidin plate and incubated on a shaker for 1 h at room temperature. 500 nM or 1000 nM purified Fabs were added to saturate the coated human BCMA for 1 h at room temperature. The plate was washed 3 times with PBS and murine APRIL was added at eight different concentrations using a two-fold dilution series in PBS buffer, ranging from 0 to 100 nM, and incubated on a shaker for 30 min. The plate was washed 3 times with PBS and anti-FLAG-HRP secondary antibody (1:4000) was added for 1 h. Again, the plate was washed 3 times with PBS and developed by adding 100 ul/well BM Blue POD (Roche). The reaction was stopped by adding 50 ul/well 1M $H_2SO_4$ and the OD was read at 450 nm (reference at 650 nm) for a final read-out of $OD_{450-650}$. Results for selected Fabs are shown in FIG. 5. The reduction (%) in OD values measured with the anti-BCMA clones in the absence vs. presence of 50 nM (1200 ng/mL) or 6.25 nM (140 ng/mL) muAPRIL (murine Δ-APRIL) is summarized in Table 10.

TABLE 10

Reduction in OD values measured (450 nm) in absence vs. presence of murine Δ-APRIL

Figure 6:
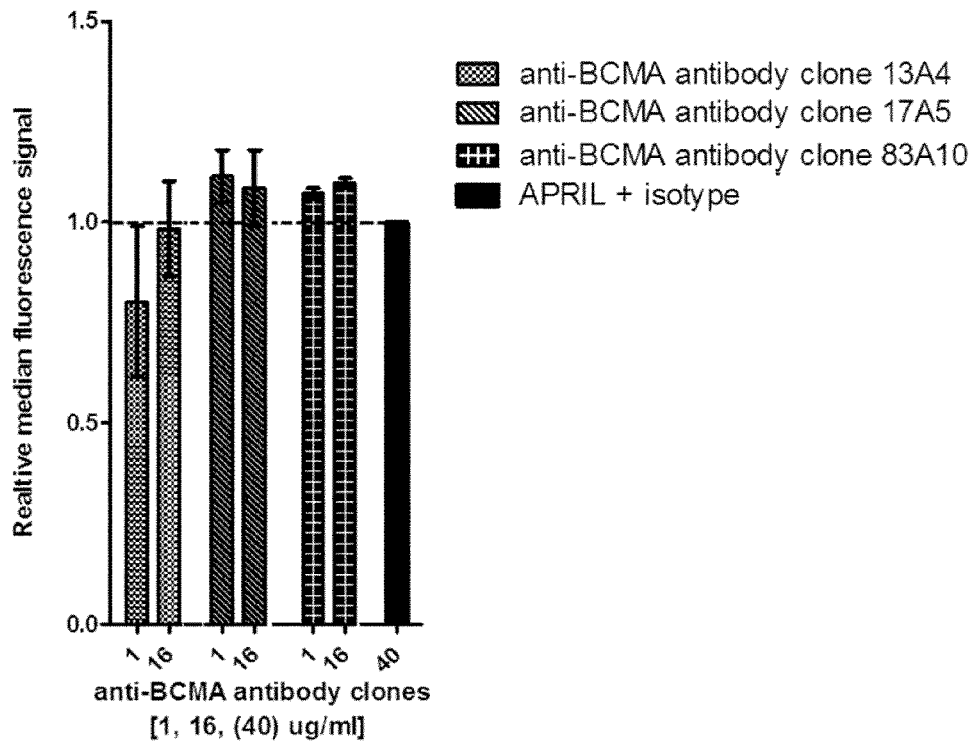
FIG. 6. Binding competition by FACS in H929 cells. Competition of murine Δ-APRIL with anti-BCMA antibodies detected by flow cytometry. Relative median fluorescence intensity of Δ-APRIL (FITC signal) used at a concentration of 1000 ng/mL detected in function of concentrations (1and 16 µg/mL) of anti-BCMA antibody clones 83A10, 17A5, and 13A4 on H929 cells. The median fluorescence intensity upon binding of Δ-APRIL in presence of the isotype control was set to one; the other signals were normalized to it. The detection of APRIL binding to BCMA-positive H929 cells in the presence of anti-BCMA antibodies was measured via anti-HA fluorochrome-conjugated antibody (see Example 5b).
Figure 7:
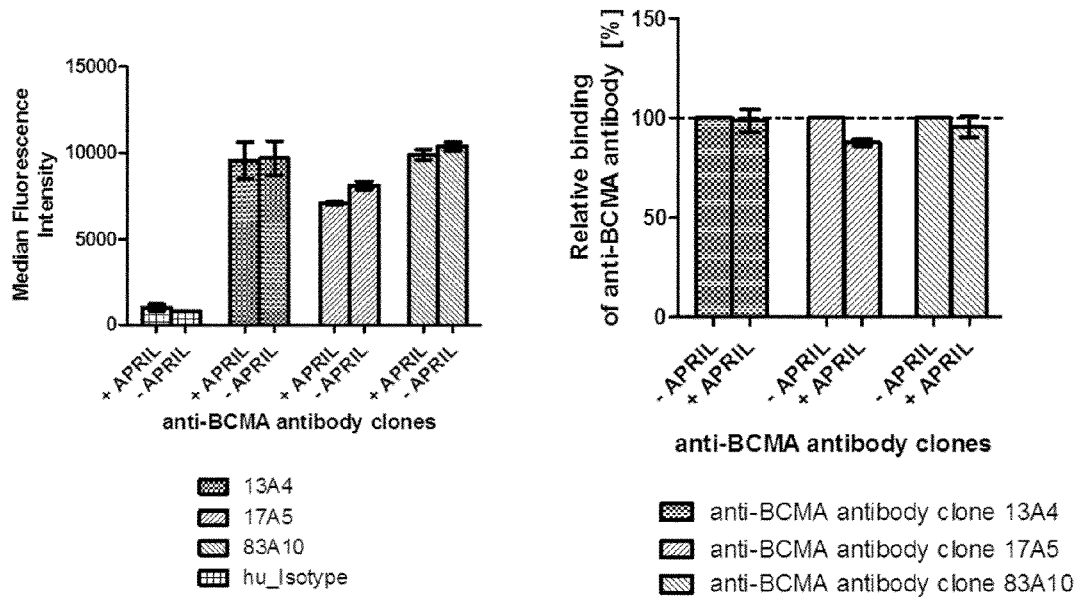
FIG. 7. Binding competition by FACS on RPMI-8226 cells. Competition of anti-BCMA antibodies with Δ-APRIL detected by flow cytometry. The relative median fluorescence intensity of anti-BCMA antibody (Alexa.Fluor 647 signal) used at a concentration of 40 µg/mL for anti-BCMA antibody clones 13A4, 17A5, 83A10 on RPMI-8226 cells detected in absence or presence of Δ-APRIL 1000 ng/mL. The median fluorescence intensity upon binding of anti-BCMA antibodies in absence of Δ-APRIL was set to one; the other signals respective to the anti-BCMA antibody in presence of Δ-APRIL were normalized to it. The detection of anti-BCMA antibodies binding to BCMA-positive RPMI-8226 cells in the presence of Δ-APRIL was measured via anti-human Fc fluorochrome-conjugated antibody (see Example 5c).

| ΔAPRIL | Anti-BCMA antibodies | | |
|---|---|---|---|
| (nM and ng/mL) | 17A5 | 83A10 | 13A4 |
| 50 nM/1200 ng/mL | ↓ 34.5% | ↓ 6.3% | ↓ 13.1% |
| 6.25 nM/140 ng/mL | ↓ 5.6% | no ↓ | ↓ 7.7% | b) Competition of Δ-APRIL with anti-BCMA antibodies detected by flow cytometry. The assessment of the eventual competition between Δ-APRIL and anti-BCMA antibodies was performed on H929 cells by quantifying the binding of Δ-APRIL in presence of increasing concentrations of anti-BCMA antibodies (clones 17A5, 83A10, 13A4). Briefly, cultured cells were harvested, counted and cell viability evaluated using ViCell. Viable cells were adjusted to 1×10$^6$ cells per ml in BSA-containing FACS Stain Buffer (BD Biosciences). 100 μl of this cell suspension are further aliquoted per well into a round-bottom 96-well plate and incubated with 30 μl of the anti-BCMA antibodies or corresponding IgG control for 30 min at 4° c. All anti-BCMA antibodies (and isotype control) were titrated and analyzed at final concentrations of 1, 16 and 40 μg/ml. Cells are then centrifuged (5 min, 350×g), washed with 120 μl/well FACS Stain Buffer (BD Biosciences), resuspended and incubated with 1 ug/ml recombinant mouse Δ-APRIL tagged with hemagglutinin (HA) (R&D Systems Europe, #7907-AP-010) for additional 30 min at 4° C. Cells were then washed once with 120 μl/well FACS Buffer and incubated with FITC-conjugated anti-HA antibody (Sigma Aldrich, #H7411) for 30 min at 4° C. At the end of incubation time, cells were washed with 120 μl/well FACS Buffer, fixed using 100 ul BD Fixation buffer per well (#BD Biosciences, 554655) at 4° C. for 20 min, resuspended in 80 μl FACS buffer and analyzed using BD FACS Fortessa. FIG. 6 shows the relative median fluorescence intensity of Δ-APRIL (FITC signal) detected in function of increasing concentrations of anti-BCMA antibody clones 13A4 on H929 cells. The median fluorescence intensity upon binding of Δ-APRIL in presence of the isotype control was set to one; the other signals were normalized to it.

c) Competition of anti-BCMA antibodies with Δ-APRIL detected by flow cytometry. The assessment of the eventual competition between Δ-APRIL and anti-BCMA antibodies was performed on RPMI cells by quantifying the binding of anti-BCMA antibodies (clones 13A4, 17A5, 83A10) in presence or absence of Δ-APRIL. Briefly, cultured cells were harvested, counted and cell viability evaluated using ViCell. Viable cells were adjusted to 1×10$^6$ cells per ml in BSA-containing FACS Stain Buffer (BD Biosciences). 100 μl of this cell suspension were further aliquoted per well into a round-bottom 96-well plate and incubated with 30 μl of the anti-BCMA antibodies or corresponding IgG control for 20 min at 4° C. All anti-BCMA antibodies and isotype control were analyzed at final concentrations 40 ug/ml. Cells were then centrifuged (5 min, 350×g), washed with 120 μl/well FACS Stain Buffer (BD Biosciences), resuspended and incubated with 1 μg/ml recombinant mouse Δ-APRIL tagged with hemagglutinin (HA) (R&D Systems Europe, #7907-AP-010) for additional 40 min at 4° C. Cells were then washed once with 120 μl/well FACS Buffer and incubated with with Alexa.Fluor 647-conjugated anti-human Fc antibody (Jackson Immuno Research Lab, #109-606-008) for 30 min at 4° C. At the end of incubation time, cells were washed with 120 μl/well FACS Buffer, fixed using 100 ul BD Fixation buffer per well (#BD Biosciences, 554655) at 4° C. for 20 min, resuspended in 80 μl FACS buffer and analyzed using BD FACS Fortessa. FIG. 7 shows the relative median fluorescence intensity of anti-BCMA antibody (Alexa.Fluor 647 signal) clones 13A4, 17A5, 83A10 on RPMI8226 cells detected in absence or presence of 1000 ng/mL of Δ-APRIL. The median fluorescence intensity upon binding of anti-BCMA antibodies in absence of Δ-APRIL was set to one; the other signals respective to the anti-BCMA antibody in presence of Δ-APRIL were normalized to it.

d) Competition of anti-BCMA antibodies with Δ-APRIL after simultaneous incubation detected by flow cytometry. The assessment of the eventual competition between Δ-APRIL and anti-BCMA antibodies was performed on H929 cells (NCI-H929, ATCC® CRL-9068™) by quantifying the binding of anti-BCMA antibodies (clones 13A4, 17A5, 83A10) in presence or absence of Δ-APRIL. Briefly, cultured cells were harvested, counted and cell viability evaluated using ViCell. Viable cells were adjusted to 1×10$^6$ cells per ml in BSA-containing FACS Stain Buffer (BD Biosciences). 100 μl of this cell suspension were further aliquoted per well into a round-bottom 96-well plate and incubated with 30 μl of the anti-BCMA antibodies or corresponding IgG control and 30 μl of Δ-APRIL tagged with hemagglutinin (HA) (R&D Systems Europe, #7907-AP-010) for 40 min at 4° C. All anti-BCMA antibodies and isotype control were analyzed at final concentrations 20 ug/ml; Δ-APRIL at final concentrations 2.5 ug/ml. Cells were then centrifuged (5 min, 350×g) and washed with 120 μl/well FACS Stain Buffer (BD Biosciences). After that, cells were incubated with with Alexa.Fluor 647-conjugated anti-human Fc antibody (Jackson Immuno Research Lab, #109-606-008) and FITC-conjugated anti-HA antibody (Sigma Aldrich, #H7411) for 30 min at 4° C. At the end of incubation time, cells were washed with 120 FACS Buffer, fixed using 100 ul BD Fixation buffer per well (#BD Biosciences, 554655) at 4° C. for 20 min, resuspended in 80 μl FACS buffer and analyzed using BD FACS Cantoll. FIG. 8A shows the mean fluorescence intensity and the relative fluorescence signal of the anti-BCMA antibody clone (Alexa.Fluor 647 signal) and FIG. 8B shows the mean fluorescence intensity and the relative fluorescence signal of Δ-APRIL (FITC signal) and the anti-BCMA antibody clone (Alexa.Fluor 647 signal). Detection of anti-BCMA antibody in presence of Δ-APRIL with FITC-conjugated anti-human Fc antibody was normalized to the signal of anti-BCMA antibody clone in absence Δ-APRIL. Detection of Δ-APRIL in presence of the anti-BCMA antibody clone with Alexa.Fluor 647-conjugated anti-HA antibody was normalized to Δ-APRIL signal in presence of the isotype control. Reduction in binding of anti-BCMA antibodies (20 μg/mL) clones 13A4, 17A5 and 83A10 in presence of Δ-APRIL (2.5 μg/mL) as detected with fluorochrome-conjugated anti-human Fc antibody is summarized in Table 11.

TABLE 11

Reduction in binding of anti-BCMA antibodies
to H929 cells in presence of APRIL

| Anti-BCMA antibody clones | Reduction (↓) in binding of anti-BCMA antibodies in presence of APRIL |
|---|---|
| 13A4 | 25% |
| 17A5 | 20% |
| 83A10 | 10% |

Example 6: Anti-BCMA Antibodies do not Induce NF-κB Activation Alone (Luminescence Assay)

Figure 9:
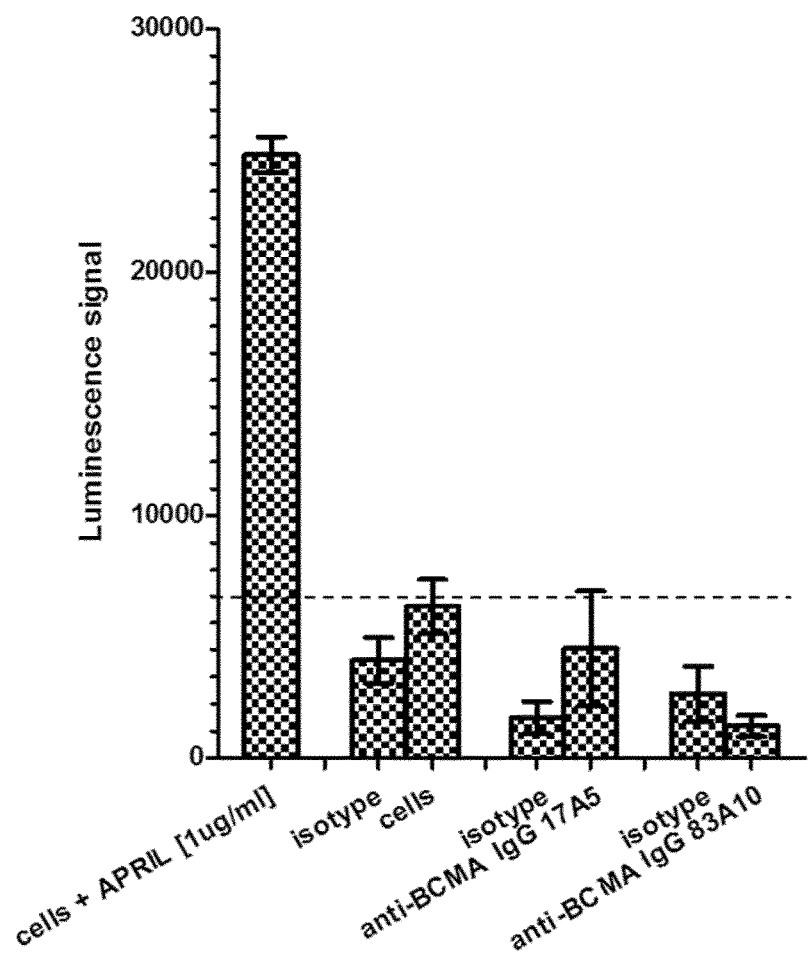
FIG. 9. Effect of anti-BCMA antibodies upon binding to H929 cells on NF-κB activation in absence of APRIL as detected by chemiluminescence ELISA-based assay. Detection of NF-κB activation upon binding of anti-BCMA antibodies (17A5, 83A10) and isotype control antibodies to BCMA-expressing H929 cells was measured using chemiluminescence ELISA-based assay (see Example 6).

It was assessed whether binding of anti-BCMA antibodies to BCMA-expressing H929 cells would induce NF-κB activation, a known signaling pathway downstream of BCMA. Briefly, H929 cells were starved in RPMI1640 with 0.25 FCS for 24 h at 37° C. in cell incubator. At the end of the starvation time, cells were harvested, counted and cell viability evaluated using ViCell. Viable cells were adjusted to $4 \times 10^6$ cells per ml in BSA-containing FACS Stain Buffer (BD Biosciences). 30 µl of this cell suspension were further aliquoted per well into a round-bottom 96-well plate and incubated with 30 µl of the anti-BCMA antibodies at 100 or 350 nM (14 or 50 ug/ml) for 20 min at 37° C. As negative controls, cells were either left untreated or incubated with the corresponding IgG isotype control antibodies 100 nM (14 µg/ml) for 20 min at 37° C. As positive controls, cells were incubated with 1 µg/ml recombinant mouse Δ-APRIL tagged with hemagglutinin (HA) (R&D Systems Europe, #7907-AP-010) for 20 min at 37° C. At the end of incubation time, cells were harvested, washed, lysed, and processed according to the manufacturer's protocol of the Nuclear Extract Kit (Active Motif, #40410). Protein extracts were analyzed for NF-κB activity using a TransAm© NF-κB p65 Chemi Assay kit (Active Motif, #40097) following manufacturer's instructions. Luminescent signal was read using the Spectra Max M5 luminometer (Molecular Devices). As depicted in FIG. 9, a 4.2-fold increase in luminescence signal was reached when H929 cells were exposed to APRIL 1 µg/ml as compared to H929 cells alone. Minimal background luminescence signals were observed with H929 cells alone or in presence of isotype control antibodies and could be explained by the basal NF-κB activation observed in multiple myeloma cell lines as previously reported (Demchenko et al., Blood 2010; 115 (17): 3541-3552). Addition of anti-BCMA antibodies (17A5, 83A10) alone did not further induce NF-κB activation as compared to the respective control isotype antibodies. The results suggest that anti-BCMA antibodies do not induce NF-κB activation upon binding to BCMA-positive cells.

Example 7: Generation of Anti-BCMA/Anti-CD3 T Cell Bispecific Antibodies

Example 7.1: Anti-CD3 Antibodies

The term "CD3ε or CD3" as used herein relates to human CD3ε described under UniProt P07766 (CD3ε_HUMAN). The term "antibody against CD3, anti CD3 antibody" relates to an antibody binding to CD3ε. Preferably the antibody comprises a variable domain VH comprising the heavy chain CDRs of SEQ ID NO: 1, 2 and 3 as respectively heavy chain CDR1, CDR2 and CDR3 and a variable domain VL comprising the light chain CDRs of SEQ ID NO: 4, 5 and 6 as respectively light chain CDR1, CDR2 and CDR3. Preferably the antibody comprises the variable domains of SEQ ID NO:7 (VH) and SEQ ID NO:8 (VL).

Anti-CD3 antibody as described above was used to generate the T cell bispecific antibodies which were used in the following examples.

Example 7.2: Generation of Anti-BCMA/Anti-CD3 T Cell Bispecific Antibodies of Fc-Containing 2+1 Format cDNAs encoding the full heavy and light chains of the corresponding anti-BCMA IgG1 antibodies as well as the anti-CD3 VH and VL cDNAs were used as the starting materials. For each bispecific antibody, four protein chains were involved comprising the heavy and light chains of the corresponding anti-BCMA antibody and the heavy and light chains of the anti-CD3 antibody described above, respectively. In order to minimize the formation of side-products with mispaired heavy chains, for example with two heavy chains of the anti-CD3 antibody, a mutated heterodimeric Fc region is used carrying "knob-into-hole mutations" and an engineered disulphide bond, as described in WO2009080251 and in WO2009080252. In order to minimize the formation of side-products with mispaired light chains, for example with two light chains of the anti-BCMA antibody, a CH1×constant kappa crossover is applied to the heavy and light chains of the anti-CD3 antibody using the methodology described in WO2009080251 and in WO2009080252.

a) An anti-BCMA/anti-CD3 T cell bispecific antibody with a 2+1 format i.e. bispecific (Fab)₂×(Fab) antibody that is bivalent for BCMA and monovalent for CD3 would have advantages on potency, predictability for efficacy and safety because it would preferentially bind to the tumor target BCMA and avoid CD3 antibody sink, thus higher probability for drug exposure focused to the tumor.

Anti-BCMA/anti-CD3 T cell bispecific of the 2+1 format (i.e. bispecific (Fab)₂×(Fab) antibody bivalent for BCMA and monovalent for CD3 with Fc were produced for the human BCMA antibodies previously selected. cDNAs encoding the full Fabs (heavy chain VH and CH1 domains plus light chain VL and CL domains) of the corresponding anti-BCMA IgG1 antibodies as well as the anti-CD3 VH and VL cDNAs, were used as the starting materials. For each bispecific antibody, four protein chains were involved comprising the heavy and light chains of the corresponding anti-BCMA antibody and the heavy and light chains of the anti-CD3 antibody described above, respectively, with Fc regions.

Briefly, each bispecific antibody is produced by simultaneous cotransfection of four mammalian expression vectors encoding, respectively: a) the full light chain cDNA of the corresponding BCMA antibody, b) a fusion cDNA generated by standard molecular biology methods, such as splice-overlap-extension PCR, encoding a fusion protein made of (in N- to C-terminal order) secretory leader sequence, Fab (VH followed by CH1 domains) of the corresponding anti-BCMA antibody described above, a flexible glycine(Gly)-serine(Ser) linker with the sequence Gly-Gly-Gly-Gly-Ser-Gly-Gly-Gly-Gly-Ser, Fab (VH followed by CH1 domains) of the corresponding anti-BCMA antibody described above, a flexible glycine(Gly)-serine(Ser) linker with the sequence Gly-Gly-Gly-Gly-Ser-Gly-Gly-Gly-Gly-Ser, the VH of the anti-CD3 antibody described above and the constant kappa domain of a human light chain cDNA, c) a fusion cDNA generated by standard molecular biology methods, such as splice-overlap-extension PC, encoding a fusion protein made of (in N- to C-terminal order) secretory leader sequence, VL of the anti-CD3 antibody described above, constant CH1 domain of a human IgG1 cDNA. Co-transfection of mammalian cells and antibody production and purification using the methods described above for production of human or humanized IgG1 antibodies, with one modification: for purification of antibodies, the first capture step is not done using ProteinA, but instead is done using an affinity chromatography column packed with a resin binding to human kappa light chain constant region, such as KappaSelect (GE Healthcare Life Sciences). In addition, a disulfide can be included to increase the stability and yields as well as additional residues forming ionic bridges and increasing the heterodimerization yields (EP 1870459A1).

b) For the generation of BCMAxCD3 bispecific antibody vectors, the IgG1 derived bispecific molecules consist at least of two antigen binding moieties capable of binding specifically to two distinct antigenic determinants CD3 and BCMA. The antigen binding moieties were Fab fragments composed of a heavy and a light chain, each comprising a variable and a constant region. At least one of the Fab fragments was a "Crossfab" fragment, wherein the constant domains of the Fab heavy and light chain were exchanged. The exchange of heavy and light chain constant domains within the Fab fragment assures that Fab fragments of different specificity do not have identical domain arrangements and consequently do not interchange light chains. The bispecific molecule design was monovalent for CD3 and bivalent for BCMA where one Fab fragment is fused to the N-terminus of the inner CrossFab (2+1). The bispecific molecule contained an Fc part in order to have a longer half-life. A schematic representation of the constructs is given in FIG. 2; the sequences of the preferred constructs are shown in SEQ ID NOs 41, and 43 to 52. The molecules were produced by co-transfecting HEK293 EBNA cells growing in suspension with the mammalian expression vectors using polymer-based transfection. For preparation of 2+1 CrossFab-IgG constructs, cells were transfected with the corresponding expression vectors in a 1:2:1:1 ratio ("vector Fc(knob)":"vector light chain":"vector light chain Cross-Fab":"vector heavy chain-CrossFab").

Example 7.3: Generation of Anti-BCMA/Anti-CD3 T Cell Bispecific Antibodies for Comparison The generation of APRIL- and BAFF-blocking J6M0-TCBcv and BCMA50-sc(Fv)$_2$ (also known as BCMA50-BiTE®) anti-BCMA/anti-CD3 T cell bispecific antibodies and the amino acid sequences used were according to WO2012163805 and WO2013072406/WO2013072415, respectively.

Example 8: Production and Purification of Anti-BCMA/Anti-CD3 Fc-Containing (2+1) T Cell Bispecific Antibodies with or without Charge Variants For the production of the bispecific antibodies, bispecific antibodies were expressed by transient co-transfection of the respective mammalian expression vectors in HEK293-EBNA cells, which were cultivated in suspension, using polymer-based transfection. One day prior to transfection the HEK293-EBNA cells were seeded at 1.5 Mio viable cells/mL in Ex-Cell medium, supplemented with 6 mM of L-Glutamine. For every mL of final production volume 2.0 Mio viable cells were centrifuged (5 minutes at 210×g). The supernatant was aspirated and the cells resuspended in 100 µL of CD CHO medium. The DNA for every mL of final production volume was prepared by mixing 1 µg of DNA (Ratio heavy chain:modified heavy chain:light chain:modified light chain=1:1:2:1) in 100 µL of CD CHO medium. After addition of 0.27 µL of polymer-based solution (1 mg/mL) the mixture was vortexed for 15 seconds and left at room temperature for 10 minutes. After 10 minutes, the resuspended cells and DNA/polymer-based solution mixture were put together and then transferred into an appropriate container which was placed in a shaking device (37° C., 5% $CO_2$). After a 3 hours incubation time 800 µL of Ex-Cell Medium, supplemented with 6 mM L-Glutamine, 1.25 mM valproic acid and 12.5% Pepsoy (50 g/L), was added for every mL of final Production volume. After 24 hours, 70 µL of Feed solution was added for every mL of final production volume. After 7 days or when the cell viability was equal or lower than 70%, the cells were separated from the supernatant by centrifugation and sterile filtration. The antibodies were purified by an affinity step and one or two polishing steps, being cation exchange chromatography and size exclusion chromatography. When required, an additional polishing step was used.

For the affinity step the supernatant was loaded on a protein A column (HiTrap Protein A FF, 5 mL, GE Healthcare) equilibrated with 6 CV 20 mM sodium phosphate, 20 mM sodium citrate, pH 7.5. After a washing step with the same buffer the antibody was eluted from the column by step elution with 20 mM sodium phosphate, 100 mM sodium chloride, 100 mM Glycine, pH 3.0. The fractions with the desired antibody were immediately neutralized by 0.5 M Sodium Phosphate, pH 8.0 (1:10), pooled and concentrated by centrifugation. The concentrate was sterile filtered and processed further by cation exchange chromatography and/or size exclusion chromatography.

For the cation exchange chromatography step the concentrated protein was diluted 1:10 with the elution buffer used for the affinity step and loaded onto a cation exchange colume (Poros 50 HS, Applied Biosystems). After two washing steps with the equilibration buffer and a washing buffer resp. 20 mM sodium phosphate, 20 mM sodium citrate, 20 mM TRIS, pH 5.0 and 20 mM sodium phosphate, 20 mM sodium citrate, 20 mM TRIS, 100 mM sodium chloride pH 5.0 the protein was eluted with a gradient using 20 mM sodium phosphate, 20 mM sodium citrate, 20 mM TRIS, 100 mM sodium chloride pH 8.5. The fractions containing the desired antibody were pooled, concentrated by centrifugation, sterile filtered and processed further a size exclusion step.

For the size exclusion step the concentrated protein was injected in a XK16/60 HiLoad Superdex 200 column (GE Healthcare), and 20 mM Histidine, 140 mM Sodium Chloride, pH 6.0 with or without Tween20 as formulation buffer. The fractions containing the monomers were pooled, concentrated by centrifugation and sterile filtered into a sterile vial.

Determination of the antibody concentration was done by measurement of the absorbance at 280 nm, using the theoretical value of the absorbance of a 0.1% solution of the antibody. This value was based on the amino acid sequence and calculated by GPMAW software (Lighthouse data).

Purity and monomer content of the final protein preparation was determined by CE-SDS (Caliper LabChip GXII system (Caliper Life Sciences)) resp. HPLC (TSKgel G3000 SW XL analytical size exclusion column (Tosoh)) in a 25 mM potassium phosphate, 125 mM Sodium chloride, 200 mM L-arginine monohydrochloride, 0.02% (w/v) Sodium azide, pH 6.7 buffer.

To verify the molecular weight of the final protein preparations and confirm the homogeneous preparation of the molecules final protein solution, liquid chromatography-mass spectometry (LC-MS) was used. A deglycosylation step was first performed. To remove heterogeneity introduced by carbohydrates, the constructs were treated with PNGaseF (ProZyme). Therefore, the pH of the protein solution was adjusted to pH7.0 by adding 2 μl 2 M Tris to 20 μg protein with a concentration of 0.5 mg/ml. 0.8 μg PNGaseF was added and incubated for 12 h at 37° C. The LC-MS online detection was then performed. LC-MS method was performed on an Agilent HPLC 1200 coupled to a TOF 6441 mass spectrometer (Agilent). The chromatographic separation was performed on a Macherey Nagel Polysterene column; RP1000-8 (8 μm particle size, 4.6×250 mm; cat. No. 719510). Eluent A was 5% acetonitrile and 0.05% (v/v) formic acid in water, eluent B was 95% acetonitrile, 5% water and 0.05% formic acid. The flow rate was 1 ml/min, the separation was performed at 40° C. and 6 μg (15 μl) of a protein sample obtained with a treatment as described before.

| Time (min.) | % B |
|---|---|
| 0.5 | 15 |
| 10 | 60 |
| 12.5 | 100 |
| 14.5 | 100 |
| 14.6 | 15 |
| 16 | 15 |
| 16.1 | 100 |

During the first 4 minutes, the eluate was directed into the waste to protect the mass spectrometer from salt contamination. The ESI-source was running with a drying gas flow of 12 l/min, a temperature of 350° C. and a nebulizer pressure of 60 psi. The MS spectra were acquired using a fragmentor voltage of 380 V and a mass range 700 to 3200 m/z in positive ion mode using. MS data were acquired by the instrument software from 4 to 17 minutes.

Figure 10:
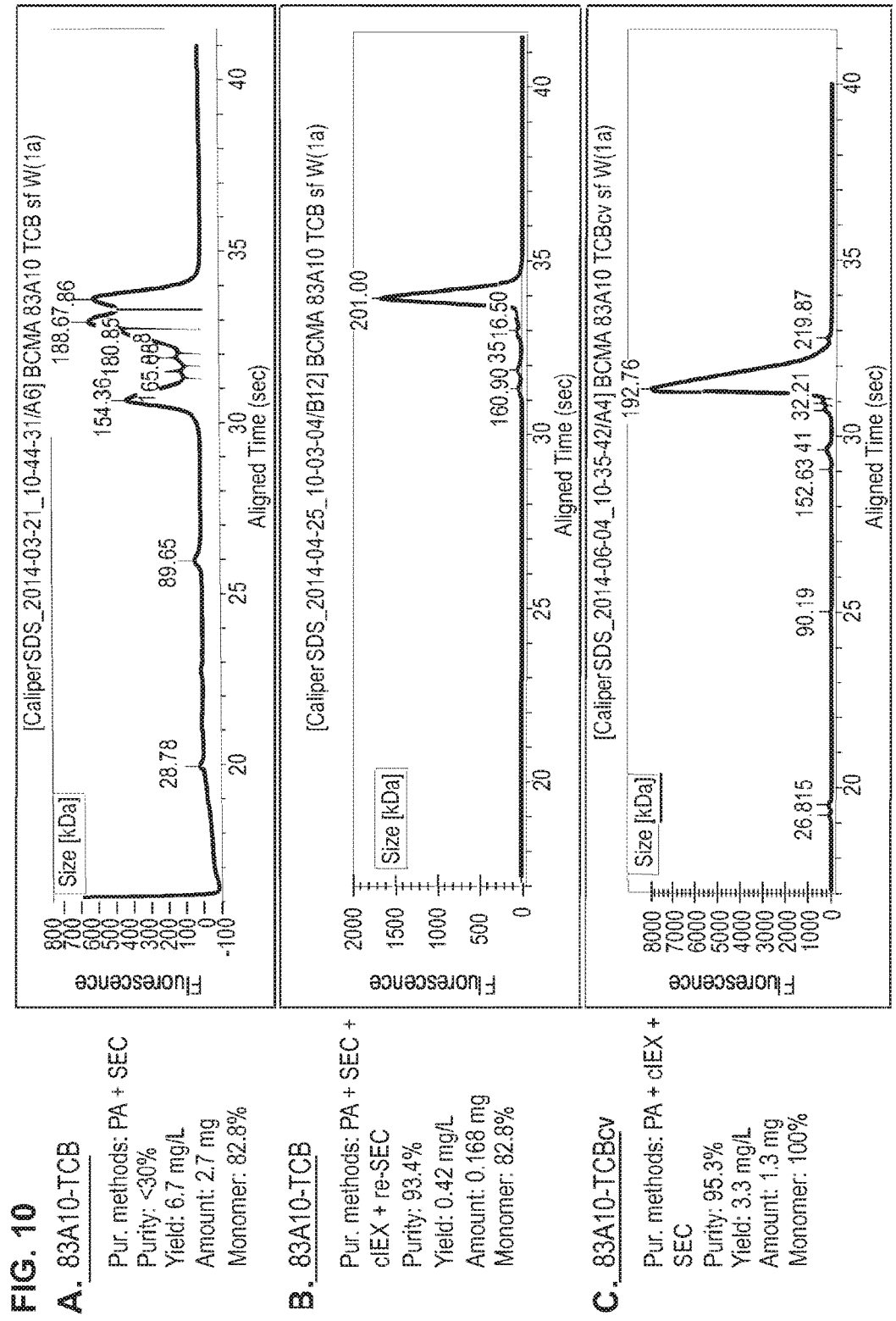
FIG. 10. Production and purification of 83A10-TCB without charge variant vs. 83A10-TCBcv with charge variant. CE-SDS (non-reduced) graphs of the final protein preparations after different methods of purification for 83A10-TCB and 83A10-TCBcv antibodies. Protein A (PA) affinity chromatography and size exclusion chromatographic (SEC) purification steps applied to 83A10-TCB antibody (A). (B) Additional purification steps: cation exchange chromatography (cIEX) and a final size exclusion chromatographic (re-SEC) steps applied to the final protein preparations in (A). (C) 83A10-TCBcv antibody after PA+cIEX+SEC purification steps. 83A10-TCB and 83A10-TCBcv molecules are both of molecular format as described in FIG. 2a (see Example 8).

FIG. 10 depicts the CE-SDS (non-reduced) graphs of the final protein preparations after different methods of purification for 83A10-TCB and 83A10-TCBcv antibodies. Protein A (PA) affinity chromatography and size exclusion chromatographic (SEC) purification steps applied to 83A10-TCB antibody resulted in a purity of <30% and 82.8% of monomer content (A). When additional purifications steps including cation exchange chromatography (cIEX) and a final size exclusion chromatographic (re-SEC) steps were applied to the final protein preparations in (A), the purity was increased to 93.4% but the monomer content remained the same and the yield was significantly reduced to 0.42 mg/L. However, when specific charge modifications were applied to 83A10 anti-BCMA Fab CL-CH1, namely 83A10-TCBcv antibody, a superior production/purification profile of the TCB molecule, as demonstrated by a purity of 95.3%, monomer content of 100% and yield of up to 3.3 mg/L, could already be observed even when PA+cIEX+SEC purification steps were applied (C) in comparison to (B) with a production/purification profile showing a 7.9-fold lower yield and 17.2% lower monomer content despite including an additional re-SEC purification step.

Figure 11:
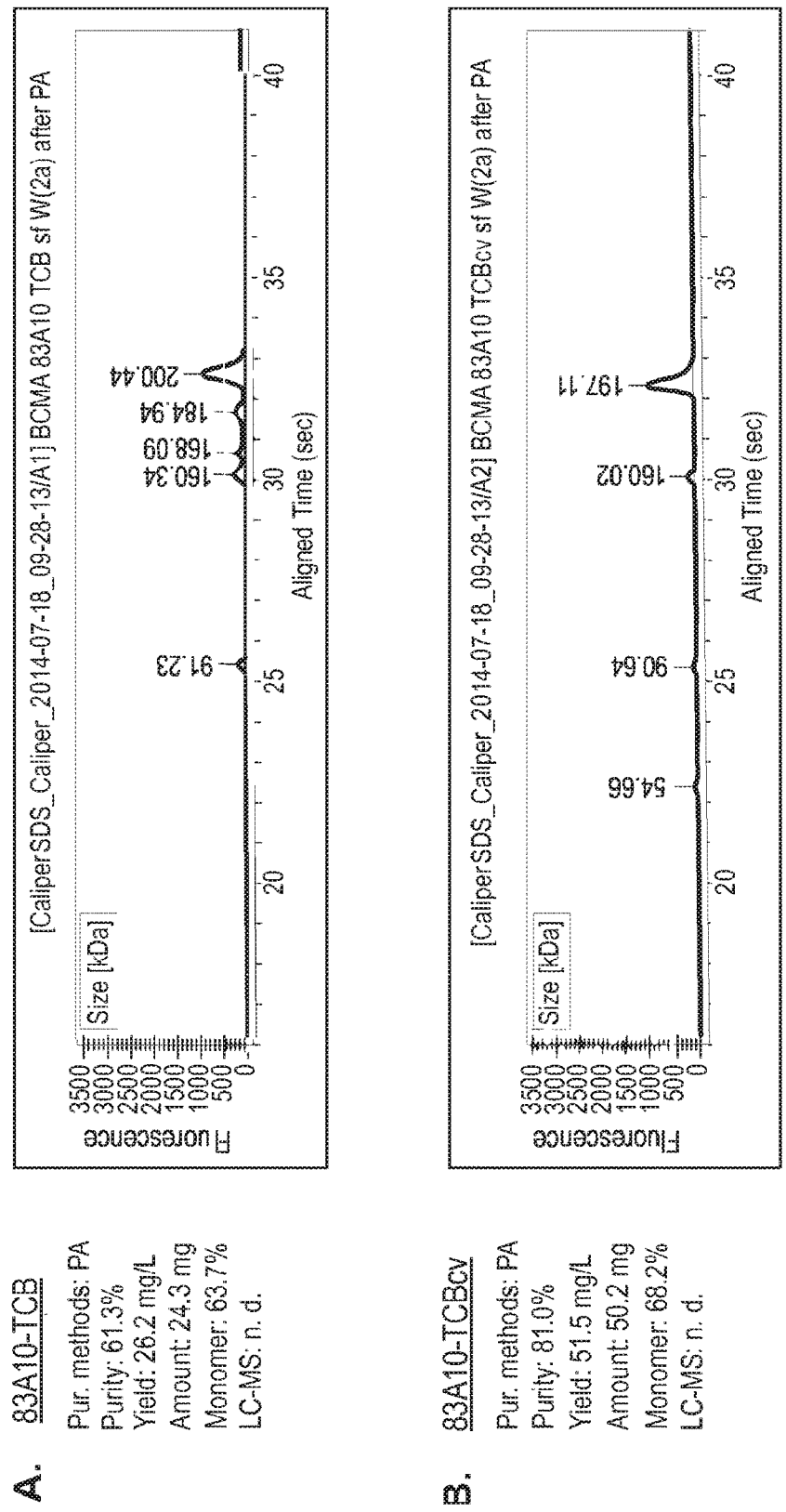
FIG. 11. Head-to-head comparison study: Production of 83A10-TCB without charge vs. 83A10-TCBcv with charge variant. Properties (e.g. purity, yield, monomer content) of 83A10-TCB and 83A10-TCBcv antibodies were measured side-by-side and compared after each purification steps 1) PA affinity chromatography only (A, B), 2) PA affinity chromatography then SEC (C, D) and 3) PA affinity chromatography then SEC then cIEX and re-SEC (E, F). CE-SDS (non-reduced) graphs of the final protein solutions after the respective methods of purification for 83A10-TCB and 83A10-TCBcv antibodies. (A) PA affinity chromatography purification step applied to 83A10-TCB antibody. (B) PA affinity chromatography purification step applied to 83A10-TCBcv antibody. (C) PA affinity chromatography+SEC purification steps applied to 83A10-TCB antibody. (D) PA affinity chromatography+SEC purification steps applied to 83A10-TCBcv antibody. (E) PA affinity chromatography+/–SEC+cIEX+SEC purification steps applied to 83A10-TCB antibody. (F) PA affinity chromatography+/–SEC+cIEX+SEC purification steps applied to 83A10-TCBcv antibody. Purity, yield, monomer content were measured. Percentage of correct molecule detected by liquid chromatography—mass spectrometry (LC-MS) (see Example 8).
Figure 11:
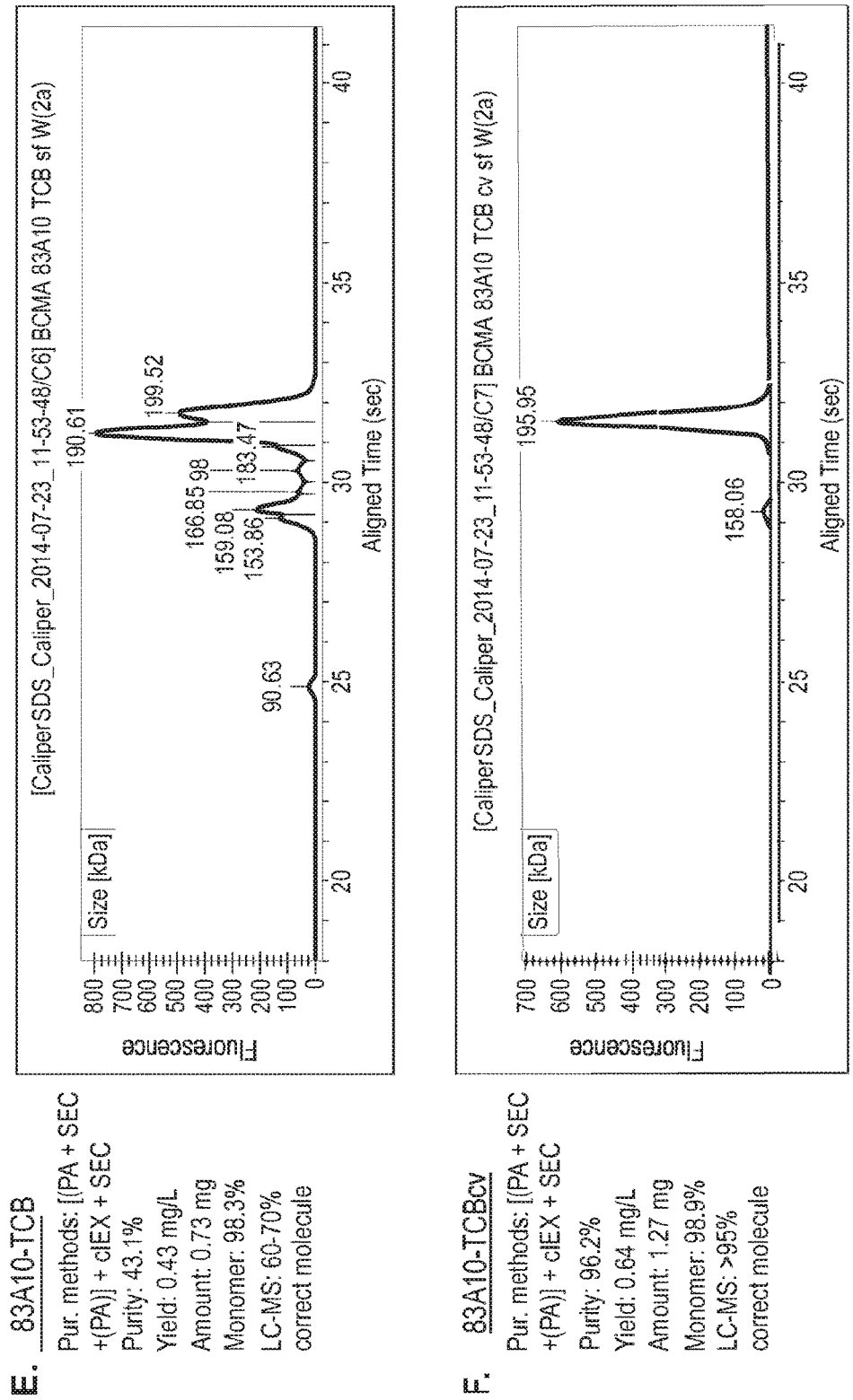

A head-to-head production run to compare the production/purification profile of 83A10-TCB vs. 83A10-TCBcv antibodies was then conducted to further evaluate the advantages of the CL-CH1 charge modifications applied to the antibodies. 83A10-TCB and 83A10-TCBcv molecules are both of molecular format as described in FIG. 2a. As depicted in FIG. 11, properties of 83A10-TCB and 83A10-TCBcv antibodies were measured side-by-side and compared after each purification steps 1) PA affinity chromatography only (A, B), 2) PA affinity chromatography then SEC (C, D) and 3) PA affinity chromatography then SEC then cIEX and re-SEC (E, F). The CE-SDS (non-reduced) graphs of the final protein solutions after the respective methods of purification for 83A10-TCB and 83A10-TCBcv antibodies are demonstrated in FIG. 11. As shown in FIGS. 11A and 11B, improvements with applying the charge variants to the TCB antibody were already observed after purification by PA affinity chromatography only. In this head-to-head study, PA affinity chromatography purification step applied to 83A10-TCB antibody resulted in a purity of 61.3%, a yield of 26.2 mg/L and 63.7% of monomer content (11A). In comparison, when 83A10-TCBcv antibody was purified by PA affinity chromatography all the properties were improved with a better purity of 81.0%, a better yield of 51.5 mg/L and 68.2% of monomer content (11B). When an additional SEC purification step was applied to the final protein preparations as seen in FIGS. 12A and 12B, 83A10-TCB gained a purity of 69.5%, a yield of 14.1 mg/L and 74.7% of monomer content (C) as compared to 83A10-TCBcv with improved purity and monomer content of up to 91.0% and 83.9% respectively, and a yield of 10.3 mg/L (D). Even though the yield was slightly less (i.e. 27% less) for 83A10-TCBcv than for 83A10-TCB in this particular experiment, the percentage of correct molecule was much better for 83A10-TCBcv than for 83A10-TCB, respectively 90% vs. 40-60%, as measured by LC-MS. In the third head-to-head comparison, 83A10-TCB and 83A10-TCBcv final protein preparations from FIGS. 11C and 11D were pooled with approximately 1 L (equivolume) of respective final protein preparations from another purification batch (same production) following PA affinity chromatography purification step only. The pooled protein preparations were then being further purified by cIEX and SEC purification methods. As depicted in FIGS. 11E and 11F, improvement of the production/purification profile of the TCB antibody with the charge variants was consistently observed when compared to TCB antibody without charge variant. After several steps of purification methods (i.e. PA+/−SEC+cIEX+SEC) were used to purify 83A10-TCB antibody, only 43.1% purity was reached and 98.3% of monomer content could be achieved but to the detriment of the yield which was reduced to 0.43 mg/L. The percentage of correct molecule as measured by LC-MS was still poor with 60-70%. At the end, the quality of the final protein preparation was not acceptable for in vitro use. In stark contrast, when the same multiple purification steps with the same chronology were applied to 83A10-TCBcv antibody, 96.2% purity and 98.9% of monomer content were reached as well as 95% of correct molecule as measured by LC-MS. The yield however was also greatly reduced to 0.64 mg/L after cIEX purification step. The results show that better purity, higher monomer content, higher percentage of correct molecule and better yield can be achieved with 83A10-TCBcv antibody only after two standard purification steps i.e. PA affinity chromatography and SEC (FIG. 11D) while such properties could not be achieved with 83A10-TCB even when additional purification steps were applied (FIG. 11E).

Table 12 summarizes the properties of 83A10-TCB as compared to 83A10-TCVcv following PA purification step.

Table 13 summarizes the properties of 83A10-TCB as compared to 83A10-TCVcv following PA and SEC purification steps. Table 14 summarizes the properties of 83A10-TCB as compared to 83A10-TCVcv following PA and SEC plus PA alone then cIEX and re-SEC purification steps. For Tables 12 to 14, the values in bold highlight the superior property as compared between 83A10-TCB vs. 83A10-TCVcv. With one exception (i.e. yield respectively amount, see Table 13) which may not be representative, all the production/purification parameters and values resulting from the 3 head-to-head comparison experiments were superior for 83A10-TCBcv as compared to 83A10-TCB. The overall results clearly demonstrate that advantages in production/purification features could be achieved with applying CL-CH1 charge modifications to TCB antibodies and that only two purification steps (i.e PA affinity chromatography and SEC) were required to achieve already high quality protein preparations with very good developability properties.

TABLE 12

Production/purification profile of anti-BCMA/anti-CD3 T cell bispecific antibodies following protein A affinity chromatography purification step

|  | 83A10-TCB | 83A10-TCBcv |
|---|---|---|
| Purity (%) | 61.3 | 81.0 |
| Yield (mg/L) | 26.2 | 51.5 |
| Amount (mg) | 24.3 | 50.2 |
| Monomer (%) | 63.7 | 68.2 |
| Correct molecule by LC-MS (%) | n.d. | n.d |

TABLE 13

Production/purification profile of anti-BCMA/anti-CD3 T cell bispecific antibodies following protein A affinity chromatography and size exclusion chromatography purification steps

|  | 83A10-TCB | 83A10-TCBcv |
|---|---|---|
| Purity (%) | 69.5 | 91.0 |
| Yield (mg/L) | 14.1 | 10.3 |
| Amount (mg) | 13.1 | 10.0 |
| Monomer (%) | 74.7 | 83.9 |
| Correct molecule by LC-MS (%) | 40-60 | 90 |

TABLE 14

Production/purification profile of anti-BCMA/anti-CD3 T cell bispecific antibodies following 1.a) protein A affinity chromatography and size exclusion chromatography and 1.b) protein A affinity chromatography only pooled together then 2) cation exchange chromatography and 3) final size exclusion chromatography purification steps

|  | 83A10-TCB | 83A10-TCBcv |
|---|---|---|
| Purity (%) | 43.1 | 96.2 |
| Yield (mg/L) | 0.43 | 0.64 |
| Amount (mg) | 0.73 | 1.27 |
| Monomer (%) | 98.3 | 98.9 |
| Correct molecule by LC-MS (%) | 60-70% | >95% |

Example 9: Stability (Aggregation/Fragmentation) of Anti-BCMA/Anti-CD3 TCB Antibodies in Formulation Buffer To assess anti-BCMA/anti-CD3 TCBcv antibodies and compare with BCMA×CD3 (scFV)$_2$ bispecific antibody format for their stability with regard to aggregation/fragmentation, samples are incubated for 10 days, preferably 2 to 4 weeks at 37-40° C. in standard formulation buffer (e.g. 20 mM citrate, 180 mM sucrose, 20 mM arginine, 0.02% polysorbate 20 or e.g. 20 mM histidine, 140 mM NaCl, 0.01% Tween20, pH 6.0) at a protein concentration of approximately 1 mg/mL. A respective control sample is stored for 2-4 weeks at −80° C.

Size exclusion chromatography for the quantification of aggregates and low-molecular weight (LMW) species are performed by HPLC. An amount of 25 µg of protein is applied to a Tosoh TSKgel G3000SWXL column in 5 mM K2HPO4, 125 mM NaCl, 200 mM L-Arginine Monohydrochloride, 0.02% (w/v) NaN3, pH 6.7 on an Agilent 1200 HPLC system (Agilent). The eluted protein is quantified by UV absorbance at 280 nm.

Example 10: Binding of Anti-BCMA/Anti-CD3 T-Cell Bispecific Antibodies to Recombinant Cells Expressing Human, Cynomolgus Monkey or Mouse BCMA on their Surface (Flow Cytometry)

a) Binding of anti-BCMA/anti-CD3 TCB antibodies were demonstrated on HEK cells transiently expressing mouse BCMA (muBCMA-HEK) or cynomolgus BCMA (cyBCMA-HEK) by flow cytometry. Briefly, BCMA-expressing HEK cells were harvested, counted and cell viability was evaluated using ViCell. Viable cells were then adjusted to $2\times10^6$ cells per ml in BSA-containing FACS Stain Buffer (BD Biosciences). 100 µl of this cell suspension were further aliquoted per well into a round-bottom 96-well plate and incubated with 30 µl of the anti-BCMA/anti-CD3 TCB antibodies or corresponding TCB control antibody for 30 min at 4° c. All anti-BCMA/anti-CD3 TCB antibodies and TCB control antibody were titrated and analyzed in final concentration range between 2-300 nM. Cells were then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 µl BD Fixation buffer per well (#BD Biosciences, 554655) at 4° C. for 20 min, resuspended in 120 µl FACS buffer and analyzed using BD FACS CantoII. As depicted in FIG. 12, 83A10-TCB binds to HEK cells transiently expressing mouse BCMA (A) and cynomolgus monkey BCMA (B) in a specific and concentration-dependent manner as measured by an increased in median fluorescence intensity. As a negative control TCB antibody, DP47-TCB did not bind to muBCMA-HEK cells and cyBCMA-HEK cells. The same binding properties as observed with 83A10-TCB are expected for 83A10-TCBcv as the VL and VH CDRs are identical between the two molecules (see Example 19).

b) Binding of anti-BCMA/anti-CD3 TCB antibodies is also performed on CHO cells stably expressing mouse BCMA, cynomolgus BCMA or BCMA by flow cytometry. Briefly, BCMA-expressing HEK cells are harvested, counted and cell viability is evaluated using ViCell. Viable cells are then adjusted to $2\times10^6$ cells per ml in BSA-containing FACS Stain Buffer (BD Biosciences). 100 µl of this cell suspension are further aliquoted per well into a round-bottom 96-well plate and incubated with 30 µl of the anti-BCMA/anti-CD3 TCB antibodies or corresponding TCB control antibody for 30 min at 4° c. All anti-BCMA/anti-CD3 TCB antibodies and TCB control antibody are titrated and analyzed in final concentration range between 2-300 nM. Cells are then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells are then washed twice with Stain Buffer (BD Biosciences), fixed using 100 µl BD Fixation buffer per well (#BD Biosciences, 554655) at 4° C. for 20 min, resuspended in 120 µl FACS buffer and analyzed using BD FACS Cantoll.

c) Binding of anti-BCMA/anti-CD3 T-cell bispecific antibodies to recombinant cells stably expressing human BCMA or cynomolgus monkey BCMA on their surface as measured by flow cytometry. Binding of anti-BCMA/anti-CD3 TCB antibodies were demonstrated on HEK293T cell line stably expressing human BCMA (huBCMA-HEK293T) or cynomolgus BCMA (cynoBCMA-HEK293T) by flow cytometry. The cell surface expression level of human BCMA and cynomolgus BCMA were similar as confirmed by intracellular FLAG expression. Briefly, BCMA-expressing HEK293T cells were harvested, counted and cell viability was evaluated using ViCell. Viable cells were then adjusted to $2 \times 10^6$ cells per ml in BSA-containing FACS Stain Buffer (BD Biosciences). 100 µl of this cell suspension were further aliquoted per well into a round-bottom 96-well plate and incubated with 30 µl of the anti-BCMA/anti-CD3 TCB antibodies or corresponding TCB control antibody for 30 min at 4° c. All anti-BCMA/anti-CD3 TCB antibodies and TCB control antibody were titrated and analyzed in final concentration range between 2-300 nM. Cells were then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 µl BD Fixation buffer per well (#BD Biosciences, 554655) at 4° C. for 20 min, resuspended in 120 µl FACS buffer and analyzed using BD FACS Cantoll. EC50 values of binding of 83A10-TCBcv to huBCMA-HEK293T cells and cynoBCMA-HEK293T cells was measured (Table 14A).

TABLE 14A

Binding of anti-BCMA/anti-CD3 T cell bispecific antibodies to HEK293T cells expressing same levels of human BCMA or cynomolgus BCMA on the surface.

| BCMA-TCB antibodies | Cell Binding EC50 (nM) | |
|---|---|---|
| | huBCMA-HEK293T | cynoBCMA-HEK293T |
| 83A10-TCBcv | 15.6 | 7.8 |

Example 11: Binding of Anti-BCMA/Anti-CD3 T-Cell Bispecific Antibodies to BCMA-Positive Multiple Myeloma Cell Lines (Flow Cytometry)

Figure 13:
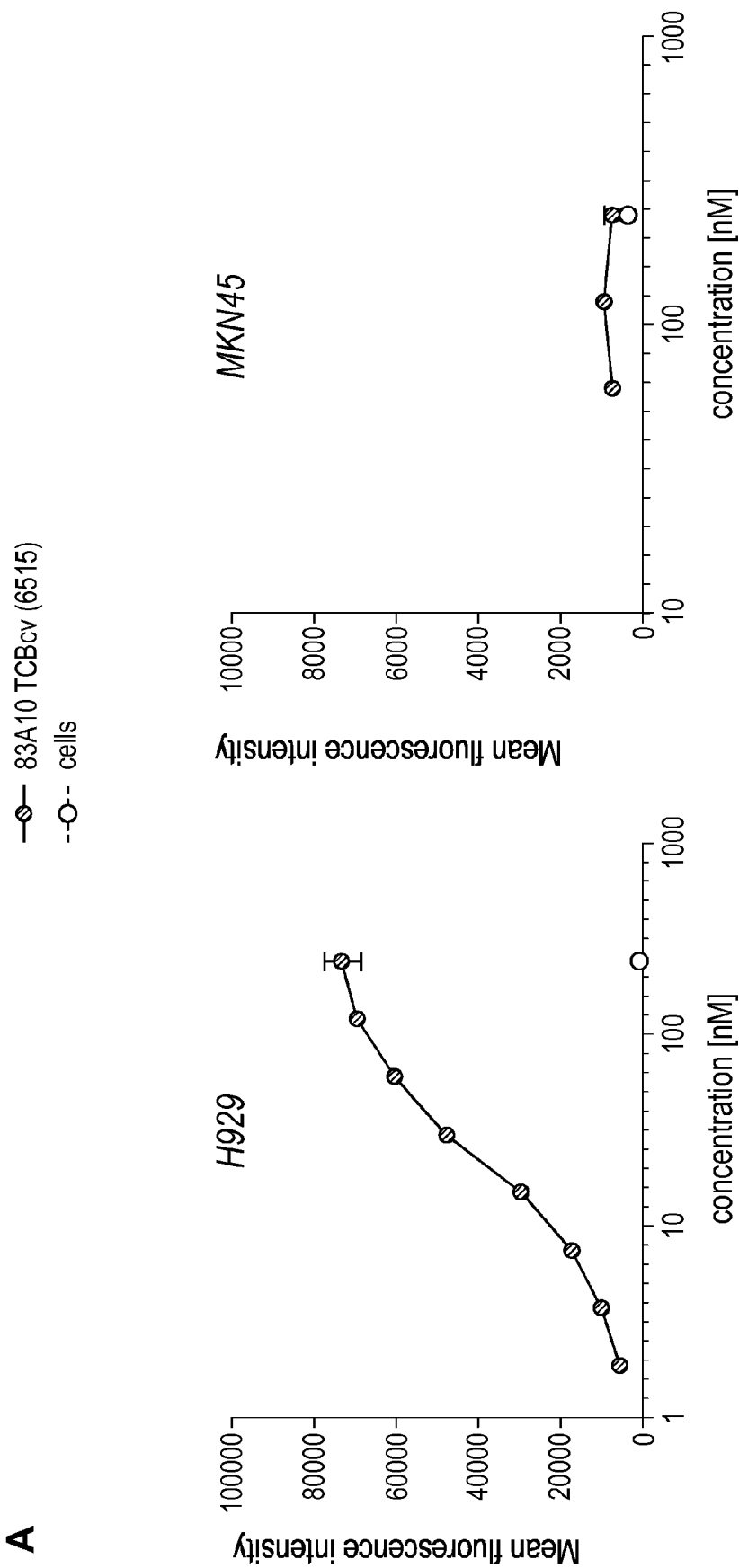
FIG. 13. Binding of anti-BCMA/anti-CD3-TCBcv antibodies on BCMA-positive H929 cells by flow cytometry. The mean fluorescence intensity of anti-BCMA/anti-CD3 TCB antibodies were plotted in function of antibody concentrations; (A) 83A10-TCBcv on H929 cells and MKN45 cells, (B) 17A5-TCBcv on H929 cells and MKN45 cells (see Example 11).
Figure 13:
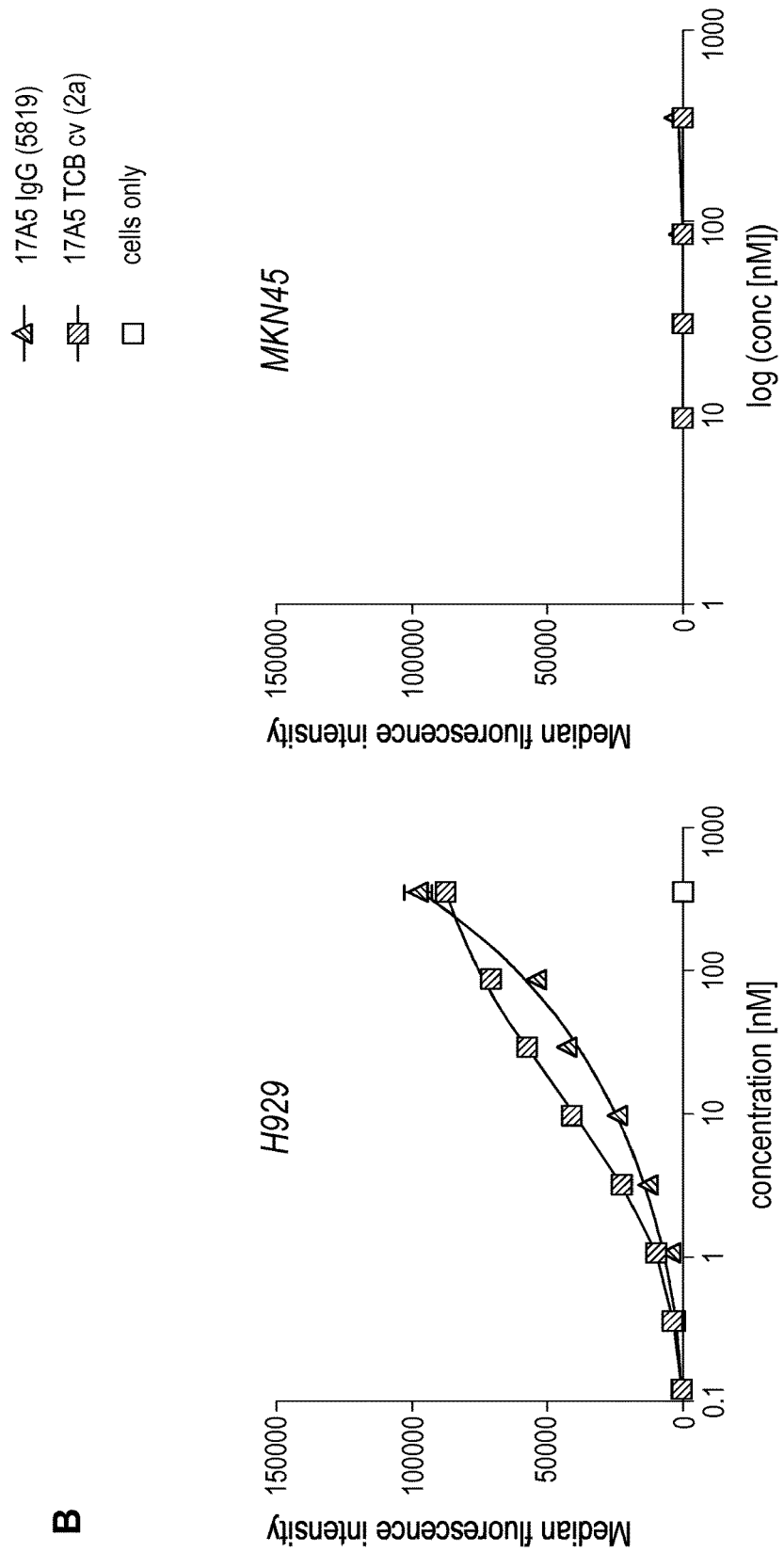

Anti-BCMA/anti-CD3 TCB antibodies (13A4-TCBcv, 17A5-TCBcv, 83A10-TCBcv) were analyzed by flow cytometry for binding to human BCMA on BCMA-expressing H929 and L363 cells. MKN45 (human gastric adenocarcinoma cell line that does not express BCMA) was used as negative control. Briefly, cultured cells are harvested, counted and cell viability was evaluated using ViCell. Viable cells are then adjusted to $2 \times 10^6$ cells per ml in BSA-containing FACS Stain Buffer (BD Biosciences). 100 µl of this cell suspension were further aliquoted per well into a round-bottom 96-well plate and incubated with 30 µl of the anti-BCMA antibodies or corresponding IgG control for 30 min at 4° c. All Anti-BCMA/anti-CD3 TCB antibodies (and TCB controls) were titrated and analyzed in final concentration range between 1-300 nM. Cells were then centrifuged (5 min, 350×g), washed with 120 µl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 ul BD Fixation buffer per well (#BD Biosciences, 554655) at 4° C. for 20 min, resuspended in 120 µl FACS buffer and analyzed using BD FACS CantoII. As depicted in FIG. 13, the mean fluorescence intensity of anti-BCMA/anti-CD3 TCB antibodies were plotted in function of antibody concentrations; (A) 83A10-TCBcv on H929 cells and MKN45 cells, (B) 17A5-TCBcv on H929 cells and MKN45 cells, (C) 13A4-TCBcv on H929 cells and MKN45 cells. When applicable, EC50 were calculated using Prism GraphPad (LaJolla, Calif., USA) and EC50 values denoting the antibody concentration required to reach 50% of the maximal binding for the binding of anti-BCMA/anti-CD3 TCB antibodies to H929 cells are summarized in Table 15. Table 15A shows the EC50 values for binding of 83A10-TCBcv to L363 MM cells.

TABLE 15

EC50 values for binding of anti-BCMA/anti-CD3 TCB antibodies to H929 cells

| Anti-BCMA/anti-CD3 TCB molecules | EC50 (nM) | EC50 (µg/ml) |
|---|---|---|
| 83A10-TCB (Experiment 1) | 9.8 | 1.9 |
| 83A10-TCBcv (Experiment 1) | 14.5 | 2.4 |
| 83A10-TCB (Experiment 2) | 16.9 | 3.25 |
| 83A10-TCBcv (Experiment 2) | 14.5 | 2.4 |
| 83A10-TCBcv (Experiment 3) | 12.0 | 1.725 |
| 17A5-TCBcv | no EC50 value | no EC50 value |

TABLE 15A

EC50 values for binding of anti-BCMA/anti-CD3 T-cell bispecific antibodies to L363 multiple myeloma cells

| Estimated EC50 | 83A10-TCBcv |
|---|---|
| nM | 17.4 |
| µg/ml | 2.507 |

Example 12: Binding of Anti-BCMA/Anti-CD3 T-Cell Bispecific Antibodies to CD3-Positive Jurkat T Cell Line (Flow Cytometry)

Figure 14:
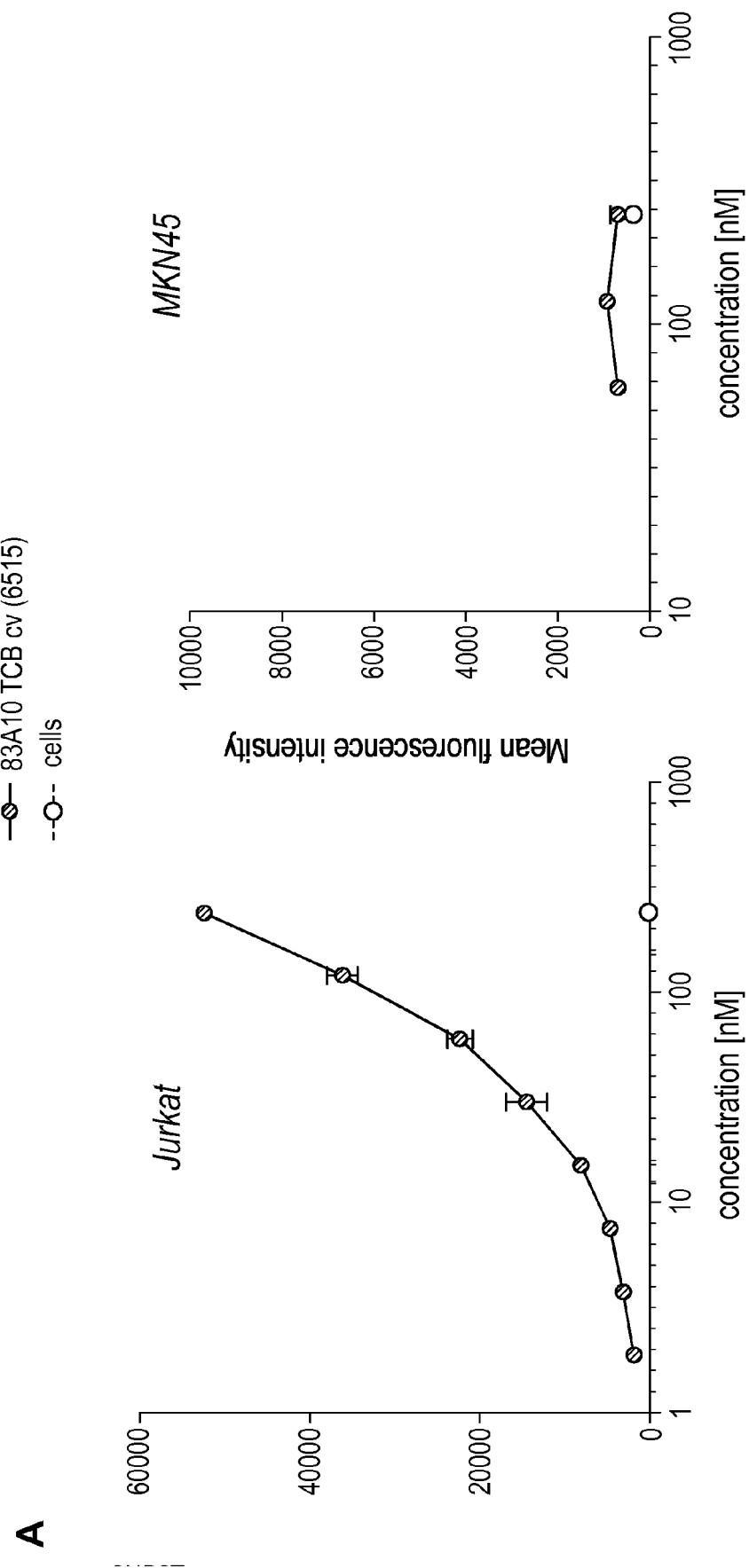
FIG. 14. Binding of anti-BCMA/anti-CD3-TCBcv antibodies on CD3-positive Jurkat T cells as measured by flow cytometry. Median fluorescence intensity for anti-BCMA/anti-CD3 TCB antibodies (83A10-TCBcv (A); 17A5-TCBcv (B)) binding to Jurkat T cells and plotted in function of antibody concentration. Non-binding to BCMA-negative and CD3-negative MKN45 cells (see Example 12).
Figure 14:
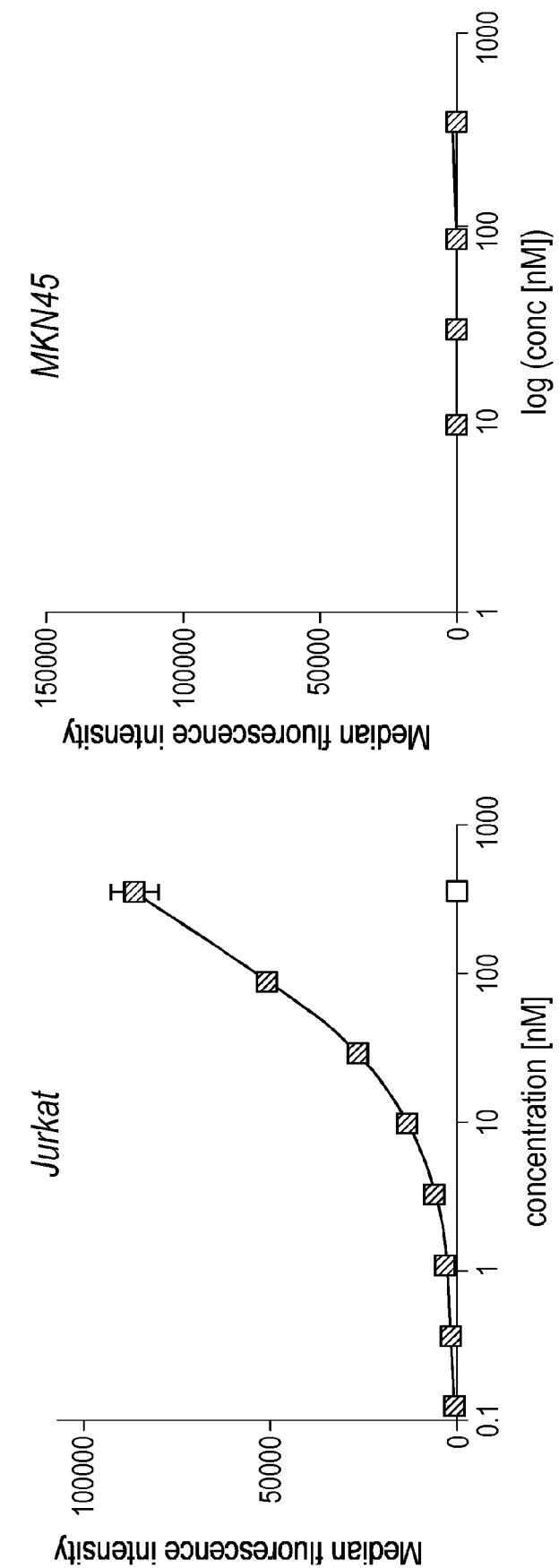

Anti-BCMA/anti-CD3 TCB antibodies (13A4-TCBcv, 17A5-TCBcv, 83A10-TCBcv) were also analyzed by flow cytometry for their binding properties to human CD3 expressed on human leukemic T cells Jurkat (ATCC TIB- 152). Jurkat T cells were cultured in RPMI supplemented with 10% heat-inactivated FCS. Briefly, cultured cells were harvested, counted and cell viability was evaluated using ViCell. Viable cells were then adjusted to $2\times10^6$ cells per ml in FACS Stain Buffer (BD Biosciences) containing 0.1% BSA. 100 µl of this cell suspension were further aliquoted per well into a round-bottom 96-well plate. 30 µl of the anti-BCMA/anti-CD3 TCB antibodies or corresponding IgG control were added to the cell-containing wells to obtain final concentrations of 3 nM to 500 nM or 0.1 pM to 200 nM. Anti-BCMA/anti-CD3 TCB antibodies and control IgG were used at the same molarity. After incubation for 30 min at 4° C., cells were centrifuged (5 min, 350×g), washed twice with 150 µl/well BSA-containing FACS Stain Buffer (BD Biosciences), then cells were fixed using 100 ul BD Fixation buffer per well (#BD Biosciences, 554655) at 4° C. for 20 min, resuspended in 120 µl FACS buffer and analyzed using BD FACS CantoII. Binding of the anti-BCMA/anti-CD3 TCB antibodies to T cells were evaluated and the median fluorescence intensity was determined gated on CD3-expressing Jurkat T cells and plotted in histograms or dot plots. FIG. 14 shows the median fluorescence intensity for anti-BCMA/anti-CD3 TCB antibodies (83A10-TCBcv (A); 17A5-TCBcv (B)) binding to Jurkat T cells and plotted in function of antibody concentration. EC50 values and maximal binding of anti-BCMA/anti-CD3 TCB antibodies to CD3-positive Jurkat T cells were not reached. Isotype control antibody did not bind to Jurkat T cells and BCMA/anti-CD3 TCB antibodies ((A), 83A10-TCBcv); (B) 17A5-TCBcv) did not bind to BCMA-negative and CD3-negative MKN45 cells.

Example 13: Anti-BCMA/Anti-CD3 T-Cell Bispecific Antibodies do not Block APRIL-Dependent NF-κB Activation as Detected by Intracellular Phosphorylated NF-κB (Flow Cytometry)

In order to test whether the anti-BCMA/anti-CD3 TCB antibodies block or further induce APRIL-dependent NF-κB activation, the detection of intracellular phosphorylated NF-κB was measured by flow cytometry, as described in Lafarge et al. BMC Molecular Biol 2007; 8:64. The phospho flow cytometry method is an alternative to the detection of NF-κB activation by ELISA-based luminescence assay which may not be sensitive enough and contains laborious steps (Perez and Nolan. Nat Biotechnol 2002; 20(2):155-62). It was assessed whether binding of anti-BCMA/anti-CD3 TCB antibodies to BCMA-positive H929 myeloma cells blocks or further induces APRIL-dependent NF-κB activation, a known nuclear factor signaling pathway downstream of BCMA receptor. Briefly, H929 cells were starved in RPMI1640 without FCS for 24 h at 37° C. in cell incubator. At the end of the starvation time, cells were harvested, counted and cell viability evaluated using ViCell. Viable cells were adjusted to $1\times10^6$ cells per ml in BSA-containing FACS Stain Buffer (BD Biosciences). 100 µl of this cell suspension were further aliquoted per well into a round-bottom 96-well plate and incubated with 25 µl of the anti-BCMA/anti-CD3 TCB antibodies or isotype control antibodies at saturating concentration 400 nM (77 µg/ml) for 20 min at 37° C. followed by direct incubation of 100 ng/mL or 1 µg/mL recombinant mouse Δ-APRIL (R&D Systems Europe) for additional 15 min at 37° C. As negative controls, cells were either left untreated or incubated with the corresponding IgG isotype control antibodies 400 nM (77 µg/ml) for a total of 45 min at 37° C. As positive controls, cells were incubated with 100 ng/mL or 1 µg/ml recombinant mouse Δ-APRIL alone (R&D Systems Europe) for 15 min at 37° C. At the end of the stimulation, the cells were centrifuged (360×g, 4 min), the cell pellet immediately fixed in pre-warmed Cytofix Buffer (BD Biosciences, #554655) and incubated at 37° C. for 10 minutes. The cells were then centrifuged, supernatant was removed and the cell pellet was disrupted by vortex. The cells were then permeabilized in ice cold Phosflow Perm Buffer III (BD Biosciences, #558050) for 30 min on ice. The cells were then centrifuged, supernatant was removed and the cell pellet was disrupted by vortex. Cells were resuspended in 100 µL Phosflow Perm Buffer III and the permeabilized cells were stained with anti-NF-κB p65 (pS529) antibody (BD Biosciences, #558423) or an isotype control antibody (Mouse IgG2b, κ, BD Biosciences #555058) for 60 min at room temperature protected from light. After the staining period, the cells were washed with PBS+0.1% BSA in PBS+0.1% BSA prior to flow cytometric analysis. The relative median fluorescence intensity obtained from H929 cells treated as described above was measured. The median fluorescence intensity (MFI) signal obtained upon binding of Δ-APRIL in presence of the isotype control was set to one; the other signals were normalized to it. As depicted in FIG. 15, the effect of anti-BCMA/anti-CD3 TCB antibodies with an APRIL non-competing BCMA binding arm (83A10-TCBcv) compared to an APRIL competing BCMA binding arm (J6M0-TCB) was tested on 1000 ng/mL APRIL mediated NF-κB activation in H929 cells (A). As compared to H929 cells in presence of 1000 ng/mL APRIL, non-APRIL competing 83A10-TCBcv reduced 29.9% of the APRIL-induced NF-κB activation signal (A). Considering there could be approximately 20% of experimental variability, 83A10-TCBcv showed a minimal reduction of NF-κB phosphorylation mediated by APRIL. On the contrary, when APRIL competing BCMA binding arm J6M0-TCB was compared to H929 cells in presence of 1000 ng/mL APRIL there was at least 79.3% decrease in the NF-κB activation signal as measured by phosphoflow cytometry. J6M0 anti-BCMA antibody (WO2012163805) has been reported to block APRIL-induced NF-κB activation. J6M0-TCB was generated using the exact same TCB format as 83A10-TCBcv.

In a second set of experiment, the effect of APRIL non-competing 83A10-TCBcv and APRIL competing J6M0-TCB was verified in presence of a saturating concentration of APRIL i.e. 5000 ng/mL which induced a stronger signal for NF-κB activation in H929 cells and to confirm the first observations using the phosphoflow cytometry technique. As compared to H929 cells in presence of 5000 ng/mL APRIL, an increase of 30% in the NF-κB activation was observed with non-APRIL competing 83A10-TCBcv (FIG. 15B). However, considering that 20-30% is still in the variability of the assay, therefore neither an increase nor a reduction of the activation signal can be concluded for 83A10-TCBcv. On the other hand, when APRIL competing J6M0-TCB was compared to H929 cells in presence of 5000 ng/mL APRIL, there was a 69% decrease in the NF-κB activation signal as measured by phosphoflow cytometry, even considering the variability of the assay, this is a reduction of the activation signal.

The overall results corroborate with the dataset of APRIL competition studies for binding to BCMA and to BCMA-positive cells (FIGS. 5-8) and confirm that 83A10 anti-BCMA IgG antibody and 83A10-TCBcv minimally compete with APRIL and does not block or minimally block the binding of APRIL to BCMA on cells as well as only minimally affect NF-κB downstream signaling/signal transduction upon APRIL binding to BCMA on cells. The current results also confirm that J6M0 is an anti-BCMA antibody that is competing with APRIL for binding to BCMA and which blocks APRIL downstream signaling.

Example 14: Anti-BCMA/Anti-CD3 T-Cell Bispecific Antibodies do not Directly Induce NF-κB Activation in Absence of Exogenous APRIL as Measured by Phosphorylated NF-κB (Flow Cytometry)

It was assessed whether binding of anti-BCMA/anti-CD3 TCB antibodies to BCMA-positive H929 myeloma cells induces NF-κB activation, a known nuclear factor signaling pathway downstream of BCMA receptor. Briefly, H929 cells were starved in RPMI1640 without FCS for 24 h at 37° C. in cell incubator. At the end of the starvation time, cells were harvested, counted and cell viability evaluated using ViCell. Viable cells were adjusted to 1×10$^6$ cells per ml in BSA-containing FACS Stain Buffer (BD Biosciences). 100 μl of this cell suspension were further aliquoted per well into a round-bottom 96-well plate and incubated with 25 μl of the anti-BCMA/anti-CD3 TCB antibodies or isotype control antibodies at saturating concentration 400 nM (77 μg/ml) for 20 min at 37° C. followed by direct incubation of 100 ng/mL or 1 μg/mL or saturating concentrations 3 μg/mL up to 5 μg/mL of recombinant mouse Δ-APRIL (R&D Systems Europe) for additional 15 min at 37° C. As negative controls, cells were either left untreated or incubated with the corresponding IgG isotype control antibodies 400 nM (77 μg/ml) for a total of 45 min at 37° C. As positive controls, cells were incubated with 100 ng/mL or 1 μg/ml recombinant mouse Δ-APRIL alone (R&D Systems Europe) for 15 min at 37° C. to show that a positive signal was detectable and that lack of/minimal signal was not due to a technical error. At the end of the stimulation, the cells were centrifuged (360×g, 4 min), the cell pellet immediately fixed in pre-warmed Cytofix Buffer (BD Biosciences, #554655) and incubated at 37° C. for 10 minutes. The cells were then centrifuged, supernatant was removed and the cell pellet was disrupted by vortex. The cells were then permeabilized in ice cold Phosflow Perm Buffer III (BD Biosciences, #558050) for 30 min on ice. The cells were then centrifuged, supernatant was removed and the cell pellet was disrupted by vortex. Cells were resuspended in 100 μL Phosflow Perm Buffer III and the permeabilized cells were stained with anti-NF-κB p65 (pS529) antibody (BD Biosciences, #558423) or an isotype control antibody (Mouse IgG2b, κ, BD Biosciences #555058) for 60 min at room temperature protected from light. After the staining period, the cells were washed with PBS+0.1% BSA in PBS+0.1% BSA prior to flow cytometric analysis. The relative median fluorescence intensity obtained from H929 cells treated as described above was measured. The median fluorescence intensity signal obtained upon binding of Δ-APRIL in presence of the isotype control was set to one; the other signals were normalized to it. The effect of anti-BCMA/anti-CD3 TCB antibodies (83A10-TCBcv) on NF-κB signaling upon binding to H929 cells in absence of exogenous APRIL is shown in FIG. 16. FIG. 16A shows that binding of anti-BCMA/anti-CD3 83A10-TCBcv to H929 cells did not cause an increase in NF-κB activation in the absence of APRIL but a slight 18.1% decrease in the basal signal was observed which is within experimental variability, as compared to H929 cells alone and as measured by detection of intracellular NF-κB p65 (pS529) by phospho-flow cytometry. This observation was confirmed in a second experiment showing that anti-BCMA/anti-CD3 83A10-TCBcv did not inhibit nor induce NF-κB activation by binding to BCMA-positive H929 cells (FIG. 16B). As previously reported in past publications, H929 myeloma cells showed a basal level of activation in the NF-κB pathway, a known pathological feature of multiple myeloma cell lines (Demchenko et al., Blood 2010; 115 (17): 3541-3552). The lack of activation of NF-κB pathway upon binding of anti-BCMA/anti-CD3 TCB antibodies to BCMA-positive cells may be advantageous especially that due to the higher binding affinity of anti-BCMA/anti-CD3 TCB antibodies to BCMA tumor target vs. to CD3 on T cells, it is preferable that NF-κB pathway is not further activated and that myeloma cell survival is increased when anti-BCMA/anti-CD3 TCB antibodies temporarily bind to BCMA-positive myeloma cells without binding yet to T cells.

Example 15: Activation of Human T Cells Upon Binding of Anti-BCMA/Anti-CD3 T Cell Bispecific Antibodies to CD3-Positive T Cells and BCMA-Positive Multiple Myeloma Cell Lines (Flow Cytometry)

Figure 17:
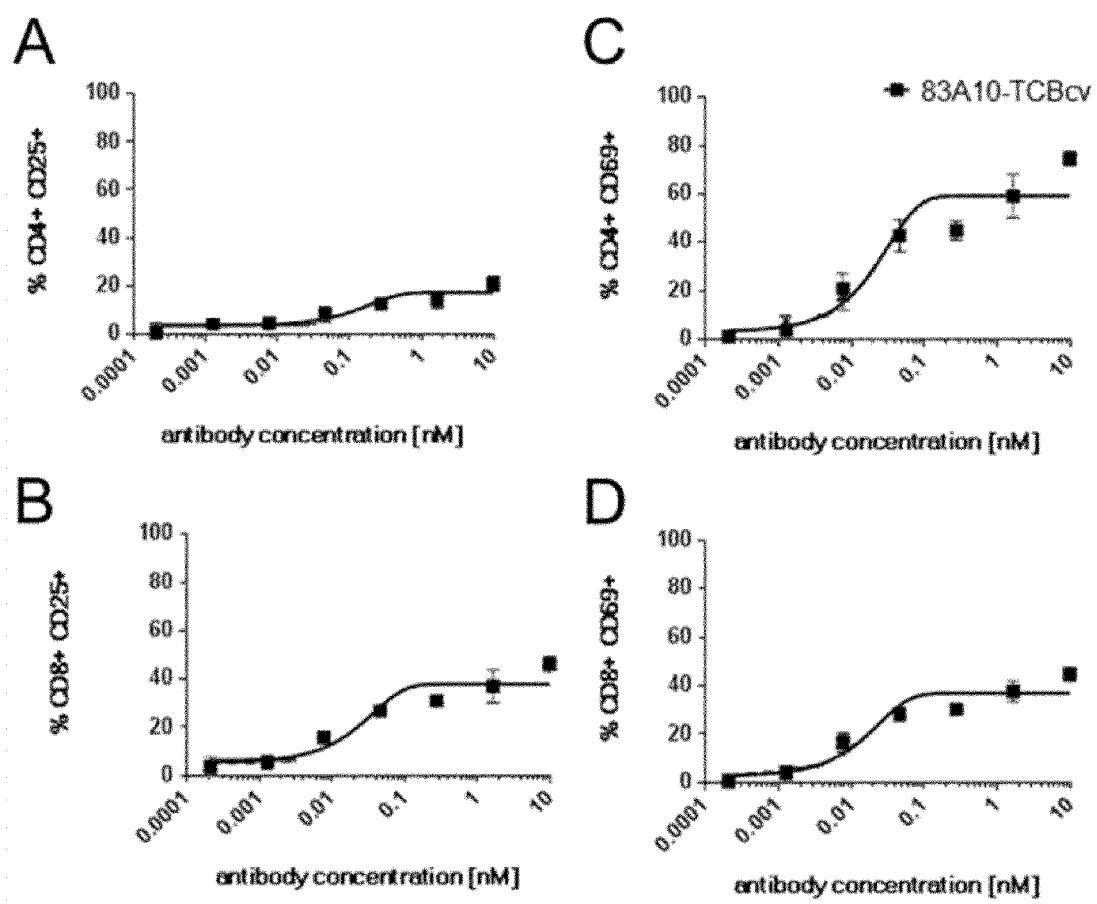
FIG. 17. T-cell activation mediated by anti-BCMA/anti-CD3 TCBcv antibodies in presence of H929 cells as detected by flow cytometry. Expression level of the early activation marker CD69 (C, D), and the late activation marker CD25 (A, B) on $CD4^+$ and $CD8^+$ T cells after 48 hours of incubation. 83A10-TCBcv antibody induced an up-regulation of CD69 and CD25 activation markers in a concentration-dependent and specific manner in the presence of BCMA-positive target cells. E:T ratio used as 10 PBMCs:1 H929 cell; cells were incubated for 48 h before measurement of CD69 and CD25 upregulation. Representative results from two independent experiments (see Example 15).

Anti-BCMA/anti-CD3 TCB antibodies were analyzed by flow cytometry for their ability to induce T cell activation by evaluating the surface expression of the early activation marker CD69, or the late activation marker CD25 on CD4$^+$ and CD8$^+$ T cells in the presence or absence of human BCMA-expressing MM cells. Briefly, BCMA-positive H929 cells were harvested with Cell Dissociation buffer, counted and checked for viability. Cells were adjusted to 0.3×10$^6$ (viable) cells per ml in modified RPMI-1640 medium, 100 μl of this cell suspension were pipetted per well into a round-bottom 96-well plate (as indicated). 50 μl of the (diluted) anti-BCMA/anti-CD3 TCB antibodies were added to the cell-containing wells to obtain a final concentration of 0.3 pM-30 nM. Human PBMC effector cells were isolated from fresh blood of a healthy donor and adjusted to 6×10$^6$ (viable) cells per ml in modified RPMI-1640 medium. 50 μl of this cell suspension was added per well of the assay plate to obtain a final E:T ratio of PBMC to myeloma tumor cells of 10:1. To analyze whether the anti-BCMA/anti-CD3 TCB antibodies were able to activate T cells specifically in the presence of target cells expressing human BCMA, wells were included that contained 3 nM of the respective anti-BCMA/anti-CD3 TCB molecules, as well as PBMCs, but no target cells. After incubation for 15-28 h (CD69), or 24-48 h (CD25) at 37° C., 5% CO$_2$, cells were centrifuged (5 min, 350×g) and washed twice with 150 μl/well PBS containing 0.1% BSA. Surface staining for CD4 (mouse IgG1,K; clone RPA-T4), CD8 (mouse IgG1,K; clone HIT8a; BD #555635), CD69 (mouse IgG1; clone L78; BD #340560) and CD25 (mouse IgG1,K; clone M-A251; BD #555434) was performed at 4° C. for 30 min, according to the supplier's suggestions. Cells were washed twice with 150 μl/well PBS containing 0.1% BSA and fixed for 15 min at 4° C., using 100 μl/well fixation buffer (BD #554655). After centrifugation, the samples were resuspended in 200 μl/well PBS with 0.1% BSA and analyzed using a FACS CantoII machine (Software FACS Diva). FIG. 17 depicts the expression level of the early activation marker CD69 (C, D), and the late activation marker CD25 (A, B) on $CD4^+$ and $CD8^+$ T cells after 48 hours of incubation (representative results from two independent experiments). 83A10-TCBcv antibody induced an up-regulation of CD69 and CD25 activation markers in a concentration-dependent and specific manner in the presence of BCMA-positive target cells. No activation of $CD4^+$ and CD8+ T cells was observed when human PBMCs were treated with DP47-TCB control antibody, suggesting that despite binding to CD3 on the T cells T-cell activation does not occur when the TCB antibody does not bind to BCMA-positive target cells (data not shown).

Example 16: Cytokine Production from Activated T Cells Upon Binding of Anti-BCMA/Anti-CD3 T Cell Bispecific Antibodies to CD3-Positive T Cells and BCMA-Positive Multiple Myeloma Cell Lines (Cytokine Release Assay CBA Analysis)

Anti-BCMA/anti-CD3 T cell bispecific antibodies are analyzed for their ability to induce T-cell mediated cytokine production de novo in the presence or absence of human BCMA-expressing MM cells. Briefly, human PBMCs are isolated from Buffy Coats and 0.3 million cells per well are plated into a round-bottom 96-well plate. Alternatively, 280 μl whole blood from a healthy donor are plated per well of a deep-well 96-well plate. Tumor target cells (e.g. H929, RPMI-8226, U266, or L363 myeloma cells) are added to obtain a final E:T-ratio of 10:1. Anti-BCMA/anti-CD3 TCB antibodies and controls are added for a final concentration of 0.3 pM-30 nM. After an incubation of up to 24 h at 37° C., 5% $CO_2$, the assay plate is centrifuged for 5 min at 350×g and the supernatant is transferred into a new deep-well 96-well plate for the subsequent analysis. The CBA analysis is performed on FACS CantoII according to manufacturer's instructions, using either the Human Th1/Th2 Cytokine Kit II (BD #551809) or the combination of the following CBA Flex Sets: human granzyme B (BD #560304), human IFN-γ Flex Set (BD #558269), human TNF Flex Set (BD #558273), human IL-10 Flex Set (BD #558274), human IL-6 Flex Set (BD #558276), human IL-4 Flex Set (BD #558272), human IL-2 Flex Set (BD #558270). Tables 15C and 15D show the EC50 values and amount of secreted cytokines/proteases per anti-BCMA/anti-CD3 T-cell bispecific antibody concentrations when H929 cells and RPMI-8226 cells were used as tumor target cells, respectively.

TABLE 15C

Secretion of cytokine and proteases induced by anti-BCMA/anti-CD3 T-cell bispecific antibodies in presence of H929 cells

| Cytokines/proteases | EC50 (nM) | 83A10-TCBcv concentration (nM) | | | | | | |
|---|---|---|---|---|---|---|---|---|
| | | 0.0002 | 0.0013 | 0.008 | 0.046 | 0.28 | 1.67 | 10 |
| IFN-γ (pg/mL) | 3.25 | 4.34 | 5.97 | 18.13 | 123.02 | 820.91 | 1563.53 | 2768.75 |
| IL-2 (pg/mL) | 0.22 | 153.81 | 154.25 | 156.48 | 166.46 | 202.94 | 238.43 | 239.50 |
| TNF-α (pg/mL) | 0.99 | 10.39 | 10.84 | 13.81 | 34.46 | 162.79 | 209.01 | 463.95 |
| IL-10 (pg/mL) | 2.31 | 23.64 | 24.14 | 20.96 | 24.08 | 29.03 | 46.54 | 70.88 |
| Granzyme B (pg/mL) | 13.5 | 161.58 | 140.50 | 229.89 | 874.36 | 2425.32 | 5772.46 | 12018.26 |
| IL-6 (pg/mL) | / | 11.28 | 10.55 | 12.58 | 24.19 | 46.57 | 68.79 | 193.07 |

TABLE 15D

Secretion of cytokine and proteases induced by anti-BCMA/anti-CD3 T-cell bispecific antibodies in presence of RPMI-8226 cells

| Cytokines/proteases | EC50 (nM) | 83A10-TCBcv concentration (nM) | | | | | | |
|---|---|---|---|---|---|---|---|---|
| | | 0.00064 | 0.0032 | 0.016 | 0.08 | 0.4 | 2 | 10 |
| TNF-α (pg/mL) | 0.52 | −6.95 | −6.49 | −0.65 | 46.72 | 161.24 | 315.11 | 371.47 |
| IL-10 (pg/mL) | 0.30 | −9.21 | 1.95 | 25.17 | 125.82 | 401.42 | 602.64 | 680.05 |
| Granzyme B (pg/mL) | 0.34 | 220.54 | 331.55 | 889.13 | 5855.02 | 15862.84 | 21270.43 | 27120.52 |

Example 17: Redirected T-Cell Cytotoxicity of Cynomolgus BCMA-Transfected Cells Induced by Anti-BCMA/Anti-CD3 T Cell Bispecific Antibodies (LDH Release Assay)

a) Anti-BCMA/anti-CD3 TCB antibodies are analyzed for their ability to induce T cell-mediated apoptosis in cynomolgus monkey BCMA-expressing CHO cells upon cross-linking of the TCB construct via binding of the antigen binding moieties to BCMA on cells. Briefly, cynomolgus monkey BCMA-expressing CHO target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Cynomolgus monkey PBMC are used as effector cells, a final E:T ratio of 10:1 is used. Negative control groups are represented by effector or target cells only. As a positive control for the activation of cynomolgus monkey T cells, 1 μg/ml PHA-M (Sigma #L8902) is used. For normalization, maximal lysis of the cynomolgus monkey BCMA-expressing CHO target cells (=100%) is determined by incubation of the target cells with a final concentration of 1% Triton X-100, inducing cell death. Minimal lysis (=0%) was represented by target cells co-incubated with effector cells only, i.e. without any T cell bispecific antibody. After 20-24 h incubation at 37° C., 5% $CO_2$, LDH release from the apoptotic/necrotic cynomolgus monkey BCMA-expressing CHO target cells into the supernatant was then measured with the LDH detection kit (Roche Applied Science), following the manufacturer's instructions. The percentage of LDH release is plotted against the concentrations of anti-BCMA/anti-CD3 TCB antibodies in concentration-response curves. The EC50 values are measured using Prism software (GraphPad) and determined as the TCB antibody concentration that results in 50% of maximum LDH release.

b) Anti-BCMA/anti-CD3 TCB antibodies are analyzed for their ability to induce T cell-mediated apoptosis in cynomolgus monkey BCMA-expressing HEK293T cells upon crosslinking of the TCB construct via binding of the antigen binding moieties to BCMA on cells. Briefly, cynomolgus monkey BCMA-expressing HEK293T target cells are harvested with Cell Dissociation Buffer, washed and resuspended in RPMI 1640 medium supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Cynomolgus monkey PBMC are used as effector cells, a final E:T ratio of 10:1 is used. Negative control groups are represented by effector or target cells only. For normalization, maximal lysis of the cynomolgus monkey BCMA-expressing HEK target cells (=100%) is determined by incubation of the target cells with a final concentration of 1% Triton X-100, inducing cell death. Minimal lysis (=0%) was represented by target cells co-incubated with effector cells only, i.e. without any T cell bispecific antibody. After 20-24 h incubation at 37° C., 5% $CO_2$, LDH release from the apoptotic/necrotic cynomolgus monkey BCMA-expressing HEK target cells into the supernatant was then measured with the LDH detection kit (Roche Applied Science), following the manufacturer's instructions. The percentage of LDH release is plotted against the concentrations of anti-BCMA/anti-CD3 TCB antibodies in concentration-response curves. The EC50 values are measured using Prism software (GraphPad) and determined as the TCB antibody concentration that results in 50% of maximum LDH release. Table 15E shows the EC50 values for target cell lysis of cynoBCMA-HEK cells by 83A10-TCBcv.

TABLE 15E

EC50 values of potency of anti-BCMA/anti-CD3 T cell bispecific antibodies to induce lysis of cynoBCMA-HEK cells

| Target cells | Effector cells | EC50 (pM) 83A10-TCBcv |
|---|---|---|
| CynoBCMA-HEK | Cyno PBMCs donor 1 | 3.5 |
| CynoBCMA-HEK | Cyno PBMCs donor 2 | 2.7 |
| | Mean EC50 = | 3.1 ± 0.57 |

Example 18: Redirected T-Cell Cytotoxicity of BCMA-High Expressing H929 Myeloma Cells Induced by Anti-BCMA/Anti-CD3 T Cell Bispecific Antibodies (Colorimetric LDH Release Assay)

Figure 18:
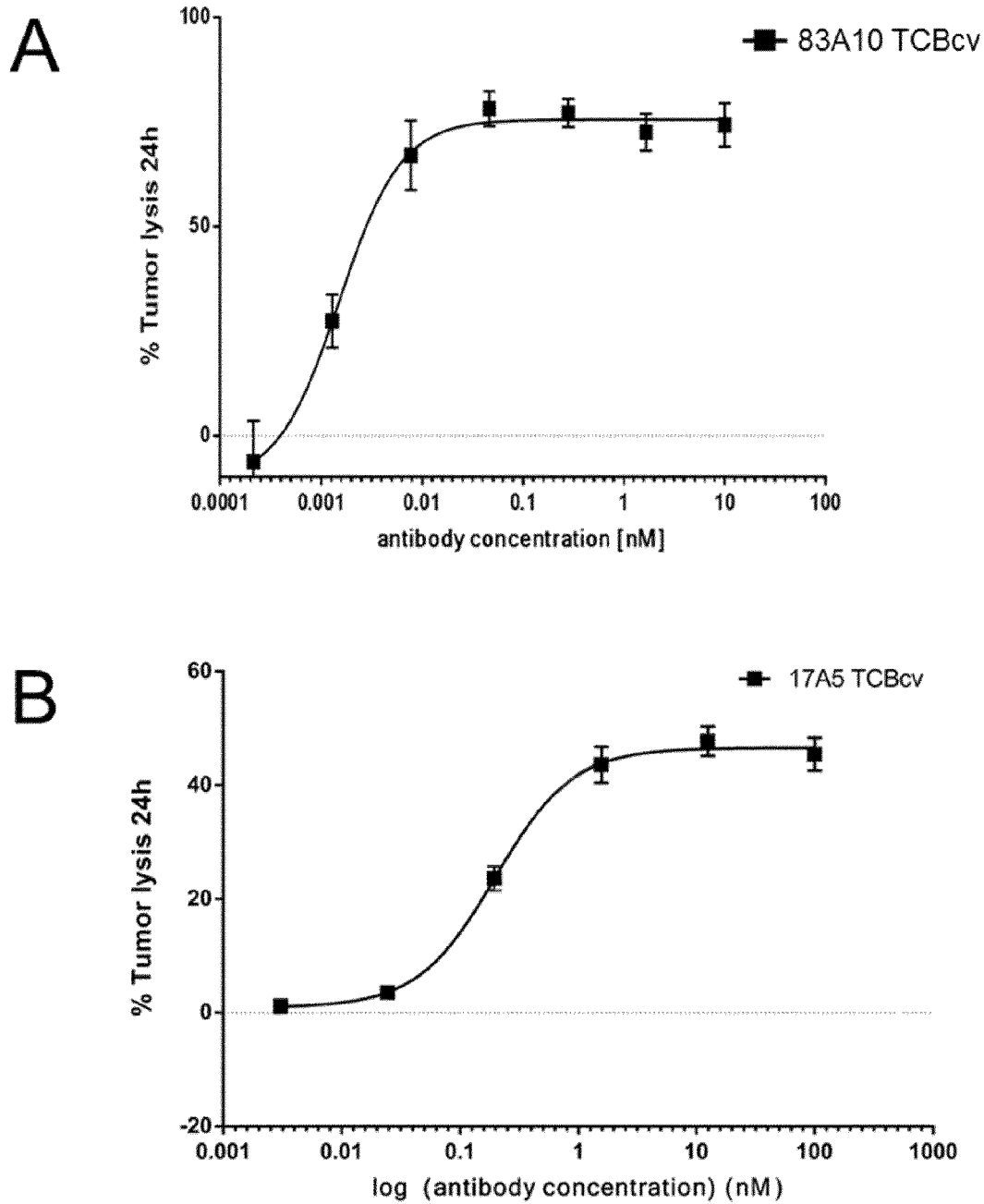
FIG. 18. Anti-BCMA/anti-CD3 TCBcv antibodies induce T-cell redirected killing of BCMA-positive H929 myeloma cells as detected by colorimetric LDH release assay. Anti-BCMA/anti-CD3 TCB antibodies ((A) 83A10-TCBcv, (B) 17A5-TCBcv) induced a concentration-dependent killing of BCMA-positive H929 myeloma cells as measured by LDH release. E:T ratio used as 10 PBMCs:1 H929 cell; cells were incubated for 24 h before measurement of LDH release (see Example 18).
Figures 1, 18:
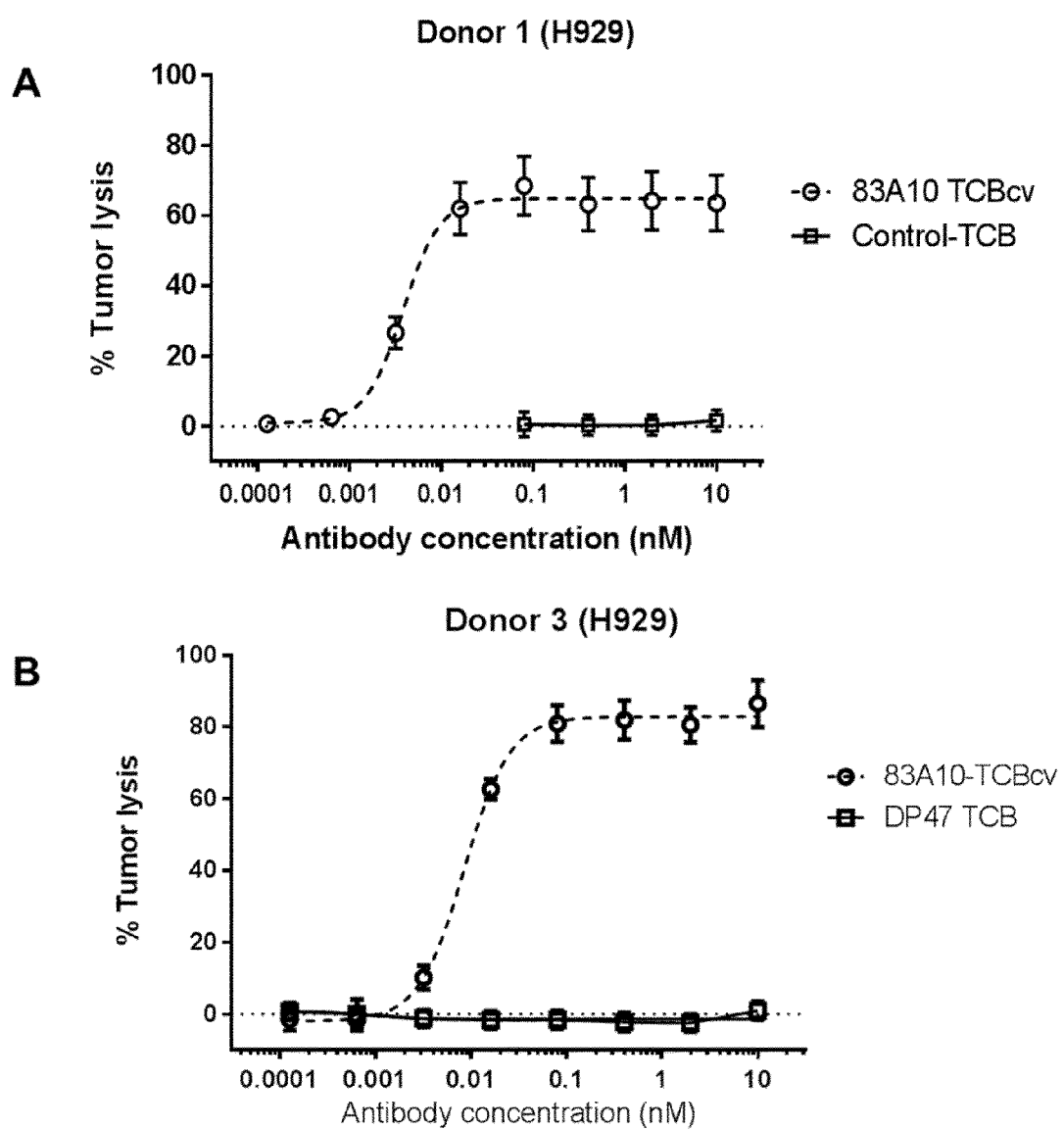
FIG. 1. Bispecific bivalent antibodies comprising only the Fab fragments (specific to CD3 and BCMA) and the Fc part as specified: (A) Fab BCMA(RK/EE)-Fc-Fab CD3; (B) Fab BCMA-Fc-Fab CD3(RK/EE). aa substitutions for RK/EE introduced in CL-CH1 to reduce LC mispairing/side products in production. The Fab CD3 includes a VL-VH crossover to reduce LC mispairing and side-products.
Figures 1, 18:
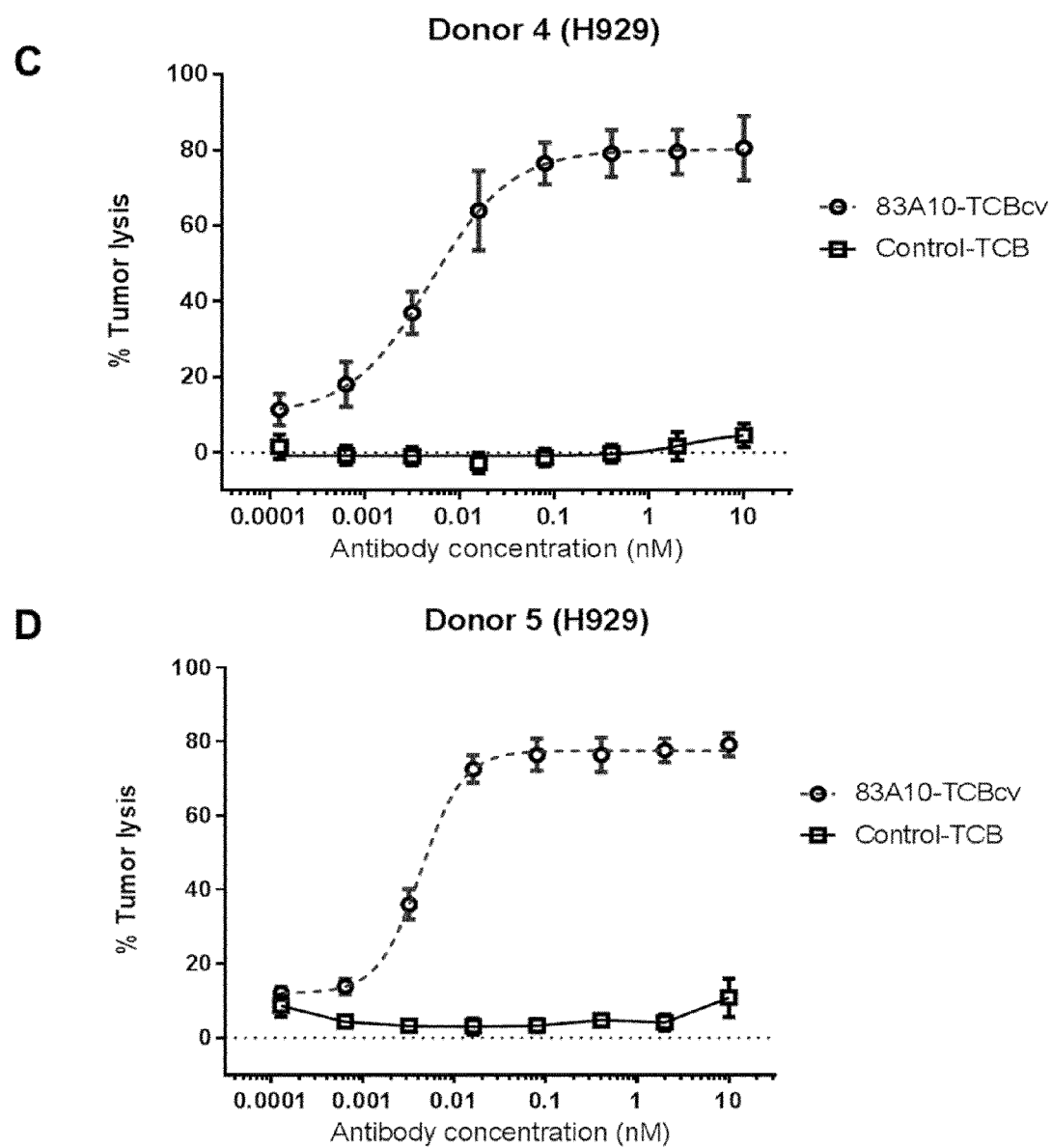
Figures 2, 18:
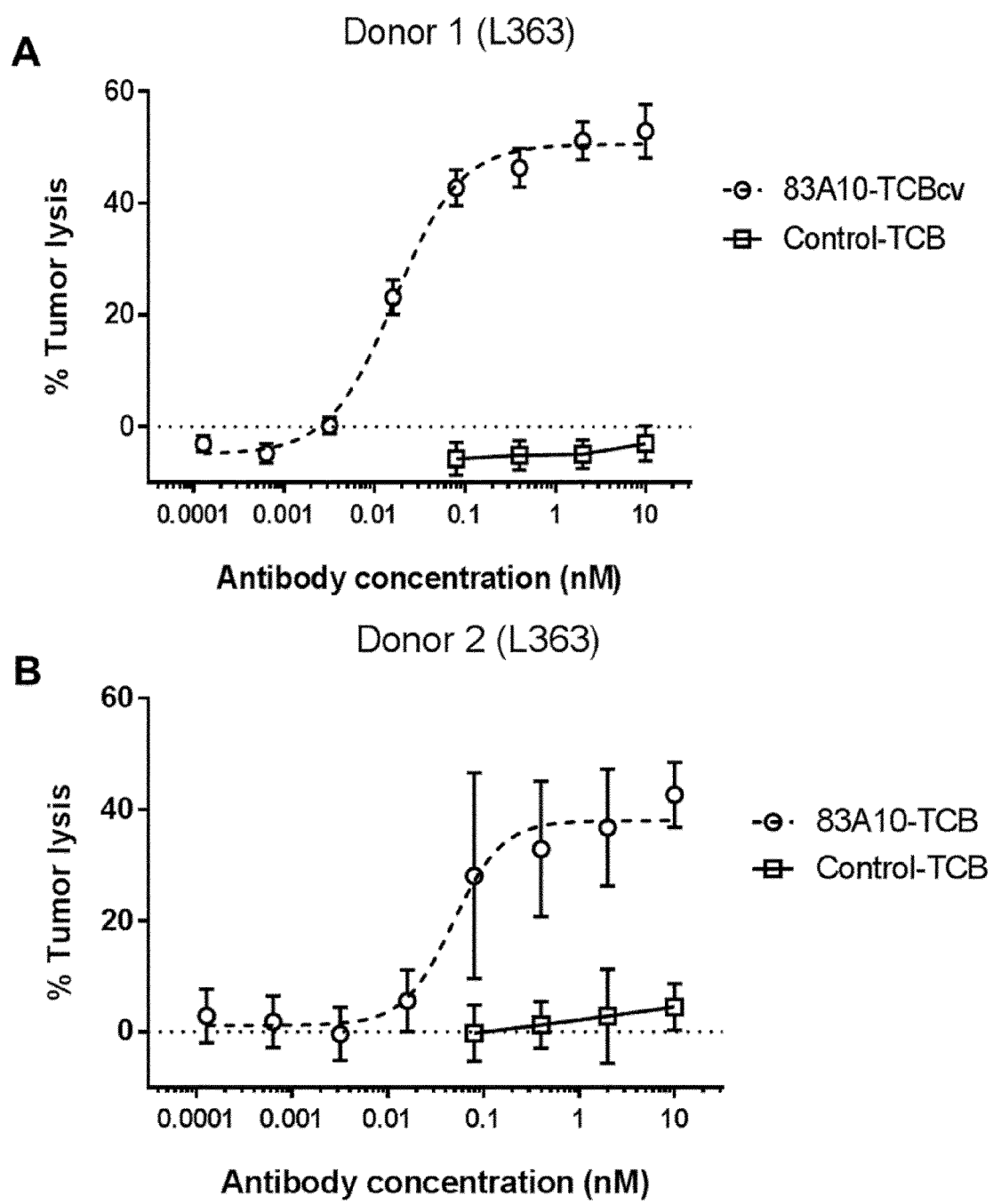
Figures 2, 18:
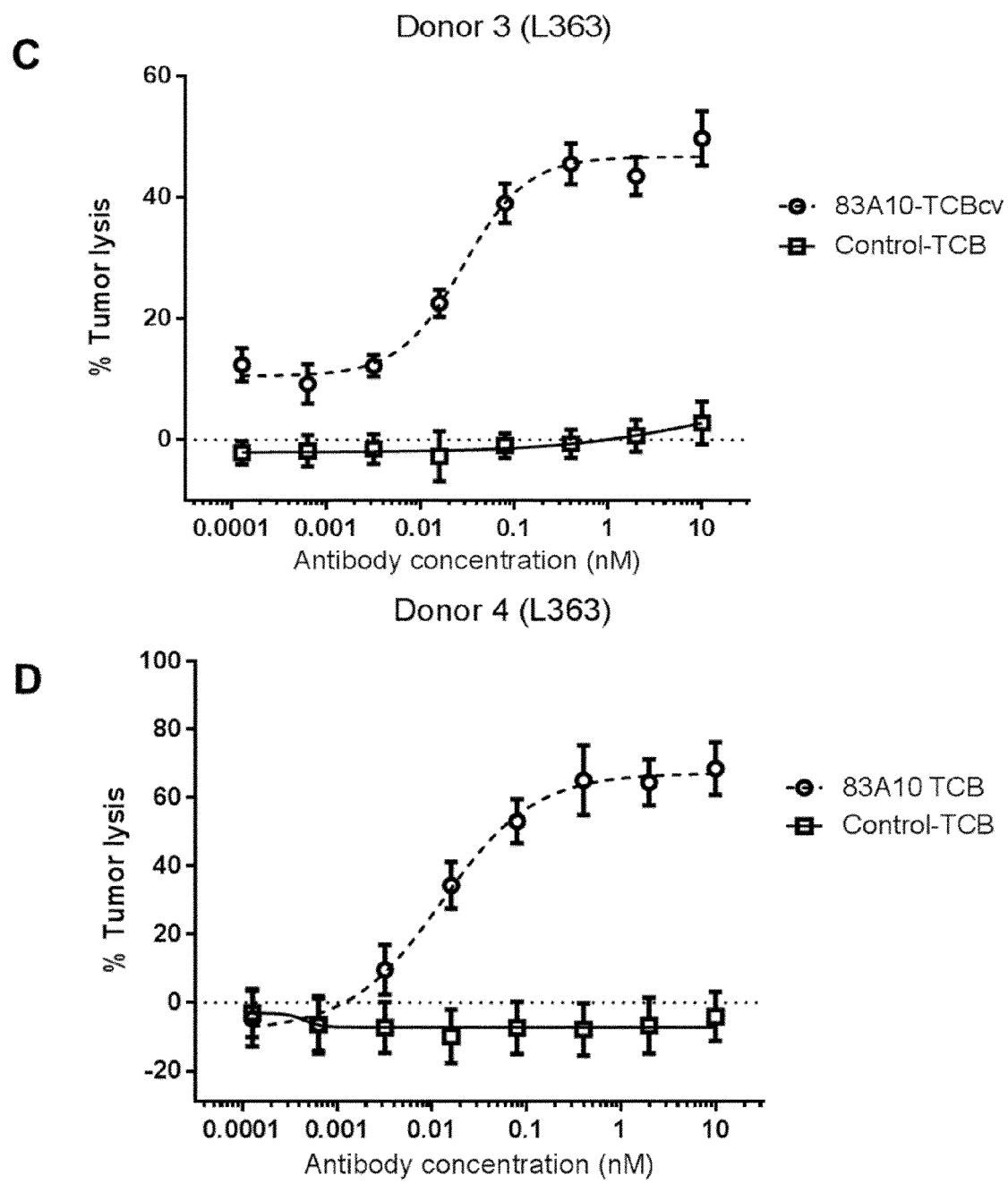
Figures 2, 18:
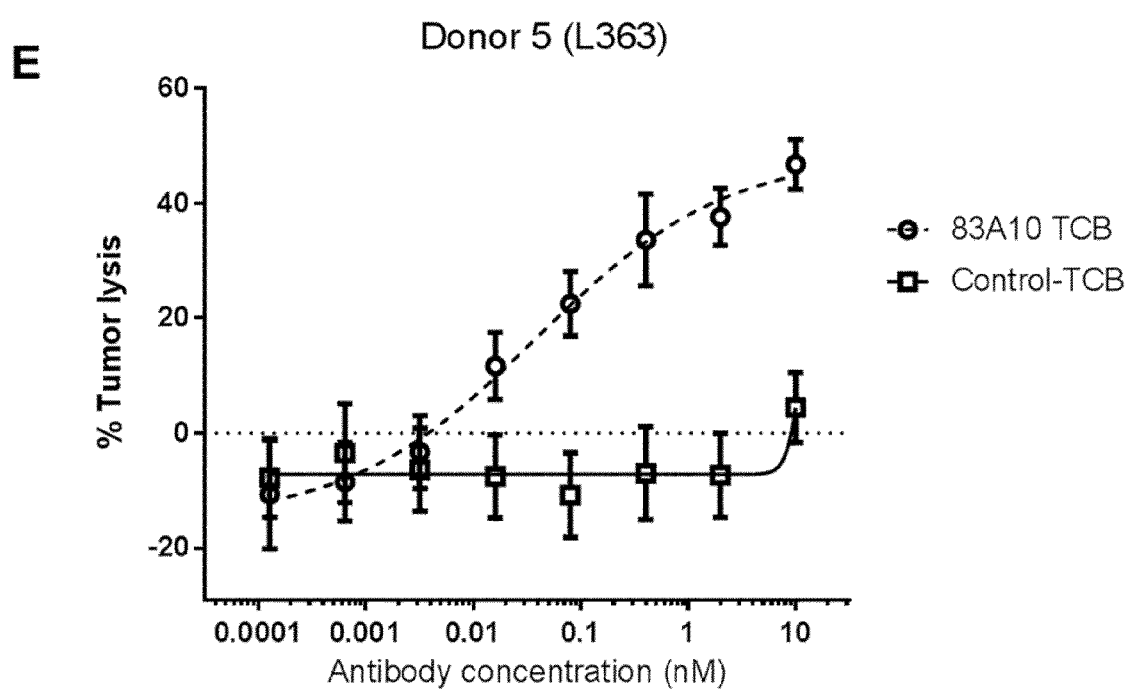
Figures 3, 18:
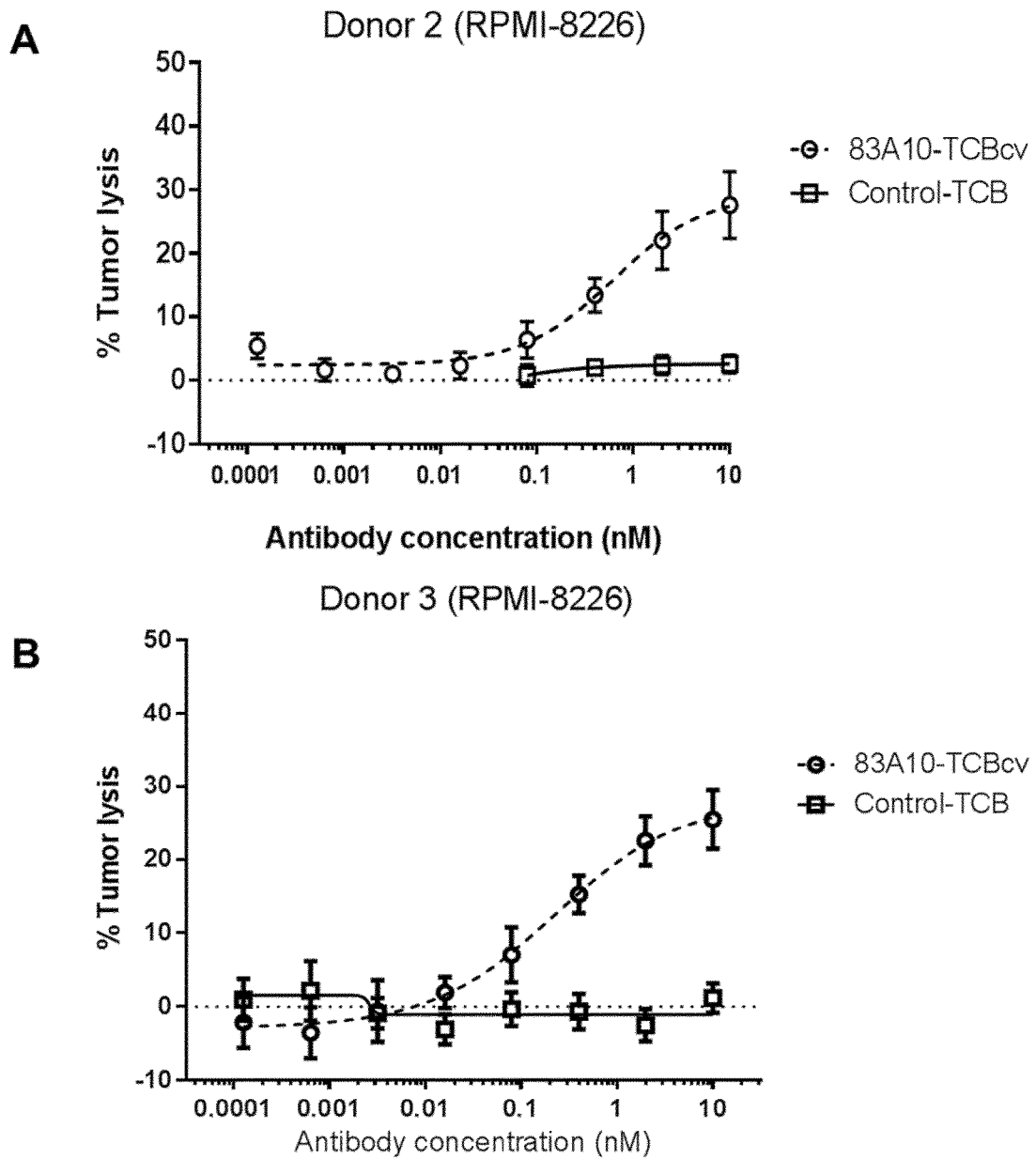
Figures 3, 18:
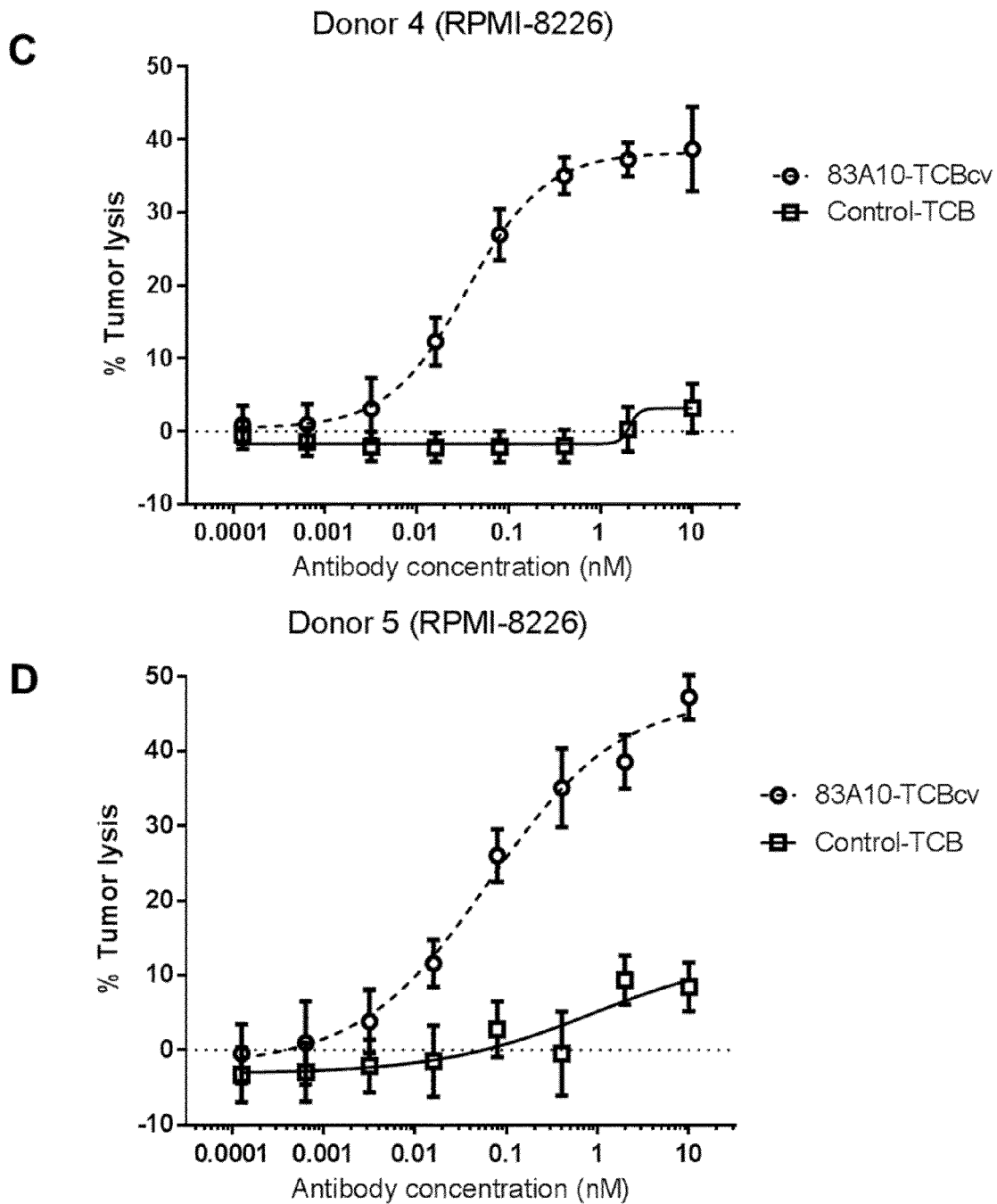
Figure 18:
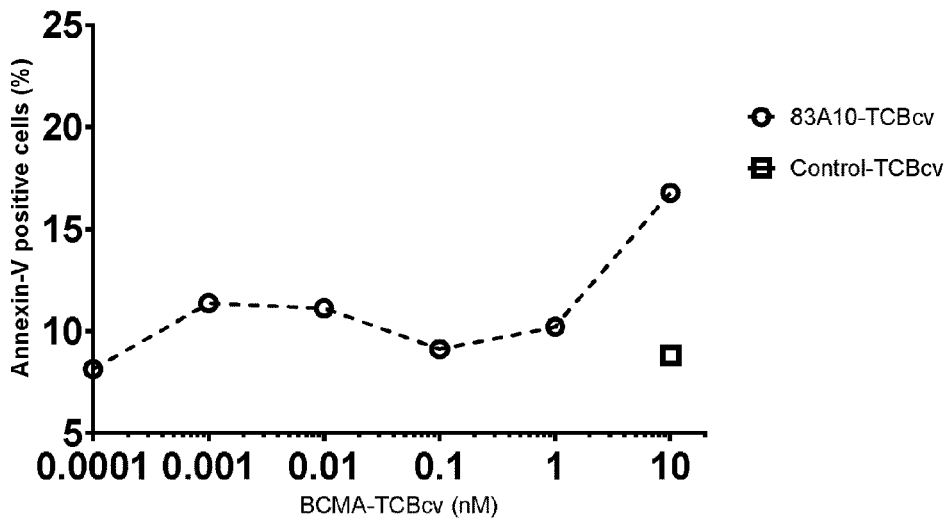
Figure 4:
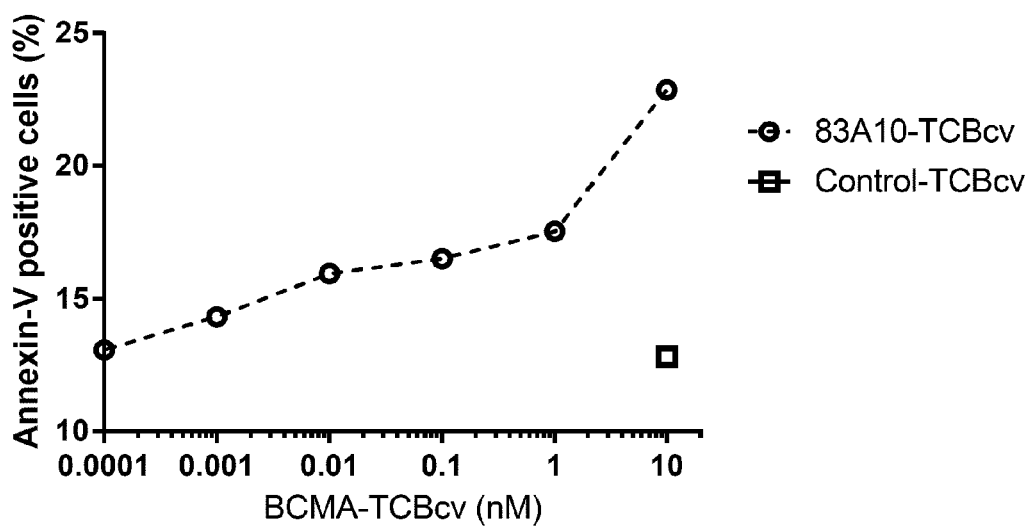
Figures 4, 18:
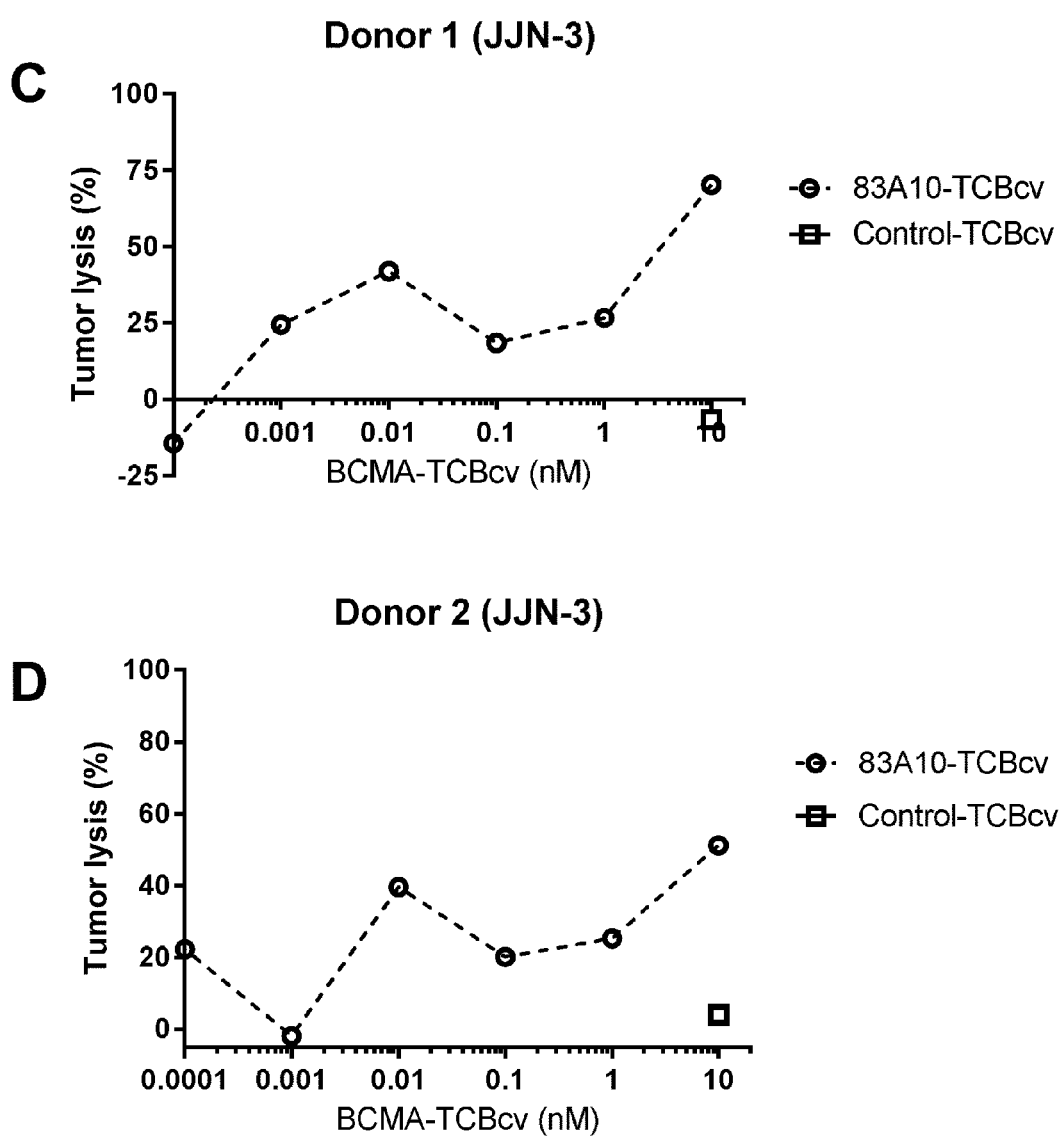

Anti-BCMA/anti-CD3 TCB antibodies were also analyzed for their potential to induce T cell-mediated apoptosis in BCMA-high expressing MM cells upon crosslinking of the construct via binding of the antigen binding moieties to BCMA on cells. Briefly, human BCMA-expressing H929 multiple myeloma target cells were harvested with Cell Dissociation Buffer, washed and resuspended in RPMI supplemented with 10% fetal bovine serum (Invitrogen). Approximately, 30,000 cells per well were plated in a round-bottom 96-well plate and the respective dilution of the construct was added for a desired final concentration (in triplicates); final concentrations ranging from 0.1 pM to 10 nM. For an appropriate comparison, all TCB constructs and controls were adjusted to the same molarity. Human total T cells (effector) were added into the wells to obtain a final E:T ratio of 5:1. When human PBMC were used as effector cells, a final E:T ratio of 10:1 was used. Negative control groups were represented by effector or target cells only. As a positive control for the activation of human pan T cells, 1 μg/ml PHA-M (Sigma #L8902) was used. For normalization, maximal lysis of the H929 MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. After 20-24 h or 48 h incubation at 37° C., 5% $CO_2$, LDH release from the apoptotic/necrotic MM target cells into the supernatant was then measured with the LDH detection kit (Roche Applied Science), following the manufacturer's instructions. The percentage of LDH release was plotted against the concentrations of anti-BCMA/anti-CD3 T cell bispecific antibodies in concentration-response curves. The EC50 values were measured using Prism software (GraphPad) and determined as the TCB antibody concentration that results in 50% of maximum LDH release. As shown in FIG. 18, anti-BCMA/anti-CD3 TCB antibodies ((A) 83A10-TCBcv, (B) 17A5-TCBcv) induced a concentration-dependent killing of BCMA-positive H929 myeloma cells as measured by LDH release. The killing of H929 cells was specific since DP47-TCB control antibody which does not bind to BCMA-positive target cells did not induce LDH release, even at the highest concentration tested (data not shown). Tables 16 and 16A summarize the EC50 values for redirected T-cell killing of BCMA-positive H929 cells induced by anti-BCMA/anti-CD3 TCB antibodies. In some experiment, 83A10-TCBcv was compared with APRIL/BAFF ligand-competing J6M0-TCB in inducing killing of H929 cells (Table 16A). FIG. 18-1 shows that 83A10-TCBcv induced a concentration-dependent killing of BCMA-positive H929 myeloma cells as measured by LDH release. The lysis of H929 cells was specific since control-TCB antibody which does not bind to BCMA-positive target cells but only to CD3 on T cells did not induce LDH release, even at the highest concentration tested.

TABLE 16

EC50 values for redirected T-cell killing of H929 cells induced by anti-BCMA/anti-CD3 TCB antibodies

| Anti-BCMA/anti-CD3 TCB molecules | EC50 (pM) | EC50 (μg/ml) |
|---|---|---|
| 83A10-TCBcv (Experiment 1) | Low pM range (approx. <20) | Single digit |
| 83A10-TCBcv (Experiment 2) | 1.5 | 0.29 |
| 17A5-TCBcv | 197 | 37.9 |

TABLE 16A

EC50 values for redirected T-cell killing of H929 cells induced by anti-BCMA/anti-CD3 TCB antibodies

| Anti-BCMA/anti-CD3 TCB antibodies | EC50 (pM) | | | | | |
|---|---|---|---|---|---|---|
| | Donor 1 | Donor 2 | Donor 3 | Donor 4 | Donor 5 | Donor 6 |
| 83A10-TCBcv | 3.9 | / | 8.5 | 5.0 | 4.3 | 1.5 |
| J6M0-TCBcv | / | / | / | / | / | 5.8 |

Example 19: Redirected T-Cell Cytotoxicity of BCMA-Low Expressing U266BI and/or L363 Myeloma Cells Induced by Anti-BCMA/Anti-CD3 T Cell Bispecific Antibodies (LDH Release Assay)

Anti-BCMA/anti-CD3 TCB antibodies are analyzed for their ability to induce T cell-mediated apoptosis in BCMA-low expressing MM cells upon crosslinking of the construct via binding of the antigen binding moieties to BCMA on cells. Briefly, human BCMA-low expressing U266 and/or L363 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Human total T cells (effector) are added into the wells to obtain a final E:T ratio of 5:1. When human PBMC are used as effector cells, a final E:T ratio of 10:1 is used. Negative control groups are represented by effector or target cells only. As a positive control for the activation of human T cells, 1 μg/ml PHA-M (Sigma #L8902) is used. For normalization, maximal lysis of the MM target cells (=100%) is determined by incubation of the target cells with a final concentration of 1% Triton X-100, inducing cell death. Minimal lysis (=0%) is represented by target cells co-incubated with effector cells only, i.e. without any T cell bispecific antibody. After 20-24 h incubation at 37° C., 5% $CO_2$, LDH release from the apoptotic/necrotic MM target cells into the supernatant is then measured with the LDH detection kit (Roche Applied Science), following the manufacturer's instructions. The percentage of LDH release is plotted against the concentrations of anti-BCMA/anti-CD3 T cell bispecific antibodies in concentration-response curves. The EC50 values are measured using Prism software (GraphPad) and determined as the TCB antibody concentration that results in 50% of maximum LDH release. As shown in FIG. 18-2, 83A10-TCBcv anti-BCMA/anti-CD3 TCB antibody induced a concentration-dependent killing of BCMA-positive L363 myeloma cells as measured by LDH release. The lysis of L363 cells was specific since control-TCB antibody which does not bind to BCMA-positive target cells but only to CD3 on T cells did not induce LDH release, even at the highest concentration tested. Table 16B summarizes the EC50 values for the redirected T-cell killing of BCMA medium/low-expressing L363cells induced by anti-BCMA/anti-CD3 TCB antibodies.

TABLE 16B

EC50 values for redirected T-cell killing of L363 cells induced by anti-BCMA/anti-CD3 TCB antibodies

| Anti-BCMA/anti-CD3 TCB antibodies | EC50 (pM) | | | | |
|---|---|---|---|---|---|
| | Donor 1 | Donor 2 | Donor 3 | Donor 4 | Donor 5 |
| 83A10-TCBcv | 16.8 | 47.8 | 28.4 | 12.6 | 39.0 |

Example 19A: Redirected T-Cell Cytotoxicity of BCMA-Medium/Low Expressing RPMI-8226 Myeloma Cells Induced by Anti-BCMA/Anti-CD3 T Cell Bispecific Antibodies (LDH Release Assay)

Anti-BCMA/anti-CD3 TCB antibodies were analyzed for their ability to induce T cell-mediated apoptosis in BCMA medium/low-expressing MM cells upon crosslinking of the construct via binding of the antigen binding moieties to BCMA on cells. Briefly, human BCMA medium/low-expressing L363 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Human PBMCs (effector cells) were added into the wells to obtain a final E:T ratio of 10:1, corresponding to a E:T ratio of approximately 3 to 5 T cells for 1 tumor target cells. Negative control groups were represented by effector or target cells only. For normalization, maximal lysis of the MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. After 20-24 h incubation at 37° C., 5% $CO_2$, LDH release from the apoptotic/necrotic MM target cells into the supernatant was then measured with the LDH detection kit (Roche Applied Science), following the manufacturer's instructions. The percentage of LDH release was plotted against the concentrations of anti-BCMA/anti-CD3 T cell bispecific antibodies in concentration-response curves. The EC50 values were measured using Prism software (GraphPad) and determined as the TCB antibody concentration that results in 50% of maximum LDH release. As shown in FIG. 18-3, 83A10-TCBcv anti-BCMA/anti-CD3 TCB antibody induced a concentration-dependent killing of BCMA-positive RPMI-8226 myeloma cells as measured by LDH release. The lysis of RPMI-8226 cells was specific since control-TCB antibody which does not bind to BCMA-positive target cells but only to CD3 on T cells did not induce LDH release, even at the highest concentration tested. Table 16C summarizes the EC50 values for the redirected T-cell killing of BCMA medium/low-expressing RPMI-8226 cells induced by anti-BCMA/anti-CD3 TCB antibodies.

TABLE 16C

EC50 values for redirected T-cell killing of RPMI-8226 cells induced by anti-BCMA/anti-CD3 TCB antibodies

| Anti-BCMA/anti-CD3 TCB antibodies | EC50 (pM) | | | | |
|---|---|---|---|---|---|
| | Donor 1 | Donor 2 | Donor 3 | Donor 4 | Donor 5 |
| 83A10-TCBcv | / | 620.5 | 229.3 | 35.0 | 64.9 |

Example 19B: Redirected T-Cell Cytotoxicity of BCMA-Low Expressing JJN-3 Myeloma Cells Induced by Anti-BCMA/Anti-CD3 T Cell Bispecific Antibodies (Flow Cytometry and LDH Release)

Anti-BCMA/anti-CD3 TCB antibodies were analyzed for their ability to induce T cell-mediated apoptosis in BCMA low-expressing MM cells upon crosslinking of the construct via binding of the antigen binding moieties to BCMA on cells. Briefly, human BCMA low-expressing JJN-3 multiple myeloma target cells are harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct is added for a desired final concentration (in triplicates); final concentrations ranging from 0.1 pM to 10 nM. For an appropriate comparison, all TCB constructs and controls are adjusted to the same molarity. Human PBMCs (effector cells) were added into the wells to obtain a final E:T ratio of 10:1, corresponding to a E:T ratio of approximately 3 to 5 T cells for 1 tumor target cells. Negative control groups were represented by effector or target cells only. For normalization, maximal lysis of the MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. i) After 48 h incubation at 37° C., 5% $CO_2$, the cultured myeloma cells were collected, washed and stained with fluorochrome-conjugated antibodies and Annexin-V for determination of apoptotic myeloma cells. The staining panel comprised CD138-APCC750/CD38-FITC/CD5-B V510/CD56-PE/CD19-PerCP-Cy7/CD45-V450/Annexin-V-PerCP-Cy5.5. Fluorochrome-labelled antibodies used were purchased from BD Biosciences (San Jose, Calif.) and Caltag Laboratories (San Francisco Calif.). Acquisition was performed using a multicolor flow cytometer and installed software (e.g. CantoII device running FACS Diva software or FACSCalibur flow cytometer using the CellQUEST software). The Paint-A-Gate PRO program (BD Biosciences) was used for data analysis. Annexin-V was measured on JJN-3 cells and the percentage of annexin-v-positive JJN-3 cells was plotted against the concentration of anti-BCMA/anti-CD3 T cell bispecific antibodies. The percentage of lysis of JJN-3 cells induced by a specific concentration of anti-BCMA/anti-CD3 T cell bispecific antibody was also determined by measuring the absolute count of annexin-V-negative JJN-3 cells at a given TCB concentration and subtracting it from the absolute count of annexin-V-negative JJN-3 cells without TCB; divided by the absolute count of annexin-V-negative JJN-3 cells without TCB. FIG. 18-4 shows that 83A10-TCBcv anti-BCMA/anti-CD3 TCB antibody induced a concentration-dependent killing of BCMA low-expressing JJN-3 myeloma cells as measured by flow cytometry. The lysis of JJN-3 cells was specific since control-TCB antibody which does not bind to BCMA-positive target cells but only to CD3 on T cells did not induce increase in annexin-V positive JJN-3 cells or JJN-3 cell lysis, even at the highest concentration tested. Tables 16D and 16E summarize respectively the percentages of annexin-v positive JJN-3 cells and percentages of lysis of JJN-3 cells induced by anti-BCMA/anti-CD3 TCB antibodies.

TABLE 16D

Redirected T-cell killing of BCMA low-expressing JJN-3 cells induced by anti-BCMA/anti-CD3 TCB antibodies: percentages of annexin-V positive cells

| Annexin-V positive JJN-3 cells (%) | Anti-BCMA/anti-CD3 TCB concentration (pM) | | | | | | |
|---|---|---|---|---|---|---|---|
| | 10000 | 1000 | 100 | 10 | 1 | 0.1 | 0 |
| Experiment 1 | | | | | | | |
| 83A10-TCBcv | 16.78 | 10.21 | 9.12 | 11.11 | 11.36 | 8.14 | 9.6 |
| Control-TCB | 8.84 | / | / | / | / | / | / |
| Experiment 2 | | | | | | | |
| 83A10-TCBcv | 22.86 | 17.53 | 16.5 | 15.94 | 14.32 | 13.07 | 10.74 |
| Control-TCB | 12.82 | / | / | / | / | / | / |

TABLE 16E

Redirected T-cell killing of BCMA low-expressing JJN-3 cells induced by anti-BCMA/anti-CD3 TCB antibodies: percentages of lysis of JJN-3 cells

| Lysis of JJN-3 cells (%) | Anti-BCMA/anti-CD3 TCB concentration (pM) | | | | | | |
|---|---|---|---|---|---|---|---|
| | 10000 | 1000 | 100 | 10 | 1 | 0.1 | 0 |
| Experiment 1 | | | | | | | |
| 83A10-TCBcv | 70.30 | 26.66 | 18.43 | 41.88 | 24.42 | −14.45 | 0.00 |
| Control-TCB | −6.55 | / | / | / | / | / | / |
| Experiment 2 | | | | | | | |
| 83A10-TCBcv | 51.18 | 25.30 | 20.12 | 39.58 | −1.88 | 22.28 | 0.00 |
| Control-TCB | 4.18 | / | / | / | / | / | / |

Example 20: Comparison of Anti-BCMA/Anti-CD3 T Cell Bispecific Antibodies Containing APRIL Non-Blocking/Non-Competing Anti-BCMA Antibody Vs. APRIL-Blocking/Competing Anti-BCMA Antibody on the Redirected T-Cell Killing of BCMA-Positive Multiple Myeloma Cell Lines in Presence of High Concentrations of the Ligand In certain hematological malignancies such as multiple myeloma, the level of circulating BCMA-ligands APRIL and BAFF can be elevated (Moreaux et al. 2004; Blood 103(8): 3148-3157). Thus, the inventors recognize that high levels of ligands in the serum may interfere with the binding of anti-BCMA/anti-CD3 TCB antibodies to BCMA receptor on the tumor cells. In comparison to healthy donors, the levels of circulating APRIL (the high affinity ligand to BCMA) in multiple myeloma patient blood are ~100 ng/mL vs. ~10 ng/mL. For BAFF (the low affinity ligand to BCMA), the levels can fluctuate from 1-1000 ng/mL as compared to ~3 ng/mL in healthy donors. Nearby the tumor cells i.e. in the bone marrow microenvironment of multiple myeloma patients (the bone marrow being an organ constitutively rich in APRIL), APRIL/BAFF concentrations may very well be higher than the levels measured in the serum. More importantly, APRIL is constitutively expressed in the bone marrow microenvironment being an important survival factor to malignant myeloma cells and also being mainly produced and secreted by bone marrow myeloid precursor cells (Matthes et al. Blood 2011; 118 (7): 1838-1844). Thus, the concentrations of APRIL in the bone marrow of myeloma patients, which are expected to be of higher magnitude, up to 1000 ng/mL or even more, are of high relevance in this context. In certain autoimmune diseases such as systemic lupus erythematosus, the levels of circulating APRIL are also elevated with ~85 ng/mL (Koyama et al. 2005; Ann Rheum Dis 64: 1065-1067).

To verify whether APRIL non-blocking/non-competing anti-BCMA/anti-CD3 TCB antibodies would be advantageous over APRIL blocking/competing anti-BCMA/anti-CD3 TCB antibodies, APRIL non-blocking/non-competing anti-BCMA/anti-CD3 TCB antibodies were analyzed for their potential to induce T cell-mediated killing of BCMA-expressing myeloma cells upon crosslinking of the construct via binding of the antigen binding moieties to BCMA on cells in the presence of elevated concentrations of APRIL found in multiple myeloma patients (i.e. 100 ng/mL to 1000 ng/mL). Since APRIL binds to human BCMA with up to 1000-fold higher affinity than BAFF binds to the receptor, high concentrations of APRIL are more relevant in this context than those of BAFF. High levels of APRIL would most likely influence the efficacy of TCB antibodies, especially when the therapeutic is given at very low doses in patients (Bargou et al. Science 2008; 321 (5891); 974-7). Thus, the following experiments were performed in presence of APRIL.

Briefly, human BCMA-positive H929 multiple myeloma target cells were harvested with Cell Dissociation Buffer, washed and resuspended in RPMI supplemented with 10% fetal bovine serum (Invitrogen). Approximately, 30,000 cells per well were plated in a round-bottom 96-well plate and the respective dilution of the TCB constructs were added for a desired final concentration (in triplicates); final concentrations of anti-BCMA/anti-CD3 TCBs ranging from 0.1 pM to 10 nM, in presence or absence of APRIL at final concentration of 100 ng/mL or 1000 ng/mL. For an appropriate comparison, all TCB constructs and controls were adjusted to the same molarity. Human PBMCs (effector) were added into the wells to obtain a final E:T ratio of 10:1. Negative control groups were represented by effector or target cells only. As a positive control for the activation of human pan T cells, 1 µg/ml PHA (Sigma #L8902) was used. For normalization, maximal lysis of the H929 MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. After 24 h incubation at 37° C., 5% $CO_2$, LDH release from the apoptotic/necrotic H929 myeloma target cells into the supernatant was then measured with the LDH detection kit (Roche Applied Science), following the manufacturer's instructions. The percentage of LDH release was plotted against the concentrations of anti-BCMA/anti-CD3 T cell bispecific antibodies in concentration-response curves. The EC50 values were measured using Prism software (GraphPad) and determined as the TCB antibody concentration that results in 50% of maximum LDH release. As shown in FIG. 19, anti-BCMA/anti-CD3 TCB antibodies induced killing BCMA-positive H929 myeloma cells in presence or absence of exogenous APRIL. As depicted in FIG. 19A, APRIL non-blocking/non-competing 83A10-TCBcv induced a concentration-dependent killing of BCMA-positive H929 myeloma with a low picomolar potency ($EC50_{APRIL0}$=1.5 pM) in the absence of exogenous APRIL. When 100 ng/mL of APRIL was added into the culture, a concentration of APRIL that could be found in the blood of multiple myeloma patients, such concentration of ligand only minimally affected the killing potency mediated by 83A10-TCBcv as reflected by an 2.9-fold increase in the EC50 ($EC50_{APRIL100}$=4.3 pM). When a 10-fold higher concentration of APRIL (i.e. 1000 ng/mL), which could be found in the bone marrow of multiple myeloma patients, was added into the culture the killing potency mediated by 83A10-TCBcv was slightly reduced as reflected by a 6-fold increase in the EC50 ($EC50_{APRIL1000}$=9.0 pM). Despite this small reduction in the killing potency in presence of 1000 ng/mL of APRIL, APRIL non-blocking/non-competing 83A10-TCBcv could still efficiently kill BCMA-positive H929 myeloma cells with a potency in the low picomolar range. Table 17 summarizes the EC50 values of APRIL non-blocking/non-competing 83A10-TCBcv in absence and presence of exogenous APRIL.

TABLE 17

EC50 values for redirected T-cell killing of H929 cells induced by APRIL non-blocking/non-competing anti-BCMA/anti-CD3 TCB antibodies

| Anti-BCMA/anti-CD3 TCB molecules | EC50 (pM) | Fold increase |
|---|---|---|
| 83A10-TCBcv (no exogenous APRIL) | 1.5 | — |
| 83A10-TCBcv with 100 ng/mL APRIL | 4.3 | 2.9x |
| 83A10-TCBcv with 1000 ng/mL APRIL | 9.0 | 6x |

As depicted in FIG. 19B, APRIL blocking/competing J6M0-TCB induced a concentration-dependent killing of BCMA-positive H929 myeloma with a low picomolar potency ($EC50_{APRIL0}$=5.8 pM) in the absence of exogenous APRIL. When 100 ng/mL of APRIL was added into the culture, such concentration of ligand only minimally affected the killing potency mediated by J6M0-TCB as shown with an 2.4-fold increase in the EC50 ($EC50_{APRIL100}$=14.2 pM). However, when 1000 ng/mL of APRIL was added into the culture the killing potency mediated by J6M0-TCB was greatly reduced as reflected by an increase in the EC50 of 84.3-fold (EC50$_{APRIL1000}$=488.9 pM). Table 18 summarizes the EC50 values of APRIL blocking/competing J6M0-TCB in absence and presence of exogenous APRIL.

The overall results suggest that APRIL non-blocking/non-competing anti-BCMA/anti-CD3 TCB antibodies could have a clear advantage over APRIL blocking/competing anti-BCMA/anti-CD3 TCB antibodies by not being and/or being less influenced by high concentrations of APRIL which could well be present in the bone marrow microenvironment of multiple myeloma patients. Despite this small reduction in the killing potency in presence of 1000 ng/mL of APRIL, APRIL non-blocking/non-competing 83A10-TCBcv could still efficiently kill BCMA-positive H929 myeloma cells with a potency in the low picomolar range. Translating these observations into the clinical situation means that at a given low therapeutic dose of a TCB like 83A10-TCBcv in patients with high levels of APRIL in the bone marrow, the myeloma cells may still be killed. The situation could be different if a TCB like J6M0-TCB is used; the antitumor effect in patients with high levels of APRIL could well be lost. Alternative is to use a much higher therapeutic dose, but this increases the risk of side-effects (for the TCB blinatumomab, dose-dependent side-effects have been reported).

TABLE 18

EC50 values for redirected T-cell killing of H929 cells induced by APRIL blocking/competing anti-BCMA/anti-CD3 TCB antibodies

| Anti-BCMA/anti-CD3 TCB molecules | EC50 (pM) | Fold increase |
| --- | --- | --- |
| J6M0-TCB (no exogenous APRIL) | 5.8 | — |
| J6M0-TCB with 100 ng/mL APRIL | 14.2 | 2.4x |
| J6M0-TCB with 1000 ng/mL APRIL | 488.9 | 84.3x |

Example 21: 83A10-TCB without Charge Variant and 83A10-TCBcv with Charge Variant Show Similar Biological Properties It is expected that a TCB antibody with charge modifications in the CL-CH1 would behave similarly in cell-based assays and would display similar biological properties as their wildtype TCB counterpart without charge modification since the VL and VH CDRs remain identical in both molecules.

Figure 20:
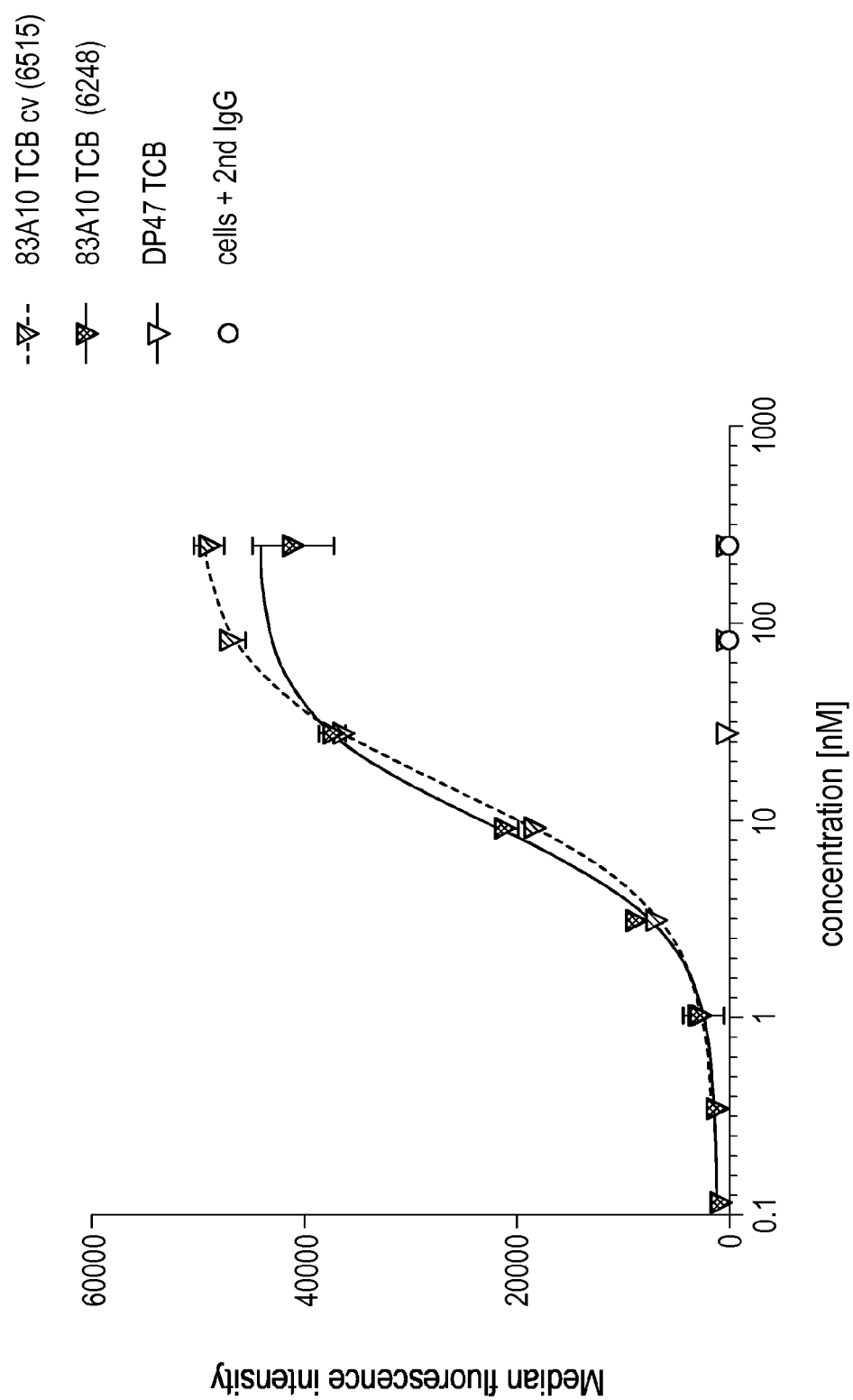
FIG. 20. Comparison between 83A10-TCB without charge variant and 83A10-TCBcv with charge variant on biological properties. (A) Head-to-head comparison: binding of 83A10-TCB and 83A10-TCBcv antibodies to H929 cells as detected by flow cytometry (experiment 1); (B) Head-to-head comparison: binding of 83A10-TCB and 83A10-TCBcv antibodies to H929 cells and MKN45 cells as detected by flow cytometry (experiment 2); (C-F) Comparison of 83A10-TCB antibody (C, D) and 83A10-TCBcv antibody (E, F) to induce T-cell redirected killing of BCMA-positive H929 myeloma cells. E:T ratio used as 10 PBMCs:1 H929 cell; cells were incubated for 24 h before measurement of LDH release (see Example 21).
Figure 20:
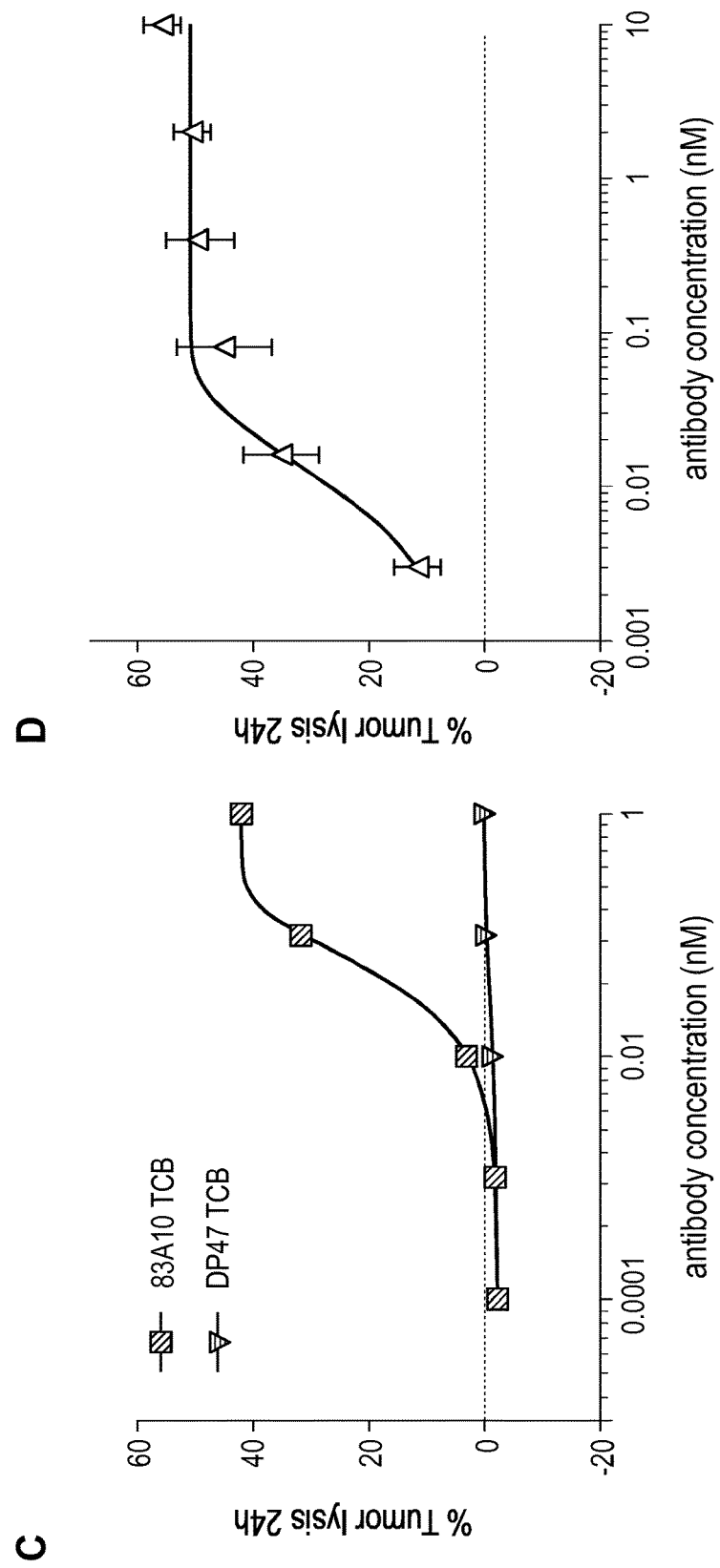
Figure 20:
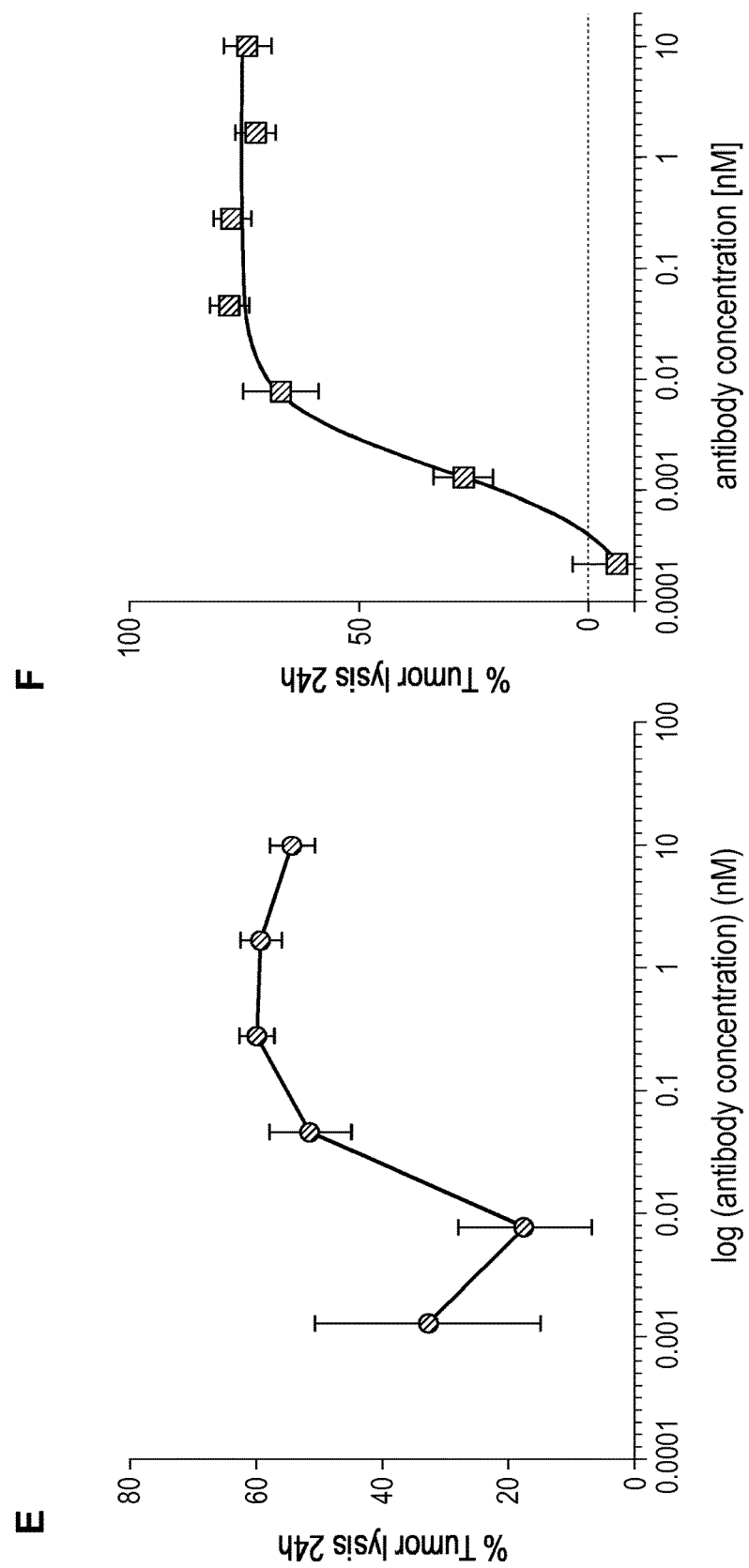

One of the most relevant biological properties to compare TCB with charge variant vs. TCB without charge variant would be the capacity of the TCB antibodies to bind to cells. FIG. 20A depicts the binding of 83A10-TCB and 83A10-TCBcv to BCMA-positive H929 cells in a concentration-dependent manner and with similar potency, respectively EC50=9.8 nM vs. EC50=14.5 nM. DP47-TCB control antibody did not bind to BCMA-positive H929 myeloma cells as measured by a lack of increase in median fluorescence intensity. In a second head-to-head comparison experiment, 83A10-TCB and 83A10-TCBcv were evaluated for binding to BCMA-positive H929 cells and lack of binding to BCMA/CD3-negative MKN45 cells. As depicted in FIG. 20B, 83A10-TCB and 83A10-TCBcv bind to BCMA-positive H929 cells in a concentration-dependent manner and with similar potency, respectively EC50=16.9 nM and EC50=14.5 nM. EC50 values for the binding of 83A10-TCB and 83A10-TCBcv to H929 cells for both experiments are summarized in Table 19.

TABLE 19

EC50 values for binding of 83A10-TCB antibody and 83A10-TCBcv antibody to H929 cells (Experiments 1 and 2).

| Anti-BCMA/anti-CD3 TCB molecules | EC50 (nM) | EC50 (µg/ml) |
| --- | --- | --- |
| Experiment 1 | | |
| 83A10-TCB | 9.8 | 1.9 |
| 83A10-TCBcv | 14.5 | 2.8 |
| Experiment 2 | | |
| 83A10-TCB | 16.9 | 3.25 |
| 83A10-TCBcv | 14.5 | 2.8 |

Another relevant biological property to compare TCB antibodies with charge variant vs. TCB antibodies without charge variant would be their capacity to induce redirected T-cell killing of target cells. As shown in FIG. 20C-F, anti-BCMA/anti-CD3 TCB antibodies ((C, D) 83A10-TCB, (E, F) 83A10-TCBcv) induced a concentration-dependent killing of BCMA-positive H929 myeloma cells as measured by LDH release. The killing of H929 cells was specific since DP47-TCB control antibody which does not bind to BCMA-positive target cells did not induce LDH release, even at the highest concentration of nM (C). Even though EC50 values were not measurable with Prism (GraphPad) statistical software for 83A10-TCB (C, D) and 83A10-TCBcv (E, Experiment 1), the magnitude of EC50 values could be approximately estimated to low picomolar range potency for both non-charged and charged TCB molecules. In a second experiment, the effect of 83A10-TCBcv was evaluated in the redirected T-cell killing assay and an EC50 value could be measured to 1.5 pM (F). The authors could not exclude that the slightly lower EC50 value (slightly better potency) could be due to blood donor variability. However, the magnitude of potency to kill H929 cells was definitely in the low picomolar range. The overall results suggest that 83A10-TCB (without charge variant) vs. 83A10-TCBcv (with charge variant) shows similar biological properties in cell-based assays. EC50 values for the redirected T-cell killing of H929 cells induced by 83A10-TCB and 83A10-TCBcv are summarized in Table 20.

TABLE 20

EC50 values and estimations for redirected T-cell killing of H929 cells induced by 83A10-TCB and 83A10-TCBcv antibodies

| Anti-BCMA/anti-CD3 TCB molecules | EC50 (pM) | EC50 (µg/ml) |
| --- | --- | --- |
| 83A10-TCB (Experiment 1) | Low pM range (approx. <20) | Single digit |
| 83A10-TCB (Experiment 2) | Low pM range (approx. <20) | Single digit |
| 83A10-TCBcv (Experiment 1) | Low pM range (approx. <20) | Single digit |
| 83A10-TCBcv (Experiment 2) | 1.5 | 0.3 |

Example 22: BCMA Expression on Bone Marrow Myeloma Cells from Multiple Myeloma Patients Human cell lines expressing the tumor target of interest are very useful and practical tools for the measurement of TCB antibody potency to induce tumor cell cytotoxicity in presence of T cells and determination of EC50 values and for the ranking of TCB molecules. However, despite being readily accessible and practical human myeloma cell lines have the caveat of not representing the heterogeneity of multiple myeloma, a very complex disease which is characterized by a significant heterogeneity at the molecular level. In addition, myeloma cell lines do not express BCMA receptor with the same intensity and density as some cells express BCMA more strongly than others (e.g. H929 cells vs. U266 or RPMI-8226 cells), suggesting that such heterogeneity at the cellular level may also been observed among different patients. Throughout academic collaborations with key opinion leaders in multiple myeloma, determination of BCMA expression and density in patient samples and evaluation of the anti-BCMA/anti-CD3 TCB antibodies with clinical patient samples are being investigated. Blood and bone marrow aspirates are collected from multiple myeloma patients after informed consent is given, in accordance with local ethical committee guidelines and the Declaration of Helsinki.

a) BCMA Expression as Detected by Flow Cytometry (Median Fluorescence Intensity)

To determine the expression of BCMA receptor on bone marrow myeloma cells, immunophenotypic analyses are performed using freshly isolated bone marrow aspirates. Erythrocyte-lysed $K_3$-EDTA (ethylenediaminetetraacetic acid) anticoagulated whole bone marrow samples are used for the immunophenotypic analyses. A total of $2 \times 10^6$ cells per tube are stained, lysed, and then washed using a direct immunofluorescence technique and multicolor staining, which is aimed at the specific identification and immunophenotypic characterization of malignant plasma cells identified as $CD138^+$ $CD38^+$ $CD45^+$ $CD19^-$ $CD56^+$. The cells are then stained using a panel of fluorochrome-conjugated antibodies including at least CD38-FITC/CD56-PE/CD19-PerCP-Cy7/CD45-V450/BCMA-APC. Fluorochrome-labelled antibodies used are purchased from BD Biosciences (San Jose, Calif.) and Caltag Laboratories (San Francisco Calif.). In-house APC-conjugated anti-human BCMA antibody is used in the immunophenotypic analyses. Acquisition is performed using a multicolor flow cytometer and installed software (e.g. Cantoll device running FACS Diva software or FACSCalibur flow cytometer using the CellQUEST software). The Paint-A-Gate PRO program (BD Biosciences) is used for data analysis. BCMA expression is measured gated on the malignant plasma cell population and median fluorescence intensity values are determined and compared among the myeloma patients.

TABLE 21

BCMA expression on patient bone marrow myeloma plasma cells as detected by multiparameter flow cytometry (mean fluorescence intensity)

| Patient No | $MFI_{BCMA}$ |
|---|---|
| P1 | 2863 |
| P2 | 3528 |
| P3 | 602 |
| P4 | 389 |
| P5 | 955 |
| P6 | 1475 |
| P7 | 282 |
| P8 | 1621 |
| P9 | 116 |
| P10 | 125 |
| P11 | 1495 |
| P12 | 2451 |
| P13 | 398 |
| P14 | 2040 |
| P15 | 678 |
| P16 | 945 |
| P17 | 1672 |
| P18 | 1491 |

TABLE 21-continued

BCMA expression on patient bone marrow myeloma plasma cells as detected by multiparameter flow cytometry (mean fluorescence intensity)

| Patient No | $MFI_{BCMA}$ |
|---|---|
| P19 | 2198 |
| P20 | 1058 |
| P21 | 3594 |
| P22 | 615 |
| P23 | 159 | b) Determination of BCMA Antigen Copy Number (Quantitative Flow Cytometry Analysis)

(i) The Qifikit (Dako) method is used to quantify BCMA antigen copy number on the cell surface of H929 cells. H929 cells are once washed with FACS buffer (100 µl/well; 350×g for 5 min) and adjusted to 1 Mio cells/ml. 50 µl (=0.5 Mio cells) of the cell suspension are transferred into each well of a 96 round bottom well plate, as indicated. Then, 50 µl of mouse anti-human BCMA IgG (BioLegend #357502) or a mouse IgG2a isotype control (BioLegend #401501) diluted in FACS buffer (PBS, 0.1% BSA) to a final concentration of 25 µg/ml (or at saturation concentrations) are added and staining is performed for 30 min at 4° C. in the dark. Next, 100 µl of the Set-up or Calibration Beads are added in separate wells and the cells, as well as the beads are washed twice with FACS buffer. Cells and beads are resuspended in 25 µl FACS buffer, containing fluorescein conjugated anti-mouse secondary antibody (at saturation concentrations), provided by the Qifikit. Cells and beads are stained for 45 min at 4° C. in the dark. The cells are washed once and all samples are resuspended in 100 µl FACS buffer. Samples are analyzed on a multicolor flow cytometer and installed software (e.g. Cantoll device running FACS Diva software or FACSCalibur flow cytometer using the CellQUEST software). Alternatively, in some studies instead of using a commercial mouse anti-human BCMA IgG as primary antibody, in-house anti-human BCMA IgG antibodies (e.g. 83A10 IgG, 17A5-IgG or 13A4) IgG with optimal binding properties are used followed by an additional incubation step with a commercial unconjugated first secondary antibody against human IgG-Fc (Abcam, Cat no. ABM121) before the calibration beads are incubated with the cells in presence of FACS buffer containing fluorescein conjugated anti-mouse second secondary antibody. When primary and secondary antibodies are used at saturating concentrations, the number of bound primary antibody molecules corresponds to the number of antigenic sites present on the cell surface and the fluorescence is correlated with the number of bound primary antibody molecules on the cells and on the beads.

(ii) The Qifikit (Dako) method was used to quantify BCMA specific antigen binding capacity (SABC) on the cell surface of patient bone marrow myeloma plasma cells. Myeloma plasma cells isolated from whole bone marrow aspirates were stained with 50 µl of mouse anti-human BCMA IgG (BioLegend #357502) or a mouse IgG2a isotype control (BioLegend #401501) diluted in FACS buffer (PBS, 0.1% BSA) to a final concentration of 25 µg/ml (or at saturation concentrations) and staining was performed for 30 min at 4° C. in the dark. Next, 100 µl of the Set-up or Calibration Beads were added in separate wells and the cells, as well as the beads were washed twice with FACS buffer. Cells and beads were resuspended in 25 µl FACS buffer, containing fluorescein conjugated anti-mouse secondary antibody (at saturation concentrations), provided by the Qifikit. Cells and beads were stained for 45 min at 4° C. in the dark. The cells were washed once and all samples were resuspended in 100 µl FACS buffer. Samples were analyzed immediately on a multicolor flow cytometer and installed software (e.g. Cantoll device running FACS Diva software or FACSCalibur flow cytometer using the CellQUEST software).

TABLE 22

BCMA specific antigen binding capacity on patient bone marrow myeloma plasma cells as measured by quantitative flow cytometry analysis

| Patient No | $SABC_{BCMA}$ |
|---|---|
| P1 | n/a |
| P2 | n/a |
| P3 | 679 |
| P4 | 145 |
| P5 | 957 |
| P6 | 969 |
| P7 | 554 |
| P8 | 4479 |
| P9 | 350 |
| P10 | 414 |
| P11 | 2756 |
| P12 | 2911 |
| P13 | 1267 |
| P14 | 3453 |
| P15 | 1006 |
| P16 | 1097 |
| P17 | 1622 |
| P18 | 429 |
| P19 | 1684 |
| P20 | 383 |
| P21 | 1602 |
| P22 | 799 |
| P23 | 204 |

Example 23: Redirected T-Cell Cytotoxicity of Bone Marrow Patient Myeloma Cells Induced by Anti-BCMA/Anti-CD3 T Cell Bispecific Antibodies (Flow Cytometry)

a) One of the most meaningful and critical in vitro characterization during preclinical evaluation of TCB antibody candidates for multiple myeloma is whether the TCB molecule could activate the patients' T cells and induce redirected T-cell killing of primary myeloma cells from the patients' bone marrow. To evaluate the effect of anti-BCMA/anti-CD3 TCB antibodies to induce redirected T-cell killing of bone marrow myeloma cells, autologous blood T cells isolated from whole blood and erythrocyte-lysed whole bone marrow samples are collected and prepared. In the first experimental setting, autologous marrow-infiltrated T cells are used as effector cells and TCB antibodies are spiked directly in the erythrocyte-lysed whole bone marrow samples. The ratio of effector cells to tumor cells (E:T ratio) present in the whole bone marrow sample is determined and measured by flow cytometry. Preferably, an E:T ratio of 1-3 $CD3^+$ cells for 1 myeloma cell is used. In a second experimental setting, autologous blood T cells isolated from patient whole blood are added into the whole bone marrow sample to obtain an E:T ratio of 1-3 $CD3^+$ cells for 1 myeloma cell. Briefly, 200 µl of the prepared erythrocyte-lysed whole bone marrow sample are transferred to 96 deep-well plates. Anti-BCMA/anti-CD3 TCB antibody and control antibody dilutions are prepared in sterile PBS and 10 µl of the preparation are added to the respective wells for final concentrations ranging from 0.1 pM to 100 nM. The whole bone marrow-antibody suspension is mixed by gentle shaking and then incubated at 37° C., 5% $CO_2$ for 24 h to 48 h, sealed with paraffin film. After the incubation period, 20 µl of a corresponding FACS antibody solution prepared based on an antibody-panel including CD138-APCC750/CD38-FITC/CD5-B V510/CD56-PE/CD19-PerCP-Cy7/CD45-V450/BCMA-APC/Annexin-V-PerCP-Cy5.5 are added into a 96-U-bottom plate. Fluorochrome-labelled antibodies are purchased from BD Biosciences (San Jose, Calif.) and Caltag Laboratories (San Francisco Calif.) and in-house APC-conjugated anti-human BCMA antibody is used. The samples are then incubated for 15 minutes in the dark at room temperature and acquired and analyzed using a multicolor flow cytometer. Cell death of the myeloma cells is determined by evaluating annexin-V positive expression gated on the myeloma cell populations $CD138^+$ $CD38^+$ $CD45^+$ $CD19^-$ and $CD138^+$ $CD38^+$ $CD45^+$ $CD19^-$ $BCMA^+$. Percentages of myeloma cell death is then determined.

Figure 21:
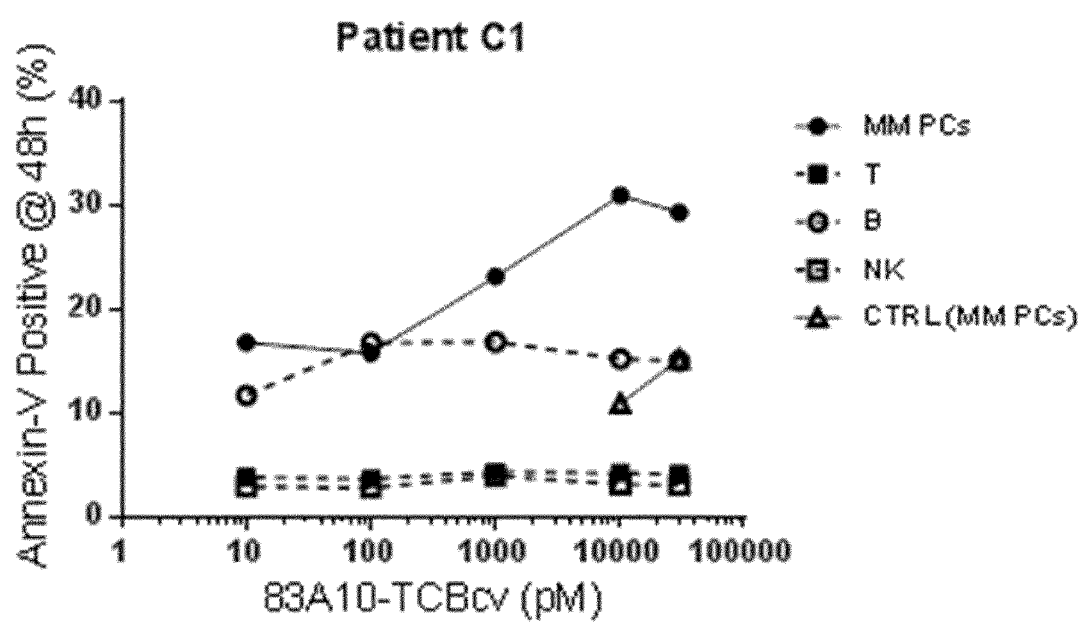
FIG. 21. Redirected T-cell lysis of multiple myeloma patient bone marrow myeloma plasma cells in presence of autologous bone marrow infiltrating T cells (patient's whole bone marrow aspirates) induced by anti-BCMA/anti-CD3 T-cell bispecific antibodies as measured by multiparameter flow cytometry. Percentage of annexin-V positive myeloma plasma cells was determined and plotted against TCB concentrations. Concentration-dependent and specific lysis of patient myeloma plasma cells were observed with 83A10-TCBcv while lysis of T cells, B cells, and NK cells was not observed based on an 8-color multiparameter panel. No induction of cell death of myeloma plasma cells with control-TCB at the highest concentration of TCB antibodies tested (see Example 23).

To evaluate whether anti-BCMA/anti-CD3 TCB antibodies induce activation of myeloma patient $CD4^+$ and $CD8^+$ T cells (e.g. bone marrow infiltrated T cells (MILs) and blood T cells), the samples from the respective treated, untreated and control groups are also stain with a FACS antibody solution prepared based on an antibody-panel including CD8-APCH7/CD69-FITC/CD107-B V510/CD16-PE/CD25-PerCP-Cy7/CD4-PacB/HLD-DR-APC/CD3-PerCP-Cy5.5. The samples are then incubated for 15 minutes in the dark at room temperature and acquired and analyzed using a multicolor flow cytometer. T-cell activation is determined by evaluating CD25 and/or CD69 positive expression gated on $CD4^+$ and $CD8^+$ T-cell populations. Percentages of T-cell activation are then measured.

b) To evaluate the effect of anti-BCMA/anti-CD3 TCB antibodies to induce redirected T-cell killing of bone marrow myeloma plasma cells, whole bone marrow aspirates were collected from multiple myeloma patients in EDTA-coated tubes and immediately used or the cell culture assays. The ratio of effector cells to tumor cells (E:T ratio) present in the whole bone marrow samples was determined and measured by flow cytometry. Briefly, 200 µl of bone marrow samples were transferred into 96 deep-well plates. Anti-BCMA/anti-CD3 TCB antibody and control antibody dilutions were prepared in sterile medium and 10 µl of the preparation were added to the respective wells for final concentrations ranging from 0.1 pM to 30 nM. The bone marrow-antibody suspension is mixed by gentle shaking and then incubated at 37° C., 5% CO2 for 48 h, sealed with paraffin film. After the incubation period, 20 µl of a corresponding FACS antibody solution prepared based on an antibody-panel including CD138-APCC750/CD38-FITC/CD5-B V510/CD56-PE/CD19-PerCP-Cy7/CD45-V450/BCMA-APC/Annexin-V-PerCP-Cy5.5 were added into a 96-U-bottom plate. Fluorochrome-labelled antibodies were purchased from BD Biosciences (San Jose, Calif.) and Caltag Laboratories (San Francisco Calif.) and in-house APC-conjugated anti-human BCMA antibody was used. The samples were then incubated for 15 minutes in the dark at room temperature and acquired and analyzed using a multicolor flow cytometer. Cell death of the myeloma cells was determined by evaluating annexin-V positive expression gated on the myeloma cell populations CD138+ CD38+ CD45+ CD19− CD56+. Percentage of myeloma cell death was then determined. The percentage of lysis of patient bone marrow myeloma plasma cells induced by a specific concentration of anti-BCMA/ anti-CD3 T cell bispecific antibody was also determined by measuring the absolute count of annexin-V-negative myeloma plasma cells at a given TCB concentration and subtracting it from the absolute count of annexin-V-negative myeloma plasma cells without TCB; divided by the absolute count of annexin-V-negative myeloma plasma cells without TCB. To verify the specificity of the anti-BCMA/anti-CD3 T cell bispecific antibodies, annexin-V expression was also measured in other bone marrow cell types such as T cells, B cells and NK cells. As shown in FIG. 21, there was a concentration-dependent and specific lysis of patient myeloma plasma cells while lysis of T cells, B cells, and NK cells was not observed. In addition, control-TCB which binds to CD3 only but not to BCMA did not induce cell death of myeloma plasma cells at the highest concentrations of TCB antibodies. As shown in Table 23, percentage of annexin-V positive patient bone marrow myeloma cells at the highest concentration (30 nM) reached up to 29.31% for 83A10-TCBcv, suggesting that 83A10-TCBcv is potent to induce killing of patient bone marrow myeloma plasma cells.

TABLE 23

Percentage of annexin-V positive myeloma plasma cells from patient bone marrow aspirates induced by anti-BCMA/anti-CD3 T cell bispecific antibodies.

Figure 22:
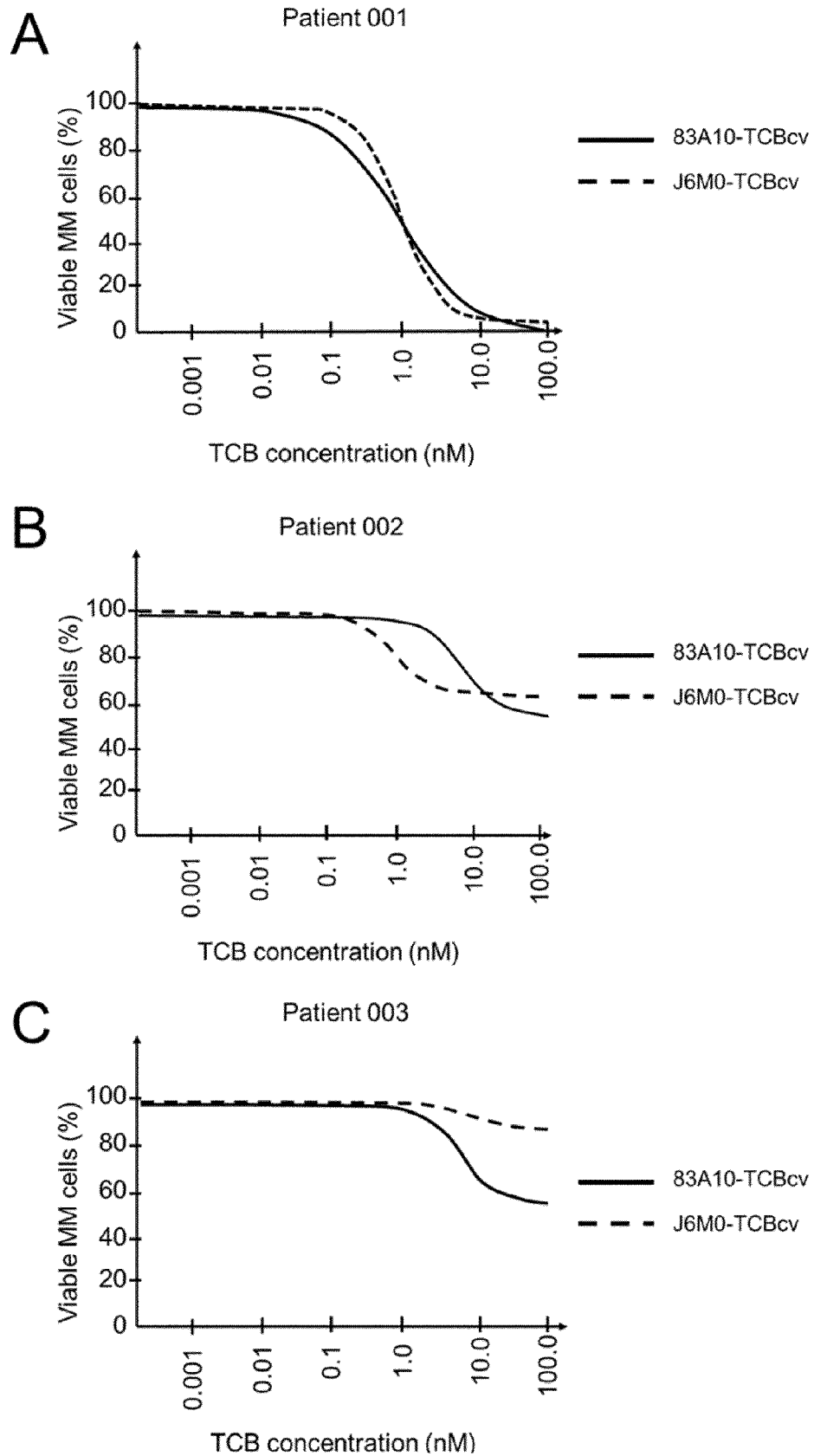
FIG. 22. Redirected T-cell lysis of multiple myeloma patient bone marrow myeloma plasma cells in presence of autologous bone marrow infiltrating T cells induced by anti-BCMA/anti-CD3 T-cell bispecific antibodies as measured by flow cytometry. Percentage of viable myeloma plasma cells was determined by gating on annexin-V negative cell population and plotted against the concentration of 83A10-TCBcv anti-BCMA/anti-CD3 T cell bispecific antibody for Patient 001 (A), Patient 002 (B) and Patient 003 (c). 83A10-TCBcv induced lysis of myeloma plasma cells in myeloma patient bone marrow aspirate samples. Concentration-dependent reduction of viable myeloma cells was observed in 3/3 patient samples treated with 83A10-TCBcv. Comparison of 83A10-TCBcv with J6M0-TCBcv (an antibody reported to be competing with APRIL on the binding to BCMA (Tai et al., Blood 2014)): In 3/3 patient samples, 83A10-TCBcv induced more lysis of myeloma plasma cells from patient bone marrow aspirates than with J6M0-TCB at equimolar maximum dose of 30 nM (see Example 23).

| Annexin-V positive myeloma plasma cells (%) | Anti-BCMA/anti-CD3 T cell bispecific antibody concentration (pM) | | | | | |
|---|---|---|---|---|---|---|
| | 30000 | 10000 | 1000 | 100 | 10 | 0 |
| 83A10-TCBcv | 29.31 | 30.95 | 23.14 | 15.74 | 16.76 | 13.11 | c) In another study in bone marrow aspirates from 3 MM patients, the percentage of viable myeloma plasma cells was determined by gating on annexin-V negative cell population and plotted against the concentration of anti-BCMA/anti-CD3 T cell bispecific antibody. The EC50 values were measured and determined as the TCB antibody concentration that results in 50% of maximum viable myeloma plasma cells. EMAX (%) was determined as maximum of viable myeloma plasma cells in presence of respective anti-BCMA/anti-CD3 T cell bispecific antibody. 83A10-TCBcv was potent in inducing lysis of myeloma plasma cells in myeloma patient bone marrow aspirate samples (Table 24; FIG. 22). Concentration-dependent reduction of viable myeloma cells was observed in 3/3 patient samples treated with 83A10-TCBcv. FIG. 22 and Table 24 also show the comparison of 83A10-TCBcv with J6M0-TCBcv (J6M0 is an antibody reported to be competing with APRIL on the binding to BCMA (Tai et al., Blood 2014) in respect to EC50 and EMAX (%) values, performed in a subsequent study. In 3/3 patient samples, 83A10-TCBcv induced more lysis of myeloma plasma cells from patient bone marrow aspirates than with J6M0-TCBcv at equimolar maximum dose of 30 nM as reflected by the EMAX values representing the percentage of viable myeloma plasma cells (the lower this percentage is, the higher the percentage of lysed cells). The EC50 values also showed that 83A10-TCBcv was also more potent than J6M0-TCBcv in 2/3 patient samples.

TABLE 24

EC50 (nM) and EMAX (%) values in respect to annexin-V negative myeloma plasma cells from patient bone marrow aspirates in presence of by anti-BCMA/anti-CD3 T cell bispecific antibodies.

Figure 23:
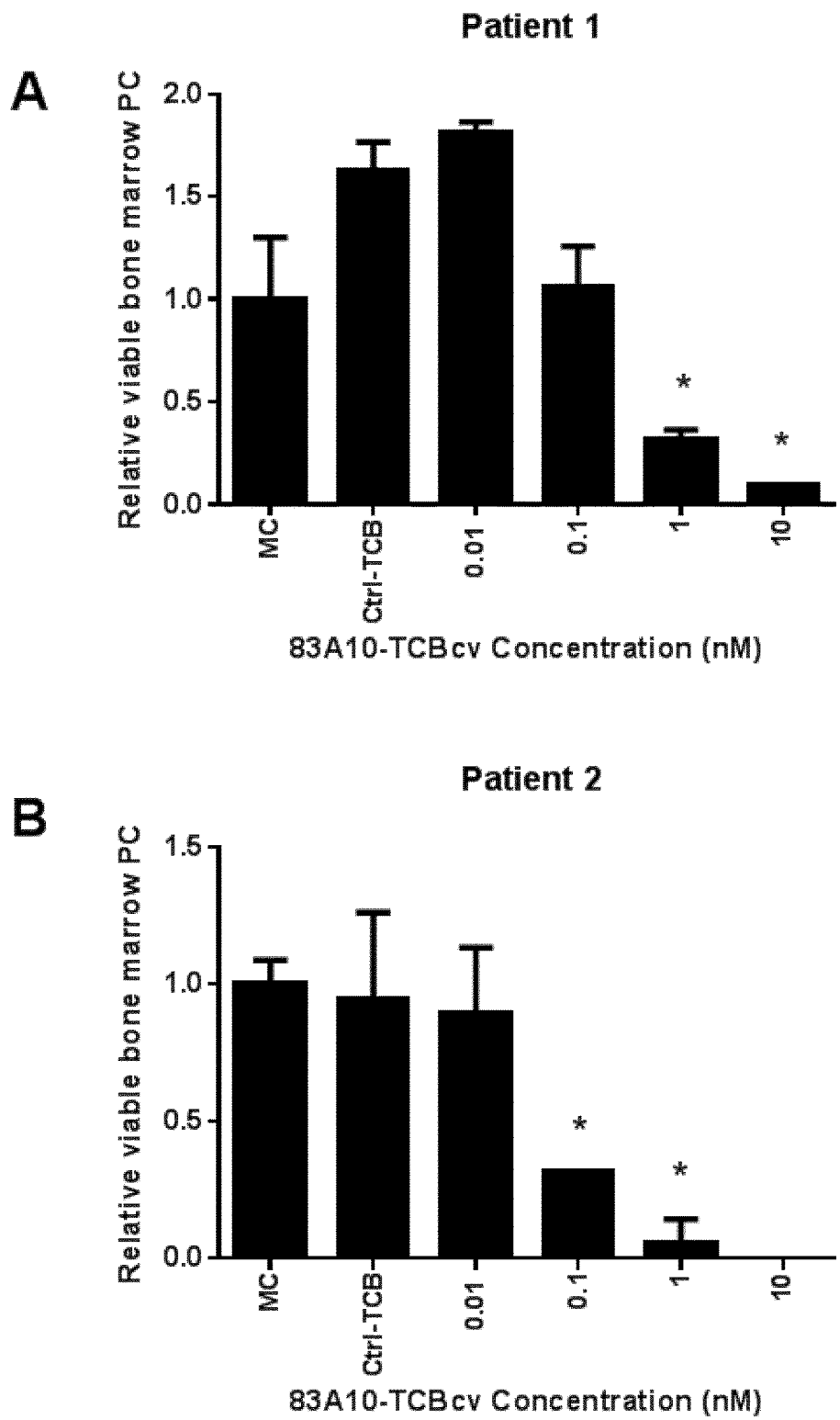
FIG. 23. Redirected T-cell lysis of multiple myeloma patient bone marrow myeloma plasma cells in presence of autologous bone marrow infiltrating T cells induced by anti-BCMA/anti-CD3 T-cell bispecific antibodies as measured by flow cytometry. Percentage of propidium iodide negative myeloma plasma cells was determined and the percentage of viable bone marrow plasma cells relative to the medium control (MC) was plotted against TCB concentrations. Concentration-dependent and specific lysis of patient myeloma plasma cells were observed with 83A10-TCBcv (A-G) while lysis of bone marrow microenvironment (BMME) was not observed (H). No induction of cell death of myeloma plasma cells observed with control-TCB at the highest concentration of TCB antibodies tested. 83A10-TCBcv induced potent killing of patient bone marrow myeloma plasma cells as reflected by the concentration-dependent reduction of viable (propidium iodide negative) myeloma plasma cells. An effect was considered statistically significant if the P-value of its corresponding statistical test was <5% (*), <1% () or <0.1% (*). Experiments performed using bone marrow aspirate samples collected from patient 1 (A), patient 2 (B), patient 3 (C), patient 4 (D), patient 5 (E), patient 6 (F), and patient 7 (G, H) (see Example 23).
Figure 23:
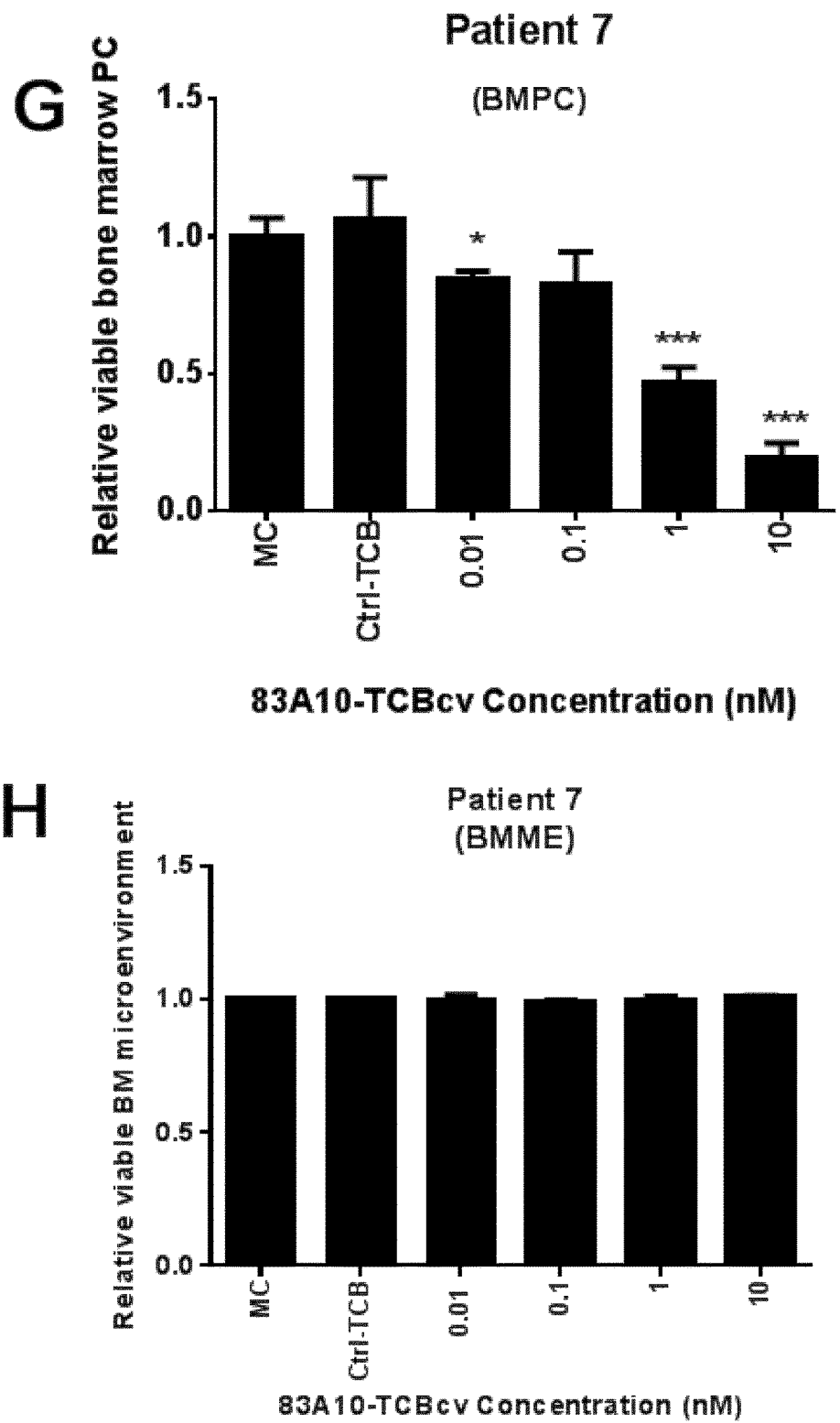

| Bone marrow aspirate patient sample | 83A10-TCBcv | | J6M0-TCBcv | |
|---|---|---|---|---|
| | EC50 (nM) | EMAX (%) | EC50 (nM) | EMAX (%) |
| Patient 001 | 1.0 | 0.62 | 1.0 | 4.43 |
| Patient 002 | 8.24 | 55.5 | 1.0 | 63.6 |
| Patient 003 | 8.02 | 56.0 | 9.5 | 87.5 | d) In a further investigations of the new anti-BCMA/anti-CD3 T cell bispecific antibodies of this invention compared to 83A10-TCBcv, seven freshly taken patient whole bone marrow samples/aspirates were stained with CD138 magnetic microbeads (Miltenyi Biotec, Bergisch Gladbach, Germany), passed through an autoMACS cell separation column and the collected fractions with sufficient remaining number of MM plasma cells of usually >4% myeloma plasma cells were used for further experiments. In 24-well plates, 500,000 cells/well were incubated and cultured for 48 hours. Anti-BCMA/anti-CD3 TCB antibodies and control antibody dilutions were added to the respective wells for a final TCB concentration of 0.1. pM to 10 nM. Each dose point was done in triplicates. Viability of the plasma cells and cells of the bone marrow microenvironment was investigated by propidium iodide/CD138-FITC double-staining using flow cytometry (FACSCalibur; Becton Dickinson). Data analysis was performed using FACSDiva Software (Becton Dickinson). As depicted in FIG. 23, bar plots show mean values normalized on the mean over the triplicates of the respective medium control (MC). For statistical analysis, a one-sided t-test was used. The maximum inhibition of MM plasma cell growth at a concentration of 10 nM (IMAX10) and the inhibition measured at 1 nM (IMAX1), respectively, were given in percent as referred to the medium control. The maximum inhibition of the control-TCB antibody (10 nM) compared to the medium control was also depicted. Computations were performed using R 3.1.19, and Bioconductor 2.1310, but for calculation of the IMAX values (Microsoft Excel®; Microsoft Office Professional 2013). An effect was considered statistically significant if the P-value of its corresponding statistical test was <5% (*), <1% () or <0.1% (*). As shown in FIGS. 23A-23G, the results clearly show that there were less viable bone marrow myeloma plasma cells with 83A10-TCBcv (i.e. more lysis of the bone marrow myeloma plasma cells) in 7/7 patient samples as compared to medium control. Table 25 demonstrates the percentage of viable myeloma plasma cells from patient bone marrow aspirates induced by anti-BCMA/anti-CD3 T cell bispecific antibodies relative to medium control. Table 26 shows the IMAX10 and IMAX1 values. The results demonstrate that 83A10-TCBcv is potent to induce killing of patient bone marrow myeloma plasma cells. Despite specific lysis of bone marrow plasma cells (BMPC) induced by the anti-BCMA/anti-CD3 T cell bispecific antibodies and observed in all bone marrow patient samples, the bone marrow microenvironment (BMME) was unaffected in the respective samples (FIG. 23H, representative of 7 patient samples).

TABLE 25

Relative percentage of propidium iodide negative viable myeloma plasma cells from patient bone marrow aspirates induced by anti-BCMA/anti-CD3 T cell bispecific antibodies.

| | Anti-BCMA/anti-CD3 T cell bispecific antibody concentration (nM) | | | |
|---|---|---|---|---|
| | 0.01 | 0.1 | 1 | 10 |
| Patient sample No. 1/Viable myeloma plasma cells (%) | | | | |
| 83A10-TCBcv | 181.3 | 106.3 | 31.3 | 9.4 |
| Ctrl-TCB | / | / | / | 162.5 |
| Patient sample No. 2/Viable myeloma plasma cells (%) | | | | |
| 83A10-TCBcv | 89.5 | 31.6 | 5.3 | 0 |
| Ctrl-TCB | / | / | / | 94.7 |
| Patient sample No. 3/Viable myeloma plasma cells (%) | | | | |
| 83A10-TCBcv | 76.7 | 35.0 | 1.7 | 0 |
| Ctrl-TCB | / | / | / | 86.7 |
| Patient sample No. 4/Viable myeloma plasma cells (%) | | | | |
| 83A10-TCBcv | 93.9 | 51.5 | 9.1 | 6.1 |
| Ctrl-TCB | / | / | / | 127.3 |
| Patient sample No. 5/Viable myeloma plasma cells (%) | | | | |
| 83A10-TCBcv | 100 | 91.4 | 62.9 | 20.0 |
| Ctrl-TCB | / | / | / | 85.7 |
| Patient sample No. 6/Viable myeloma plasma cells (%) | | | | |
| 83A10-TCBcv | 55.6 | 22.2 | 6.7 | 4.4 |
| Ctrl-TCB | / | / | / | 117.8 |
| Patient sample No. 7/Viable myeloma plasma cells (%) | | | | |
| 83A10-TCBcv | 84.4 | 82.6 | 46.8 | 19.3 |
| Ctrl-TCB | / | / | / | 106.4 |

TABLE 26

IMAX10 and IMAX1 values in respect to maximal inhibition of MM plasma cell growth at 10 nM IMAX10 and inhibition at 1 nM IMAX1 based on propidium iodide negative viable myeloma plasma cells from patient bone marrow aspirates in presence of by anti-BCMA/anti-CD3 T cell bispecific antibodies.

| | 83A10-TCBcv | | Ctrl-TCB |
|---|---|---|---|
| Patient Sample No. | IMAX10 (%) | IMAX1 (%) | IMAX10 (%) |
| 1 | 90.6 | 68.8 | −62.5 |
| 3 | 100 | 94.7 | 5.3 |
| 4 | 100 | 98.3 | 13.3 |
| 5 | 93.9 | 90.9 | −27.3 |
| 6 | 80.0 | 37.1 | 14.3 |
| 7 | 95.6 | 93.3 | −17.8 |
| 8 | 80.7 | 53.2 | −6.4 |

Example 23A: T-Cell Activation of Patient Bone Marrow T Cells Induced by Anti-BCMA/Anti-CD3 T Cell Bispecific Antibodies (Multiparameter Flow Cytometry)

Figure 24:
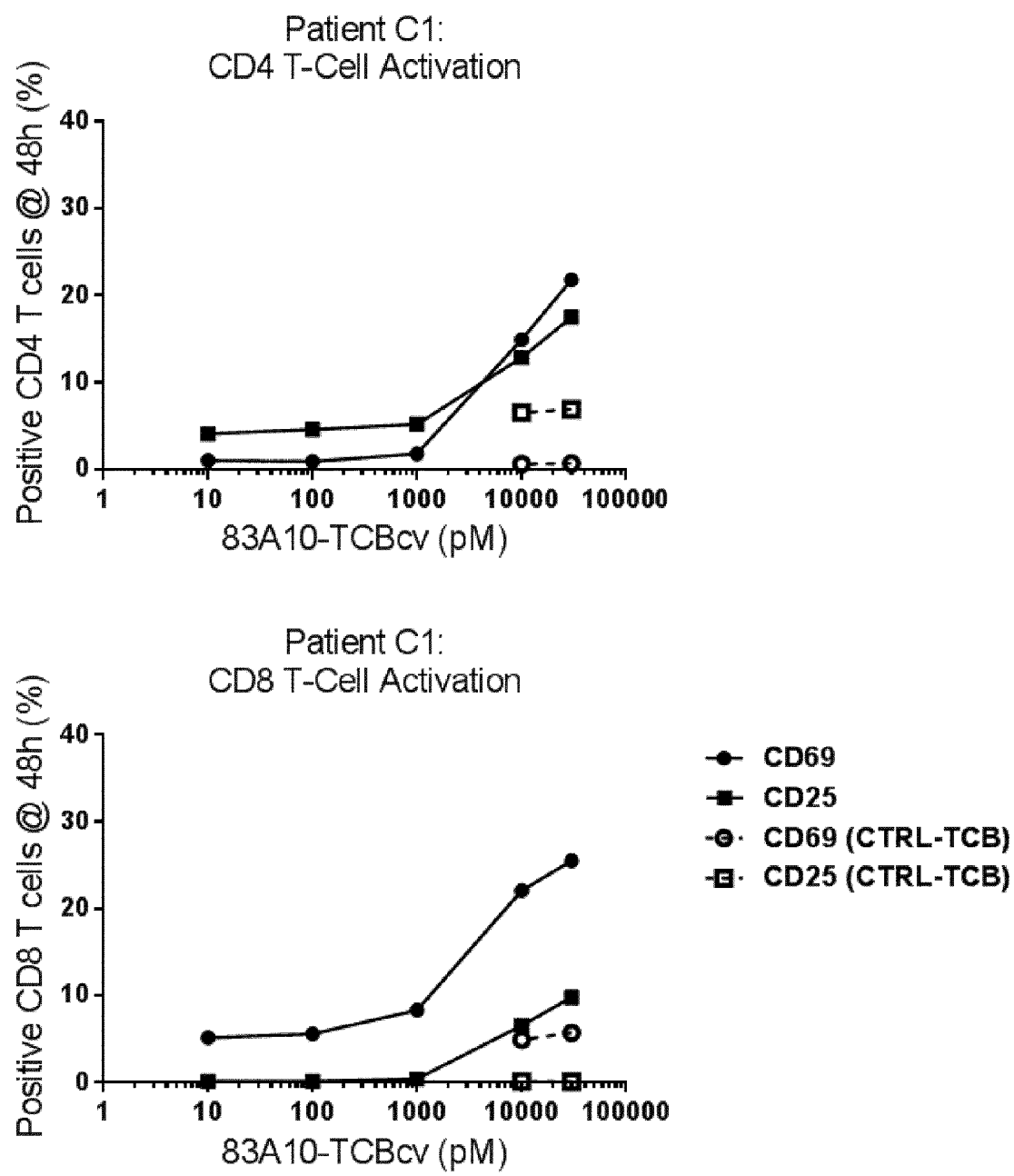
FIG. 24. Activation of myeloma patient bone marrow T cells in presence of bone marrow plasma cells (patient whole bone marrow aspirates) induced by 83A10-TCBcv anti-BCMA/anti-CD3 T-cell bispecific antibody as measured by multiparameter flow cytometry (8-color staining panel). CD4 T-cell activation (top) and CD8 T-cell activation (bottom) (see Example 23A).

To evaluate whether anti-BCMA/anti-CD3 TCB antibodies induce activation of myeloma patient CD4$^+$ and CD8$^+$ T cells (i.e. bone marrow infiltrated T cells (MILs)), the samples from the respective treated, untreated and control groups after 48 h of incubation were also stain with a FACS antibody solution prepared based on an antibody-panel including eight markers: CD8/CD69/TIM-3/CD16/CD25/CD4/HLA-DR/PD-1. The samples were then incubated for 15 minutes in the dark at room temperature and acquired and analyzed using a multicolor flow cytometer. T-cell activation was determined by evaluating CD25, CD69 and/or HLA-DR positive expression gated on CD4$^+$ and CD8$^+$ T-cell populations. Percentages of T-cell activation were then measured. FIG. 24 shows a concentration-dependent upregulation of CD69 and CD25 on bone marrow-infiltrated CD4$^+$ and CD8$^+$ T cells from multiple myeloma patients. Table 26A summarizes the increase of CD69 and CD25 expression on CD4$^+$ and CD8$^+$ T cells induced by anti-BCMA/anti-CD3 TCB antibodies; data from one patient.

TABLE 26A

EC50 values for T-cell activation of myeloma patient autologous T cells induced by anti-BCMA/anti-CD3 T-cell bispecific antibodies in presence of patient bone marrow myeloma plasma cells

| | Anti-BCMA/anti-CD3 T cell bispecific antibody concentration (pM) | | | | | |
|---|---|---|---|---|---|---|
| | 30000 | 10000 | 1000 | 100 | 10 | 0 |
| CD69+/CD4 T cells (%) | | | | | | |
| 83A10-TCBcv | 21.8 | 14.93 | 1.80 | 0.93 | 1.02 | 0.85 |
| Control-TCB | 0.7 | 0.62 | / | / | / | / |
| CD69+/CD8 T cells (%) | | | | | | |
| 83A10-TCBcv | 25.50 | 22.07 | 8.330 | 5.60 | 5.14 | 5.30 |
| Control-TCB | 5.71 | 4.93 | / | / | / | / |
| CD25+/CD4 T cells (%) | | | | | | |
| 83A10-TCBcv | 17.47 | 12.86 | 5.18 | 4.58 | 4.07 | 7.5 |
| Control-TCB | 6.90 | 6.50 | / | / | / | / |
| CD25+/CD8 T cells (%) | | | | | | |
| 83A10-TCBcv | 9.79 | 6.560 | 0.42 | 0.13 | 0.12 | 0.12 |
| Control-TCB | 0.09 | 0.100 | / | / | / | / |

Example 24: Pharmacokinetic Study in Mice

A clear advantage an anti-BCMA/anti-CD3 TCBcv antibody could have over other bispecific antibodies such as (scFV)$_2$ (e.g. BCMA×CD3 bispecific T-cell engager BiTE as described in WO2013/072415 and WO2013/072406) is the much longer elimination half-life/lower clearance in vivo which could allow a twice or once a week i.v. or s.c. administration as compared to the very short elimination half-life of (scFV)$_2$ (e.g. 1 to 4 hours) requiring treatment administered via a pump carried by the patients for weeks to months (Topp et al. J Clin Oncol 2011; 29(18): 2493-8). A twice or once a week administration is much more convenient for the patients and also much less risky (e.g. failure of pump, issues with the catheter).

Figure 25:
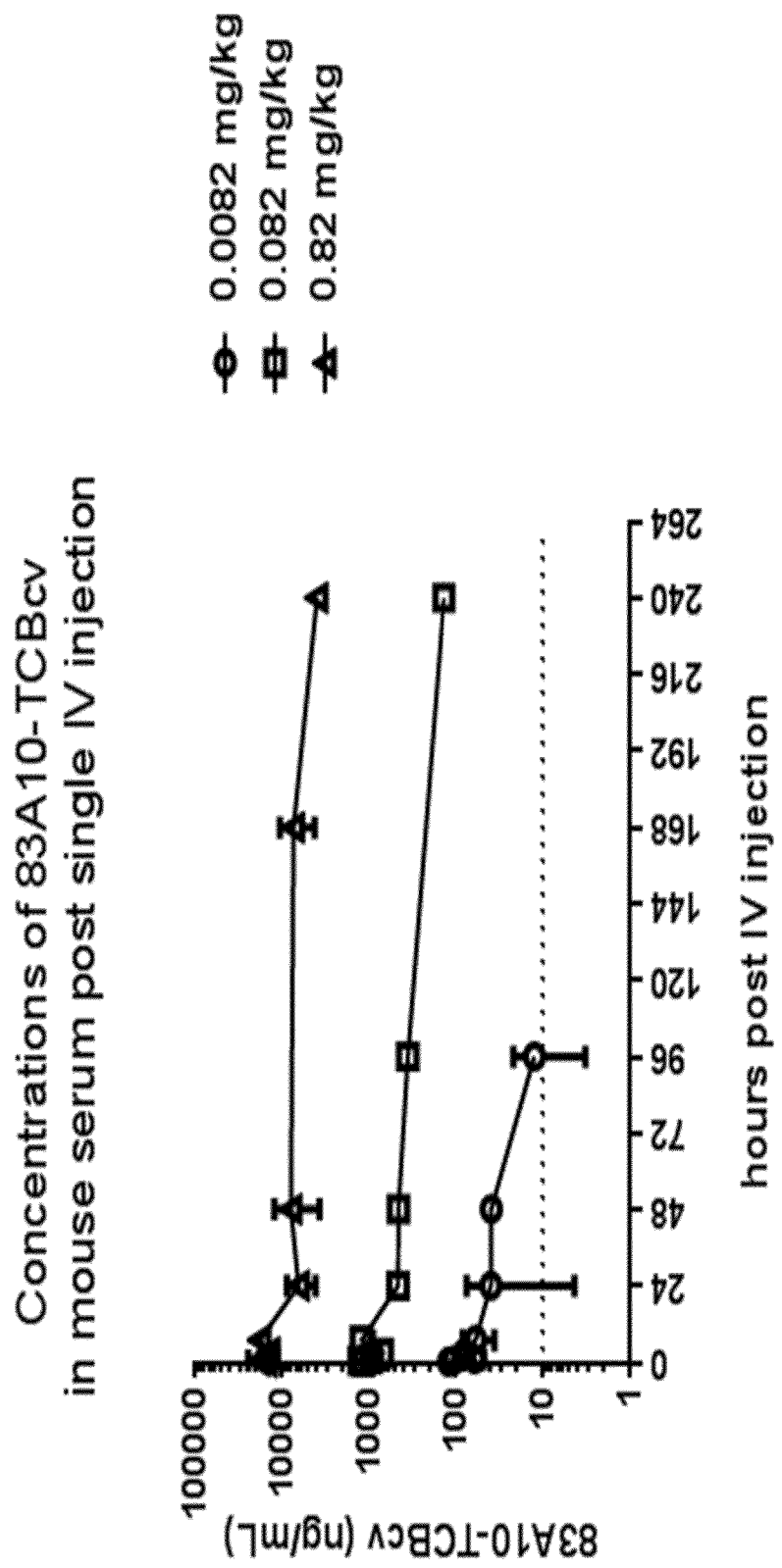
FIG. 25. Concentrations of 83A10-TCBcv measured from serum samples after single intravenous (IV) injection in immunodeficient NOD/Shi-scid IL2rgamma(null) (NOG) mice with 0.0082, 0.082 and 0.82 mg/kg of 83A10-TCBcv. Serum samples collection was performed at pre-dose and 0.25, 0.5, 1, 3, 7, 24, 48, 96, 168, 240 h after dosing (see Example 24).

To verify the elimination half-life/clearance of anti-BCMA/anti-CD3 TCBcv antibody in vivo, immunodeficient male and/or female mice (e.g. NOD/SCID or NOD/Shi-scid IL2rgamma(null) (NOG) mice, 6-10 weeks old and weighing 18-25 g are obtained from recognized vendors such as Charles River, The Jackson Laboratory and/or Taconic and allowed to acclimatise under appropriate conditions for at least one week. Throughout the acclimatisation period and experimental period, animals had access to standard pellet diet and water ad libitum. Animal housing and all procedures are conducted at experienced CROs and/or authorized laboratories in accordance with the federal guidelines and applicable animal welfare regulations.

a) In order to conduct pharmacokinetic studies, animals are randomized to groups of n=1 to n=6, preferably n=2 to n=4, assigned to selected treatments and/or doses and/or time points for blood collection. Groups are kept in separate cages and individual animals are marked with appropriate methods. Animals are administered with single i.v. doses of the anti-BCMA/anti-CD3 TCBcv antibody at doses ranging from 1 µg/kg to 20 mg/kg, preferably 5 µg/kg to 0.5 mg/kg. Administration volumes range from 5 to 10 mL/kg. In some group, mice may receive for the reason of comparison i.v. doses of a BCMA×CD3 (scFV)$_2$. Blood withdrawals are scheduled according to the experimental protocol(s) at multiple time points before and after administration ranging from 10 min to 14 days after i.v. injection of the test item, preferably from 15 min to 168 hours. Blood samples of about 200 µl are collected using hematocrit capillaries into Microvettes© by either puncture of the retro bulbar venous plexus or, at the time of euthanasia, by cardiac puncture. Blood samples are stored at 4° C. immediately and centrifuged for 2-5 min at up to 9000×g. Serum or plasma supernatants of at least 80 µl are separated and stored at −20° C. to −80° C. until analysis. Serum or plasma concentrations of the antibody(ies) under investigation are measured using a standard ELISA assay to detect human IgG (abcam; Cat. # ab1000547). From serum and/or plasma concentrations, pharmacokinetic parameters are calculated, e.g. maximum serum/plasma concentration, volume of distribution, area under concentration time curve, clearance, mean residence time and/or half-life time. For detection of serum concentrations of BCMA×CD3 (scFV)$_2$ lacking human IgG Fc, a biological assay is used for quantitating the sub-ng/ml concentrations of BCMA×CD3 (scFV)$_2$ in serum samples from the treated mice. The basis for the biological assay is the observation that BCMA×CD3 (scFV)$_2$ induces an upregulation of T-cell activation surface markers (CD69 and/or CD25) in a concentration-dependent manner as previously reported (Schlereth et al. Cancer Immunol Immunother 2006; 55:503-514). BCMA×CD3 (scFV)$_2$ concentrations ranging from 3 ng/ml to 200 pg/ml are used for the generation of standard curves to measure immunological responses of CD3-positive T cells in the presence of BCMA×CD3 (scFV)$_2$ bound to BCMA-positive H929 cells. Cells are incubated with an E:T ratio of 10:1 at 37° C., 5% $CO_2$ overnight. Blank samples (without BCMA×CD3 (scFV)$_2$) are used to measure background marker expression. Test samples are processed neat as well as diluted 1:2 and 1:4 in human pooled serum equivalent to the procedure for standards. The expression levels of immunological surface markers are determined by FACS analysis using anti-CD25 and/or anti-CD69 FITC- or PE-labeled detection antibodies (BD biosciences). BCMA×CD3 (scFV)$_2$ concentrations of unknown test samples are determined by plotting the amount of the respective marker from the standard curves against known BCMA×CD3 (scFV)$_2$ concentrations using the "interpolated X values" function of the Prism Software (GraphPad). A subcutaneous pharmacokinetic study in mice may follow since subcutaneous administration may be finally the preferred clinical route of administration.

b) In a single dose pharmacokinetic study, animals were randomized to 3 treatment groups of n=9 mice per group, and then further assigned to selected time points for blood collection (n=3 per timepoint per treatment group). Animals were administered with single IV doses of the anti-BCMA/anti-CD3 83A10-TCBcv antibody at doses ranging from 0.0082 mg/kg to 0.82 mg/kg. Administration volumes were given at 5 mL/kg. Blood withdrawals were scheduled according to the experimental protocol at multiple time points: 0.25, 0.5, 1, 3, 7, 24, 48, 96, 168, 240 h after i.v. injection of the test item 83A10-TCBcv. Blood samples of approximately 100 µl per animal were collected using hematocrit capillaries into Microvettes© by either puncture of the retro bulbar venous plexus (for an individual mouse blood from retro bulbar plexus was only taken at 2 or maximal 3 timepoints after injection) or, at the time of euthanasia, by cardiac puncture. Blood samples were kept at room temperature to allow for clotting for approximately 60 min until centrifugation for 2.5 min at 9300 g. The serum supernatants of at least 50 µl were collected, transferred into clean 200 µl Eppendorf tubes d and stored between −85° C. to −70° C. until analysis. Serum concentrations of 83A10-TCBcv under investigation were measured using standard biochemical assays to detect human Fc or CH1/kappa as described in Stubenrauch et al. J Pharm Biomed Anal 2009 and Stubenrauch et al. J Pharm Biomed Anal 2013. The serum concentrations reported in Table 27 and FIG. 25 have been measured by using the ELISA detecting human Fc. Table 27 and FIG. 25 show the serum concentrations measured by ELISA at the 3 doses. FIG. 25 suggests a dose linearity in the investigated dose range. Concentration time curves seem to show in the first few hours after injection a relatively faster decline than the decline of concentrations observed in the period between 24 hours and 240 hours after injection. At the mid dose (0.082 mg/kg) the decline between 24 and 240 hours reflects a rather linear behavior and an elimination half-life of approx 6 to 7 days can be taken from the slope of the linear decline. The decline of the concentration time curve at high dose (0.82 mg/kg) appears to be even slower, i.e. elimination half-life is at least 6 to 7 days but may be even longer. Elimination half-life between 24 and 240 hours at low dose (0.0082 mg/kg) cannot be fully evaluated because serum levels at 240 hours are below detection limit. However, FIG. 25 suggests that elimination half-life between 24 hours and 96 hours may be shorter than 6 to 7 days, possibly closer to 3 to 5 days. The concentration time curves observed for 83A10-TCBcv support the opportunity for convenient once or twice a week administration of the drug.

TABLE 27

Serum concentrations of 83A10-TCBcv after single IV treatment in mice; according to study protocol at each collection timepoint, blood has been collected from retrobulbar plexus from 2, 3 or maximal 4 different mice. Therefore, mean concentrations and SD are given for the values measured in 2, 3 or 4 samples, respectively (BLQ, means below level of quantification).

| Collection time post treatment | Concentration of 83A10-TCBcv per treatment groups | | |
| --- | --- | --- | --- |
| | 0.0082 mg/kg (mean ± SD) | 0.082 mg/kg (mean ± SD) | 0.82 mg/kg (mean ± SD) |
| 15 min | 125 ± 19 | 1173 ± 260 | 15521 ± 2677 |
| 30 min | 109 ± 12 | 1321 ± 52 | 18956 ± 5740 |
| 1 h | 62 ± 14 | 980 ± 266 | 15648 ± 4063 |
| 3 h | 81 ± 1 | 728 ± 154 | 14410 ± 2889 |
| 7 h | 61 ± 24 | 1306 ± 294 | 18311 ± 779 |
| 24 h | 40 ± 36 | 452 ± 62 | 6570 ± 2380 |
| 48 h | 40 ± 7 | 469 ± 18 | 8095 ± 4335 |
| 96 h | 13 ± 9 | 365 ± 47 | Not measured |
| 168 h | Not measured | Not measured | 7503 ± 3241 |
| 240 h | BLQ | 141 ± 12 | 4047 ± 236 |

Figure 26:
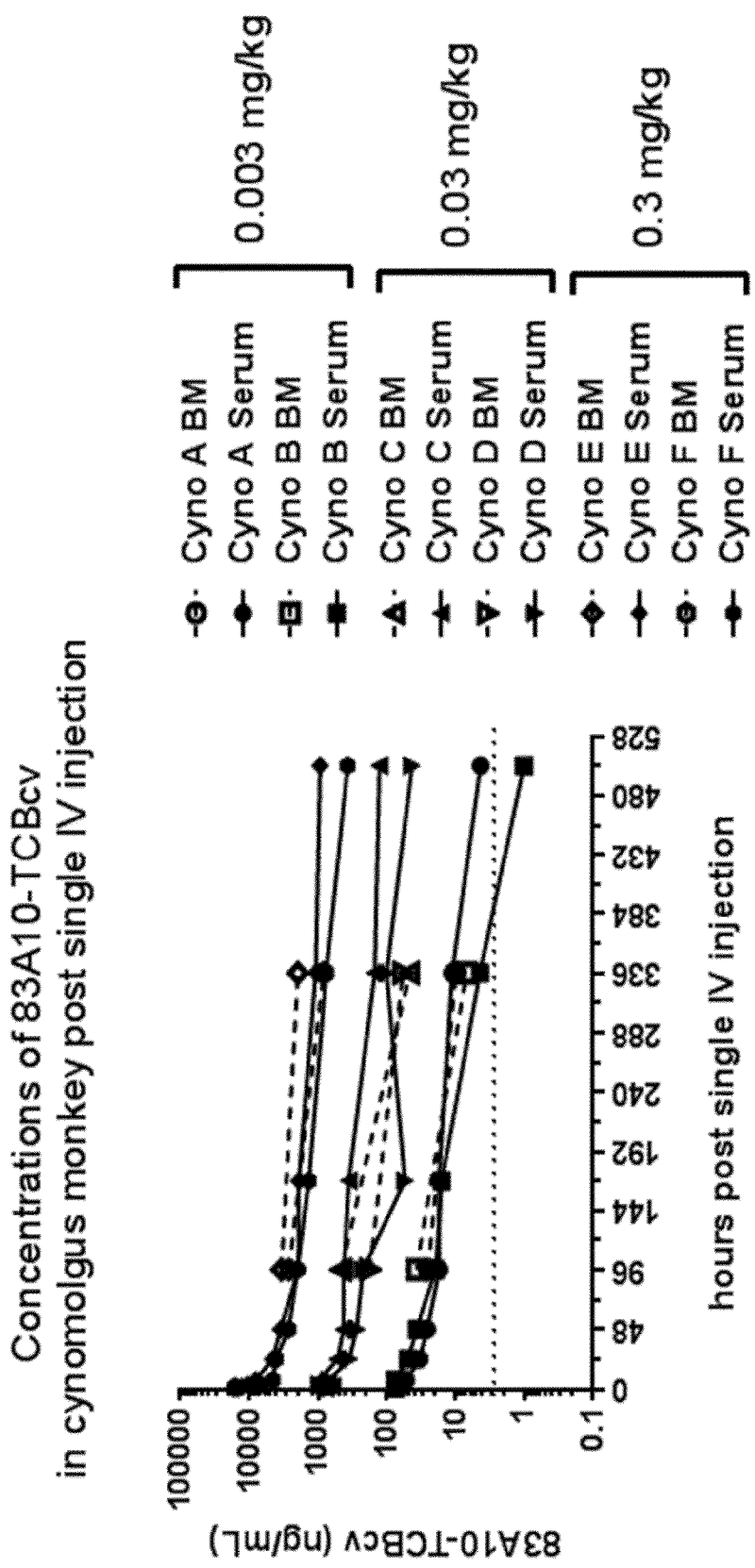
FIG. 26. Concentrations of 83A10-TCBcv measured from serum samples (closed symbols with full lines) and bone marrow samples (open symbols with dotted lines) after single intravenous (IV) injection in cynomolgus monkeys with 0.003, 0.03 and 0.1 mg/kg of 83A10-TCBcv. Serum samples collection was performed at pre-dose and 30, 90, 180 min, 7, 24, 48, 96, 168, 336, 504 h after dosing. Bone marrow samples were collected at pre-dose, and 96 and 336 h after dosing (see Example 24A).

Example 24A: Pharmacokinetic/Pharmacodynamic (PK/PD) Study in Cynomolgus Monkeys Single dose pharmacokinetic (PK) pharmacodynamic (PD) studies with anti-BCMA/anti-CD3 T-cell bispecific antibodies (83A10-TCBcv) were conducted at experienced AAALAC-accredited CRO. Biologically naïve adult cynomolgus monkeys of about two years old and weighing approximately 3 kg were acclimatized for at least 40 days and selected on the basis of body weight, clinical observations and clinical pathology examinations Animals were identified by Individual tattoos and color-coded cage cards. All the animal procedures (including housing, health monitoring, restrain, dosing, etc) and ethical revision was performed according to the current country legislation enforcing the Directive on the protection of animals used for biomedical research Animals were randomly assigned to the treatment group based on the most recent pretest body weight. After excluding animals with unacceptable pretest findings, a computer program included in the Pristima® system designed to achieve balance with respect to pretest body weights was used to exclude animals from both body weight extremes and randomize the remaining animals to the treatment group. Animals were assigned to three treatment groups with 83A10-TCBcv (n=2 animals i.e. 1 female and 1 male per group) at 0.003; 0.03; and 0.3 mg/kg. Animals received a single i.v. injection of 83A10-TCBcv and at least 0.8 mL of blood samples per timepoint were collected via the peripheral vein for PK evaluations according to the following collection schedule and procedures: Pre-dose, 30, 90, 180 min, 7, 24, 48, 96, 168, 336, 504 h after dosing. Blood samples were allowed to clot in tubes for serum separation for 60 min at room temperature. The clot was spun down by centrifugation (at least 10 min., 1200 g, +4° C.). The resultant serum (about 300 µL) was directly stored at −80° C. until further analysis. Bone marrow samples for PK evaluations were also collected at the femur under anesthesia/analgesic treatment according to the following collection schedule: Pre-dose, 96 and 336 h after dosing. Bone marrow samples were allowed to clot in tubes for serum separation for 60 min at room temperature. The clot was spun down by centrifugation (at least 10 min, 1200 g, +4° C.). The resultant bone marrow (about 1 mL) was directly stored at −80° C. until further analysis. The PK data analysis and evaluation are performed. Standard non compartmental analysis is performed using Watson package (v 7.4, Thermo Fisher Scientific Waltman, Mass., USA) or Phoenix WinNonlin system (v. 6.3, Certara Company, USA). As shown in FIG. 26, Table 28, serum concentrations of 83A10-TCBcv are measured by ELISA. Table 29 shows the concentrations of 83A10-TCBcv in bone marrow as measured by ELISA for each treatment group (BLQ, means below level of quantification).

Several information relevant for potential clinical use of 83A10-TCBcv can be taken from FIG. 26, Table 28 and Table 29:

In bone marrow aspirates from MM patients concentrations of 1 nM or 10 nM of 83A10-TCBcv induce significant or even total killing of MM plasma cells; at the dose 0.03 mg/kg in the interval from injection to 168 hours (7 days) plasma concentrations between approx. 1 nM and 4 nM have been achieved showing that once a week therapy with doses of approx. 0.03 mg/kg may well be feasible (200 ng/ml corresponds to approx. 1 nM)

FIG. 26 shows that in the investigated dose range PK is largely dose linear; that means concentrations are proportional to dose, a useful property for clinical therapy MM is a disease mainly located in the bone marrow; Concentrations of 83A10-TCBcv detected in bone marrow are close to serum concentrations (Table 29), e.g. at 96 h after injection bone marrow concentrations of approx. 1 and 2 nM have been measured; these are concentrations of TCB of this invention at which significant killing MM plasma cells is observed in bone marrow aspirates freshly taken from MM Patients; (see Tables 25 and 26) demonstrating again the opportunity for convenient dosing intervals like once a week Between 24 and 504 hours post injection the elimination is largely first order with an elimination half life of approx. 6 to 8 days confirming again the opportunity for e.g. once a week dosing

TABLE 28

Serum concentrations of 83A10-TCBcv after IV treatment in cynomolgus monkeys 83A10-TCBcv

| Conc. | 0.003 mg/ kg IV | | 0.03 mg/ kg IV | | 0.3 mg/ kg IV | |
|---|---|---|---|---|---|---|
| (ng/mL) | A | B | C | D | E | F |
| Pre-dose | 0.00 | 0.00 | 0.00 | 0.00 | 0.00 | 0.00 |
| 30 min | 75.69 | 74.99 | 668.66 | 796.54 | 17207.20 | 14943.95 |
| 90 min | 70.92 | 74.56 | 951.81 | 628.72 | 12831.54 | 16248.97 |
| 180 min | 76.54 | 62.55 | 981.42 | 722.27 | 10653.28 | 6824.72 |
| 7 h | 53.17 | 77.39 | 700.67 | 972.38 | 8204.77 | 4560.36 |
| 24 h | 33.16 | 50.41 | 358.90 | 532.11 | 4609.28 | 4127.41 |
| 48 h | 26.05 | 37.40 | 279.80 | 433.30 | 3546.09 | 2700.43 |
| 96 h | 17.28 | 19.52 | 226.01 | 429.80 | 1959.96 | 2006.92 |
| 168 h | 17.33 | 15.87 | 55.58 | 365.67 | 1918.06 | 1382.57 |
| 336 h | 11.21 | 4.43 | 102.94 | 153.54 | 1102.96 | 773.55 |
| 504 h | 4.33 | BLQ | 43.99 | 130.14 | 952.03 | 377.04 |

TABLE 29

Bone marrow concentrations of 83A10-TCBcv after single IV treatment in cynomolgus monkeys

| Conc. | 0.003 mg/kg | | 0.03 mg/kg | | 0.3 mg/kg | |
|---|---|---|---|---|---|---|
| (ng/mL) | A | B | C | D | E | F |
| Pre-dose | 0.00 | 0.00 | 0.00 | 0.00 | 0.00 | 0.00 |
| 96 h | 25.07 | 37.15 | 179.87 | 469.08 | 3432.54 | 2674.70 |
| 336 h | 9.92 | 6.90 | 59.39 | 47.22 | 1987.48 | 850.87 |

Figure 27:
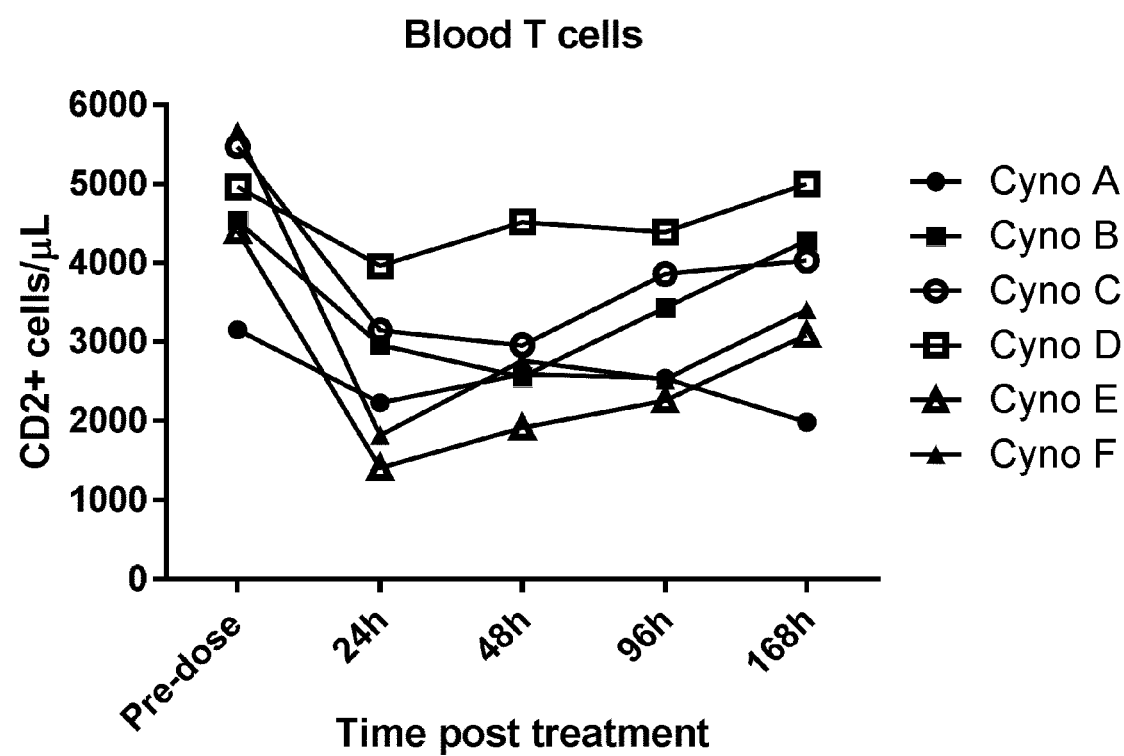
FIG. 27. Peripheral T-cell redistribution observed in cynomolgus monkeys following a single IV injection of 83A10-TCBcv (0.003, 0.03 and 0.3 mg/kg). Animals A and B, C and D, and E and F respectively received an IV injection of 0.003, 0.03 and 0.3 mg/kg of 83A10-TCBcv. Absolute blood T-cell cell counts (CD2+ cells per µL of blood) were plotted against time post treatment (see Example 24A).
Figure 28A:
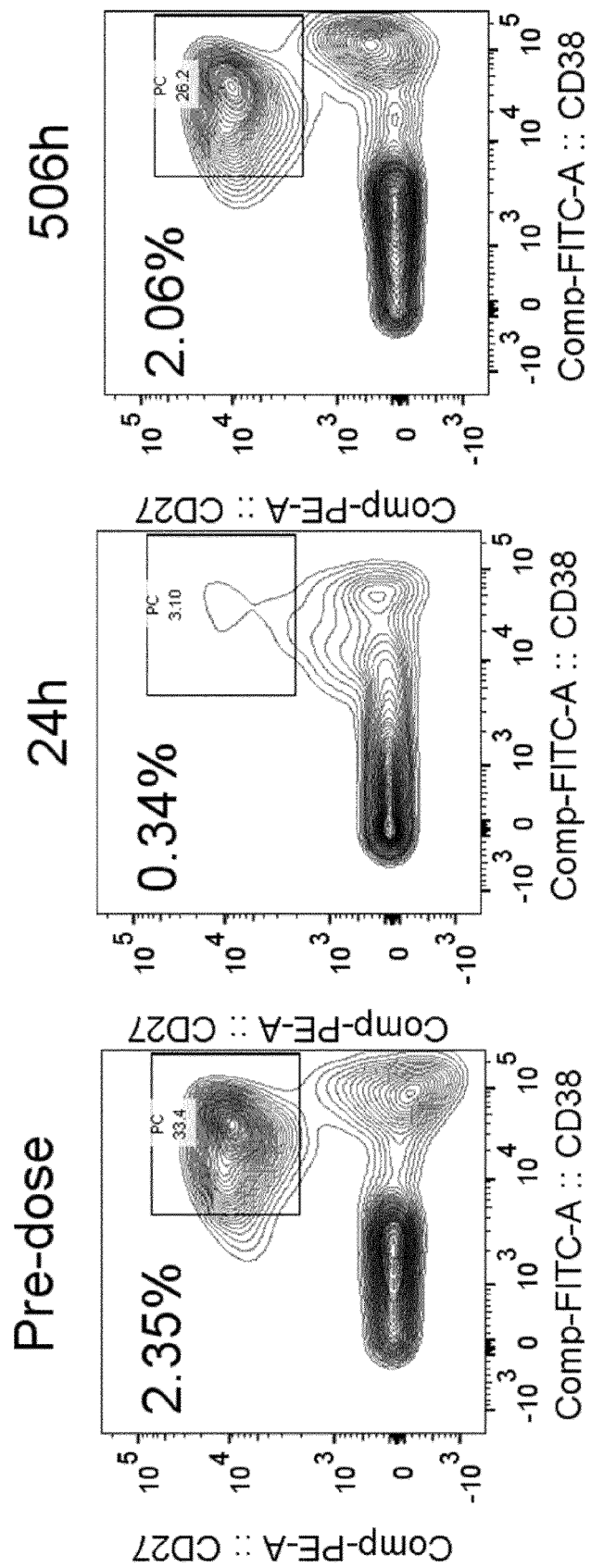
FIG. 28. Reduction of blood plasma cells observed in cynomolgus monkeys following a single IV injection of 83A10-TCBcv (0.3 mg/kg) as measured by multiparameter flow cytometry. Plasma cells (PCs) were identified based on a 6-color staining panel and percentages of PCs over lymphocytes were measured and plotted in contour plots (A). Kinetic of blood plasma cell depletion after treatment with 83A10-TCBcv 0.3 mg/kg in cynomolgus monkeys was plotted (B) (see Example 24A).
Figure 28B:
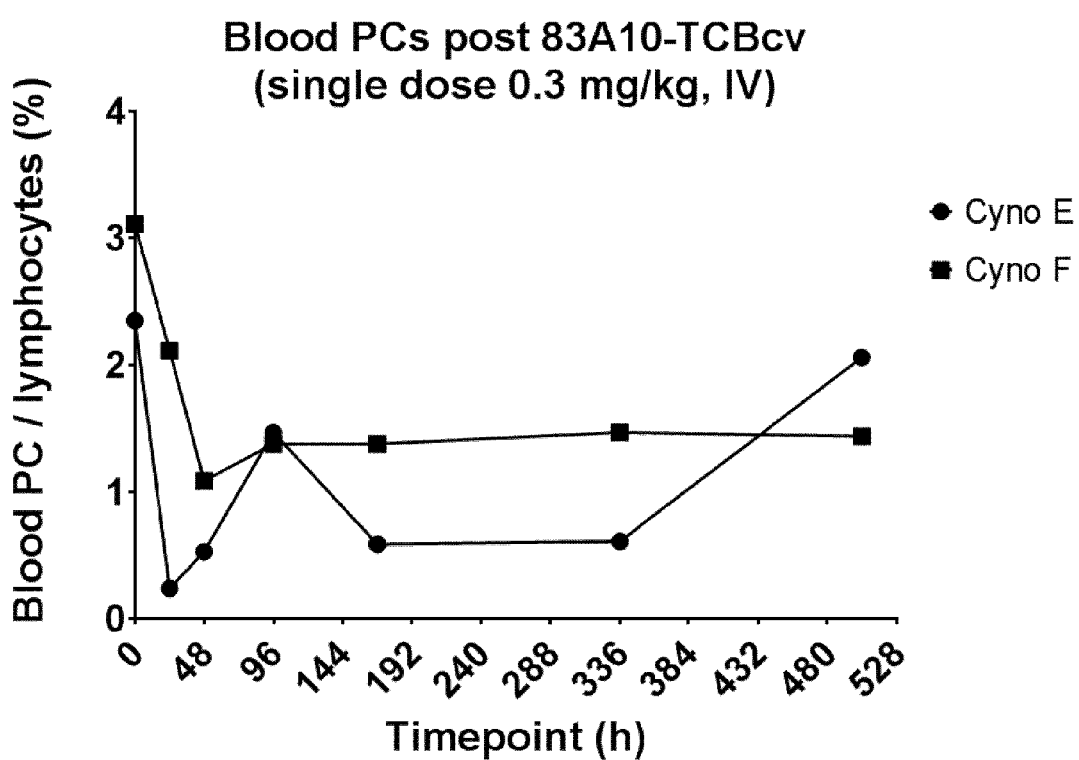

Pharmacodynamics (PD) measurements: Blood samples (timepoints: pre-dose, 24, 48, 96, 168, 336, 504 h after dosing) and bone marrow samples (timepoints: pre-dose, 96 and 336 hs after dosing) were collected in tubes containing 7.5% K3 EDTA for PD evaluation by flow cytometry to evaluate the effect of 83A10-TCBcv give i.v. as single dose on blood and bone marrow plasma cells, B cells, and T cells. A "lyse and wash" direct immunofluorescence staining method of the surface markers was applied. Briefly, 100 µL of blood or bone marrow was incubated with two antibody mixtures including CD45/CD2/CD16/CD20/CD27/CD38 or CD45/CD2/CD16/CD4/CD25/CD8 in the dark for 30 min at +4° C. To lyse red blood cells, 2 mL of lysing buffer solution was added to the sample and incubated 15 10 min at room temperature in the dark. Cells were collected by centrifugation and washed with staining buffer (PBS 2% Fetal Bovine Serum). The stained samples were kept refrigerated, protected from light, until acquisition with cytometer on the same day. FACS data acquisition was performed with a Becton Dickinson flow cytometer equipped with 488 and 635 laser lines, BD FACS Canto II. BD FACSDiva software was used for data collection and analysis. The absolute cell number enumeration was performed with a double platform, based upon the WBC count obtained by the hematology analyzer (ADVIA™ 120, Siemens). As shown in FIG. 27, peripheral T-cell redistribution was observed in all animals receiving a single dose IV treatment of 83A10-TCBcv as shown by the decrease in circulating T cell counts. As shown in FIG. 28A, already at 24 h after treatment with 83A10-TCBcv 0.3 mg/kg a decrease in blood plasma cells (BCMA-positive cells) was observed in animals treated while there was no decrease in total B cells (BCMA-negative cells). FIG. 28B shows the kinetic of plasma cell reduction in blood after treatment with 83A10-TCBcv 0.3 mg/kg in cynomolgus monkeys.

Blood samples were also processed for plasma collection for cytokine analysis (IL-1b, IL-2, IL-6, IL-10, TNF-α and IFN-γ) in accordance with the following collection schedule: Pre-dose, 30, 90, 180 min, 7, 24, 48, 96, 168 h after dosing. Blood samples were put in plastic tubes kept in an ice-water bath, then centrifuged (at least 10 min., 1200 g, +4° C.). The resultant plasma was directly stored at −80° C. until analysis. Cytokines analysis is performed with Multiplex bead-based cytokine immunoassay (Luminex Technology). Data are analyzed using Bio-Plex Manager 4.1 software (Bio-Rad): a five-parameter logistic regression model (5PL) is used.

Figure 29:
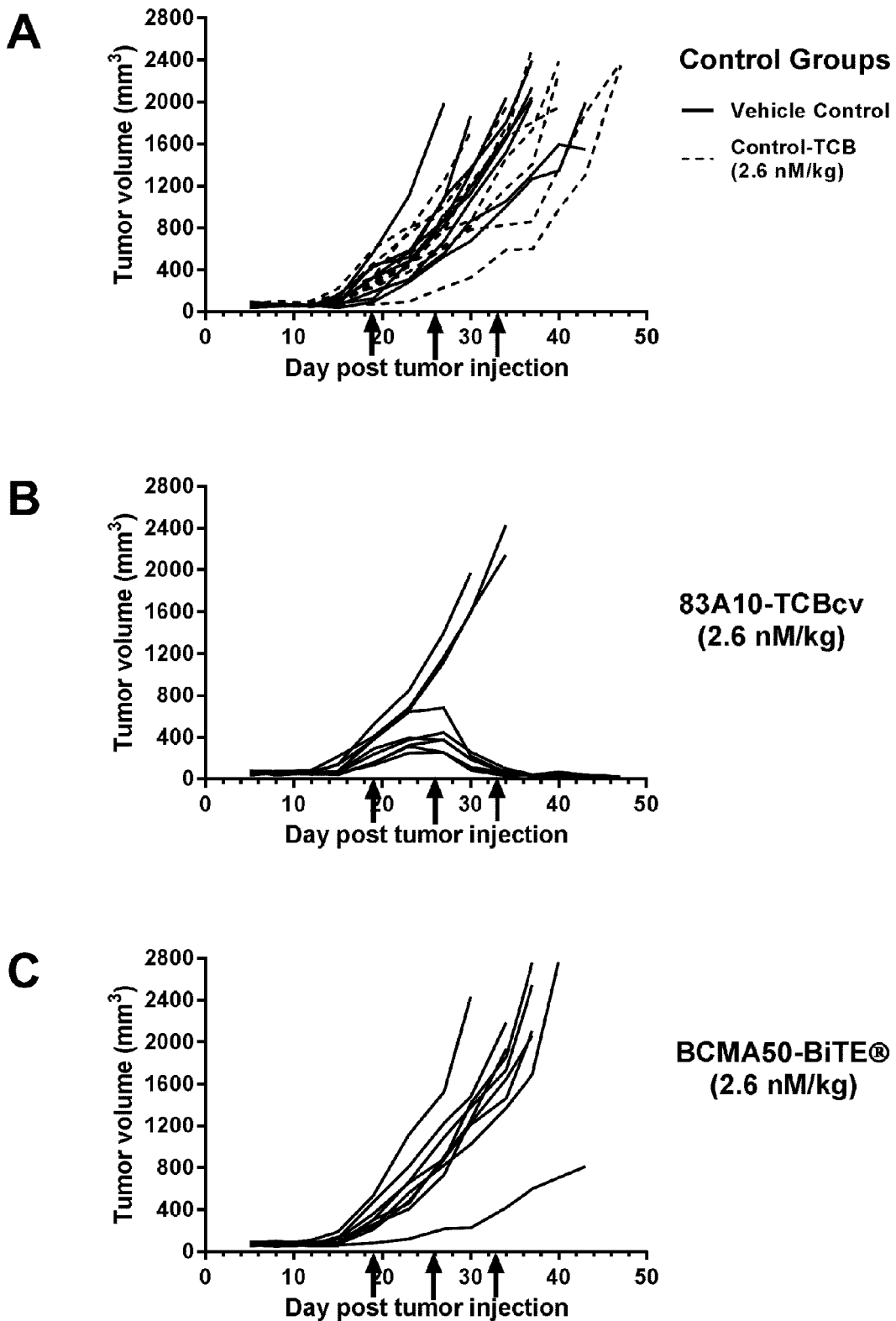
FIG. 29. Antitumoral activity induced by 83A10-TCBcv anti-BCMA/anti-CD3 T cell bispecific antibody in the H929 human myeloma xenograft model using PBMC-humanized NOG mice. Immunodeficient NOD/Shi-scid IL2rgamma (null) (NOG) received on day 0 (d0) human multiple myeloma H929 cells as a subcutaneous (SC) injection into the right dorsal flank. On day 15 (d15), NOG mice received a single intraperitoneal (IP) injection of human PBMCs. Mice were then carefully randomized into the different treatment and control groups (n=9/group) and a statistical test was performed to test for homogeneity between groups. The experimental groups were the control untreated group, control-TCB treated group, 83A10-TCBcv 2.6 nM/kg treated group and BCMA50-BiTE® (BCMA×CD3 (scFv)$_2$) 2.6 nM/kg treated group. Antibody treatment given by tail vein injection started on day 19 (d19), i.e. 19 days after SC injection of H929 tumor cells. The TCB antibody treatment schedule consisted of a once a week IV administration for up to 3 weeks (i.e. total of 3 injections of TCB antibody). Tumor volume (TV) was measured by caliper during the study and progress evaluated by intergroup comparison of TV. TV (mm3) plotted against day post tumor injection. On d19, first day of treatment, the mean tumor volume had reached 300±161 mm3 for the vehicle treated control group (A), 315±148 mm3 for the 2.6 nM/kg control-TCB treated group (A), 293±135 mm3 for the 2.6 nM/kg 83A10-TCBcv group (B) and 307±138 mm3 for the 2.6 nM/kg BCMA50-BiTE® group (C). TV of each individual mouse per experimental group were plotted against day post tumor injection: (A) control groups including vehicle control (full line) and control-TCB (dotted line), (B) 83A10-TCBcv (2.6 nM/kg) group, and (C) BCMA50-BiTE® (2.6 nM/kg). Black arrows show the TCB treatement given by IV injection. In the 83A10-TCBcv (2.6 nM/kg) group, 6 out of 9 mice (67%) had their tumor regressed even below TV recorded at d19 i.e. first TCB treatment and tumor regression was maintained until termination of study. The 3 mice in the 83A10-TCBcv (2.6 nM/kg) treated group which failed to show tumor regression had their TV equal to 376, 402 and 522 mm3 respectively at d19. In contrast, none of the 9 mice (0%) treated with an equimolar dose of BCMA50-BiTE® (2.6 nM/kg) at a once a week schedule for 3 weeks had their tumor regressed at any timepoint (see Example 25).
Figure 30:
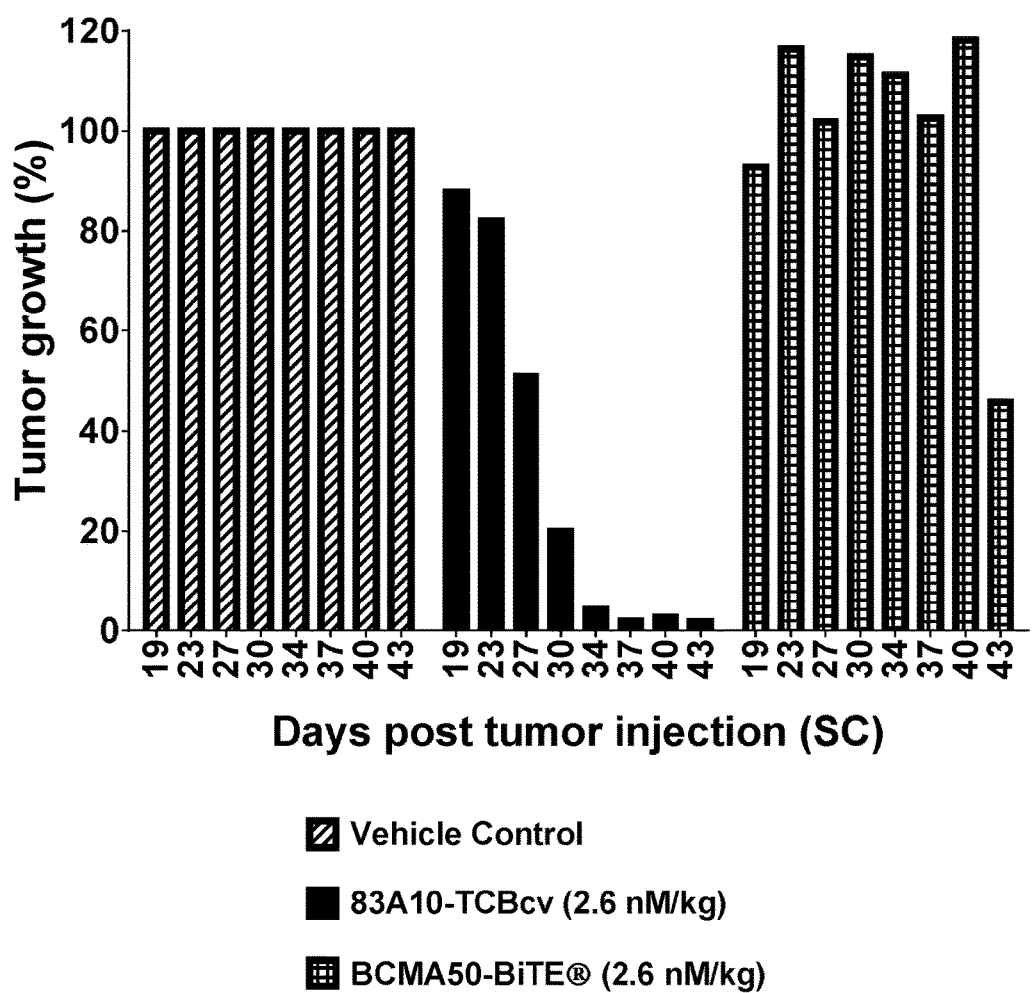
FIG. 30. Percentage of tumor growth (TG) calculated for d19 to d43 and compared between 83A10-TCBcv (2.6 nM/kg) group and BCMA50-BiTE® (2.6 nM/kg). The percentage of tumor growth defined as TG (%) was determined by calculating TG (%)=100× (median TV of analysed group)/(median TV of control vehicle treated group). For ethical reason, mice were euthanized when TV reached at least 2000 mm3 TG (%) was consistently and significantly reduced in the 83A10-TCBcv (2.6 nM/kg) group as well as the TG (%) was always lower when compared to BCMA50-BiTE® (2.6 nM/kg) (see Example 25).

Example 25: Therapeutic Efficacy of Anti-BCMA/Anti-CD3 T Cell Bispecific Antibody in Human Myeloma Xenograft Mouse Models a) The in vivo effect of anti-BCMA/anti-CD3 TCBcv antibody is evaluated in a human myeloma xenograft mouse model. Briefly, on day 0 (d0) of the study, $5 \times 10^6$ to $100 \times 10^6$ cells of human myeloma cell line NCI-H929 (NCI-H929, ATCC® CRL-9068™) are subcutaneously injected into the right dorsal flank of immunodeficient NOD/Shi-scid IL2rgamma(null) (NOG) adult mice (The Jackson Laboratory and/or Taconic) and left to engraft for 7 to 21 days or until the tumor size reaches 50-300 cm$^3$, preferably 100-200 cm$^3$. Transplanted mice are randomly assigned to different treatment groups (n=5 to 12). NOG mice are one of the most appropriate strain for humanized mouse models as reflected by the complete lack of immune cells including resident NK cell population which could be observed in non-irradiated SCID or RAG immunodeficient mice and which could in turn affect tumor engraftment of human xenogeneic cells (Ito et al. Curr Top Microbiol Immunol 2008; 324: 53-76). On day 7 to day 21 (d7 d21) when the tumor graft reaches approximately a volume of 50-300 cm$^3$, preferably 100-200 cm$^3$, $5 \times 10^6$ to $100 \times 10^6$ of human PBMC isolated from buffy coats are injected into the peritoneal cavity of the host mice. Mice from control groups do not receive human PBMCs and are used as untransplanted control mice for comparison with control vehicle treated mice receiving human PBMCs to monitor the impact of T cells on tumor growth. The TCB treatment schedule is based on the pharmacokinetic data previously obtained and consists of once a week i.v., s.c. or i.p. administration for up to 3-6 injections of anti-BCMA/anti-CD3 TCBcv antibody. Two days after reconstitution of the recipients with human PBMCs (d9 to d23), a first dose of the anti-BCMA/anti-CD3 2TCBcv antibody, ranging from 1 μg/kg to 20 mg/kg, preferably 5 μg/kg to 0.5 mg/kg, is given via tail vein injection or by s.c. or i.p. injection. In some mice of satellite groups, bleeding time points are performed 5 min, 1 hr, 8 hr and 24 h after injection of the anti-BCMA/anti-CD3 2+1 Fc-containing TCB antibody for pharmacokinetic analyses. Three to 7 days after the first TCB treatment, recipient mice are treated with a second dose of anti-BCMA/anti-CD3 TCBcv antibody. One hour prior to the second TCB injection, blood is collected to obtain trough levels of the treatment antibody. Three to 7 days after the second TCB treatment, recipient mice are treated with a third dose of anti-BCMA/anti-CD3 TCBcv antibody, etc. Treatment is planned to go over 3 weeks, i.e. 6 doses at twice a week schedule respectively 3 doses at a once a week schedule. One hour prior to the second (at once a week dosing schedule) respectively fourth TCB injection, blood is collected for pharmacokinetic analyses. Between the second and third respectively the fourth and fifth TCB treatment, some mice of satellite groups are euthanized and used for demonstration of pharmacodynamics effect and measurement of secondary endpoints such as T-cell activation and T-cell function in the treated mice. Primary endpoint is measured by tumor volume. Tumors are measured by caliper during the study and progress evaluated by intergroup comparison of tumor volume (TV). The tumor growth inhibition T/C (%) is determined by calculation TC as T/C %=100× (median TV of analysed group)/(median TV of control vehicle treated group). In some studies, survival of the host mice is used as primary or secondary endpoint. Alternatively to H929 cell line, human myeloma cell lines RPMI-8226 (ATCC® CCL-155™), U266B1 (ATCC® TIB-196™) or L-363 cell line (Leibniz Institute DSMZ-German collection of microorganisms and cell cultures; DSMZ No. ACC 49) may be used as xenograft. In some studies, NOD-Rag1 (null)-γ chain(null) (NRG) adult mice (The Jackson Laboratory) may be used as transplant recipients. In some studies, recipient mice are treated with comparative doses of BCMA×CD3 (scFV)$_2$ (e.g. BCMA×CD3 bispecific T-cell engager BiTE as described in WO2013/072415 and WO2013/072406) for a treatment schedule of twice and/or once a week.

b) Antitumoral activity induced by anti-BCMA/anti-CD3 T cell bispecific antibody in H929 human myeloma xenograft model in PBMC-humanized NOG mice. With a long elimination half-life, Fc-containing anti-BCMA/anti-CD3 TCBcv antibodies could be more efficacious than (scFv)$_2$-based bispecific antibodies such as BCMA50-BITE® given at equimolar doses, in a once a week schedule. The in vivo effect of 83A10-TCBcv and BCMA50-BITE® (as described in WO2013072415 and WO2013072406) was compared and evaluated in the H929 human myeloma xenograft model in PBMC-humanized NOG mice. NOG mice are appropriate for humanized mouse models as they completely lack of immune cells including resident NK cell population and are therefore more permissive to tumor engraftment of human xenogeneic cells (Ito et al. Curr Top Microbiol Immunol 2008; 324: 53-76). Briefly, on day 0 (d0) of the study, 5×106 human myeloma cell line NCI-H929 (NCI-H929, ATCC® CRL9068™) in 100 μL RPMI 1640 medium containing 50:50 matrigel (BD Biosciences, France) were subcutaneously (SC) injected into the right dorsal flank of immunodeficient NOD/Shi-scid IL2rgamma(null) (NOG) female mice of 8-10 weeks of age (Taconic, Ry, Danemark). Twenty-four to 72 hours prior to H929 tumor cell SC implantation, all mice received a whole body irradiation with a □-source (1.44 Gy, 60Co, BioMep, Bretenières, France). On day 15 (d15), NOG mice received a single intraperitoneal (IP) injection of 2×107 human PBMCs (in 500 μL PBS 1×pH7.4). Characterization of the human PBMC was performed by immunophenotyping (flow cytometry). Mice were then carefully randomized into the different treatment and control groups (n=9/group) using Vivo Manager® software (Biosystemes, Couternon, France) and a statistical test (analysis of variance) was performed to test for homogeneity between groups. Antibody treatment started on day 19 (d19), i.e. 19 days after SC injection of H929 tumor cells when the tumor volume had reached at least 100-150 mm3 in all mice, with a mean tumor volume of 300±161 mm3 for the vehicle treated control group, 315±148 mm3 for the 2.6 nM/kg control-TCB treated group, 293±135 mm3 for the 2.6 nM/kg 83A10-TCBcv group and 307±138 mm3 for the 2.6 nM/kg BCMA50-(scFv)2 (BCMA50-BiTE®) group. The TCB antibody treatment schedule was based on the pharmacokinetic results previously obtained with 83A10-TCBcv and consisted of a once a week IV administration for up to 3 weeks (i.e. total of 3 injections of TCB antibody). Four days after reconstitution of the host mice with human PBMCs (d19), a first dose of the anti-BCMA/anti-CD3 83A10-TCBcv antibody (2.6 nM/kg respectively 0.5 mg/kg) was given via tail vein injection. Blood samples were collected by jugular/mandibular vein puncture (under anesthesia) 1 h before each treatment, 2 h before the second treatment and at termination in mice from all groups treated with 83A10-TCBcv and control-TCBcv. Blood samples were immediately transferred into clot activator containing tubes (T MG tubes, cherry red top, Capiject®, Terumo®). Tubes were left at room temperature for 30 min to allow clotting. Then tubes were centrifuged at 1,300 g for 5 min for clot/serum separation. Serum aliquots were prepared, flash frozen in liquid nitrogen and stored at −80° C. until further analysis. Tumor volume (TV) was measured by caliper during the study and progress evaluated by intergroup comparison of TV. The percentage of tumor growth defined as TG (%) was determined by calculating TG (%)=100×(median TV of analysed group)/(median TV of control vehicle treated group). For ethical reason, mice were euthanized when TV reached at least 2000 mm3 FIG. 29 shows the TV of each individual mouse per experimental group: (A) control groups including vehicle control (full line) and control-TCB (dotted line), (B) 83A10-TCBcv (2.6 nM/kg) group, and (C) BCMA50-BiTE® (2.6 nM/kg). In the 83A10-TCBcv (2.6 nM/kg) group, 6 out of 9 mice (67%) had their tumor regressed even below TV recorded at d19 i.e. first TCB treatment and tumor regression was maintained until termination of study. The 3 mice in the 83A10-TCBcv (2.6 nM/kg) treated group which failed to show tumor regression had their TV equal to 376, 402 and 522 mm3 respectively at d19. In contrast, none of the 9 mice (0%) treated with an equimolar dose of BCMA50-BiTE® (2.6 nM/kg) at a once a week schedule for 3 weeks had their tumor regressed at any timepoints. Table 30 shows progression of tumor volumes over time in all experimental groups. The percentage of tumor growth was calculated for d19 to d43 and compared between 83A10-TCBcv (2.6 nM/kg) group and BCMA50-BiTE® (2.6 nM/kg) (FIG. 30). The results demonstrate that TG (%) is consistently and significantly reduced in the 83A10-TCBcv (2.6 nM/kg) group as well as the TG (%) is always lower when compared to BCMA50-BITE® (2.6 nM/kg). Table 31 shows the median tumor volume (TV) and percentage of tumor growth (TG (%)) at days 19 to 43. The overall results clearly demonstrated that 83A10-TCBcv is superior to BCMA50-BITE® to induce antitumor activity in vivo when treatment is given at equimolar dose in once a week schedule for 3 weeks.

TABLE 30

Progression of tumor volumes over time in mice from control vehicle group and mice treated with equimolar doses of control-TCB, 83A10-TCBcv and BCMA50-(scFv)$_2$ (BCMA50-BiTE ®)

| Tumor volume (mm³) | Control vehicle Group A | | | | | | | | | | |
|---|---|---|---|---|---|---|---|---|---|---|---|
| | A1 | A2 | A3 | A4 | A5 | A6 | A7 | A8 | A9 | Mean | SD |
| Day 5 | 95 | 58 | 63 | 71 | 63 | 68 | 67 | 65 | 36 | 65 | 15 |
| Day 8 | 70 | 61 | 71 | 70 | 56 | 68 | 74 | 70 | 49 | 66 | 8 |
| Day 12 | 66 | 65 | 53 | 50 | 57 | 58 | 60 | 59 | 56 | 58 | 5 |
| Day 15 | 101 | 95 | 131 | 80 | 61 | 65 | 89 | 37 | 161 | 91 | 37 |
| Day 19 | 333 | 327 | 566 | 123 | 197 | 191 | 444 | 92 | 427 | 300 | 161 |
| Day 23 | 565 | 481 | 1105 | 470 | 310 | 309 | 517 | 281 | 581 | 513 | 249 |
| Day 27 | 1071 | 877 | 1989 | 823 | 560 | 675 | 1089 | 530 | 870 | 943 | 440 |
| Day 30 | 1870 | 1129 | x | 419.2 | 867 | 1060 | 1368 | 673 | 1331 | 1090 | 450 |
| Day 34 | x | 1653 | | 507 | 1056 | 1521 | 1805 | 1008 | 2042 | 1370 | 535 |
| Day 37 | | 2140 | | 2043 | 1309 | 2017 | 2394 | 1267 | x | 1862 | 464 |
| Day 40 | | x | | x | 1592 | x | x | 1346 | | 1469 | 174 |
| Day 43 | | | | | 1548 | | | 1994 | | 1771 | 314 |
| Day 47 | | | | | x | | | x | | | |
| Day 51 | | | | | | | | | | | |

| Tumor volume (mm³) | 2.6 nM/kg Control TCB Group B | | | | | | | | | | |
|---|---|---|---|---|---|---|---|---|---|---|---|
| | B1 | B2 | B3 | B4 | B5 | B6 | B7 | B8 | B9 | Mean | SD |
| Day 5 | 68 | 65 | 84 | 83 | 46 | 63 | 73 | 74 | 67 | 69 | 11 |
| Day 8 | 55 | 64 | 54 | 73 | 60 | 103 | 56 | 55 | 76 | 66 | 16 |
| Day 12 | 45 | 92 | 73 | 76 | 83 | 78 | 103 | 69 | 76 | 77 | 16 |
| Day 15 | 72 | 169 | 64 | 99 | 69 | 150 | 223 | 115 | 88 | 117 | 54 |
| Day 19 | 257 | 334 | 71 | 318 | 268 | 460 | 602 | 236 | 285 | 315 | 148 |
| Day 23 | 430 | 773 | 95 | 444 | 553 | 738 | 808 | 381 | 461 | 520 | 227 |
| Day 27 | 924 | 1252 | 232 | 780 | 768 | 1009 | 915 | 606 | 630 | 791 | 289 |
| Day 30 | 1191 | 1714 | 326 | 867 | 1230 | 1349 | 1118 | 817 | 783 | 1044 | 398 |

TABLE 30-continued

Progression of tumor volumes over time in mice from control vehicle group and mice treated with equimolar doses of control-TCB, 83A10-TCBcv and BCMA50-(scFv)$_2$ (BCMA50-BiTE ®)

| | | | | | | | | | | | |
|---|---|---|---|---|---|---|---|---|---|---|---|
| Day 34 | 1684 | x | 592 | 1466 | 1660 | 1954 | 1765 | 1180 | 576 | 1359 | 529 |
| Day 37 | 2522 | | 597 | 1735 | 1105 | x | x | 1402 | 861 | 1370 | 691 |
| Day 40 | x | | 978 | 2388 | 1952 | | | 2211 | 1365 | 1792 | 604 |
| Day 43 | | | 1302 | x | x | | | x | 1895 | 1599 | 419 |
| Day 47 | | | 2346 | | | | | | 2373 | 2359 | 19 |
| Day 51 | | | x | | | | | | x | | |

| Tumor volume (mm$^3$) | 2.6 nM/kg 83A10-TCBcv Group C | | | | | | | | | | |
|---|---|---|---|---|---|---|---|---|---|---|---|
| | C1 | C2 | C3 | C4 | C5 | C6 | C7 | C8 | C9 | Mean | SD |
| Day 5 | 78 | 79 | 55 | 77 | 53 | 47 | 39 | 53 | 60 | 60 | 15 |
| Day 8 | 69 | 37 | 67 | 75 | 62 | 59 | 59 | 77 | 75 | 64 | 12 |
| Day 12 | 58 | 61 | 60 | 69 | 48 | 59 | 46 | 63 | 87 | 61 | 12 |
| Day 15 | 136 | 41 | 61 | 138 | 48 | 57 | 76 | 71 | 217 | 94 | 58 |
| Day 19 | 376 | 151 | 238 | 522 | 154 | 133 | 377 | 287 | 402 | 293 | 135 |
| Day 23 | 656 | 322 | 375 | 847 | 311 | 249 | 642 | 395 | 681 | 498 | 210 |
| Day 27 | 1119 | 376 | 443 | 1400 | 253 | 253 | 678 | 371 | 1166 | 673 | 441 |
| Day 30 | 1607 | 187 | 260 | 1975 | 88 | 113 | 219 | 191 | 1590 | 692 | 783 |
| Day 34 | 2143 | 68 | 100 | x | 34 | 54 | 63 | 53 | 2429 | 618 | 1033 |
| Day 37 | x | 41 | 44 | | 43 | 34 | 34 | 35 | x | 38 | 5 |
| Day 40 | | 64 | 40 | | 43 | 38 | 32 | 39 | | 43 | 11 |
| Day 43 | | 40 | 43 | | 33 | 24 | 32 | 25 | | 33 | 8 |
| Day 47 | | 14 | 21 | | 16 | 12 | 19 | 14 | | 16 | 3 |
| Day 51 | | 15 | 30 | | 20 | 20 | 15 | 18 | | 20 | 6 |

| Tumor volume (mm$^3$) | 2.6 nM/kg BCMA50-(scFv)$_2$ (BCMA50-BiTE ®) Group D | | | | | | | | | | |
|---|---|---|---|---|---|---|---|---|---|---|---|
| | D1 | D2 | D3 | D4 | D5 | D6 | D7 | D8 | D9 | Mean | SD |
| Day 5 | 75 | 92 | 78 | 86 | 57 | 91 | 74 | 58 | 62 | 75 | 13 |
| Day 8 | 51 | 87 | 61 | 99 | 70 | 88 | 90 | 73 | 71 | 77 | 15 |
| Day 12 | 70 | 73 | 63 | 76 | 84 | 76 | 85 | 58 | 113 | 78 | 16 |
| Day 15 | 142 | 72 | 61 | 128 | 87 | 77 | 121 | 60 | 188 | 104 | 44 |
| Day 19 | 232 | 212 | 81 | 474 | 303 | 260 | 360 | 304 | 539 | 307 | 138 |
| Day 23 | 560 | 483 | 121 | 811 | 665 | 408 | 654 | 457 | 1115 | 586 | 278 |
| Day 27 | 827 | 879 | 216 | 1224 | 1092 | 732 | 886 | 908 | 1526 | 921 | 359 |
| Day 30 | 1026 | 1414 | 227 | 1476 | 1373 | 1256 | 1210 | 1228 | 2433 | 1294 | 567 |
| Day 34 | 1368 | 1855 | 418 | 2185 | 1734 | 1936 | 1465 | 1645 | x | 1576 | 535 |
| Day 37 | 1691 | 2754 | 599 | | 2542 | | 2102 | 2062 | | 1958 | 765 |
| Day 40 | 2764 | x | 706 | | x | | x | x | | 1735 | 1455 |
| Day 43 | x | | 807 | | | | | | | 807 | n/a |
| Day 47 | | | | | | | | | | | |
| Day 51 | | | | | | | | | | | |

TABLE 31

Median tumor volume (TV) and percentage of tumor growth (TG (%)) at days 19 to 43: 83A10-TCBcv in comparison to BCMA50-BiTE ®.

| Tumor growth Inhibition TG$_{inh}$ (%) | Vehicle treated Control | | 83A10-TCBcv 2.6 nM/kg | | BCMA50-BiTE ® 2.6 nM/kg | | Control-TCB 2.6 nM/kg | |
|---|---|---|---|---|---|---|---|---|
| | Median TV | TG (%) | Median TV | TG (%) | Median TV | TG (%) | Median TV | TG (%) |
| Day 19 | 327 | 100 | 287 | 87.8 | 303 | 92.7 | 285 | 87.2 |
| Day 23 | 481 | 100 | 395 | 82.1 | 560 | 116.4 | 461 | 95.8 |
| Day 27 | 870 | 100 | 443 | 50.9 | 886 | 101.8 | 780 | 89.7 |
| Day 30 | 1094.5 | 100 | 219 | 20.0 | 1256 | 114.8 | 1118 | 102.1 |
| Day 34 | 1521 | 100 | 65.5 | 4.3 | 1689.5 | 111.1 | 1563 | 102.8 |
| Day 37 | 2030 | 100 | 38 | 1.9 | 2082 | 102.6 | 1253.5 | 61.7 |
| Day 40 | 1469 | 100 | 39.5 | 2.7 | 1735 | 118.1 | 1952 | 132.9 |
| Day 43 | 1771 | 100 | 32.5 | 1.8 | 807 | 45.6 | 1598.5 | 90.3 |
| Day 47 | / | / | 15 | / | / | / | 2359.5 | / |
| Day 51 | / | / | 19 | / | / | / | / | / |

The invention claimed is:

1. A bispecific bi- or trivalent antibody specifically binding to two targets which are the extracellular domain of human B cell maturation antigen (BCMA) and human CD3ε (CD3) wherein variable domains VL and VH in a light chain and a respective heavy chain are replaced by each other, wherein the antibody comprises a constant domain CL wherein the amino acid at position 124 of the CL is substituted independently by lysine (K), arginine (R) or histidine (H) (numbering according to Kabat), and in a respective constant domain CH1 the amino acid at position 147 of the CH1 and the amino acid at position 213 of the CH1 is substituted independently by glutamic acid (E), or aspartic acid (D) (numbering according to EU index of Kabat).

2. A bispecific antibody specifically binding to two targets which are the extracellular domain of human BCMA and human CD3, wherein the antibody comprises
   a) a first light chain and a first heavy chain of a first antibody which specifically binds to BCMA; and
   b) a second light chain and a second heavy chain of a second antibody which specifically binds to CD3, and wherein variable domains VL and VH in the second light chain and second heavy chain of the second antibody are replaced by each other; and wherein
   c) amino acid at position 124 of a constant domain CL of the first light chain is substituted independently by lysine (K), arginine (R) or histidine (H) (numbering according to Kabat), and wherein amino acid at position 147 and amino acid at position 213 of a constant domain CH1 of the first heavy chain are each substituted independently by glutamic acid (E), or aspartic acid (D) (numbering according to EU index of Kabat).

3. A bispecific antibody specifically binding to two targets which are the extracellular domain of human BCMA and human CD3, wherein the antibody comprises
   a) a first light chain and a first heavy chain of a first antibody which specifically binds to BCMA; and
   b) a second light chain and a second heavy chain of a second antibody which specifically binds to CD3, and wherein variable domains VL and VH in the second light chain and second heavy chain of the second antibody are replaced by each other; and wherein
   c) amino acid at position 124 of a constant domain CL of the second light chain is substituted independently by lysine (K), arginine (R) or histidine (H) (numbering according to Kabat), and wherein amino acid at positions 147 and amino acid at position 213 of a constant domain CH1 of the second heavy chain are each substituted independently by glutamic acid (E), or aspartic acid (D) (numbering according to EU index of Kabat).

4. A bispecific antibody according to claim 2, wherein said bispecific antibody comprises a Fab fragment of said first antibody (BCMA-Fab) wherein the amino acid at position 124 of a constant domain CL of said Fab fragment is substituted independently by lysine (K), arginine (R) or histidine (H) (numbering according to Kabat), and the amino acid at position 147 and the amino acid at position 213 of a constant domain CH of said Fab fragment are each substituted independently by glutamic acid (E), or aspartic acid (D) (numbering according to EU index of Kabat).

5. A bispecific antibody according to claim 4, wherein said bispecific antibody comprises a second Fab fragment of said first antibody ("BCMA-Fab").

6. A bispecific antibody according to claim 2, characterized in that in addition to the amino acid replacement at position 124 in the constant domain CL the amino acid at position 123 in the CL is substituted independently by lysine (K), arginine (R) or histidine (H).

7. A bispecific antibody according to claim 6, characterized in that amino acid 124 in the CL is K, amino acid 147 in the CH1 is E, amino acid 213 in the CH1 is E, and amino acid 123 in the CL is R.

8. A bispecific antibody specifically binding to the extracellular domain of human BCMA and to human CD3, characterized in comprising a heavy and light chain set selected from the group consisting of polypeptides
   i) SEQ ID NO:43, SEQ ID NO:44, SEQ ID NO:45, and SEQ ID NO:46 (set 1),
   ii) SEQ ID NO:45, SEQ ID NO:47, SEQ ID NO:48, and SEQ ID NO:49 (set 2), and
   iii) SEQ ID NO:45, SEQ ID NO:50, SEQ ID NO:51, and SEQ ID NO:52 (set 3).

9. A bispecific antibody according to claim 2, wherein in the antibody portion specifically binding to human CD3 comprises the heavy chain CDRs of SEQ ID NO: 1, 2 and 3 as respectively heavy chain CDR1, CDR2 and CDR3 and the variable domain comprises the light chain CDRs of SEQ ID NO: 4, 5 and 6 as respectively light chain CDR1, CDR2 and CDR3.

10. An antibody according to claim 2, characterized in that the CH3 domain of one heavy chain and the CH3 domain of the other heavy chain each meet at an interface which comprises an original interface between the antibody CH3 domains; wherein said interface is altered to promote the formation of the bispecific antibody, wherein the alteration is characterized in that:
    a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
    b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

11. A method for the preparation of a bispecific antibody according to claim 1 comprising the steps of
    a) transforming a host cell with vectors comprising nucleic acid molecules encoding a light chain and heavy chain,
    b) culturing the host cell under conditions that allow synthesis of said antibody molecule; and
    c) recovering said antibody molecule from said culture.

12. A host cell comprising vectors comprising nucleic acid molecules fully encoding the light and heavy chains of an antibody according to claim 1.

13. A pharmaceutical composition comprising an antibody according to claim 1 and a pharmaceutically acceptable excipient.

14. A method of treatment of a plasma cell disorder in a subject comprising administering an effective amount of composition according to claim 13 to said subject.

15. A method of treatment of Multiple Myeloma according to claim 14.

16. A bispecific antibody according to claim 2 wherein an antibody specifically binding to BCMA comprises a variable domain VH comprising the heavy chain CDRs of SEQ ID NO: 21, 24 and 27 as respectively heavy chain CDR1, CDR2 and CDR3 and a variable domain VL comprising the light chain CDRs of SEQ ID NO: 30, 33 and 36 as respectively light chain CDR1, CDR2 and CDR3.

* * * * *

UNITED STATES PATENT AND TRADEMARK OFFICE
CERTIFICATE OF CORRECTION

PATENT NO. : 10,253,104 B2
APPLICATION NO. : 15/501620
DATED : April 9, 2019
INVENTOR(S) : Minh Diem Vu et al.

Page 1 of 1

It is certified that error appears in the above-identified patent and that said Letters Patent is hereby corrected as shown below:

In the Claims

Column 191, Line 9, cancel the text beginning with "16. A bispecific antibody according to claim 2 wherein" and ending "light chain CDR1, CDR2 and CDR3." in Column 191, Line 15, and insert the following claim:
--16. A bispecific antibody according to claim 2 wherein an antibody portion specifically binding to BCMA comprises a variable domain VH comprising the heavy chain CDRs of SEQ ID NO: 21, 24 AND 27 as respectively heavy chain CDR1, CDR2 and CDR3 and a variable domain VL comprising the light chain CDRs of SEQ ID NO: 30, 33 and 36 as respectively light chain CDR1, CDR2 and CDR3.--

Signed and Sealed this
Ninth Day of July, 2019

Andrei Iancu
*Director of the United States Patent and Trademark Office*

UNITED STATES PATENT AND TRADEMARK OFFICE
CERTIFICATE OF CORRECTION

PATENT NO. : 10,253,104 B2  
APPLICATION NO. : 15/501620  
DATED : April 9, 2019  
INVENTOR(S) : Minh Diem Vu et al.

Page 1 of 1

It is certified that error appears in the above-identified patent and that said Letters Patent is hereby corrected as shown below:

On the Title Page

"(73) Assignee: ENGMAB AG, Pfäffikon (CH)" should read --(73) Assignee: ENGMAB SÀRL, Boudry (CH)--

"(74) Attorney, Agent, or Firm—Patrick H. Higgins; Eckert Seamas Cherin & Mellot, LLC" should read --(74) Attorney, Agent, or Firm—Patrick H. Higgins; Eckert Seamans Cherin & Mellott, LLC--

In the Claims

Column 189, Line 41, Claim 3 cancel the text beginning with "c) amino acid at position 124" and ending "(numbering according to EU index of Kabat)." in Line 50, and insert the following text:
--c) amino acid at position 124 of a constant domain CL of the second light chain is substituted independently by lysine (K), arginine (R) or histidine (H) (numbering according to Kabat), and wherein amino acid at position 147 and amino acid at position 213 of a constant domain CH1 of the second heavy chain are each substituted independently by glutamic acid (E), or aspartic acid (D) (numbering according to EU index of Kabat).--

Column 190, Line 19, Claim 9 cancel the text beginning with "9. A bispecific antibody" and ending "and CDR3." in Line 28, and insert the following claim:
--9. A bispecific antibody according to claim 2, wherein the antibody portion specifically binding to human CD3 comprises the heavy chain CDRs of SEQ ID NO: 1, 2 and 3 as respectively heavy chain CDR1, CDR2 and CDR3 and the variable domain comprises the light chain CDRs of SEQ ID NO: 4, 5 and 6 as respectively light chain CDR1, CDR2 and CDR3.--

Signed and Sealed this  
Tenth Day of August, 2021

Drew Hirshfeld  
*Performing the Functions and Duties of the  
Under Secretary of Commerce for Intellectual Property and  
Director of the United States Patent and Trademark Office*

SEQUENCE LISTING

<160> NUMBER OF SEQ ID NOS: 130

<210> SEQ ID NO 1
<211> LENGTH: 14
<212> TYPE: PRT
<213> ORGANISM: Mus musculus

<400> SEQUENCE: 1

Gly Ser Ser Thr Gly Ala Val Thr Ser Gly Tyr Tyr Pro Asn
1               5                   10

<210> SEQ ID NO 2
<211> LENGTH: 7
<212> TYPE: PRT
<213> ORGANISM: Mus musculus

<400> SEQUENCE: 2

Gly Thr Lys Phe Leu Ala Pro
1               5

<210> SEQ ID NO 3
<211> LENGTH: 9
<212> TYPE: PRT
<213> ORGANISM: Mus musculus

<400> SEQUENCE: 3

Ala Leu Trp Tyr Ser Asn Arg Trp Val
1               5

<210> SEQ ID NO 4
<211> LENGTH: 10
<212> TYPE: PRT
<213> ORGANISM: Mus musculus

<400> SEQUENCE: 4

Gly Phe Thr Phe Asn Lys Tyr Ala Met Asn
1               5                   10

<210> SEQ ID NO 5
<211> LENGTH: 19
<212> TYPE: PRT
<213> ORGANISM: Mus musculus

<400> SEQUENCE: 5

Arg Ile Arg Ser Lys Tyr Asn Asn Tyr Ala Thr Tyr Tyr Ala Asp Ser
1               5                   10                  15

Val Lys Asp

<210> SEQ ID NO 6
<211> LENGTH: 14
<212> TYPE: PRT
<213> ORGANISM: Mus musculus

<400> SEQUENCE: 6

His Gly Asn Phe Gly Asn Ser Tyr Ile Ser Tyr Trp Ala Tyr
1               5                   10

<210> SEQ ID NO 7
<211> LENGTH: 109
<212> TYPE: PRT
<213> ORGANISM: Mus musculus

<400> SEQUENCE: 7

Gln Thr Val Val Thr Gln Glu Pro Ser Leu Thr Val Ser Pro Gly Gly

```
  1               5                  10                 15
Thr Val Thr Leu Thr Cys Gly Ser Ser Thr Gly Ala Val Thr Ser Gly
            20                  25                 30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 8
<211> LENGTH: 125
<212> TYPE: PRT
<213> ORGANISM: Mus musculus

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
aagcttggat ccatgttgca gatggctggg cagtgctcc                          39

<210> SEQ ID NO 10
<211> LENGTH: 49
<212> TYPE: DNA
<213> ORGANISM: Artificial Sequence
<220> FEATURE:
<223> OTHER INFORMATION: Primer

<400> SEQUENCE: 10
gaattcgcgg ccgctcatcc tttcactgaa ttggtcacac ttgcattac               49

<210> SEQ ID NO 11
<211> LENGTH: 42
```

```
<212> TYPE: DNA
<213> ORGANISM: Artificial Sequence
<220> FEATURE:
<223> OTHER INFORMATION: Primer

<400> SEQUENCE: 11
acgttagatc tccactcagt cctgcatctt gttccagtta ac                          42

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
aacgttgcgg ccgctagttt cacaaacccc agg                                    33

<210> SEQ ID NO 13
<211> LENGTH: 45
<212> TYPE: DNA
<213> ORGANISM: Artificial Sequence
<220> FEATURE:
<223> OTHER INFORMATION: Primer

<400> SEQUENCE: 13
gaattcaagc ttgccaccat gttgcagatg gctgggcagt gctcc                       45

<210> SEQ ID NO 14
<211> LENGTH: 48
<212> TYPE: DNA
<213> ORGANISM: Artificial Sequence
<220> FEATURE:
<223> OTHER INFORMATION: Primer

<400> SEQUENCE: 14
gaattctcta gattacctag cagaaattga tttctctatc tccgtagc                    48

<210> SEQ ID NO 15
<211> LENGTH: 116
<212> TYPE: PRT
<213> ORGANISM: Homo sapiens
<220> FEATURE:
<223> OTHER INFORMATION: BCMA VH

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115
```

```
<210> SEQ ID NO 16
<211> LENGTH: 119
<212> TYPE: PRT
<213> ORGANISM: Homo sapiens
<220> FEATURE:
<223> OTHER INFORMATION: BCMA VH

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Pro Tyr Phe Ala Pro Phe Asp Tyr Trp Gly Gln Gly
            100                 105                 110

Thr Leu Val Thr Val Ser Ser
        115

<210> SEQ ID NO 17
<211> LENGTH: 116
<212> TYPE: PRT
<213> ORGANISM: Homo sapiens
<220> FEATURE:
<223> OTHER INFORMATION: BCMA VH

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 18
<211> LENGTH: 109
<212> TYPE: PRT
<213> ORGANISM: Homo sapiens
<220> FEATURE:
<223> OTHER INFORMATION: BCMA VL

<400> SEQUENCE: 18

Glu Ile Val Leu Thr Gln Ser Pro Gly Thr Leu Ser Leu Ser Pro Gly
```

```
                1               5                  10                 15
            Glu Arg Ala Thr Leu Ser Cys Arg Ala Ser Gln Ser Val Ser Ser Ser
                                20                  25                 30

Tyr Leu Ala Trp Tyr Gln Gln Lys Pro Gly Gln Ala Pro Arg Leu Leu
                                35                  40                 45

Ile Tyr Gly Ala Ser Ser Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
            65                  70                  75                  80

Pro Glu Asp Phe Ala Val Tyr Tyr Cys Gln Gln Tyr Gly Tyr Pro Pro
                                85                  90                  95

Asp Phe Thr Phe Gly Gln Gly Thr Lys Val Glu Ile Lys
                            100                 105
```

<210> SEQ ID NO 19
<211> LENGTH: 109
<212> TYPE: PRT
<213> ORGANISM: Homo sapiens
<220> FEATURE:
<223> OTHER INFORMATION: BCMA VL

<400> SEQUENCE: 19

```
            Glu Ile Val Leu Thr Gln Ser Pro Gly Thr Leu Ser Leu Ser Pro Gly
            1               5                   10                  15

Glu Arg Ala Thr Leu Ser Cys Arg Ala Ser Gln Ser Val Ser Ser Ser
                                20                  25                  30

Tyr Leu Ala Trp Tyr Gln Gln Lys Pro Gly Gln Ala Pro Arg Leu Leu
                                35                  40                  45

Ile Tyr Gly Ala Ser Ser Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
            65                  70                  75                  80

Pro Glu Asp Phe Ala Val Tyr Tyr Cys Gln Gln Tyr Gly Asn Pro Pro
                                85                  90                  95

Leu Tyr Thr Phe Gly Gln Gly Thr Lys Val Glu Ile Lys
                            100                 105
```

<210> SEQ ID NO 20
<211> LENGTH: 111
<212> TYPE: PRT
<213> ORGANISM: Homo sapiens
<220> FEATURE:
<223> OTHER INFORMATION: BCMA VL

<400> SEQUENCE: 20

```
            Asp Ile Val Met Thr Gln Ser Pro Leu Ser Leu Pro Val Thr Pro Gly
            1               5                   10                  15

Glu Pro Ala Ser Ile Ser Cys Arg Ser Ser Gln Ser Leu Leu His Ser
                                20                  25                  30

Asn Gly Tyr Asn Tyr Leu Asp Trp Tyr Leu Gln Lys Pro Gly Gln Ser
                                35                  40                  45

Pro Gln Leu Leu Ile Tyr Leu Gly Ser Asn Arg Ala Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Met Gln Ala
                                85                  90                  95
```

Met Gln Ile Pro Thr Phe Gly Gln Gly Thr Lys Val Glu Ile Lys
            100                 105                 110

<210> SEQ ID NO 21
<211> LENGTH: 5
<212> TYPE: PRT
<213> ORGANISM: Homo sapiens
<220> FEATURE:
<223> OTHER INFORMATION: CDR1H

<400> SEQUENCE: 21

Ser Tyr Ala Met Ser
1               5

<210> SEQ ID NO 22
<211> LENGTH: 5
<212> TYPE: PRT
<213> ORGANISM: Homo sapiens
<220> FEATURE:
<223> OTHER INFORMATION: CDR1H

<400> SEQUENCE: 22

Ser Tyr Ala Met Ser
1               5

<210> SEQ ID NO 23
<211> LENGTH: 5
<212> TYPE: PRT
<213> ORGANISM: Homo sapiens
<220> FEATURE:
<223> OTHER INFORMATION: CDR1H

<400> SEQUENCE: 23

Ser Tyr Trp Ile Gly
1               5

<210> SEQ ID NO 24
<211> LENGTH: 17
<212> TYPE: PRT
<213> ORGANISM: Homo sapiens
<220> FEATURE:
<223> OTHER INFORMATION: CDR2H

<400> SEQUENCE: 24

Ala Ile Ser Gly Ser Gly Gly Ser Thr Tyr Tyr Ala Asp Ser Val Lys
1               5                   10                  15

Gly

<210> SEQ ID NO 25
<211> LENGTH: 17
<212> TYPE: PRT
<213> ORGANISM: Homo sapiens
<220> FEATURE:
<223> OTHER INFORMATION: CDR2H

<400> SEQUENCE: 25

Ala Ile Ser Gly Ser Gly Gly Ser Thr Tyr Tyr Ala Asp Ser Val Lys
1               5                   10                  15

Gly

<210> SEQ ID NO 26
<211> LENGTH: 17
<212> TYPE: PRT
<213> ORGANISM: Homo sapiens
<220> FEATURE:
<223> OTHER INFORMATION: CDR2H

```
<400> SEQUENCE: 26

Ile Ile Tyr Pro Gly Asp Ser Asp Thr Arg Tyr Ser Pro Ser Phe Gln
1               5                   10                  15
Gly

<210> SEQ ID NO 27
<211> LENGTH: 7
<212> TYPE: PRT
<213> ORGANISM: Homo sapiens
<220> FEATURE:
<223> OTHER INFORMATION: CDR3H

<400> SEQUENCE: 27

Val Leu Gly Trp Phe Asp Tyr
1               5

<210> SEQ ID NO 28
<211> LENGTH: 10
<212> TYPE: PRT
<213> ORGANISM: Homo sapiens
<220> FEATURE:
<223> OTHER INFORMATION: CDR3H

<400> SEQUENCE: 28

Val Ala Pro Tyr Phe Ala Pro Phe Asp Tyr
1               5                   10

<210> SEQ ID NO 29
<211> LENGTH: 7
<212> TYPE: PRT
<213> ORGANISM: Homo sapiens
<220> FEATURE:
<223> OTHER INFORMATION: CDR3H

<400> SEQUENCE: 29

Asn Gly Tyr Leu Gly Asp Tyr
1               5

<210> SEQ ID NO 30
<211> LENGTH: 12
<212> TYPE: PRT
<213> ORGANISM: Homo sapiens
<220> FEATURE:
<223> OTHER INFORMATION: CDR1L

<400> SEQUENCE: 30

Arg Ala Ser Gln Ser Val Ser Ser Ser Tyr Leu Ala
1               5                   10

<210> SEQ ID NO 31
<211> LENGTH: 12
<212> TYPE: PRT
<213> ORGANISM: Homo sapiens
<220> FEATURE:
<223> OTHER INFORMATION: CDR1L

<400> SEQUENCE: 31

Arg Ala Ser Gln Ser Val Ser Ser Ser Tyr Leu Ala
1               5                   10

<210> SEQ ID NO 32
<211> LENGTH: 16
<212> TYPE: PRT
<213> ORGANISM: Homo sapiens
<220> FEATURE:
```

```
<223> OTHER INFORMATION: CDR1L

<400> SEQUENCE: 32

Arg Ser Ser Gln Ser Leu Leu His Ser Asn Gly Tyr Asn Tyr Leu Asp
1               5                   10                  15

<210> SEQ ID NO 33
<211> LENGTH: 7
<212> TYPE: PRT
<213> ORGANISM: Homo sapiens
<220> FEATURE:
<223> OTHER INFORMATION: CDR2L

<400> SEQUENCE: 33

Gly Ala Ser Ser Arg Ala Thr
1               5

<210> SEQ ID NO 34
<211> LENGTH: 7
<212> TYPE: PRT
<213> ORGANISM: Homo sapiens
<220> FEATURE:
<223> OTHER INFORMATION: CDR2L

<400> SEQUENCE: 34

Gly Ala Ser Ser Arg Ala Thr
1               5

<210> SEQ ID NO 35
<211> LENGTH: 7
<212> TYPE: PRT
<213> ORGANISM: Homo sapiens
<220> FEATURE:
<223> OTHER INFORMATION: CDR2L

<400> SEQUENCE: 35

Leu Gly Ser Asn Arg Ala Ser
1               5

<210> SEQ ID NO 36
<211> LENGTH: 10
<212> TYPE: PRT
<213> ORGANISM: Homo sapiens
<220> FEATURE:
<223> OTHER INFORMATION: CDR3L

<400> SEQUENCE: 36

Gln Gln Tyr Gly Tyr Pro Pro Asp Phe Thr
1               5                   10

<210> SEQ ID NO 37
<211> LENGTH: 10
<212> TYPE: PRT
<213> ORGANISM: Homo sapiens
<220> FEATURE:
<223> OTHER INFORMATION: CDR3L

<400> SEQUENCE: 37

Gln Gln Tyr Gly Asn Pro Pro Leu Tyr Thr
1               5                   10

<210> SEQ ID NO 38
<211> LENGTH: 8
<212> TYPE: PRT
<213> ORGANISM: Homo sapiens
<220> FEATURE:
<223> OTHER INFORMATION: CDR3L
```

<400> SEQUENCE: 38

Met Gln Ala Met Gln Ile Pro Thr
1               5

<210> SEQ ID NO 39
<211> LENGTH: 689
<212> TYPE: PRT
<213> ORGANISM: Homo sapiens
<220> FEATURE:
<223> OTHER INFORMATION: knob HC

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Gly Gly Gly Gly
    210                 215                 220

Ser Gly Gly Gly Gly Ser Glu Val Gln Leu Leu Glu Ser Gly Gly Gly
225                 230                 235                 240

Leu Val Gln Pro Gly Gly Ser Leu Arg Leu Ser Cys Ala Ala Ser Gly
                245                 250                 255

Phe Thr Phe Ser Thr Tyr Ala Met Asn Trp Val Arg Gln Ala Pro Gly
            260                 265                 270

Lys Gly Leu Glu Trp Val Ser Arg Ile Arg Ser Lys Tyr Asn Asn Tyr
        275                 280                 285

Ala Thr Tyr Tyr Ala Asp Ser Val Lys Gly Arg Phe Thr Ile Ser Arg
    290                 295                 300

Asp Asp Ser Lys Asn Thr Leu Tyr Leu Gln Met Asn Ser Leu Arg Ala
305                 310                 315                 320

Glu Asp Thr Ala Val Tyr Tyr Cys Val Arg His Gly Asn Phe Gly Asn
                325                 330                 335

Ser Tyr Val Ser Trp Phe Ala Tyr Trp Gly Gln Gly Thr Leu Val Thr
            340                 345                 350

Val Ser Ser Ala Ser Val Ala Ala Pro Ser Val Phe Ile Phe Pro Pro
        355                 360                 365

Ser Asp Glu Gln Leu Lys Ser Gly Thr Ala Ser Val Val Cys Leu Leu
    370                 375                 380

Asn Asn Phe Tyr Pro Arg Glu Ala Lys Val Gln Trp Lys Val Asp Asn
385                 390                 395                 400

Ala Leu Gln Ser Gly Asn Ser Gln Glu Ser Val Thr Glu Gln Asp Ser
                405                 410                 415

Lys Asp Ser Thr Tyr Ser Leu Ser Ser Thr Leu Thr Leu Ser Lys Ala
            420                 425                 430

Asp Tyr Glu Lys His Lys Val Tyr Ala Cys Glu Val Thr His Gln Gly
        435                 440                 445

Leu Ser Ser Pro Val Thr Lys Ser Phe Asn Arg Gly Glu Cys Asp Lys
    450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Gly Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Cys Arg Asp Glu Leu Thr Lys Asn Gln Val Ser Leu Trp
        595                 600                 605

Cys Leu Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 40
<211> LENGTH: 446
<212> TYPE: PRT
<213> ORGANISM: Homo sapiens
<220> FEATURE:
<223> OTHER INFORMATION: hole HC

<400> SEQUENCE: 40

Glu Val Gln Leu Leu Glu Ser Gly Gly Gly Leu Val Gln Pro Gly Gly

-continued

```
  1               5                  10                 15
Ser Leu Arg Leu Ser Cys Ala Ala Ser Gly Phe Thr Phe Ser Ser Tyr
                 20                 25                 30

Ala Met Ser Trp Val Arg Gln Ala Pro Gly Lys Gly Leu Glu Trp Val
                 35                 40                 45

Ser Ala Ile Ser Gly Ser Gly Gly Ser Thr Tyr Tyr Ala Asp Ser Val
                 50                 55                 60

Lys Gly Arg Phe Thr Ile Ser Arg Asp Asn Ser Lys Asn Thr Leu Tyr
 65              70                 75                 80

Leu Gln Met Asn Ser Leu Arg Ala Glu Asp Thr Ala Val Tyr Tyr Cys
                 85                 90                 95

Ala Lys Val Leu Gly Trp Phe Asp Tyr Trp Gly Gln Gly Thr Leu Val
                100                105                110

Thr Val Ser Ser Ala Ser Thr Lys Gly Pro Ser Val Phe Pro Leu Ala
                115                120                125

Pro Ser Ser Lys Ser Thr Ser Gly Gly Thr Ala Ala Leu Gly Cys Leu
                130                135                140

Val Lys Asp Tyr Phe Pro Glu Pro Val Thr Val Ser Trp Asn Ser Gly
145                150                155                160

Ala Leu Thr Ser Gly Val His Thr Phe Pro Ala Val Leu Gln Ser Ser
                165                170                175

Gly Leu Tyr Ser Leu Ser Ser Val Val Thr Val Pro Ser Ser Ser Leu
                180                185                190

Gly Thr Gln Thr Tyr Ile Cys Asn Val Asn His Lys Pro Ser Asn Thr
                195                200                205

Lys Val Asp Lys Lys Val Glu Pro Lys Ser Cys Asp Lys Thr His Thr
                210                215                220

Cys Pro Pro Cys Pro Ala Pro Glu Ala Ala Gly Gly Pro Ser Val Phe
225                230                235                240

Leu Phe Pro Pro Lys Pro Lys Asp Thr Leu Met Ile Ser Arg Thr Pro
                245                250                255

Glu Val Thr Cys Val Val Val Asp Val Ser His Glu Asp Pro Glu Val
                260                265                270

Lys Phe Asn Trp Tyr Val Asp Gly Val Glu Val His Asn Ala Lys Thr
                275                280                285

Lys Pro Arg Glu Glu Gln Tyr Asn Ser Thr Tyr Arg Val Val Ser Val
                290                295                300

Leu Thr Val Leu His Gln Asp Trp Leu Asn Gly Lys Glu Tyr Lys Cys
305                310                315                320

Lys Val Ser Asn Lys Ala Leu Gly Ala Pro Ile Glu Lys Thr Ile Ser
                325                330                335

Lys Ala Lys Gly Gln Pro Arg Glu Pro Gln Val Cys Thr Leu Pro Pro
                340                345                350

Ser Arg Asp Glu Leu Thr Lys Asn Gln Val Ser Leu Ser Cys Ala Val
                355                360                365

Lys Gly Phe Tyr Pro Ser Asp Ile Ala Val Glu Trp Glu Ser Asn Gly
                370                375                380

Gln Pro Glu Asn Asn Tyr Lys Thr Thr Pro Pro Val Leu Asp Ser Asp
385                390                395                400

Gly Ser Phe Phe Leu Val Ser Lys Leu Thr Val Asp Lys Ser Arg Trp
                405                410                415

Gln Gln Gly Asn Val Phe Ser Cys Ser Val Met His Glu Ala Leu His
                420                425                430
```

Asn His Tyr Thr Gln Lys Ser Leu Ser Leu Ser Pro Gly Lys
         435                 440                 445

<210> SEQ ID NO 41
<211> LENGTH: 214
<212> TYPE: PRT
<213> ORGANISM: Homo sapiens
<220> FEATURE:
<223> OTHER INFORMATION: CD3 LC

<400> SEQUENCE: 41

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 42
<211> LENGTH: 216
<212> TYPE: PRT
<213> ORGANISM: Homo sapiens
<220> FEATURE:
<223> OTHER INFORMATION: BCMA LC

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Gly Tyr Pro Pro
                    85                  90                  95

Asp Phe Thr Phe Gly Gln Gly Thr Lys Val Glu Ile Lys Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Cys
210                 215

<210> SEQ ID NO 43
<211> LENGTH: 671
<212> TYPE: PRT
<213> ORGANISM: Homo sapiens
<220> FEATURE:
<223> OTHER INFORMATION: knob HC

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Gly Gly Gly Gly
```

-continued

```
              210                 215                 220
Ser Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
                260                 265                 270

Gly Gln Ala Phe Arg Gly Leu Ile Gly Gly Thr Asn Lys Arg Ala Pro
            275                 280                 285

Gly Thr Pro Ala Arg Phe Ser Gly Ser Leu Leu Gly Gly Lys Ala Ala
            290                 295                 300

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
                325                 330                 335

Thr Val Leu Ser Ser Ala Ser Thr Lys Gly Pro Ser Val Phe Pro Leu
                340                 345                 350

Ala Pro Ser Ser Lys Ser Thr Ser Gly Gly Thr Ala Ala Leu Gly Cys
            355                 360                 365

Leu Val Lys Asp Tyr Phe Pro Glu Pro Val Thr Val Ser Trp Asn Ser
            370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
                405                 410                 415

Leu Gly Thr Gln Thr Tyr Ile Cys Asn Val Asn His Lys Pro Ser Asn
            420                 425                 430

Thr Lys Val Asp Lys Lys Val Glu Pro Lys Ser Cys Asp Lys Thr His
            435                 440                 445

Thr Cys Pro Pro Cys Pro Ala Pro Glu Ala Ala Gly Gly Pro Ser Val
            450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
            515                 520                 525

Val Leu Thr Val Leu His Gln Asp Trp Leu Asn Gly Lys Glu Tyr Lys
530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Cys Arg Asp Glu Leu Thr Lys Asn Gln Val Ser Leu Trp Cys Leu
            580                 585                 590

Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
            610                 615                 620

Asp Gly Ser Phe Phe Leu Tyr Ser Lys Leu Thr Val Asp Lys Ser Arg
625                 630                 635                 640
```

```
Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 44
<211> LENGTH: 446
<212> TYPE: PRT
<213> ORGANISM: Homo sapiens
<220> FEATURE:
<223> OTHER INFORMATION: hole HC

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335
```

```
Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 45
<211> LENGTH: 232
<212> TYPE: PRT
<213> ORGANISM: Homo sapiens
<220> FEATURE:
<223> OTHER INFORMATION: CD3 VH_CL

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
        210                 215                 220

Lys Ser Phe Asn Arg Gly Glu Cys
225                 230

<210> SEQ ID NO 46
```

<211> LENGTH: 216
<212> TYPE: PRT
<213> ORGANISM: Homo sapiens
<220> FEATURE:
<223> OTHER INFORMATION: BCMA cv LC

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Asp Phe Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 47
<211> LENGTH: 674
<212> TYPE: PRT
<213> ORGANISM: Homo sapiens
<220> FEATURE:
<223> OTHER INFORMATION: BCMA cv HC knob

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Ala Pro Tyr Phe Ala Pro Phe Asp Tyr Trp Gly Gln Gly

```
                100             105                110
Thr Leu Val Thr Val Ser Ser Ala Ser Thr Lys Gly Pro Ser Val Phe
            115                 120             125
Pro Leu Ala Pro Ser Ser Lys Ser Thr Ser Gly Gly Thr Ala Ala Leu
            130                 135             140
Gly Cys Leu Val Glu Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Glu Lys Val Glu Pro Lys Ser Cys Asp Gly
            210                 215                 220
Gly Gly Gly Ser Gly Gly Gly Ser Gln Ala Val Val Thr Gln Glu
225                 230                 235                 240
Pro Ser Leu Thr Val Ser Pro Gly Gly Thr Val Thr Leu Thr Cys Gly
                245                 250                 255
Ser Ser Thr Gly Ala Val Thr Thr Ser Asn Tyr Ala Asn Trp Val Gln
                260                 265                 270
Glu Lys Pro Gly Gln Ala Phe Arg Gly Leu Ile Gly Gly Thr Asn Lys
            275                 280                 285
Arg Ala Pro Gly Thr Pro Ala Arg Phe Ser Gly Ser Leu Leu Gly Gly
            290                 295                 300
Lys Ala Ala Leu Thr Leu Ser Gly Ala Gln Pro Glu Asp Glu Ala Glu
305                 310                 315                 320
Tyr Tyr Cys Ala Leu Trp Tyr Ser Asn Leu Trp Val Phe Gly Gly Gly
                325                 330                 335
Thr Lys Leu Thr Val Leu Ser Ser Ala Ser Thr Lys Gly Pro Ser Val
                340                 345                 350
Phe Pro Leu Ala Pro Ser Ser Lys Ser Thr Ser Gly Gly Thr Ala Ala
                355                 360                 365
Leu Gly Cys Leu Val Lys Asp Tyr Phe Pro Glu Pro Val Thr Val Ser
            370                 375                 380
Trp Asn Ser Gly Ala Leu Thr Ser Gly Val His Thr Phe Pro Ala Val
385                 390                 395                 400
Leu Gln Ser Ser Gly Leu Tyr Ser Leu Ser Ser Val Val Thr Val Pro
                405                 410                 415
Ser Ser Ser Leu Gly Thr Gln Thr Tyr Ile Cys Asn Val Asn His Lys
                420                 425                 430
Pro Ser Asn Thr Lys Val Asp Lys Lys Val Glu Pro Lys Ser Cys Asp
            435                 440                 445
Lys Thr His Thr Cys Pro Pro Cys Pro Ala Pro Glu Ala Ala Gly Gly
            450                 455                 460
Pro Ser Val Phe Leu Phe Pro Pro Lys Pro Lys Asp Thr Leu Met Ile
465                 470                 475                 480
Ser Arg Thr Pro Glu Val Thr Cys Val Val Val Asp Val Ser His Glu
                485                 490                 495
Asp Pro Glu Val Lys Phe Asn Trp Tyr Val Asp Gly Val Glu Val His
                500                 505                 510
Asn Ala Lys Thr Lys Pro Arg Glu Glu Gln Tyr Asn Ser Thr Tyr Arg
            515                 520                 525
```

```
Val Val Ser Val Leu Thr Val Leu His Gln Asp Trp Leu Asn Gly Lys
        530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys

<210> SEQ ID NO 48
<211> LENGTH: 449
<212> TYPE: PRT
<213> ORGANISM: Homo sapiens
<220> FEATURE:
<223> OTHER INFORMATION: BCMA cv HC hole

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Val Ala Pro Tyr Phe Ala Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 49
<211> LENGTH: 216
<212> TYPE: PRT
<213> ORGANISM: Homo sapiens
<220> FEATURE:
<223> OTHER INFORMATION: BCMA cv LC

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Pro Pro
                85                  90                  95

Leu Tyr Thr Phe Gly Gln Gly Thr Lys Val Glu Ile Lys Arg Thr Val
            100                 105                 110

Ala Ala Pro Ser Val Phe Ile Phe Pro Pro Ser Asp Arg Lys Leu Lys
```

```
                        115                 120                 125
Ser Gly Thr Ala Ser Val Val Cys Leu Leu Asn Asn Phe Tyr Pro Arg
            130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
            180                 185                 190
Val Tyr Ala Cys Glu Val Thr His Gln Gly Leu Ser Ser Pro Val Thr
                195                 200                 205
Lys Ser Phe Asn Arg Gly Glu Cys
            210                 215

<210> SEQ ID NO 50
<211> LENGTH: 671
<212> TYPE: PRT
<213> ORGANISM: Homo sapiens
<220> FEATURE:
<223> OTHER INFORMATION: BCMA cv HC knob

<400> SEQUENCE: 50

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
                20                  25                  30
Trp Ile Gly Trp Val Arg Gln Met Pro Gly Lys Gly Leu Glu Trp Met
            35                  40                  45
Gly Ile Ile Tyr Pro Gly Asp Ser Asp Thr Arg Tyr Ser Pro Ser Phe
        50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Asn Gly Tyr Leu Gly Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Glu Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Glu Lys Val Glu Pro Lys Ser Cys Asp Gly Gly Gly Gly
    210                 215                 220
Ser Gly Gly Gly Gly Ser Gln Ala Val Val Thr Gln Glu Pro Ser Leu
225                 230                 235                 240
Thr Val Ser Pro Gly Gly Thr Val Thr Leu Thr Cys Gly Ser Ser Thr
                245                 250                 255
Gly Ala Val Thr Thr Ser Asn Tyr Ala Asn Trp Val Gln Glu Lys Pro
```

```
            260                 265                 270
Gly Gln Ala Phe Arg Gly Leu Ile Gly Gly Thr Asn Lys Arg Ala Pro
            275                 280                 285
Gly Thr Pro Ala Arg Phe Ser Gly Ser Leu Leu Gly Gly Lys Ala Ala
            290                 295                 300
Leu Thr Leu Ser Gly Ala Gln Pro Glu Asp Glu Ala Glu Tyr Tyr Cys
305                 310                 315                 320
Ala Leu Trp Tyr Ser Asn Leu Trp Val Phe Gly Gly Gly Thr Lys Leu
                325                 330                 335
Thr Val Leu Ser Ser Ala Ser Thr Lys Gly Pro Ser Val Phe Pro Leu
            340                 345                 350
Ala Pro Ser Ser Lys Ser Thr Ser Gly Gly Thr Ala Ala Leu Gly Cys
            355                 360                 365
Leu Val Lys Asp Tyr Phe Pro Glu Pro Val Thr Val Ser Trp Asn Ser
            370                 375                 380
Gly Ala Leu Thr Ser Gly Val His Thr Phe Pro Ala Val Leu Gln Ser
385                 390                 395                 400
Ser Gly Leu Tyr Ser Leu Ser Ser Val Val Thr Val Pro Ser Ser Ser
                405                 410                 415
Leu Gly Thr Gln Thr Tyr Ile Cys Asn Val Asn His Lys Pro Ser Asn
            420                 425                 430
Thr Lys Val Asp Lys Lys Val Glu Pro Lys Ser Cys Asp Lys Thr His
            435                 440                 445
Thr Cys Pro Pro Cys Pro Ala Pro Glu Ala Ala Gly Gly Pro Ser Val
450                 455                 460
Phe Leu Phe Pro Pro Lys Pro Lys Asp Thr Leu Met Ile Ser Arg Thr
465                 470                 475                 480
Pro Glu Val Thr Cys Val Val Val Asp Val Ser His Glu Asp Pro Glu
                485                 490                 495
Val Lys Phe Asn Trp Tyr Val Asp Gly Val Glu Val His Asn Ala Lys
            500                 505                 510
Thr Lys Pro Arg Glu Glu Gln Tyr Asn Ser Thr Tyr Arg Val Val Ser
            515                 520                 525
Val Leu Thr Val Leu His Gln Asp Trp Leu Asn Gly Lys Glu Tyr Lys
            530                 535                 540
Cys Lys Val Ser Asn Lys Ala Leu Gly Ala Pro Ile Glu Lys Thr Ile
545                 550                 555                 560
Ser Lys Ala Lys Gly Gln Pro Arg Glu Pro Gln Val Tyr Thr Leu Pro
                565                 570                 575
Pro Cys Arg Asp Glu Leu Thr Lys Asn Gln Val Ser Leu Trp Cys Leu
            580                 585                 590
Val Lys Gly Phe Tyr Pro Ser Asp Ile Ala Val Glu Trp Glu Ser Asn
            595                 600                 605
Gly Gln Pro Glu Asn Asn Tyr Lys Thr Thr Pro Pro Val Leu Asp Ser
            610                 615                 620
Asp Gly Ser Phe Phe Leu Tyr Ser Lys Leu Thr Val Asp Lys Ser Arg
625                 630                 635                 640
Trp Gln Gln Gly Asn Val Phe Ser Cys Ser Val Met His Glu Ala Leu
                645                 650                 655
His Asn His Tyr Thr Gln Lys Ser Leu Ser Leu Ser Pro Gly Lys
            660                 665                 670

<210> SEQ ID NO 51
```

<211> LENGTH: 446
<212> TYPE: PRT
<213> ORGANISM: Homo sapiens
<220> FEATURE:
<223> OTHER INFORMATION: BCMA cv HC hole

<400> SEQUENCE: 51

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 52
<211> LENGTH: 218
<212> TYPE: PRT
<213> ORGANISM: Homo sapiens
<220> FEATURE:
<223> OTHER INFORMATION: BCMA cv LC

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Gln Ile Pro Thr Phe Gly Gln Gly Thr Lys Val Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 53
<211> LENGTH: 7
<212> TYPE: PRT
<213> ORGANISM: Homo sapiens

<400> SEQUENCE: 53

Ser Gly Tyr Leu Gly Asp Tyr
1               5

<210> SEQ ID NO 54
<211> LENGTH: 116
```

<212> TYPE: PRT
<213> ORGANISM: Homo sapiens

<400> SEQUENCE: 54

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Leu Gly Asp Tyr Trp Gly Gln Gly Thr Leu Val
            100                 105                 110

Thr Val Ser Ser
            115

<210> SEQ ID NO 55
<211> LENGTH: 7
<212> TYPE: PRT
<213> ORGANISM: Homo sapiens

<400> SEQUENCE: 55

Thr Gly Tyr Leu Gly Asp Tyr
1               5

<210> SEQ ID NO 56
<211> LENGTH: 116
<212> TYPE: PRT
<213> ORGANISM: Homo sapiens

<400> SEQUENCE: 56

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Thr Gly Tyr Leu Gly Asp Tyr Trp Gly Gln Gly Thr Leu Val
            100                 105                 110

Thr Val Ser Ser
            115

<210> SEQ ID NO 57
<211> LENGTH: 7
<212> TYPE: PRT
<213> ORGANISM: Homo sapiens

<400> SEQUENCE: 57

```
Glu Gly Tyr Leu Gly Asp Tyr
1               5

<210> SEQ ID NO 58
<211> LENGTH: 116
<212> TYPE: PRT
<213> ORGANISM: Homo sapiens

<400> SEQUENCE: 58

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Tyr Leu Gly Asp Tyr Trp Gly Gln Gly Thr Leu Val
            100                 105                 110

Thr Val Ser Ser
            115

<210> SEQ ID NO 59
<211> LENGTH: 7
<212> TYPE: PRT
<213> ORGANISM: Homo sapiens

<400> SEQUENCE: 59

Gln Gly Tyr Leu Gly Asp Tyr
1               5

<210> SEQ ID NO 60
<211> LENGTH: 116
<212> TYPE: PRT
<213> ORGANISM: Homo sapiens

<400> SEQUENCE: 60

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Tyr Leu Gly Asp Tyr Trp Gly Gln Gly Thr Leu Val
            100                 105                 110

Thr Val Ser Ser
            115
```

```
<210> SEQ ID NO 61
<211> LENGTH: 7
<212> TYPE: PRT
<213> ORGANISM: Homo sapiens

<400> SEQUENCE: 61

Ala Gly Tyr Leu Gly Asp Tyr
1               5

<210> SEQ ID NO 62
<211> LENGTH: 116
<212> TYPE: PRT
<213> ORGANISM: Homo sapiens

<400> SEQUENCE: 62

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ala Gly Tyr Leu Gly Asp Tyr Trp Gly Gln Gly Thr Leu Val
            100                 105                 110

Thr Val Ser Ser
        115

<210> SEQ ID NO 63
<211> LENGTH: 7
<212> TYPE: PRT
<213> ORGANISM: Homo sapiens

<400> SEQUENCE: 63

Gly Gly Tyr Leu Gly Asp Tyr
1               5

<210> SEQ ID NO 64
<211> LENGTH: 116
<212> TYPE: PRT
<213> ORGANISM: Homo sapiens

<400> SEQUENCE: 64

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

Ala Arg Gly Gly Tyr Leu Gly Asp Tyr Trp Gly Gln Gly Thr Leu Val
            100                 105                 110

Thr Val Ser Ser
        115

<210> SEQ ID NO 65
<211> LENGTH: 7
<212> TYPE: PRT
<213> ORGANISM: Homo sapiens

<400> SEQUENCE: 65

Asn Ala Tyr Leu Gly Asp Tyr
1               5

<210> SEQ ID NO 66
<211> LENGTH: 116
<212> TYPE: PRT
<213> ORGANISM: Homo sapiens

<400> SEQUENCE: 66

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Ala Tyr Leu Gly Asp Tyr Trp Gly Gln Gly Thr Leu Val
            100                 105                 110

Thr Val Ser Ser
        115

<210> SEQ ID NO 67
<211> LENGTH: 7
<212> TYPE: PRT
<213> ORGANISM: Homo sapiens

<400> SEQUENCE: 67

Asn Glu Tyr Leu Gly Asp Tyr
1               5

<210> SEQ ID NO 68
<211> LENGTH: 116
<212> TYPE: PRT
<213> ORGANISM: Homo sapiens

<400> SEQUENCE: 68

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe

```
                50              55              60
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Asn Glu Tyr Leu Gly Asp Tyr Trp Gly Gln Gly Thr Leu Val
                100                 105                 110

Thr Val Ser Ser
        115

<210> SEQ ID NO 69
<211> LENGTH: 7
<212> TYPE: PRT
<213> ORGANISM: Homo sapiens

<400> SEQUENCE: 69

Asn Gln Tyr Leu Gly Asp Tyr
1               5

<210> SEQ ID NO 70
<211> LENGTH: 116
<212> TYPE: PRT
<213> ORGANISM: Homo sapiens

<400> SEQUENCE: 70

Glu Val Gln Leu Val Gln Ser Gly Ala Glu Val Lys Lys Pro Gly Glu
1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Asn Gln Tyr Leu Gly Asp Tyr Trp Gly Gln Gly Thr Leu Val
                100                 105                 110

Thr Val Ser Ser
        115

<210> SEQ ID NO 71
<211> LENGTH: 16
<212> TYPE: PRT
<213> ORGANISM: Homo sapiens

<400> SEQUENCE: 71

Arg Ser Ser Gln Ser Leu Leu His Ser Ser Gly Tyr Asn Tyr Leu Asp
1               5                  10                  15

<210> SEQ ID NO 72
<211> LENGTH: 111
<212> TYPE: PRT
<213> ORGANISM: Homo sapiens

<400> SEQUENCE: 72

Asp Ile Val Met Thr Gln Ser Pro Leu Ser Leu Pro Val Thr Pro Gly
1               5                  10                  15
```

Glu Pro Ala Ser Ile Ser Cys Arg Ser Ser Gln Ser Leu Leu His Ser
                20                  25                  30

Ser Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Met Gln Ile Pro Thr Phe Gly Gly Gly Thr Lys Val Glu Ile Lys
                100                 105                 110

<210> SEQ ID NO 73
<211> LENGTH: 16
<212> TYPE: PRT
<213> ORGANISM: Homo sapiens

<400> SEQUENCE: 73

Arg Ser Ser Gln Ser Leu Leu His Ser Thr Gly Tyr Asn Tyr Leu Asp
 1               5                   10                  15

<210> SEQ ID NO 74
<211> LENGTH: 111
<212> TYPE: PRT
<213> ORGANISM: Homo sapiens

<400> SEQUENCE: 74

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu His Ser
                20                  25                  30

Thr Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Met Gln Ile Pro Thr Phe Gly Gln Gly Thr Lys Val Glu Ile Lys
                100                 105                 110

<210> SEQ ID NO 75
<211> LENGTH: 16
<212> TYPE: PRT
<213> ORGANISM: Homo sapiens

<400> SEQUENCE: 75

Arg Ser Ser Gln Ser Leu Leu His Ser Glu Gly Tyr Asn Tyr Leu Asp
 1               5                   10                  15

<210> SEQ ID NO 76
<211> LENGTH: 111
<212> TYPE: PRT
<213> ORGANISM: Homo sapiens

<400> SEQUENCE: 76

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu His Ser
            20                  25                  30

Glu Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Gln Ile Pro Thr Phe Gly Gln Gly Thr Lys Val Glu Ile Lys
            100                 105                 110

<210> SEQ ID NO 77
<211> LENGTH: 16
<212> TYPE: PRT
<213> ORGANISM: Homo sapiens

<400> SEQUENCE: 77

Arg Ser Ser Gln Ser Leu Leu His Ser Gln Gly Tyr Asn Tyr Leu Asp
1               5                   10                  15

<210> SEQ ID NO 78
<211> LENGTH: 111
<212> TYPE: PRT
<213> ORGANISM: Homo sapiens

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Gln Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Gln Ile Pro Thr Phe Gly Gln Gly Thr Lys Val Glu Ile Lys
            100                 105                 110

<210> SEQ ID NO 79
<211> LENGTH: 16
<212> TYPE: PRT
<213> ORGANISM: Homo sapiens

<400> SEQUENCE: 79

Arg Ser Ser Gln Ser Leu Leu His Ser Ala Gly Tyr Asn Tyr Leu Asp
1               5                   10                  15

<210> SEQ ID NO 80
<211> LENGTH: 111
<212> TYPE: PRT
<213> ORGANISM: Homo sapiens

<400> SEQUENCE: 80

Asp Ile Val Met Thr Gln Ser Pro Leu Ser Leu Pro Val Thr Pro Gly

```
            1               5                  10                 15
         Glu Pro Ala Ser Ile Ser Cys Arg Ser Ser Gln Ser Leu Leu His Ser
                        20                  25                  30

Ala Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                        50                  55                  60

Asp Arg Phe Ser Gly Ser Gly Ser Gly Thr Asp Phe Thr Leu Lys Ile
         65                  70                  75                  80

Ser Arg Val Glu Ala Glu Asp Val Gly Val Tyr Tyr Cys Met Gln Ala
                             85                  90                  95

Met Gln Ile Pro Thr Phe Gly Gln Gly Thr Lys Val Glu Ile Lys
                            100                 105                 110
```

<210> SEQ ID NO 81
<211> LENGTH: 16
<212> TYPE: PRT
<213> ORGANISM: Homo sapiens

<400> SEQUENCE: 81

```
Arg Ser Ser Gln Ser Leu Leu His Ser Gly Gly Tyr Asn Tyr Leu Asp
1               5                  10                  15
```

<210> SEQ ID NO 82
<211> LENGTH: 111
<212> TYPE: PRT
<213> ORGANISM: Homo sapiens

<400> SEQUENCE: 82

```
Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Gly Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                    85                  90                  95

Met Gln Ile Pro Thr Phe Gly Gln Gly Thr Lys Val Glu Ile Lys
                   100                 105                 110
```

<210> SEQ ID NO 83
<211> LENGTH: 16
<212> TYPE: PRT
<213> ORGANISM: Homo sapiens

<400> SEQUENCE: 83

```
Arg Ser Ser Gln Ser Leu Leu His Ser Asn Ala Tyr Asn Tyr Leu Asp
1               5                  10                  15
```

<210> SEQ ID NO 84
<211> LENGTH: 111
<212> TYPE: PRT
<213> ORGANISM: Homo sapiens

<400> SEQUENCE: 84

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Ala Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Gln Ile Pro Thr Phe Gly Gln Gly Thr Lys Val Glu Ile Lys
            100                 105                 110

<210> SEQ ID NO 85
<211> LENGTH: 16
<212> TYPE: PRT
<213> ORGANISM: Homo sapiens

<400> SEQUENCE: 85

Arg Ser Ser Gln Ser Leu Leu His Ser Asn Glu Tyr Asn Tyr Leu Asp
1               5                   10                  15

<210> SEQ ID NO 86
<211> LENGTH: 111
<212> TYPE: PRT
<213> ORGANISM: Homo sapiens

<400> SEQUENCE: 86

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Gln Ile Pro Thr Phe Gly Gln Gly Thr Lys Val Glu Ile Lys
            100                 105                 110

<210> SEQ ID NO 87
<211> LENGTH: 16
<212> TYPE: PRT
<213> ORGANISM: Homo sapiens

<400> SEQUENCE: 87

Arg Ser Ser Gln Ser Leu Leu His Ser Asn Gln Tyr Asn Tyr Leu Asp
1               5                   10                  15

<210> SEQ ID NO 88
<211> LENGTH: 111
<212> TYPE: PRT
<213> ORGANISM: Homo sapiens

<400> SEQUENCE: 88

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gln Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Gln Ile Pro Thr Phe Gly Gln Gly Thr Lys Val Glu Ile Lys
            100                 105                 110

<210> SEQ ID NO 89
<211> LENGTH: 17
<212> TYPE: PRT
<213> ORGANISM: Homo sapiens

<400> SEQUENCE: 89

Ile Ile Tyr Pro Gly Ser Ser Asp Thr Arg Tyr Ser Pro Ser Phe Gln
1               5                   10                  15

Gly

<210> SEQ ID NO 90
<211> LENGTH: 116
<212> TYPE: PRT
<213> ORGANISM: Homo sapiens

<400> SEQUENCE: 90

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Ser Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 91
<211> LENGTH: 17
<212> TYPE: PRT
<213> ORGANISM: Homo sapiens

<400> SEQUENCE: 91

Ile Ile Tyr Pro Gly Thr Ser Asp Thr Arg Tyr Ser Pro Ser Phe Gln
1               5                   10                  15

Gly

<210> SEQ ID NO 92
<211> LENGTH: 116
<212> TYPE: PRT
<213> ORGANISM: Homo sapiens

<400> SEQUENCE: 92

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Thr Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115
```

<210> SEQ ID NO 93
<211> LENGTH: 17
<212> TYPE: PRT
<213> ORGANISM: Homo sapiens

<400> SEQUENCE: 93

```
Ile Ile Tyr Pro Gly Glu Ser Asp Thr Arg Tyr Ser Pro Ser Phe Gln
1               5                   10                  15

Gly
```

<210> SEQ ID NO 94
<211> LENGTH: 116
<212> TYPE: PRT
<213> ORGANISM: Homo sapiens

<400> SEQUENCE: 94

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Glu Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115
```

```
<210> SEQ ID NO 95
<211> LENGTH: 17
<212> TYPE: PRT
<213> ORGANISM: Homo sapiens

<400> SEQUENCE: 95

Ile Ile Tyr Pro Gly Gln Ser Asp Thr Arg Tyr Ser Pro Ser Phe Gln
1               5                   10                  15

Gly

<210> SEQ ID NO 96
<211> LENGTH: 116
<212> TYPE: PRT
<213> ORGANISM: Homo sapiens

<400> SEQUENCE: 96

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Gln Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 97
<211> LENGTH: 17
<212> TYPE: PRT
<213> ORGANISM: Homo sapiens

<400> SEQUENCE: 97

Ile Ile Tyr Pro Gly Ala Ser Asp Thr Arg Tyr Ser Pro Ser Phe Gln
1               5                   10                  15

Gly

<210> SEQ ID NO 98
<211> LENGTH: 116
<212> TYPE: PRT
<213> ORGANISM: Homo sapiens

<400> SEQUENCE: 98

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Ala Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115
```

<210> SEQ ID NO 99
<211> LENGTH: 17
<212> TYPE: PRT
<213> ORGANISM: Homo sapiens

<400> SEQUENCE: 99

```
Ile Ile Tyr Pro Gly Gly Ser Asp Thr Arg Tyr Ser Pro Ser Phe Gln
1               5                   10                  15

Gly
```

<210> SEQ ID NO 100
<211> LENGTH: 116
<212> TYPE: PRT
<213> ORGANISM: Homo sapiens

<400> SEQUENCE: 100

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Gly Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115
```

<210> SEQ ID NO 101
<211> LENGTH: 17
<212> TYPE: PRT
<213> ORGANISM: Homo sapiens

<400> SEQUENCE: 101

```
Ile Ile Tyr Pro Gly Asp Ala Asp Thr Arg Tyr Ser Pro Ser Phe Gln
1               5                   10                  15

Gly
```

<210> SEQ ID NO 102
<211> LENGTH: 116
<212> TYPE: PRT
<213> ORGANISM: Homo sapiens

<400> SEQUENCE: 102

```
Glu Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ala Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 103
<211> LENGTH: 17
<212> TYPE: PRT
<213> ORGANISM: Homo sapiens

<400> SEQUENCE: 103

Ile Ile Tyr Pro Gly Asp Glu Asp Thr Arg Tyr Ser Pro Ser Phe Gln
1               5                   10                  15

Gly

<210> SEQ ID NO 104
<211> LENGTH: 116
<212> TYPE: PRT
<213> ORGANISM: Homo sapiens

<400> SEQUENCE: 104

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Glu Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 105
<211> LENGTH: 17
<212> TYPE: PRT
<213> ORGANISM: Homo sapiens

<400> SEQUENCE: 105

Ile Ile Tyr Pro Gly Asp Gln Asp Thr Arg Tyr Ser Pro Ser Phe Gln
1               5                   10                  15

Gly
```

<210> SEQ ID NO 106
<211> LENGTH: 116
<212> TYPE: PRT
<213> ORGANISM: Homo sapiens

<400> SEQUENCE: 106

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Gln Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 107
<211> LENGTH: 5
<212> TYPE: PRT
<213> ORGANISM: Homo sapiens

<400> SEQUENCE: 107

Ser Tyr Phe Ile Gly
1               5

<210> SEQ ID NO 108
<211> LENGTH: 116
<212> TYPE: PRT
<213> ORGANISM: Homo sapiens

<400> SEQUENCE: 108

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Phe Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 109
<211> LENGTH: 5
<212> TYPE: PRT

<213> ORGANISM: Homo sapiens

<400> SEQUENCE: 109

Ser Tyr Tyr Ile Gly
1               5

<210> SEQ ID NO 110
<211> LENGTH: 116
<212> TYPE: PRT
<213> ORGANISM: Homo sapiens

<400> SEQUENCE: 110

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Tyr Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
                100                 105                 110

Thr Val Ser Ser
        115

<210> SEQ ID NO 111
<211> LENGTH: 5
<212> TYPE: PRT
<213> ORGANISM: Homo sapiens

<400> SEQUENCE: 111

Ser Tyr Val Ile Gly
1               5

<210> SEQ ID NO 112
<211> LENGTH: 116
<212> TYPE: PRT
<213> ORGANISM: Homo sapiens

<400> SEQUENCE: 112

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Val Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
                100                 105                 110

Thr Val Ser Ser
         115

<210> SEQ ID NO 113
<211> LENGTH: 5
<212> TYPE: PRT
<213> ORGANISM: Homo sapiens

<400> SEQUENCE: 113

Ser Tyr Ile Ile Gly
1               5

<210> SEQ ID NO 114
<211> LENGTH: 116
<212> TYPE: PRT
<213> ORGANISM: Homo sapiens

<400> SEQUENCE: 114

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Ile Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
         115

<210> SEQ ID NO 115
<211> LENGTH: 5
<212> TYPE: PRT
<213> ORGANISM: Homo sapiens

<400> SEQUENCE: 115

Ser Tyr Leu Ile Gly
1               5

<210> SEQ ID NO 116
<211> LENGTH: 116
<212> TYPE: PRT
<213> ORGANISM: Homo sapiens

<400> SEQUENCE: 116

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Leu Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

-continued

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 117
<211> LENGTH: 5
<212> TYPE: PRT
<213> ORGANISM: Homo sapiens

<400> SEQUENCE: 117

Ser Tyr Ala Ile Gly
1               5

<210> SEQ ID NO 118
<211> LENGTH: 116
<212> TYPE: PRT
<213> ORGANISM: Homo sapiens

<400> SEQUENCE: 118

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Ala Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asn Gly Tyr Leu Gly Asp Tyr Trp Gly Gln Gly Thr Leu Val
            100                 105                 110

Thr Val Ser Ser
        115

<210> SEQ ID NO 119
<211> LENGTH: 7
<212> TYPE: PRT
<213> ORGANISM: Homo sapiens

<400> SEQUENCE: 119

Val Leu Gly Phe Phe Asp Tyr
1               5

<210> SEQ ID NO 120
<211> LENGTH: 116
<212> TYPE: PRT
<213> ORGANISM: Homo sapiens

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45
Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Gly Phe Phe Asp Tyr Trp Gly Gln Gly Thr Leu Val
                100                 105                 110

Thr Val Ser Ser
         115

<210> SEQ ID NO 121
<211> LENGTH: 7
<212> TYPE: PRT
<213> ORGANISM: Homo sapiens

<400> SEQUENCE: 121

Val Leu Gly Tyr Phe Asp Tyr
 1               5

<210> SEQ ID NO 122
<211> LENGTH: 116
<212> TYPE: PRT
<213> ORGANISM: Homo sapiens

<400> SEQUENCE: 122

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Gly Tyr Phe Asp Tyr Trp Gly Gln Gly Thr Leu Val
                100                 105                 110

Thr Val Ser Ser
         115

<210> SEQ ID NO 123
<211> LENGTH: 7
<212> TYPE: PRT
<213> ORGANISM: Homo sapiens

<400> SEQUENCE: 123

Val Leu Gly Val Phe Asp Tyr
 1               5

<210> SEQ ID NO 124
<211> LENGTH: 116
<212> TYPE: PRT
<213> ORGANISM: Homo sapiens

<400> SEQUENCE: 124
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Val Phe Asp Tyr Trp Gly Gln Gly Thr Leu Val
            100                 105                 110

Thr Val Ser Ser
        115
```

<210> SEQ ID NO 125
<211> LENGTH: 7
<212> TYPE: PRT
<213> ORGANISM: Homo sapiens

<400> SEQUENCE: 125

```
Val Leu Gly Ile Phe Asp Tyr
1               5
```

<210> SEQ ID NO 126
<211> LENGTH: 116
<212> TYPE: PRT
<213> ORGANISM: Homo sapiens

<400> SEQUENCE: 126

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Ile Phe Asp Tyr Trp Gly Gln Gly Thr Leu Val
            100                 105                 110

Thr Val Ser Ser
        115
```

<210> SEQ ID NO 127
<211> LENGTH: 7
<212> TYPE: PRT
<213> ORGANISM: Homo sapiens

<400> SEQUENCE: 127

```
Val Leu Gly Leu Phe Asp Tyr
1               5
```

```
<210> SEQ ID NO 128
<211> LENGTH: 116
<212> TYPE: PRT
<213> ORGANISM: Homo sapiens

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Leu Phe Asp Tyr Trp Gly Gln Gly Thr Leu Val
            100                 105                 110

Thr Val Ser Ser
        115

<210> SEQ ID NO 129
<211> LENGTH: 7
<212> TYPE: PRT
<213> ORGANISM: Homo sapiens

<400> SEQUENCE: 129

Val Leu Gly Ala Phe Asp Tyr
1               5

<210> SEQ ID NO 130
<211> LENGTH: 116
<212> TYPE: PRT
<213> ORGANISM: Homo sapiens

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Ala Phe Asp Tyr Trp Gly Gln Gly Thr Leu Val
            100                 105                 110

Thr Val Ser Ser
        115
```